US010763443B2

(12) United States Patent
Kim et al.

(10) Patent No.: US 10,763,443 B2
(45) Date of Patent: Sep. 1, 2020

(54) COMPOUND FOR ORGANIC ELECTRONIC ELEMENT, ORGANIC ELECTRONIC ELEMENT USING THE SAME, AND ELECTRONIC DEVICE THEREOF

(71) Applicant: Duk San Neolux Co., Ltd., Cheonan-si, Chungcheongnam-do (KR)

(72) Inventors: Wonsam Kim, Cheonan-si (KR); Yeonhee Choi, Cheonan-si (KR); Hyeryeong Kim, Cheonan-si (KR); Jaewan Jang, Cheonan-si (KR); Yuri Kim, Wonju-si (KR); Junghwan Park, Seoul (KR); Soungyun Mun, Yongin-si (KR); Seokhyun Kim, Seongnam-si (KR)

(73) Assignee: Duk San Neolux Co., Ltd (KR)

( * ) Notice: Subject to any disclaimer, the term of this patent is extended or adjusted under 35 U.S.C. 154(b) by 0 days.

(21) Appl. No.: 16/269,678

(22) Filed: Feb. 7, 2019

(65) Prior Publication Data

US 2019/0173023 A1 Jun. 6, 2019

Related U.S. Application Data

(63) Continuation of application No. 15/822,897, filed on Nov. 27, 2017, which is a continuation of application
(Continued)

(30) Foreign Application Priority Data

Dec. 24, 2012 (KR) ........................ 10-2012-0152002

(51) Int. Cl.
*H01L 51/00* (2006.01)
*C07D 403/14* (2006.01)
(Continued)

(52) U.S. Cl.
CPC ........ *H01L 51/0072* (2013.01); *C07D 209/82* (2013.01); *C07D 401/14* (2013.01);
(Continued)

(58) Field of Classification Search
CPC .. C07D 209/82; C07D 401/14; C07D 403/14; C07D 409/14; C07D 471/04;
(Continued)

(56) References Cited

U.S. PATENT DOCUMENTS 8,507,904 B2 8/2013 Kim et al.
9,017,828 B2 4/2015 Kim et al.
(Continued)

FOREIGN PATENT DOCUMENTS

JP 2012-500789 A 1/2012
KR 10-2011-0015836 A 2/2011
(Continued)

OTHER PUBLICATIONS

International Search Report for PCT/KR2013/010680 (in English and Korean), dated Feb. 13, 2014; ISA/KR.

*Primary Examiner* — Jennifer A Chriss
*Assistant Examiner* — Sean M DeGuire
(74) *Attorney, Agent, or Firm* — Harness, Dickey & Pierce, P.L.C.

(57) ABSTRACT

The present invention provides a novel compound which is capable of improving light-emitting efficiency, stability and lifespan of an element, an organic electronic element using the same, and an electronic device thereof.

7 Claims, 1 Drawing Sheet

Related U.S. Application Data

No. 14/654,917, filed as application No. PCT/KR2013/010680 on Nov. 22, 2013, now Pat. No. 10,446,762.

(51) Int. Cl.

| | |
|---|---|
| ***C07D 209/82*** | (2006.01) |
| ***C07D 401/14*** | (2006.01) |
| ***C07D 409/14*** | (2006.01) |
| ***C07D 471/04*** | (2006.01) |
| *H05B 33/20* | (2006.01) |
| *H01L 51/50* | (2006.01) |

(52) U.S. Cl.

CPC ......... *C07D 403/14* (2013.01); *C07D 409/14* (2013.01); *C07D 471/04* (2013.01); *H01L 51/0052* (2013.01); *H01L 51/0071* (2013.01); *H01L 51/0074* (2013.01); *H01L 51/5016* (2013.01); *H05B 33/20* (2013.01); *Y02E 10/549* (2013.01)

(58) Field of Classification Search

CPC ............. H01L 51/0052; H01L 51/0071; H01L 51/0072; H01L 51/0074; H01L 51/5016; H05B 33/20; Y02E 10/549

See application file for complete search history.

(56) References Cited

U.S. PATENT DOCUMENTS

| | | | | |
|---|---|---|---|---|
| 2005/0236970 | A1* | 10/2005 | Matsudate .......... | H01L 27/3244 313/500 |
| 2011/0278555 | A1 | 11/2011 | Inoue et al. | |
| 2011/0279020 | A1* | 11/2011 | Inoue .................. | C07D 209/82 313/504 |
| 2012/0018717 | A1 | 1/2012 | Kim et al. | |
| 2012/0138911 | A1 | 6/2012 | Inoue et al. | |
| 2012/0138912 | A1 | 6/2012 | Inoue et al. | |
| 2012/0235123 | A1 | 9/2012 | Lee et al. | |
| 2012/0305906 | A1 | 12/2012 | Kim et al. | |
| 2013/0001540 | A1 | 1/2013 | Kim et al. | |
| 2015/0133662 | A1 | 5/2015 | Ahn et al. | |

FOREIGN PATENT DOCUMENTS

| | | | |
|---|---|---|---|
| KR | 10-2012-0030009 | A | 3/2012 |
| KR | 20120034648 | A | 4/2012 |
| KR | 2012-0112277 | A | 10/2012 |
| KR | 20120112277 | A * | 10/2012 |
| WO | WO-2011-132684 | A1 | 10/2011 |
| WO | WO-2012-036482 | A1 | 3/2012 |
| WO | WO-2012-067425 | A1 | 5/2012 |
| WO | WO-2012-165844 | A1 | 12/2012 |

* cited by examiner

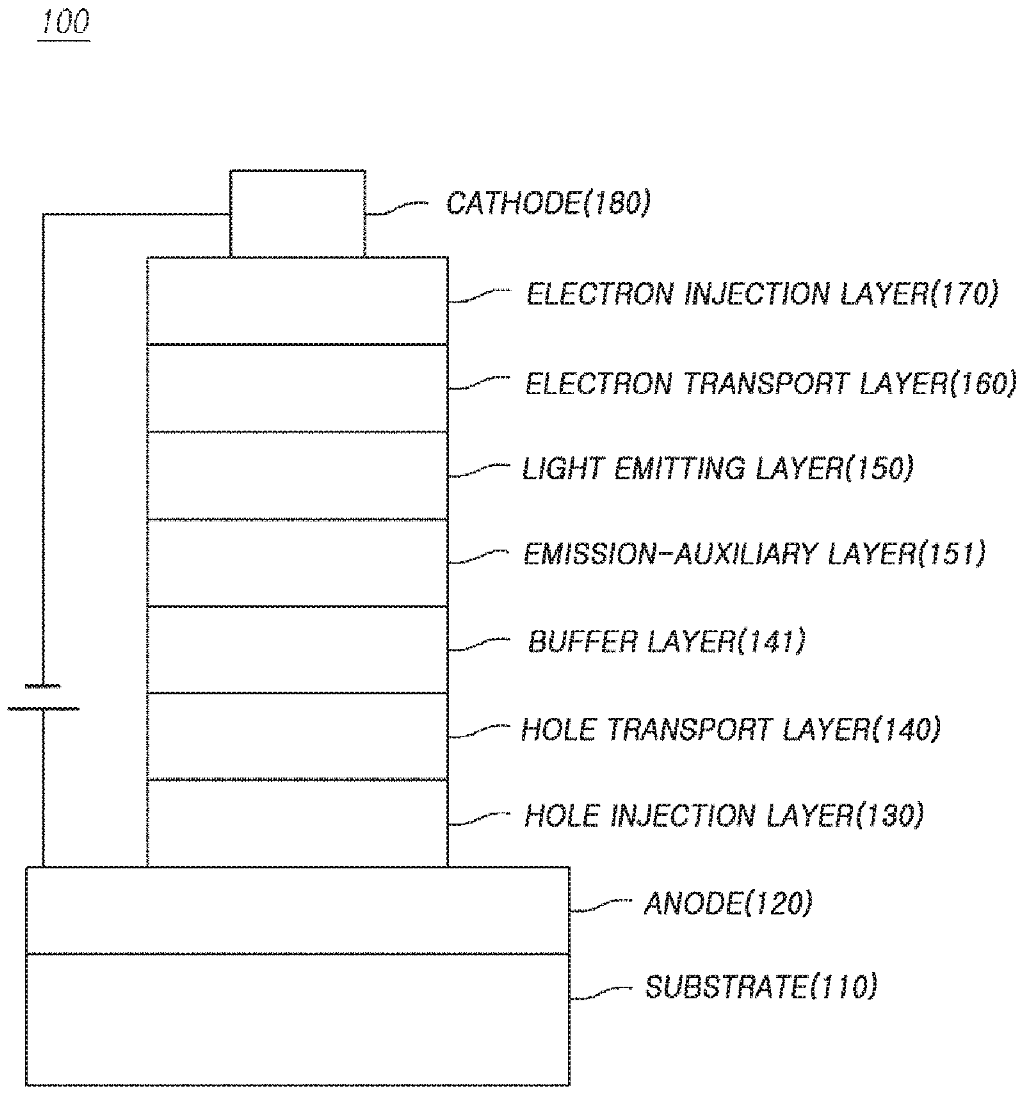
100
CATHODE(180)
ELECTRON INJECTION LAYER(170)
ELECTRON TRANSPORT LAYER(160)
LIGHT EMITTING LAYER(150)
EMISSION-AUXILIARY LAYER(151)
BUFFER LAYER(141)
HOLE TRANSPORT LAYER(140)
HOLE INJECTION LAYER(130)
ANODE(120)
SUBSTRATE(110)

COMPOUND FOR ORGANIC ELECTRONIC ELEMENT, ORGANIC ELECTRONIC ELEMENT USING THE SAME, AND ELECTRONIC DEVICE THEREOF

CROSS-REFERENCE TO RELATED APPLICATIONS

This application is a continuation of U.S. patent application Ser. No. 15/822,897, filed on Nov. 27, 2017, which is a continuation of U.S. patent application Ser. No. 14/654,917, filed on Sep. 15, 2015, which is a 371 U.S. National Stage of International Application No. PCT/KR2013/010680, filed on Nov. 22, 2013. This application also claims priority to Korean Application No. 10-2012-0152002, filed on Dec. 24, 2012. The entire disclosures of the above applications are incorporated herein by reference.

TECHNICAL FIELD

The present invention relates to a compound for an organic electronic element, an organic electronic element using the same, and an electronic device thereof.

BACKGROUND ART

In general, an organic light emitting phenomenon refers to a phenomenon in which electronic energy is converted into light energy by means of an organic material. An organic electronic element utilizing the organic light emitting phenomenon usually has a structure including an anode, a cathode, and an organic material layer interposed therebetween. Here, in many cases, the organic material layer may have a multilayered structure including multiple layers made of different materials in order to improve the efficiency and stability of an organic electronic element, and for example, may include a hole injection layer, a hole transport layer, a light emitting layer, an electron transport layer, an electron injection layer, and the like.

A material used as an organic material layer in an organic electronic element may be classified into a light emitting material and a charge transport material, for example, a hole injection material, a hole transport material, an electron transport material, an electron injection material, and the like according to its function.

It is required to develop a hole injection layer material that retards penetration/diffusion of metal oxides from an anode electrode (ITO) into an organic layer, which is one cause for the shortened lifetime of an organic electronic element, and has stability against Joule heat generated during the operation of an organic electronic element, that is, a high glass transition temperature. Also, it has been reported that a low glass transition temperature of a hole transport layer material has a great effect on the lifetime of an organic electronic element because the uniformity of a thin film surface collapses during the operation of the element. In general, deposition is a main method of forming an OLED, and thus there is an actual need to develop a material that is durable to such a deposition method, that is, a highly heat-resistant material.

That is, in order to allow an organic electronic element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material.

However, such a stable and efficient organic material layer material for an organic electronic element has not yet been fully developed. Accordingly, there is a continuous need to develop new materials for an organic material layer.

DETAILED DESCRIPTION OF THE INVENTION

Technical Problem

In order to solve the above-mentioned problems occurring in the prior art, an object of the present invention is to provide a compound that allows an organic electronic element to have high luminous efficiency, low driving voltage, and high heat resistance and to be improved in color purity and lifetime, an organic electronic element using the same, and an electronic device thereof.

Technical Solution

In accordance with an aspect of the present invention, there is provided a compound represented by Formula 1 below.

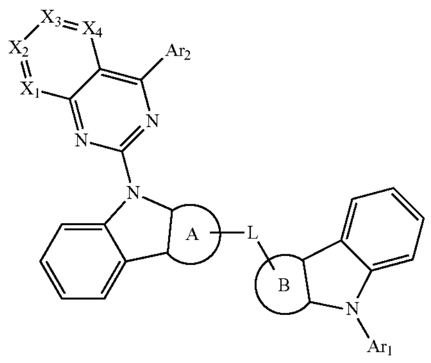

In another aspect of the present invention, there are provided an organic electronic element using the compound represented by the above formula and an electronic device.

Advantageous Effects

The inventive compound allows an organic electronic element to not only have high luminous efficiency, low driving voltage, and high heat resistance, but also be significantly improved in color purity and lifetime.

BRIEF DESCRIPTION OF THE DRAWING

The FIGURE illustrates an example of an organic light emitting diode according to an embodiment of the present invention.

MODE FOR CARRYING OUT THE INVENTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

Unless otherwise stated, the term "halo" or "halogen" as used herein includes fluorine, chlorine, bromine, and iodine.

Unless otherwise stated, the term "alkyl" or "alkyl group" as used herein has, but not limited to, 1 to 60 carbon atoms.

Unless otherwise stated, the term "alkenyl" or "alkynyl" as used herein has, but not limited to, double or triple bonds of 2 to 60 carbon atoms.

Unless otherwise stated, the term "cycloalkyl" as used herein means, but not limited to, alkyl forming a ring having 3 to 60 carbon atoms.

Unless otherwise stated, the term "alkoxy group" as used herein has, but not limited to, 1 to 60 carbon atoms.

Unless otherwise stated, the term "aryl group" or "arylene group" as used herein has, but not limited to, 6 to 60 carbon atoms.

Herein, the aryl group or arylene group means a homocyclic or heterocyclic aromatic group, and includes an aromatic ring that is formed in conjunction with an adjacent substituent linked thereto or participating in the reaction. Examples of the aryl group may include a phenyl group, a biphenyl group, a fluorine group, and a spirofluorene group.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_3$ to $C_{60}$ aryl or arylene group containing one or more heteroatoms, includes both homocyclic and heterocyclic rings, and may also be formed in conjunction with an adjacent group.

Unless otherwise stated, the term "heterocyclic alkyl" or "heterocyclic group" as used herein contains one or more heteroatoms, has 2 to 60 carbon atoms, includes both homocyclic and heterocyclic rings, and may also be formed in conjunction with an adjacent group. Also, the heterocyclic group may mean an alicyclic and/or aromatic group containing heteroatoms.

Unless otherwise stated, the term "heteroatom" as used herein represents at least one of N, O, S, P, and Si.

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "saturated or unsaturated ring" means a saturated or unsaturated aliphatic ring, an aromatic ring having 6 to 60 carbon atoms, or a hetero ring.

Hetero compounds or hetero radicals other than the above-mentioned hetero compounds each contain, but not limited to, one or more heteroatoms.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$~$C_{20}$ alkyl group, a $C_1$~$C_{20}$ alkoxy group, a $C_1$~$C_{20}$ alkylamine group, a $C_1$~$C_{20}$ alkylthio group, a $C_6$~$C_{20}$ arylthio group, a $C_2$~$C_{20}$ alkenyl group, a $C_2$~$C_{20}$ alkynyl group, a $C_3$~$C_{20}$ cycloalkyl group, a $C_6$~$C_{60}$ aryl group, a $C_6$~-$C_{20}$ aryl group substituted by deuterium, a $C_8$~$C_{20}$ arylalkenyl group, a silane group, a boron group, a germanium group, and a $C_5$~$C_{20}$ heterocyclic group.

The FIGURE illustrates an organic electronic element according to an embodiment of the present invention.

Referring to the FIGURE, an organic electronic element 100 according to the present invention includes a first electrode 120 formed on a substrate 110, a second electrode 180, and an organic material layer between the first electrode 120 and the second electrode 180, which contains the compound represented by Formula 1. Here, the first electrode 120 may be an anode (positive electrode), and the second electrode 180 may be a cathode (negative electrode). In the case of an inverted organic electronic element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electronic element according to the present invention may further include protective layer formed one side of one the first and second electrodes, which is opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150.

The organic electronic element according to an embodiment of the present invention may be manufactured using a PVD (physical vapor deposition) method. For example, the organic electronic element may be manufactured by depositing a metal, a conductive metal oxide, or a mixture thereof on the substrate 110 to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by means of a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electronic element according to the present invention may be of a top emission type, a bottom emission type, or a dual emission type.

Further, the organic electronic element according to the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electronic element, and a control unit for controlling the display device. Here, the electronic device may be a wired/wireless communication terminal which is currently used or will be used in the future, and covers all kinds of electronic devices including a mobile communication terminal such as a cellular phone, a PDA, an electronic dictionary, a PMP, a remote controller, a navigation unit, a game player, various kinds of TVs, and various kinds of computers.

Hereinafter, a compound according to an aspect of the present invention will be described.

The compound according to an aspect of the present invention is represented by Formula 1 below.

Formula 1

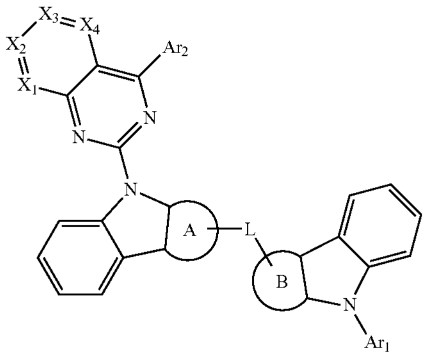

In Formula 1, Rings A and B are each independently a $C_6$~$C_{10}$ aromatic group, and phenyl, naphthalene, or the like may belong thereto. Here, both of rings A and B may be naphthalene, or both of rings A and B may not be naphthalene, that is, ring B may be naphthalene when ring A is phenyl, and ring A may be naphthalene when ring B is phenyl.

In addition, L may be selected from the group consisting of a single bond; a $C_6$~$C_{60}$ arylene group; a fluorenylene group; a $C_2$~$C_{60}$ heterocyclic group containing at least one heteroatom of O, N, S, Si, and P; and a divalent aliphatic hydrocarbon group, and for example, phenylene, naphthalene, or the like may belong thereto.

Here, the single bond means the absence of L, and it can be seen from Formulas 1-1, 1-37, and 1-40 of the present invention that L is absent.

In addition, $Ar_1$ and $Ar_2$ are each independently selected from the group consisting of a fluorenyl group; a silane group; a $C_6$~$C_{60}$ aryl group; a $C_2$~$C_{20}$ alkenyl group; a $C_2$~$C_{60}$ heterocyclic group containing at least one heteroatom of O, N, S, Si, and P; a $C_1$~$C_{50}$ alkyl group; and a fused cyclic group of a $C_6$~$C_{60}$ aromatic ring and a $C_3$~$C_{60}$ aliphatic ring.

In addition, $X_1$ to $X_4$ are each independently CR' or N; and R' may be selected from the group consisting of hydrogen; a $C_6$~$C_{60}$ aryl group; a fluorenyl group; a $C_2$~$C_{60}$ heterocyclic group containing at least one heteroatom of O, N, S, Si, and P; a $C_1$~-$C_{50}$ alkyl group; and a fused cyclic group of a $C_6$~$C_{60}$ aromatic ring and a $C_3$~$C_{60}$ aliphatic ring; and a $C_2$~$C_{20}$ alkenyl group.

Meanwhile, ring A, ring B, $Ar_1$, $Ar_2$, and R' may be further substituted with other substituents.

That is, when the aryl group, fluorenyl group, heterocyclic group, fused cyclic group, alkyl group, alkenyl group, aromatic group, aliphatic hydrocarbon group, arylene group, and fluorenylene group are further substituted with at least one substituent, each of the groups may be further substituted with at least one substituent selected from the group consisting of: deuterium; halogen; a silane group; a siloxane group; a boron group; a germanium group; a cyano group; a nitro group; an amine group; a $C_1$~-$C_{20}$ alkylthio group; a $C_1$~-$C_{20}$ alkoxy group; a $C_1$~$C_{20}$ alkyl group; a $C_2$~$C_{20}$ alkenyl group; a $C_2$~$C_{20}$ alkynyl group; a $C_6$~$C_{20}$ aryl group; a $C_6$~$C_{20}$ aryl group substituted with deuterium; a fluorenyl group; a $C_2$~$C_{20}$ heterocyclic group; a $C_3$~$C_{20}$ cycloalkyl group; a $C_7$~$C_{20}$ arylalkyl group, and a $C_8$~$C_{20}$ arylalkenyl group.

Meanwhile, Formula 1 above may be represented by one of the compounds below.

Formula 2

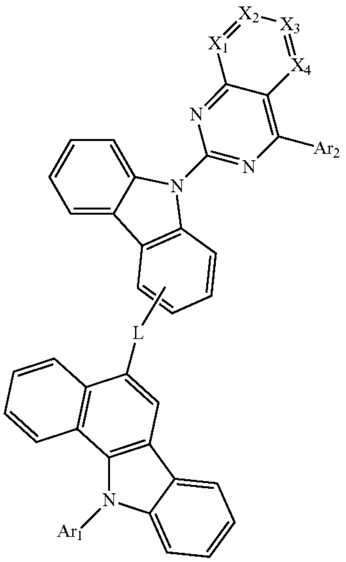

Formula 3

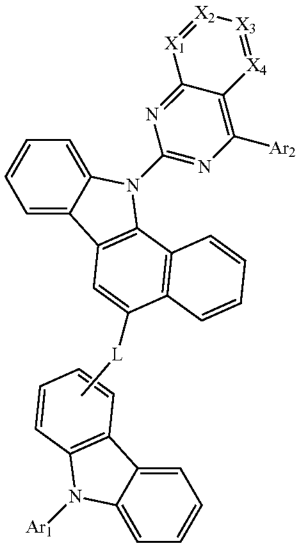

-continued
Formula 4
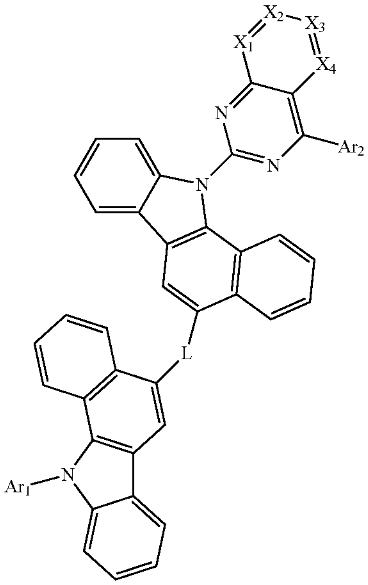
Formula 5
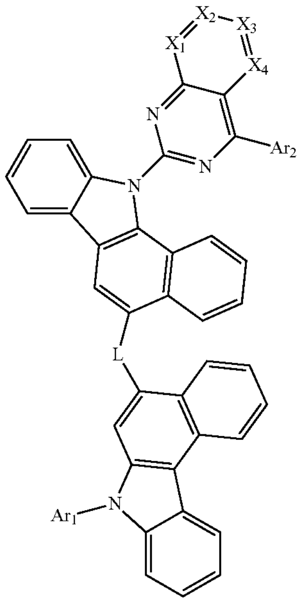
-continued
Formula 6
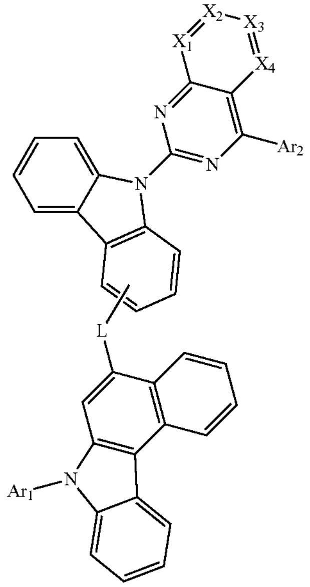
Formula 7
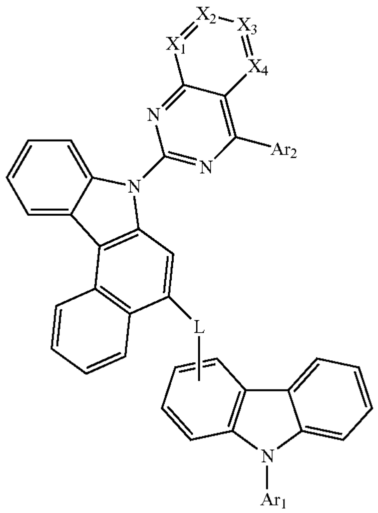
Formula 8
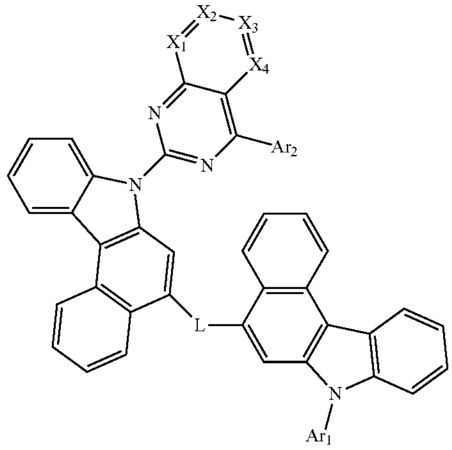

-continued
Formula 9
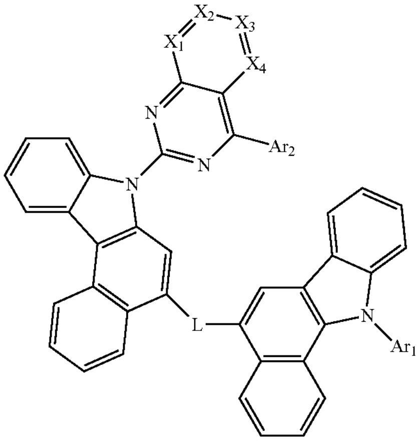
Here, in the Formulas 2 to 9 above, $Ar_1$, $Ar_2$, $X_1$ to $X_4$, and L are defined as in Formula 1.
Meanwhile, Formulas 1 to 9 above may be represented by one of the compounds below.
1-1
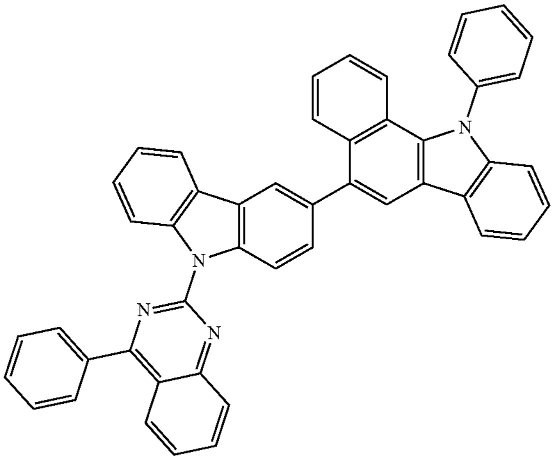
1-2
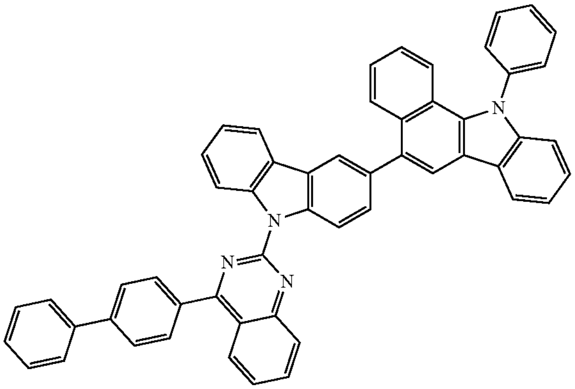
-continued
1-3
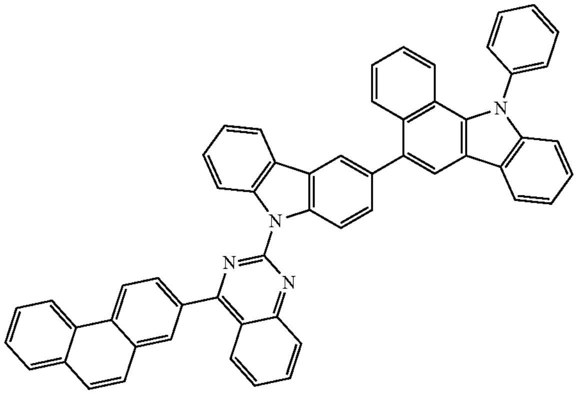
1-4
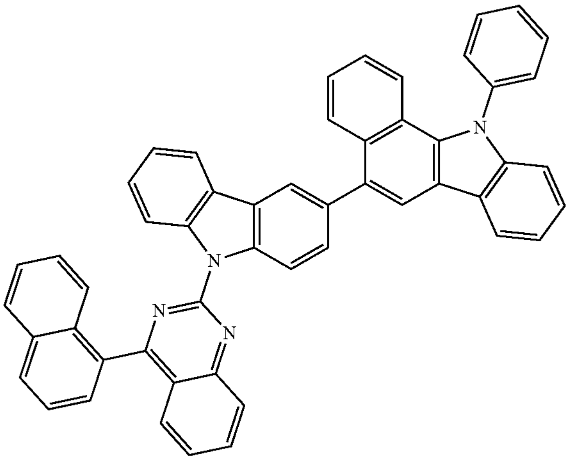
1-5
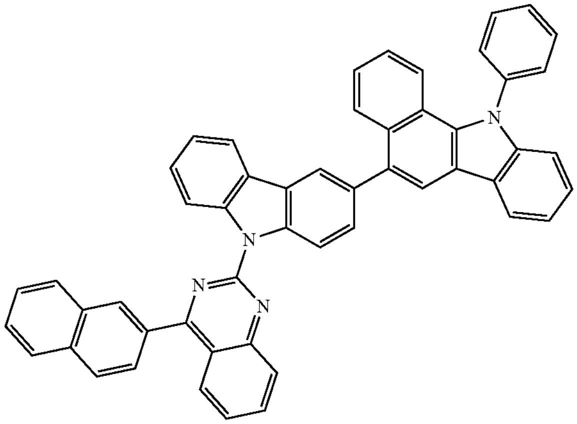

-continued
1-6
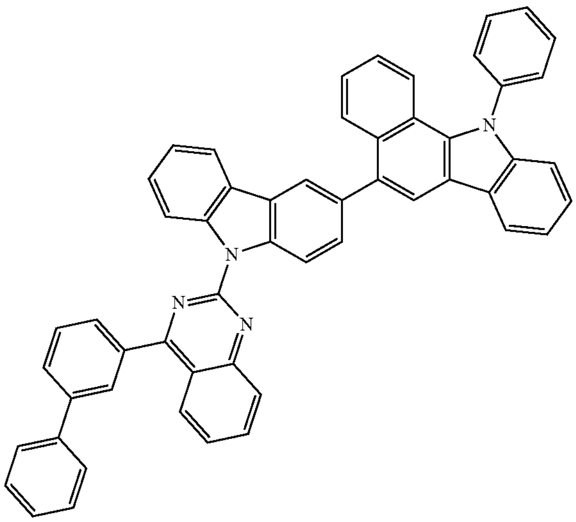
1-7
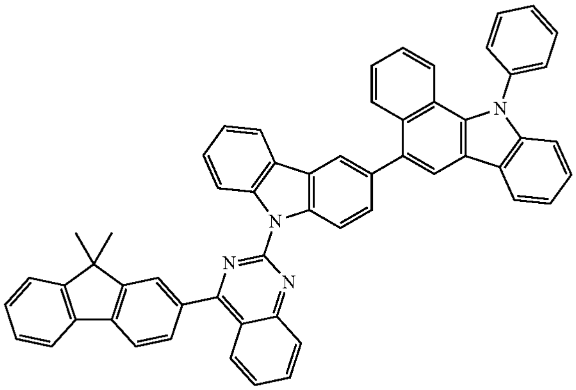
1-8
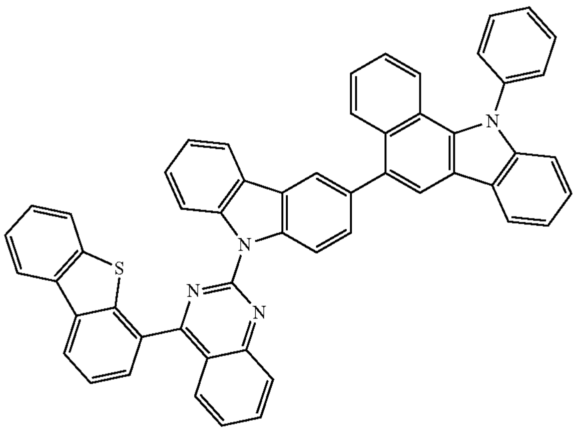
-continued
1-9
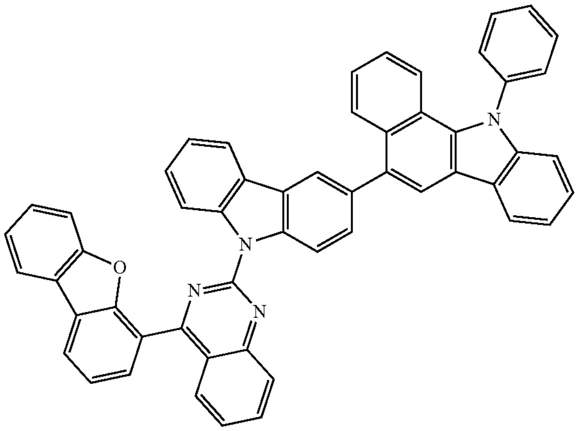
1-10
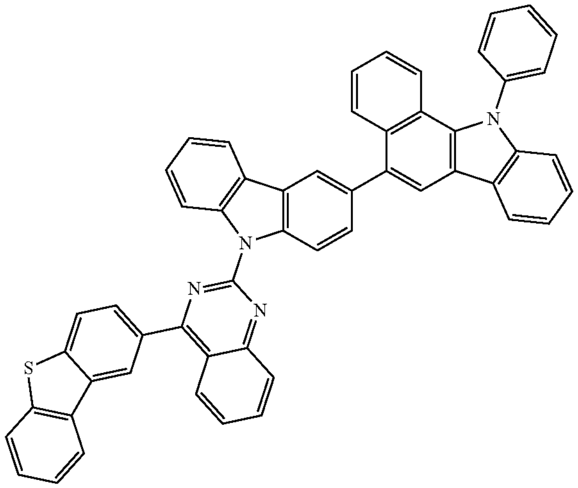
1-11
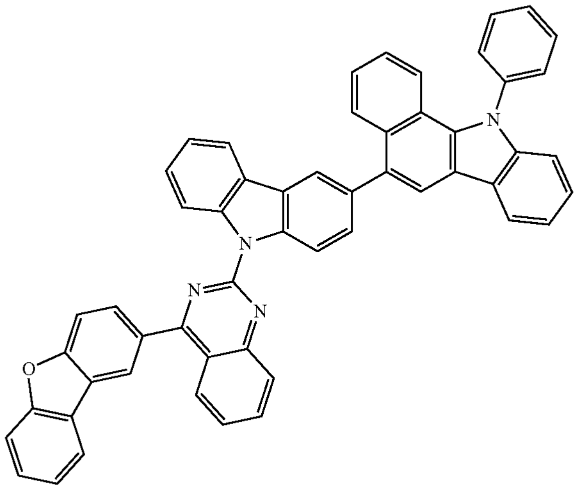

-continued
1-12
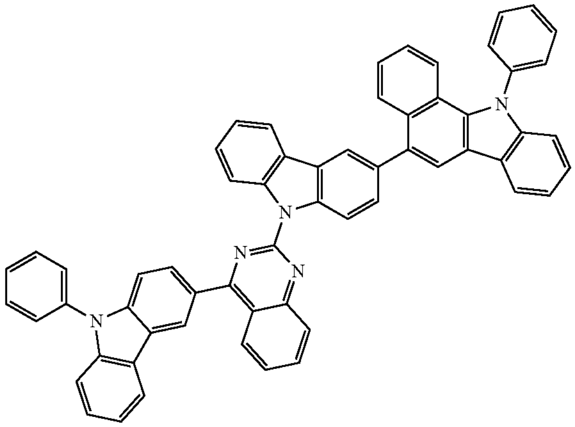
1-13
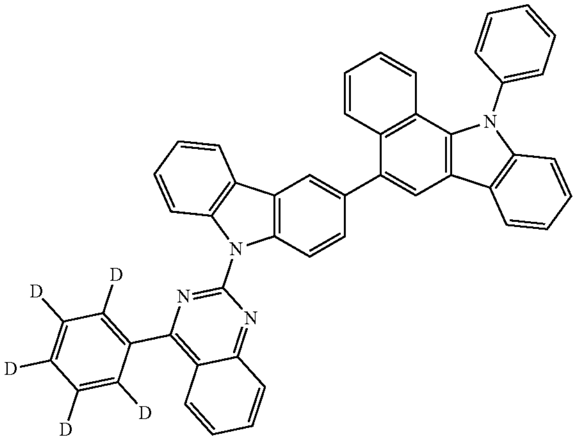
1-14
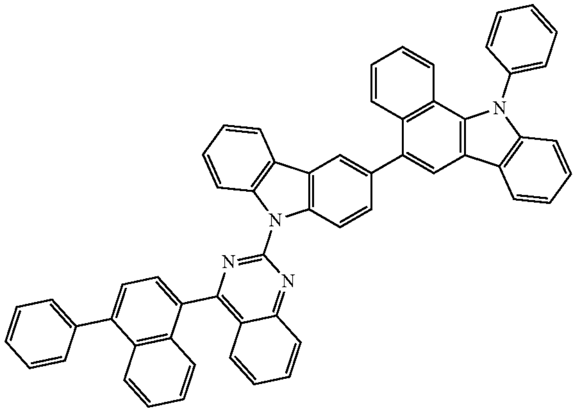
-continued
1-15
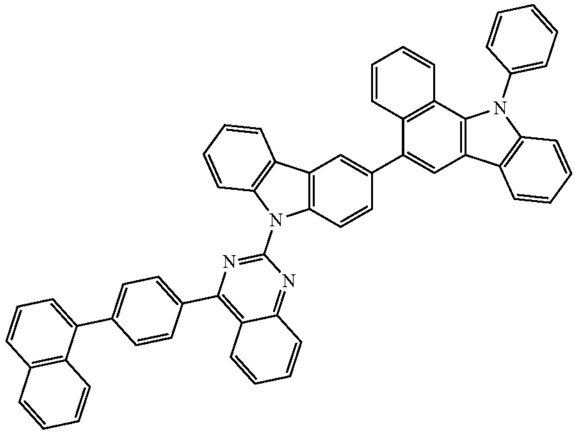
1-16
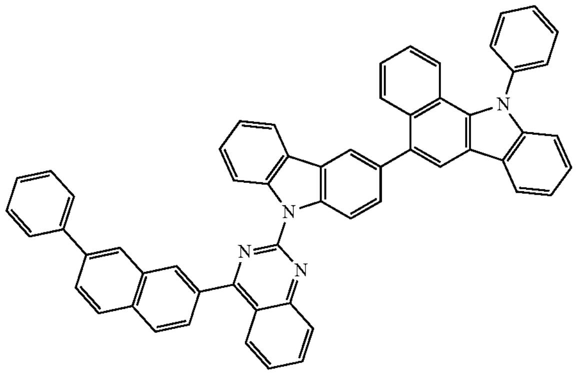
1-17
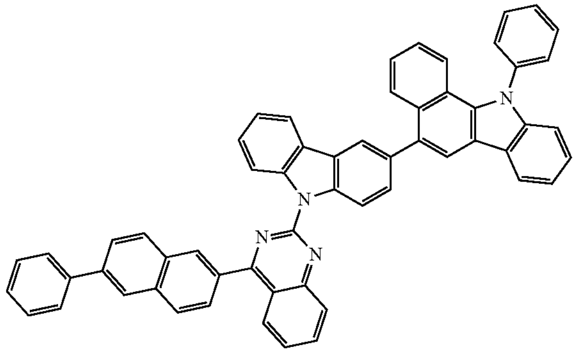

-continued
1-18
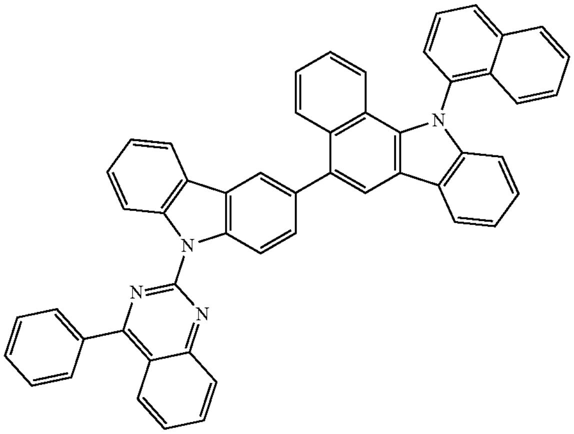
1-19
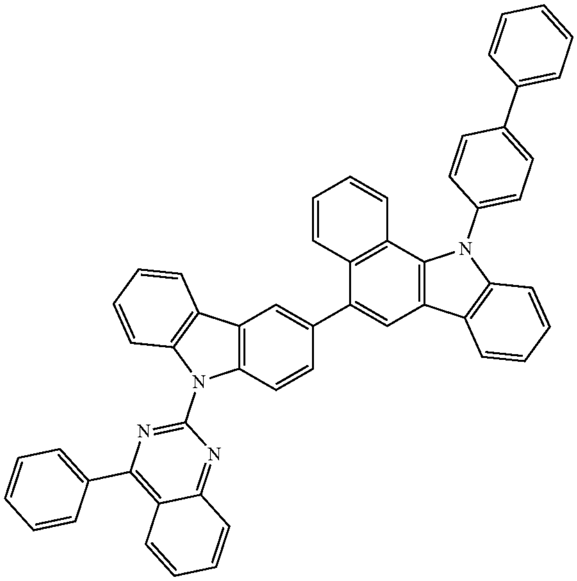
1-20
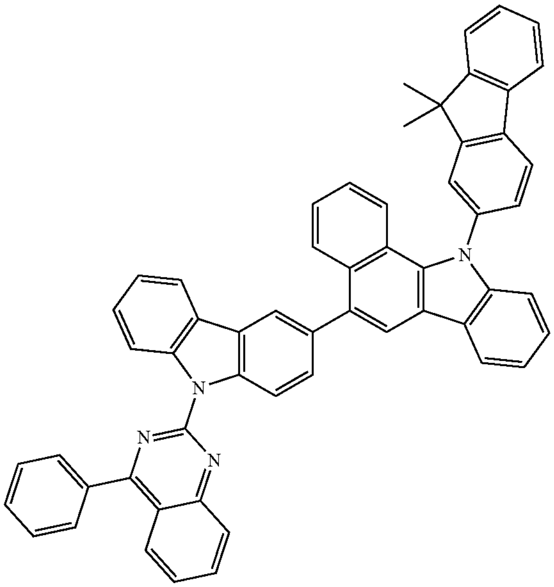
-continued
1-21
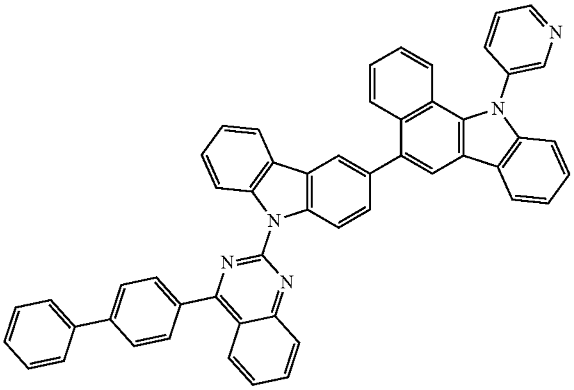
1-22
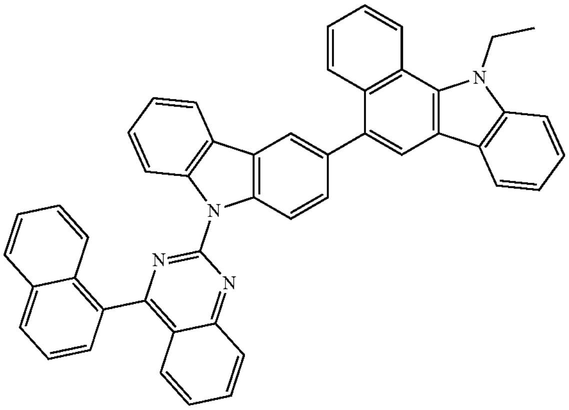
1-23
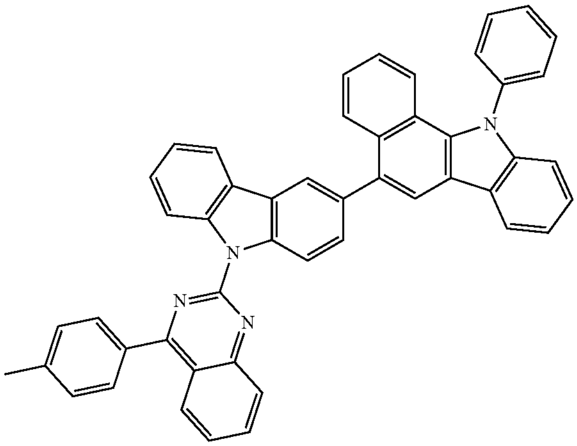

-continued
1-24
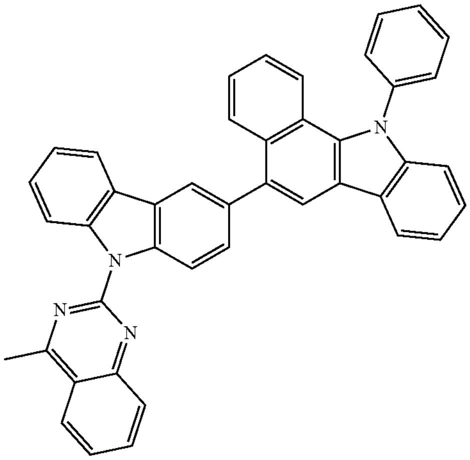
1-25
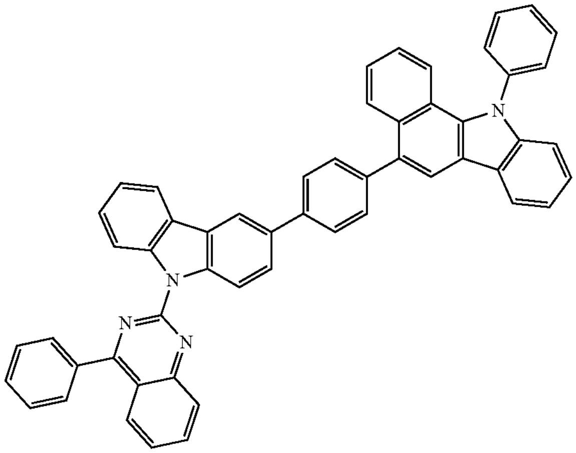
1-26
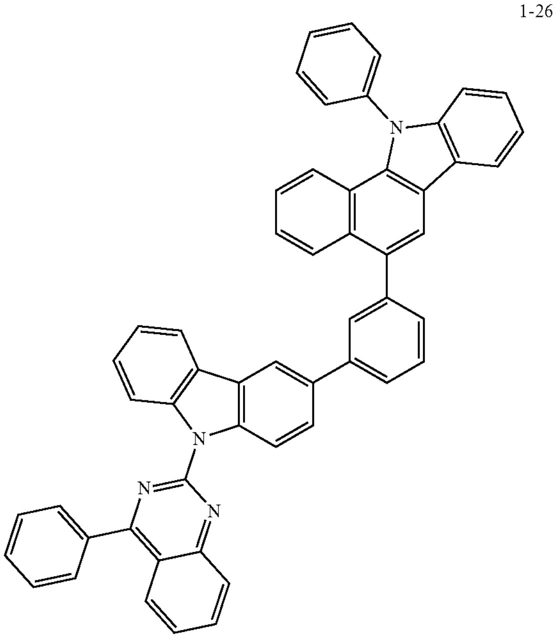
-continued
1-27
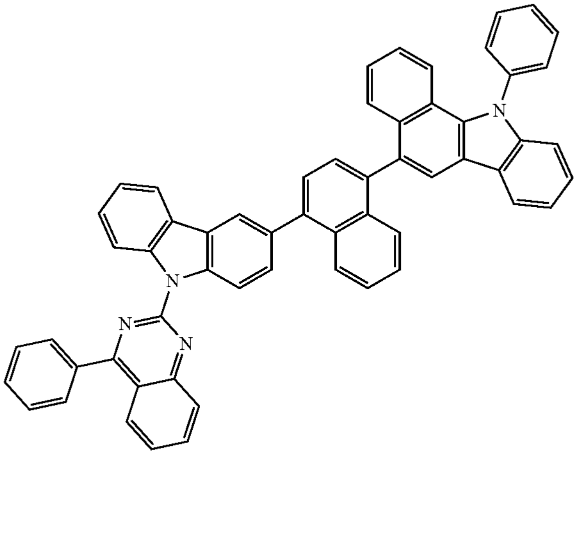
1-28
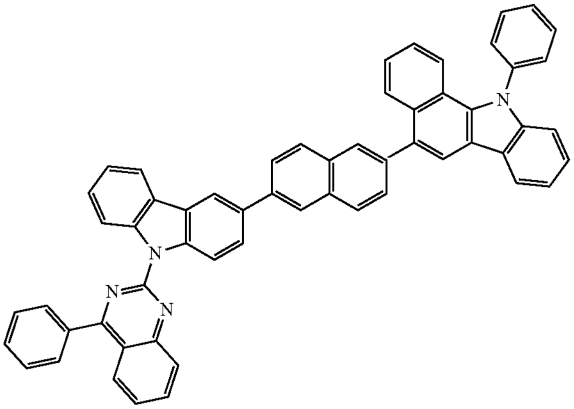
1-29
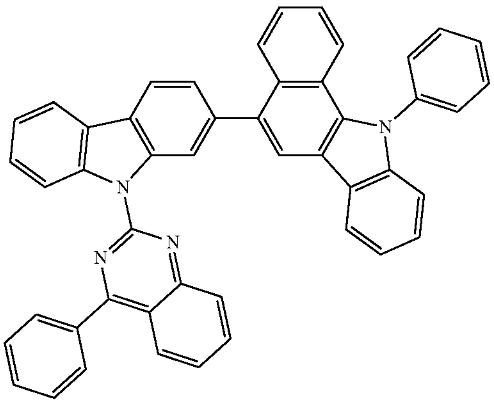

-continued
1-30
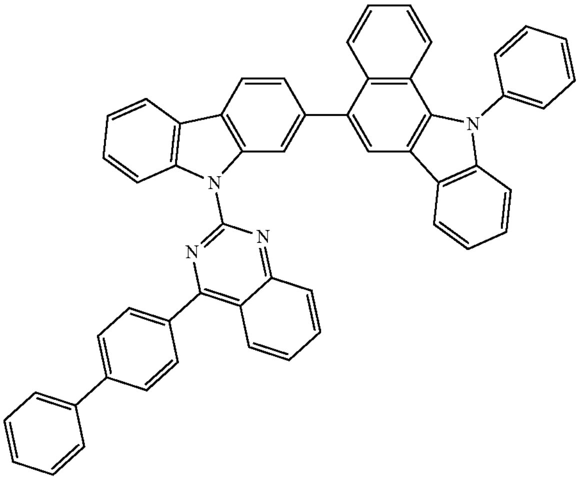
1-31
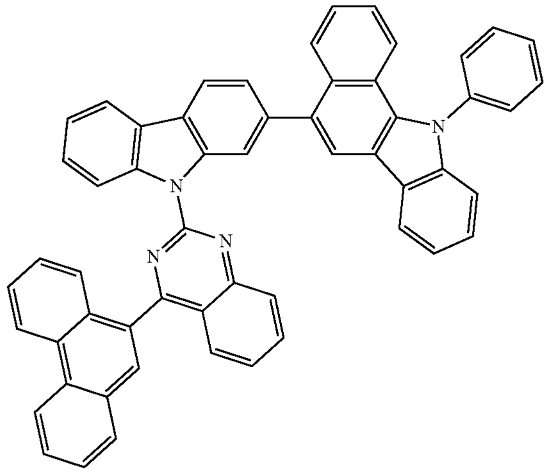
1-32
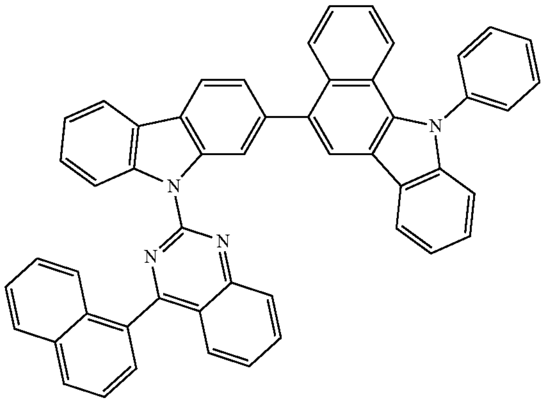
-continued
1-33
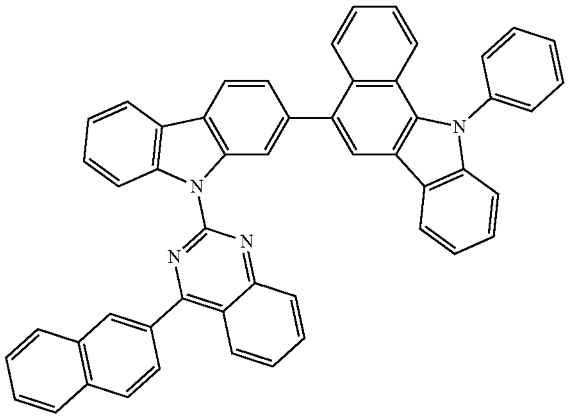
1-34
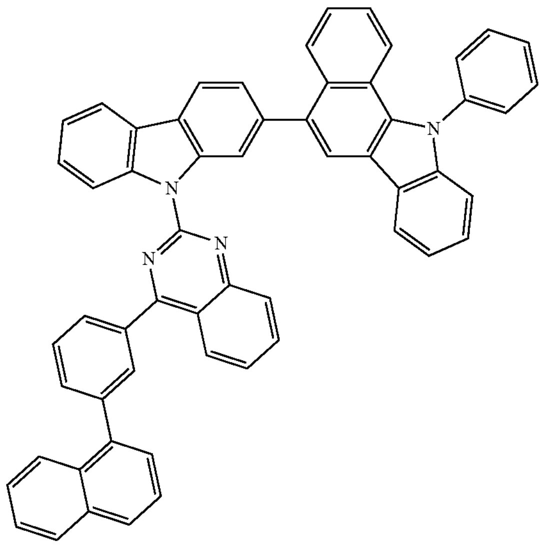
1-35
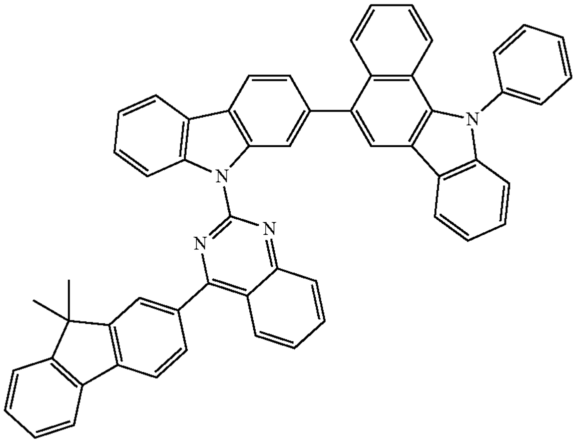

-continued
1-36
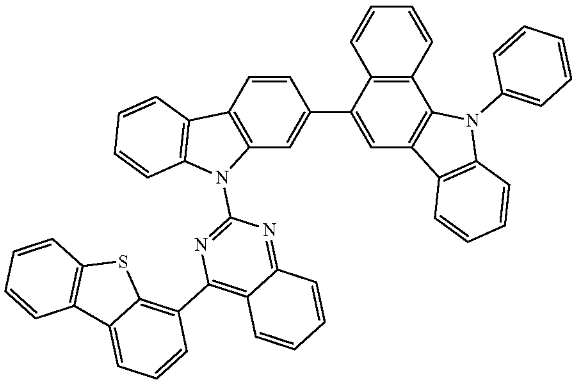
1-37
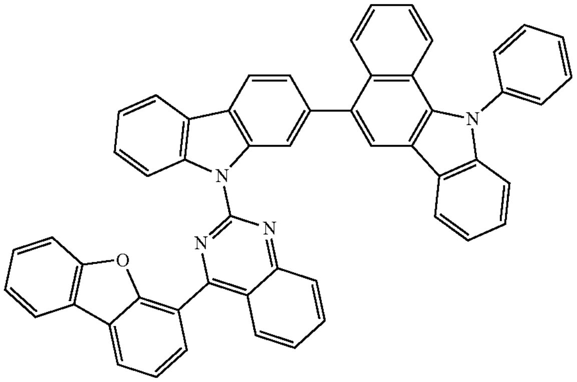
1-38
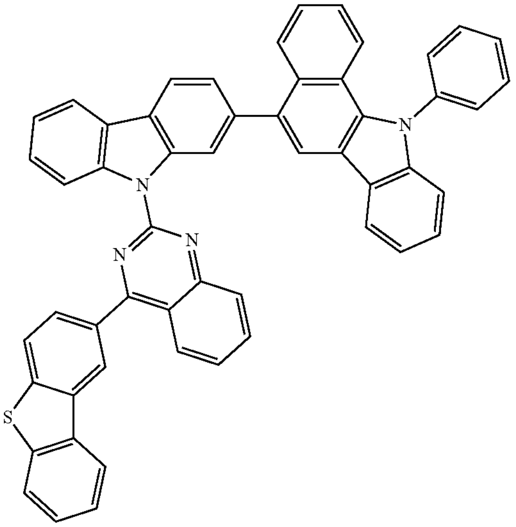
-continued
1-39
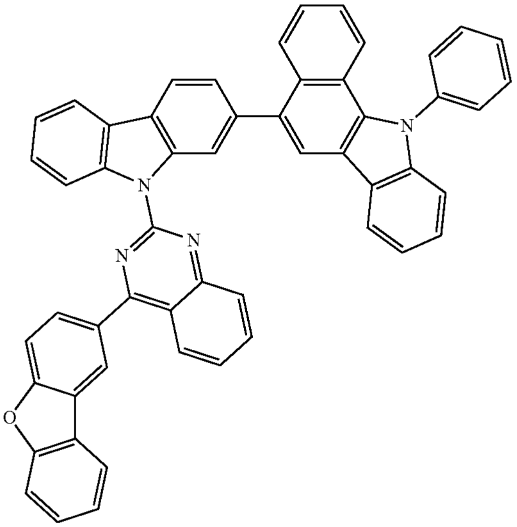
1-40
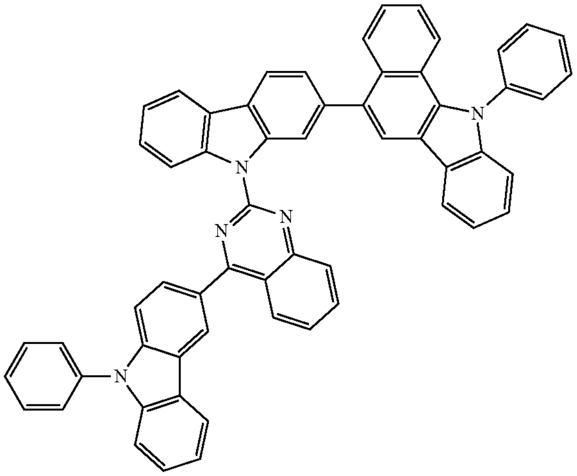
1-41
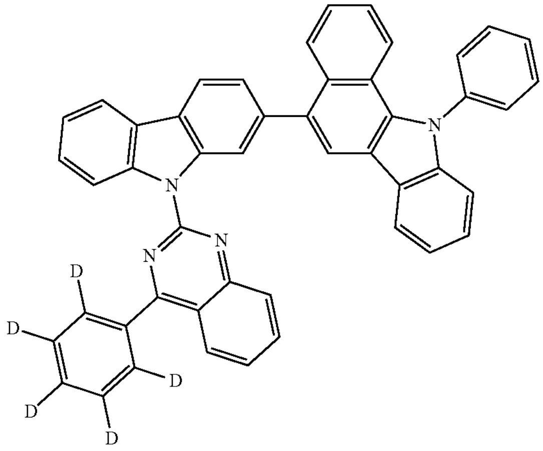

1-42
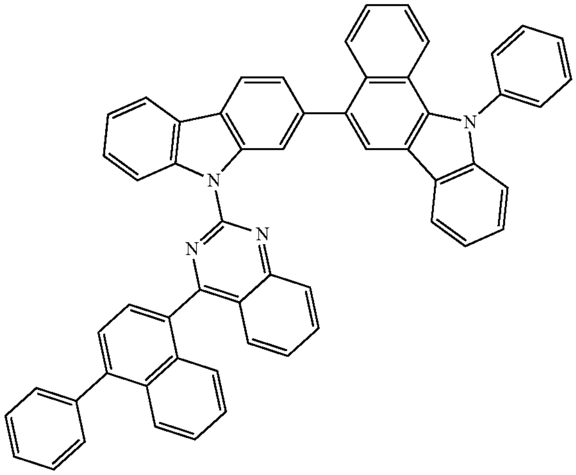
1-43
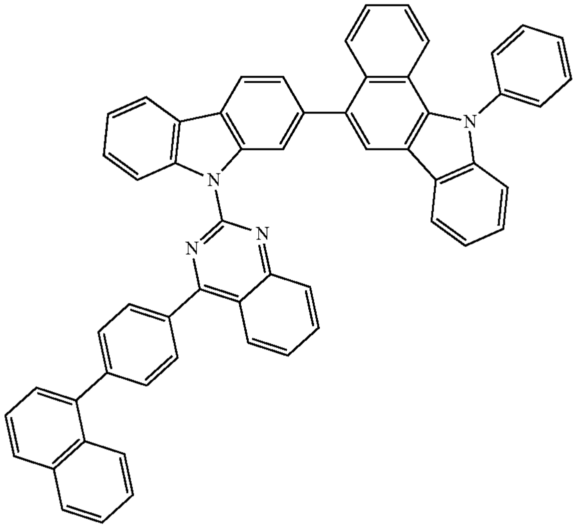
1-44
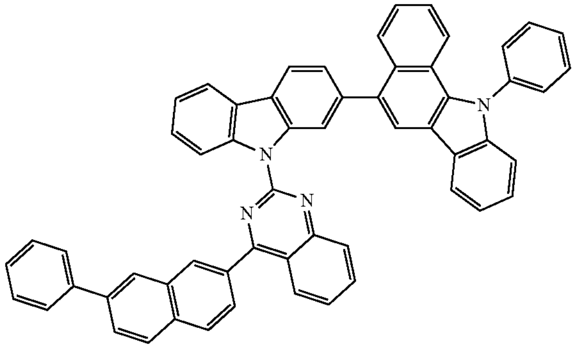
1-45
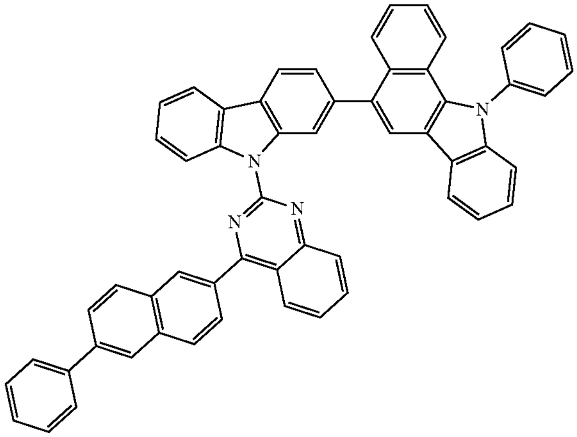
1-46
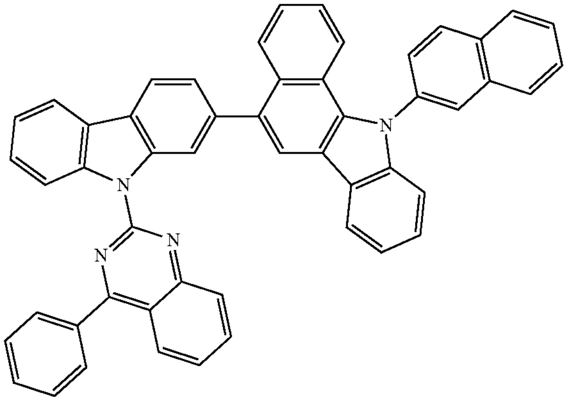
1-47
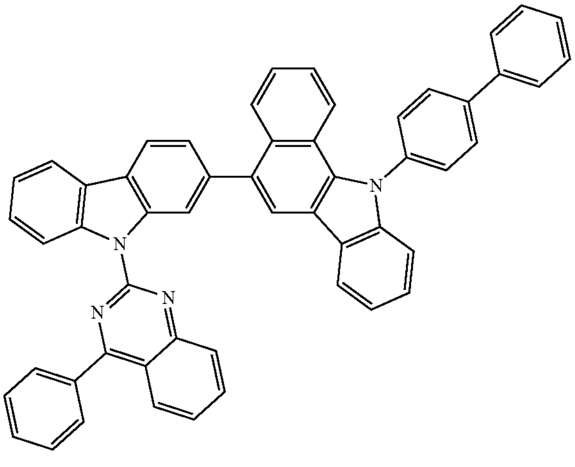

1-48
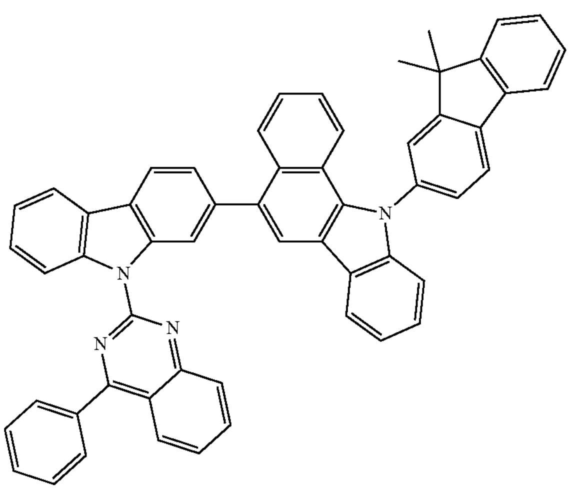
1-49
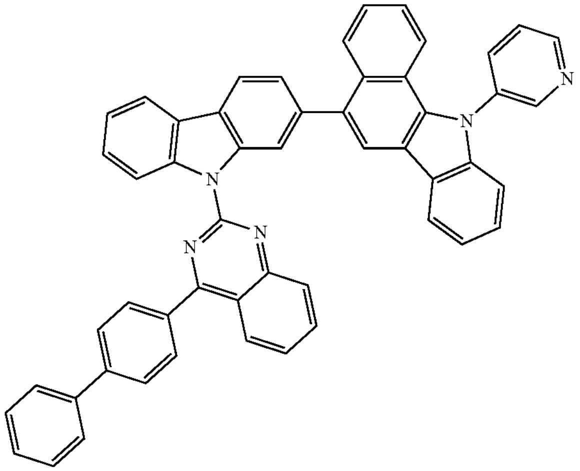
1-50
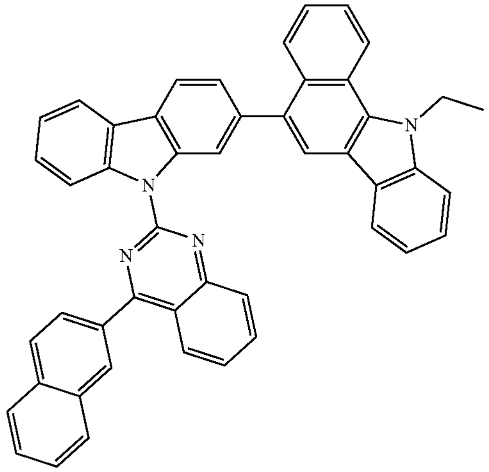
1-51
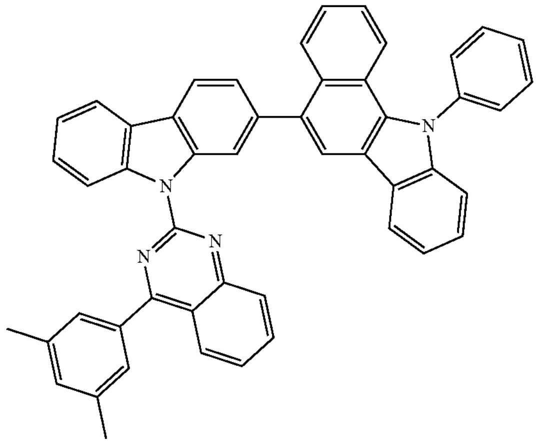
1-52
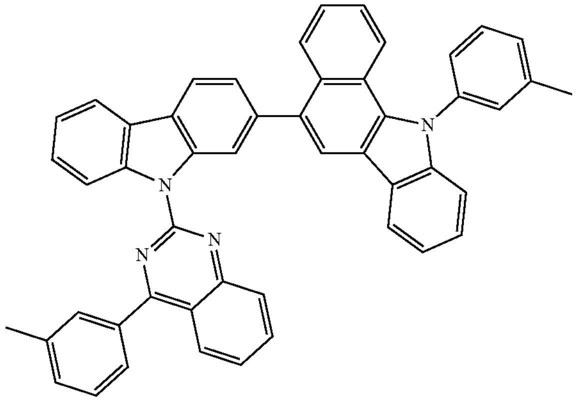
1-53
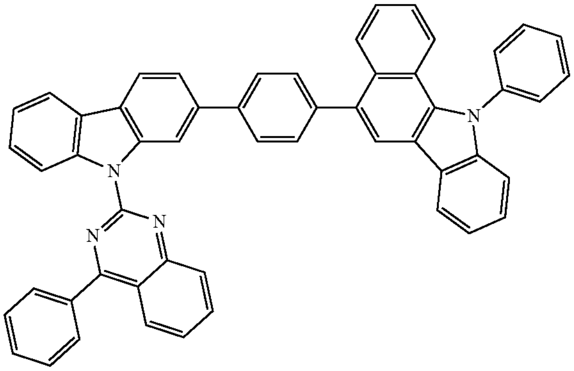
1-54
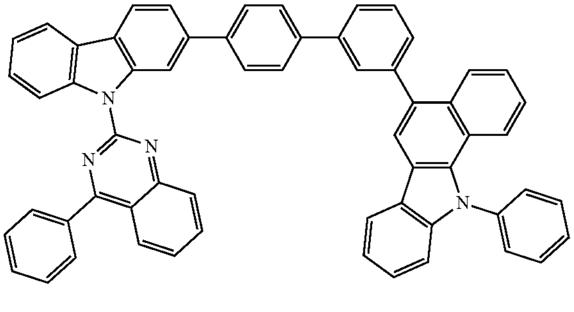

-continued
1-55
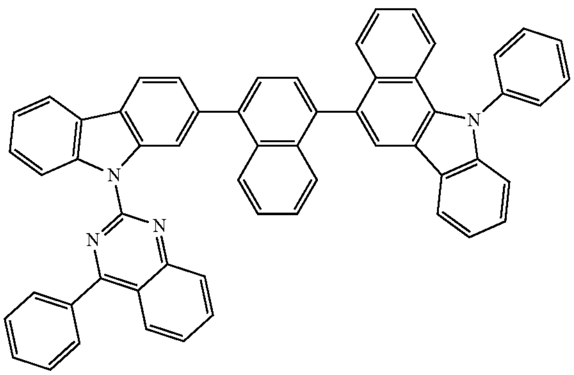
1-56
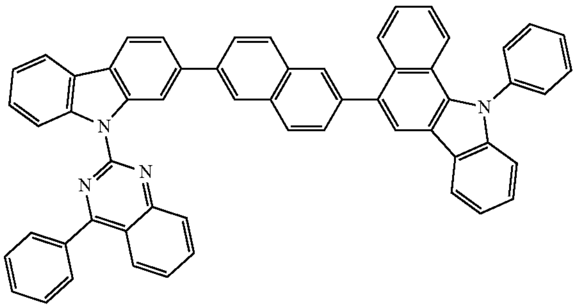
1-57
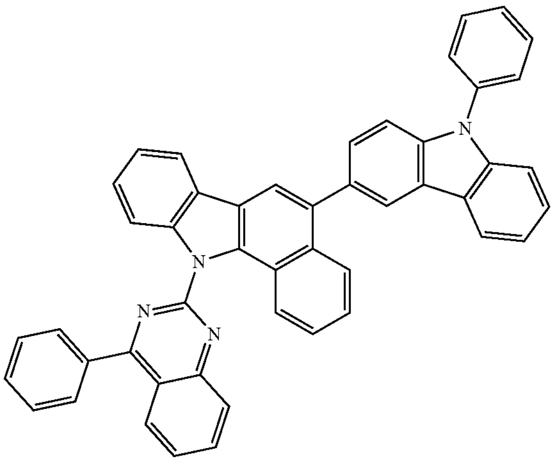
1-58
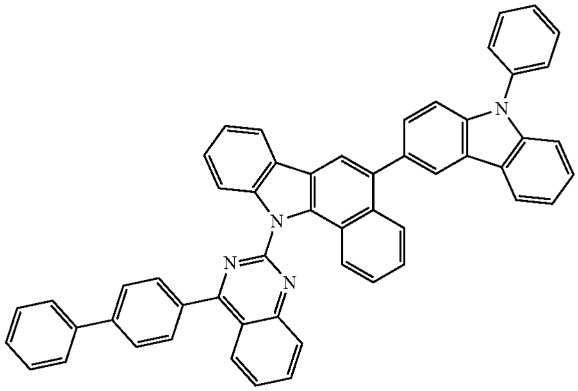
-continued
1-59
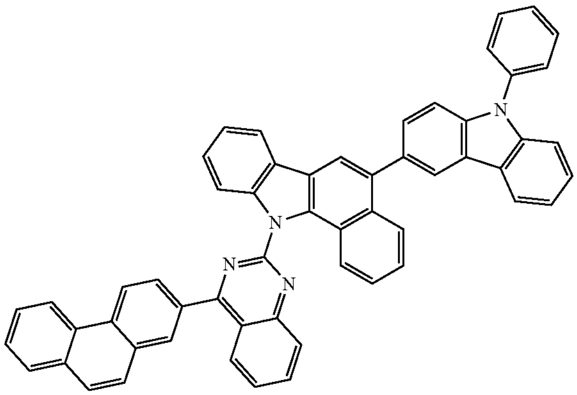
1-60
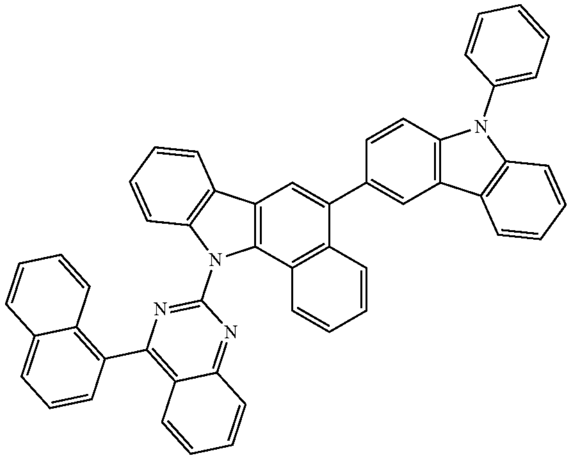
1-61
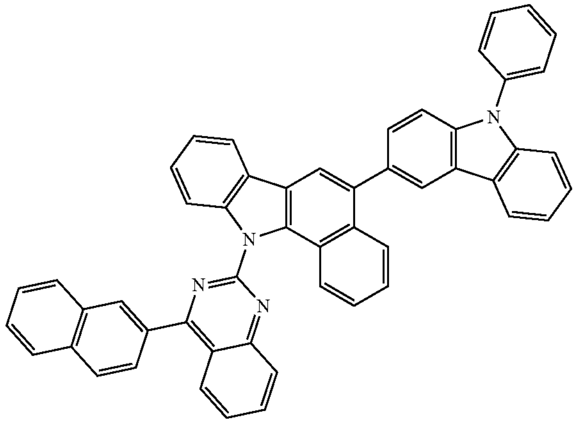

-continued
1-62
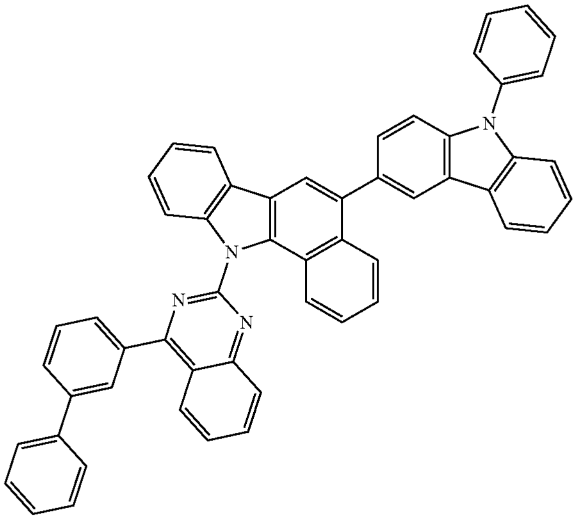
1-63
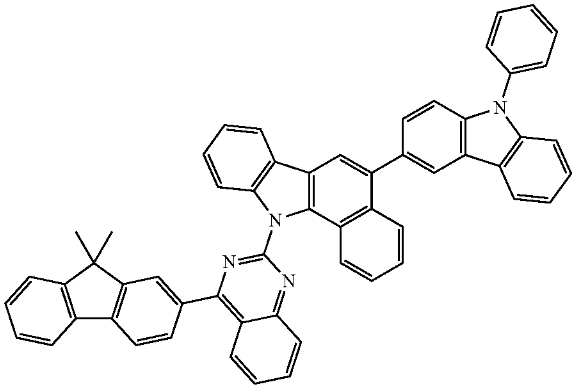
1-64
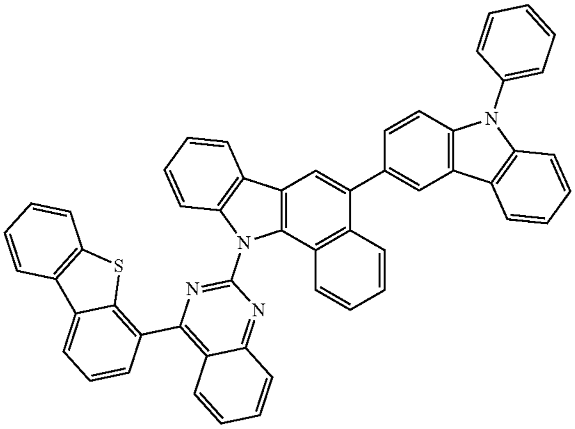
-continued
1-65
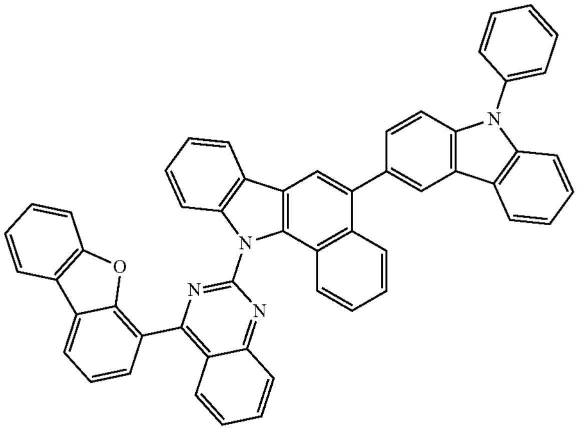
1-66
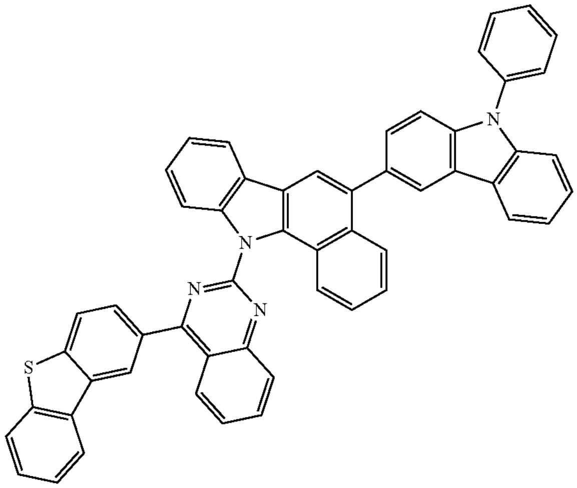
1-67
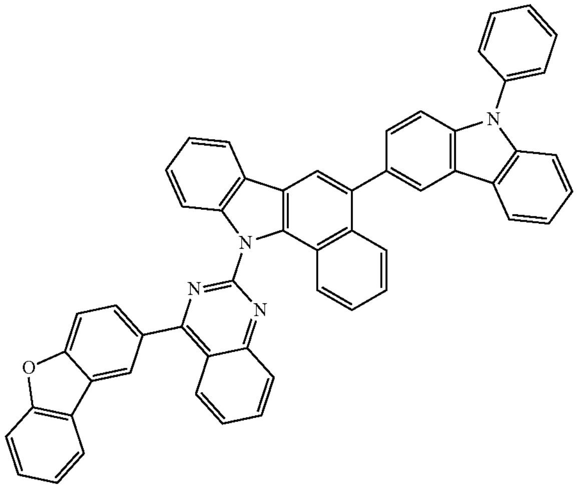

-continued
1-68
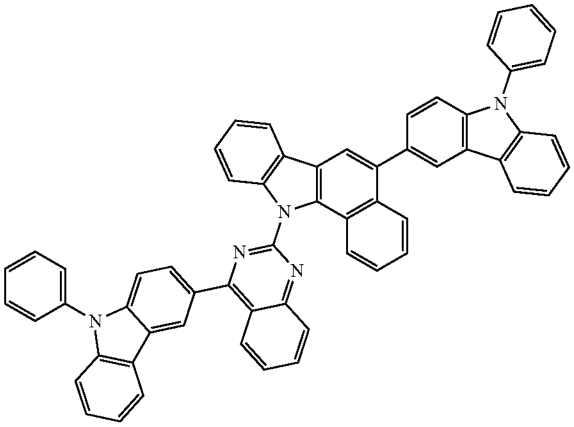
1-69
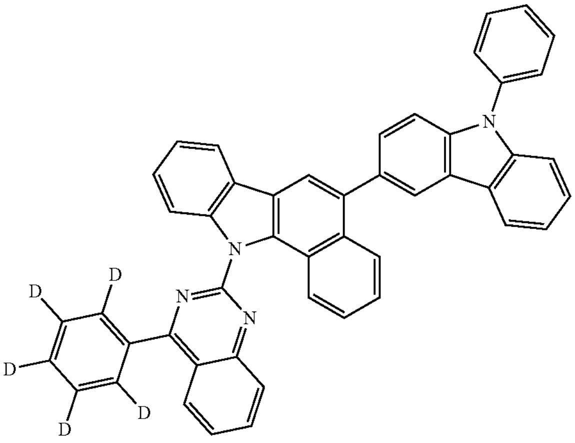
1-70
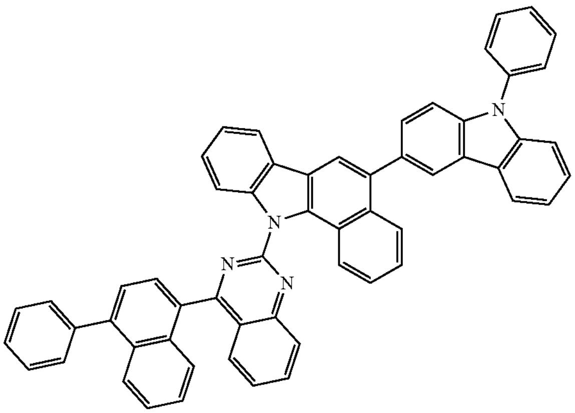
-continued
1-71
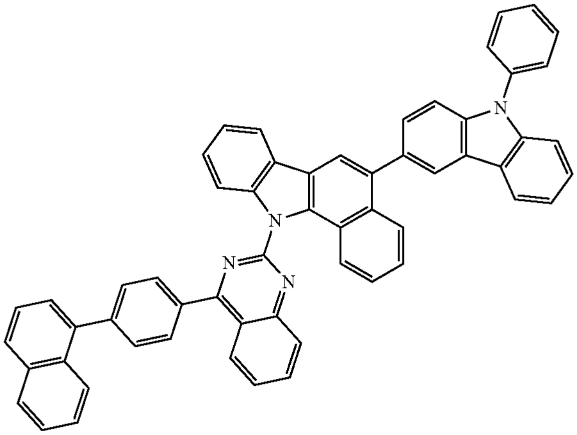
1-72
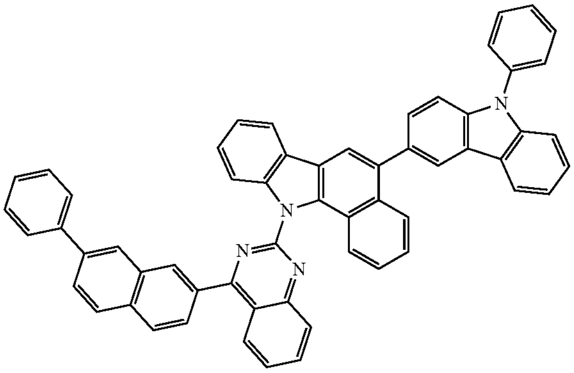
1-73
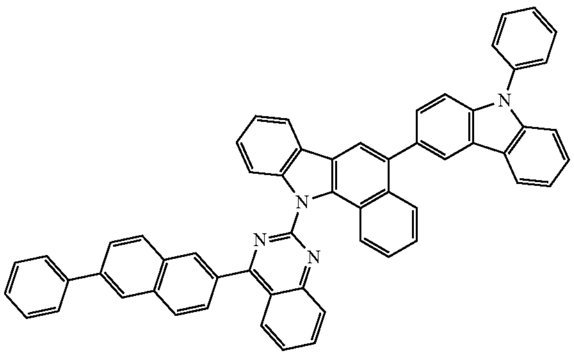

-continued
1-74
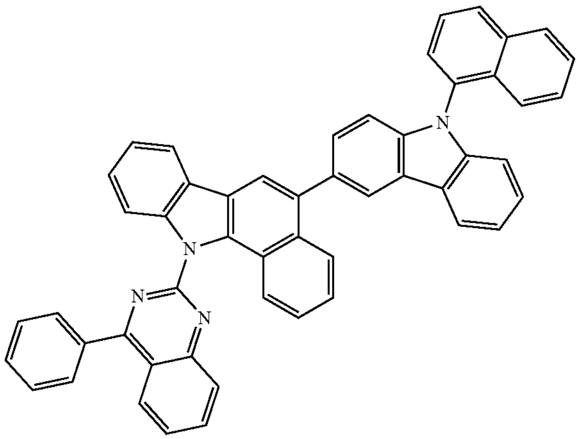
1-75
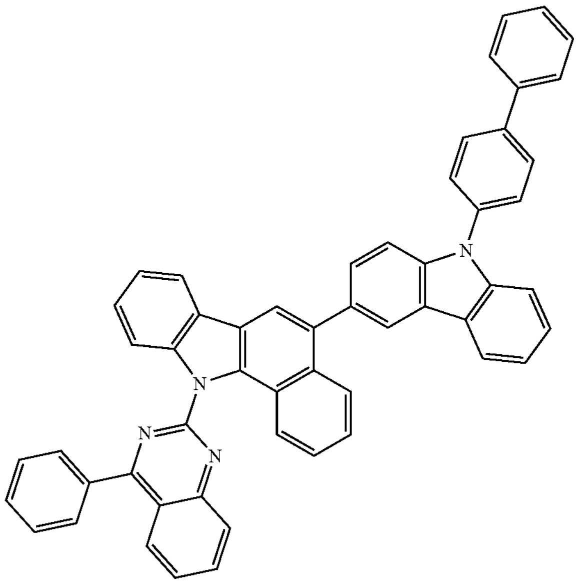
1-76
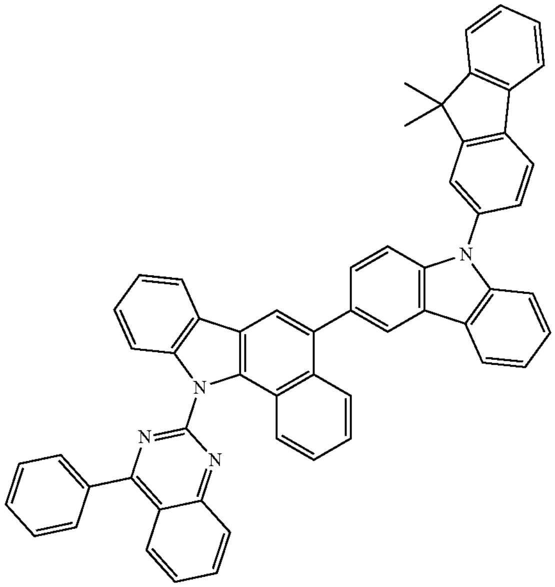
-continued
1-77
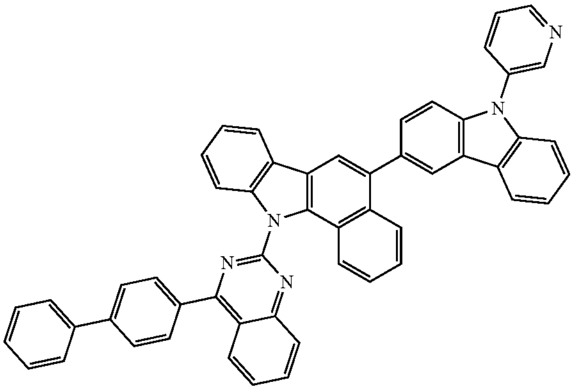
1-78
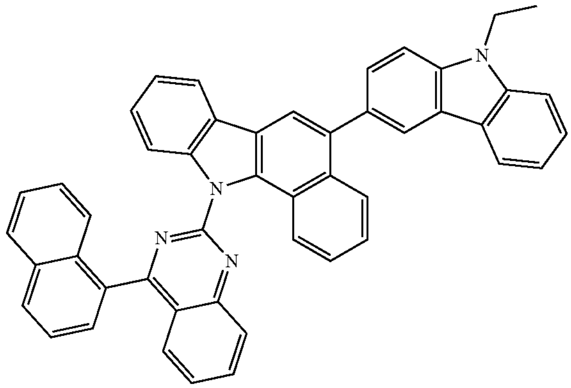
1-79
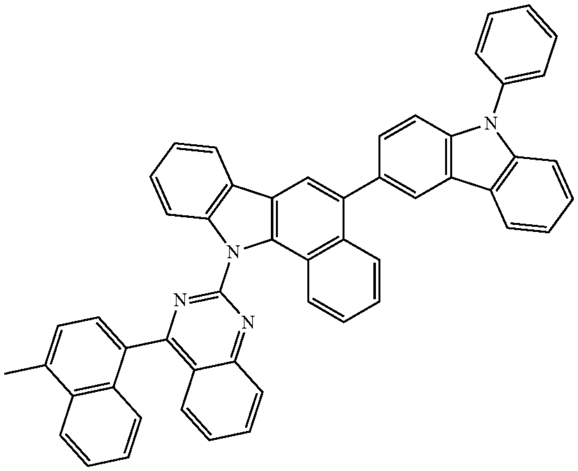

-continued
1-80
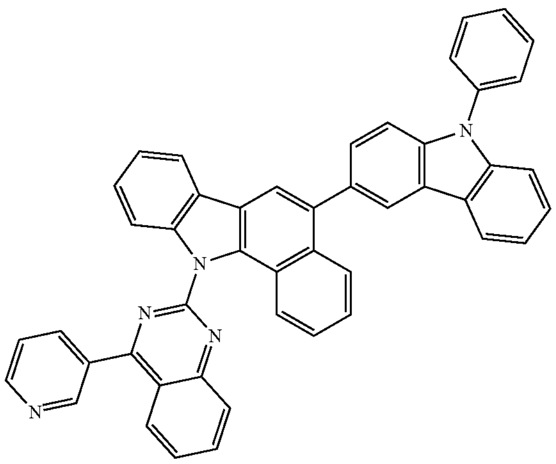
1-81
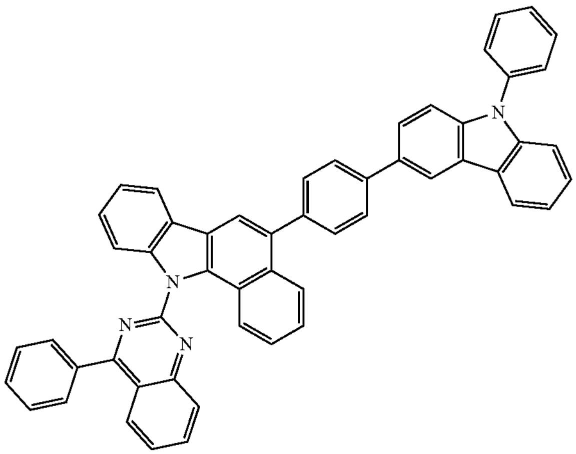
I-82
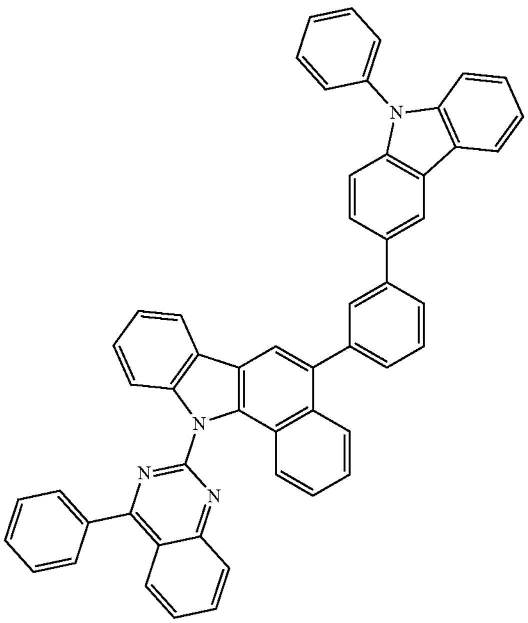
-continued
1-83
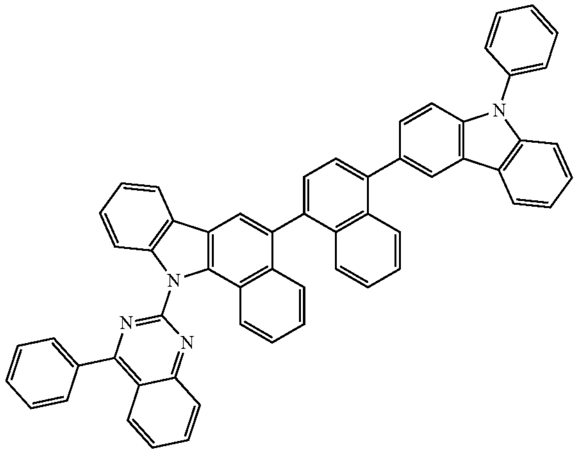
1-84
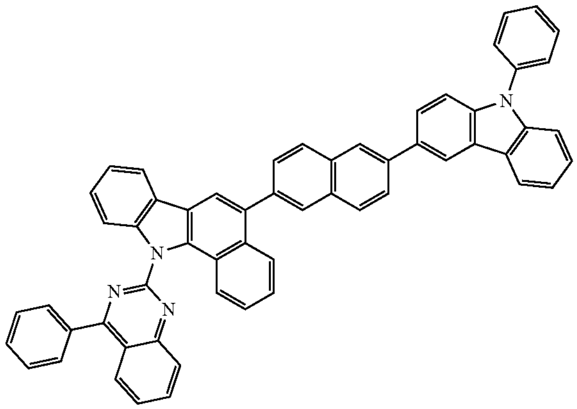
1-85
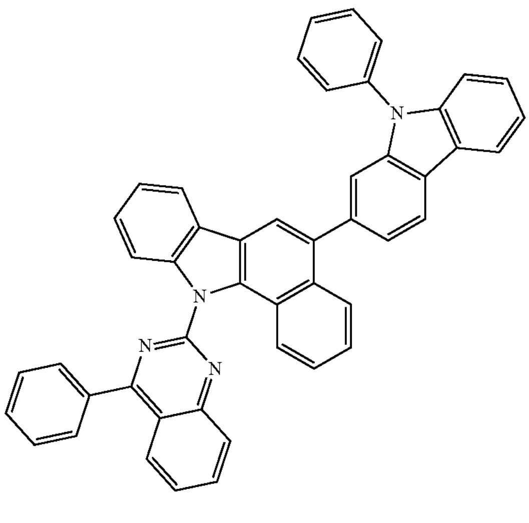

-continued
1-86
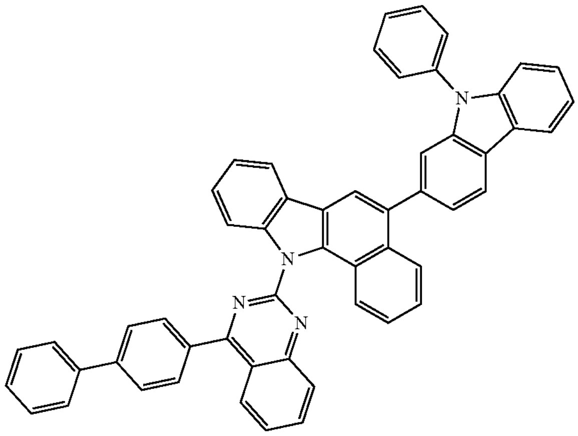
1-87
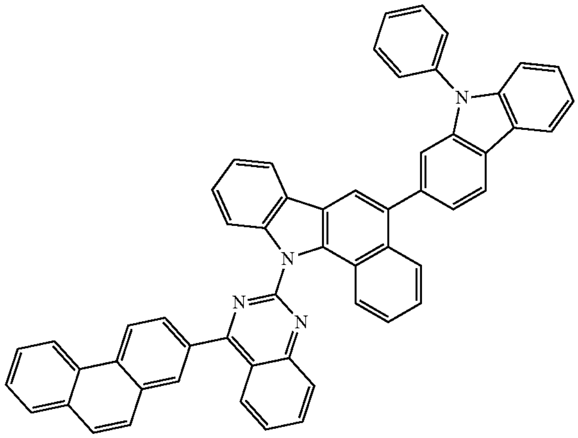
1-88
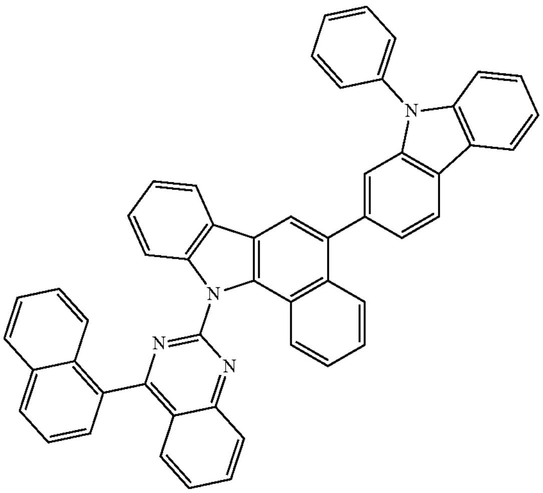
-continued
1-89
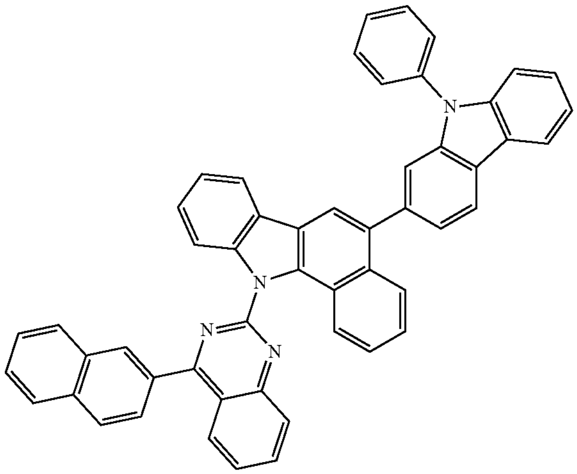
1-90
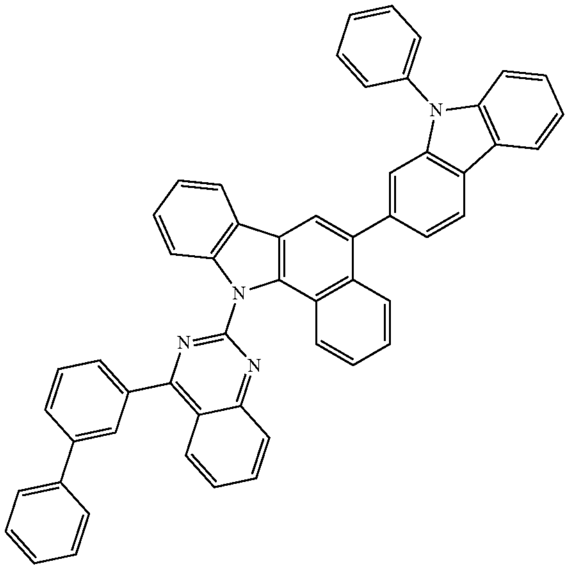
1-91
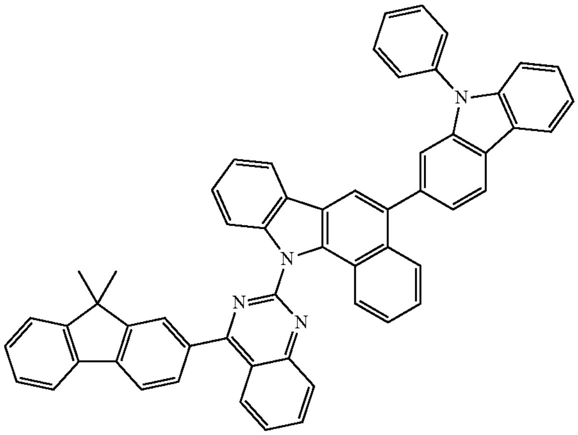

-continued
1-92
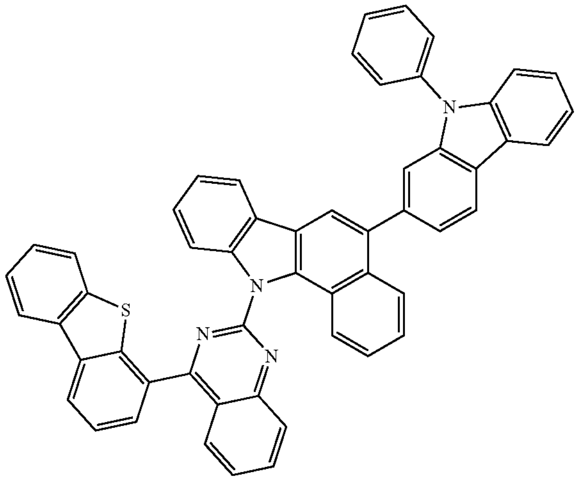
1-93
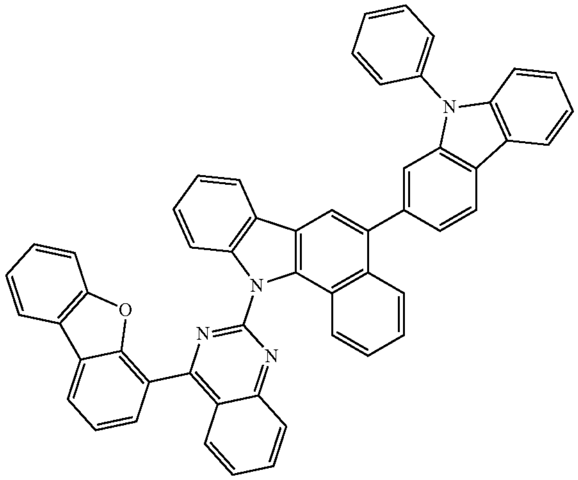
1-94
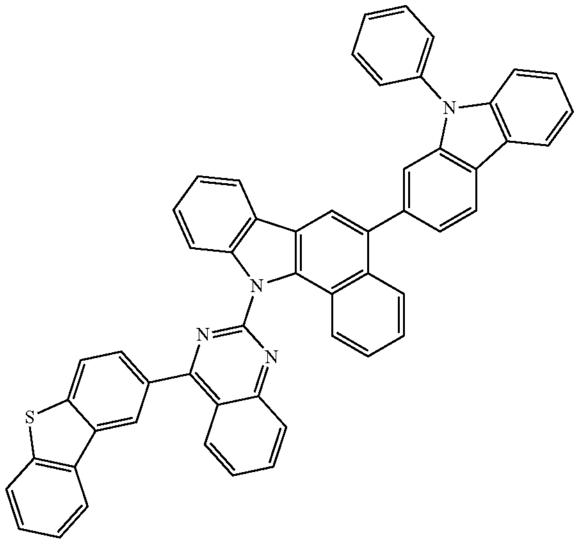
-continued
1-95
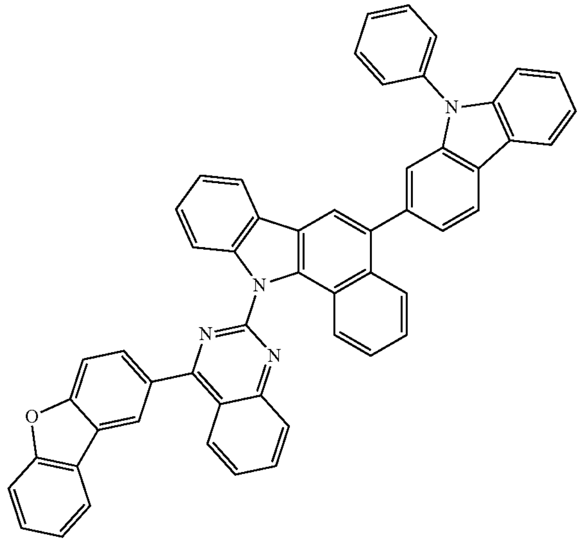
1-96
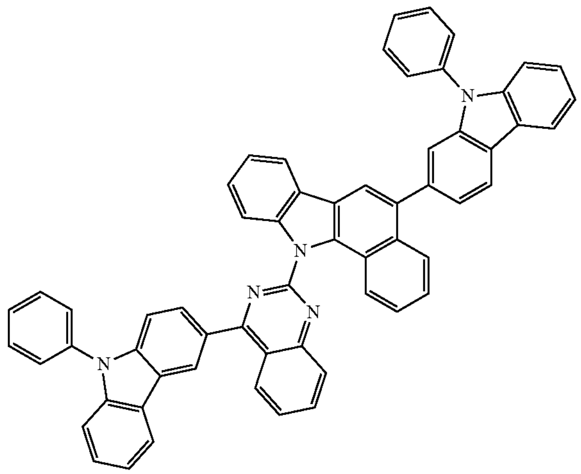
1-97
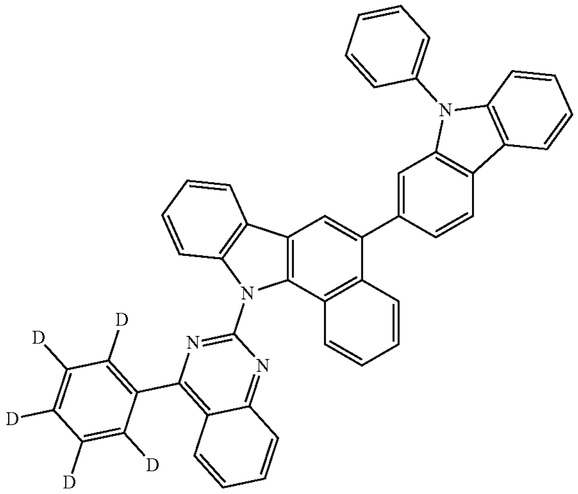

-continued
1-98
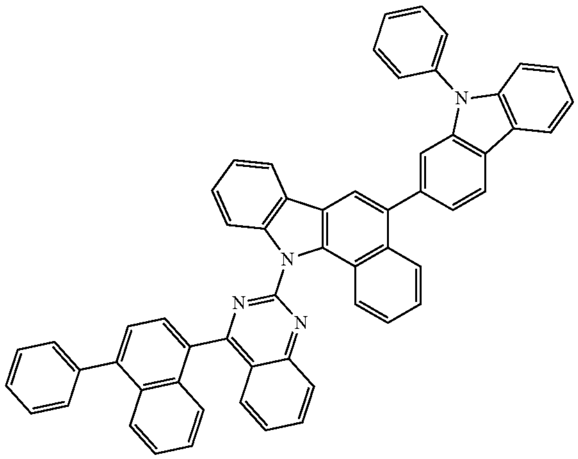
1-99
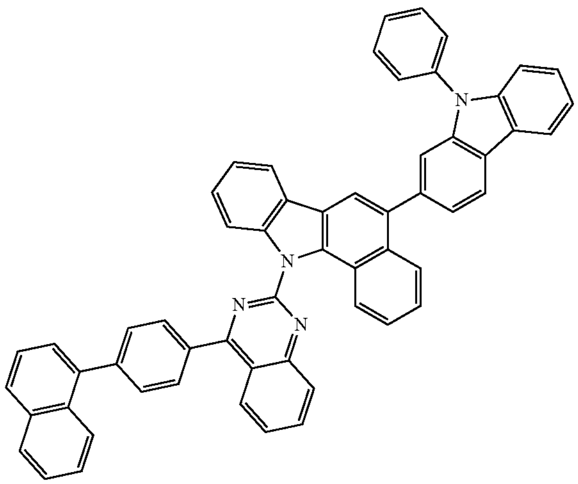
1-100
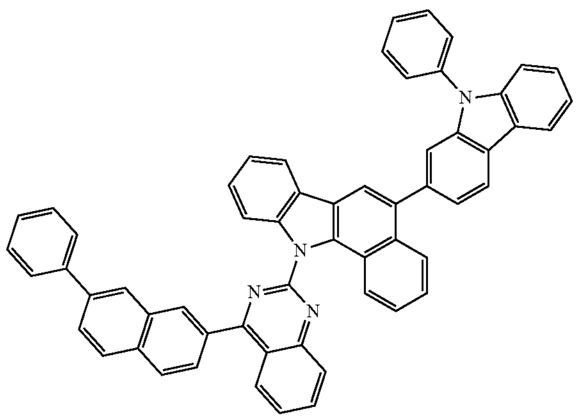
-continued
1-101
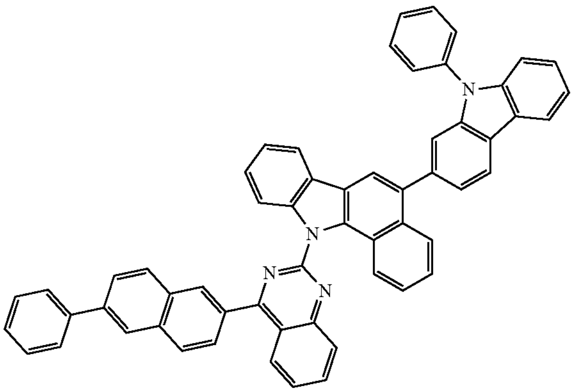
1-102
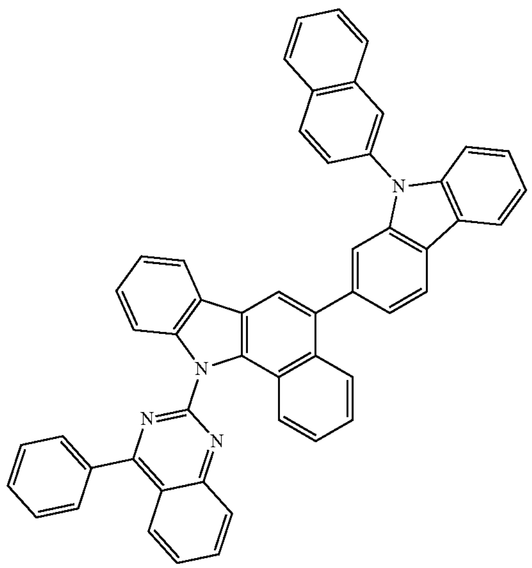
1-103
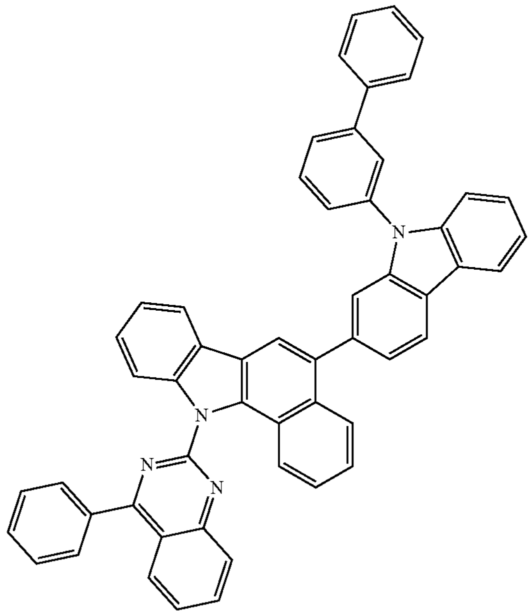

-continued
1-104
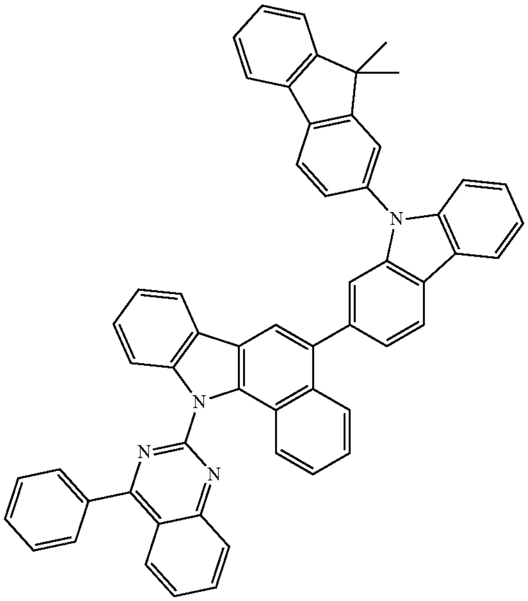
1-105
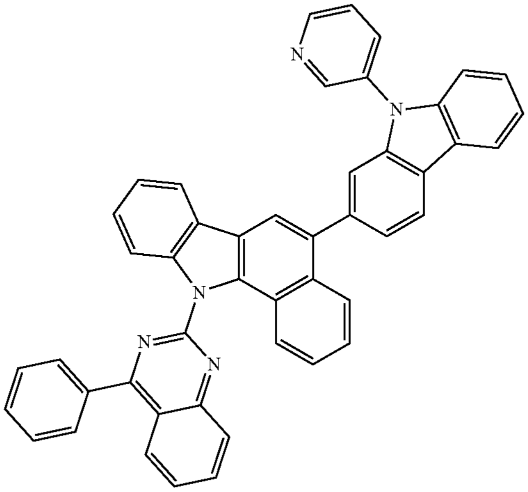
1-106
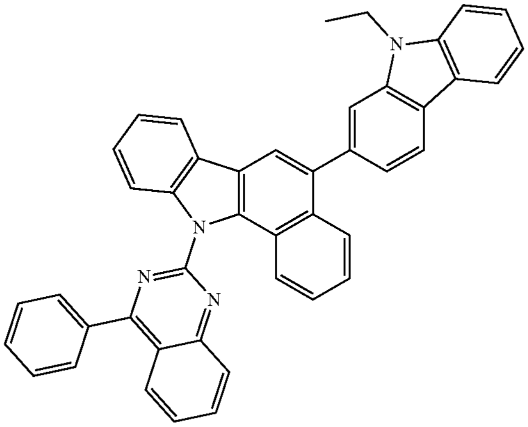
-continued
1-107
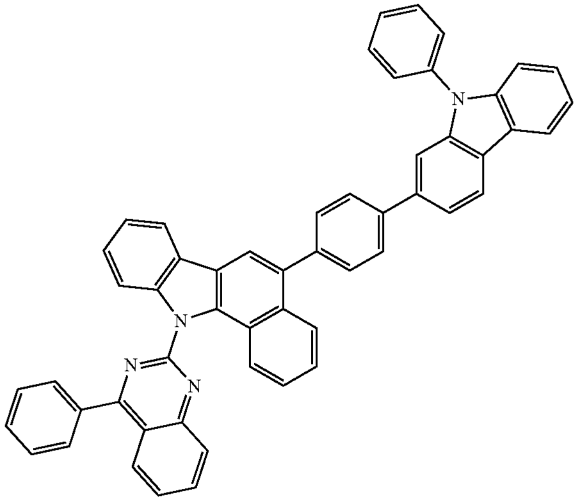
1-108
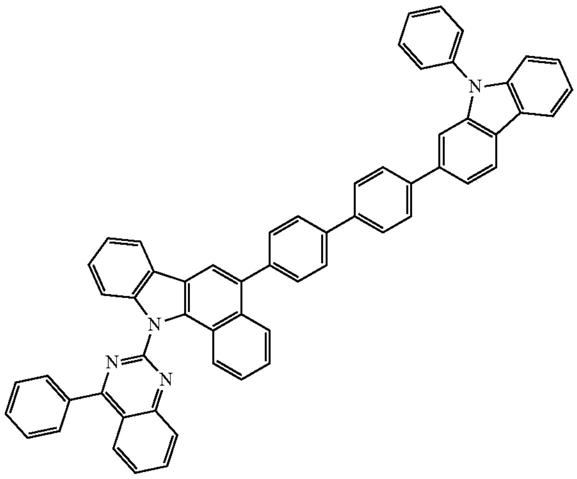
1-109
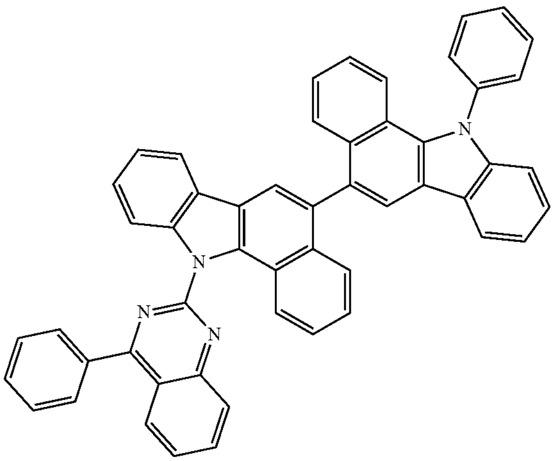

-continued
1-110
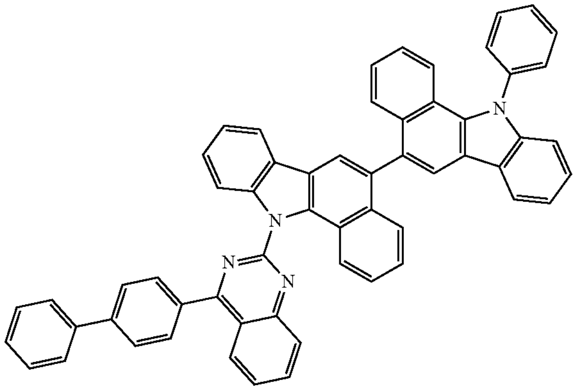
1-111
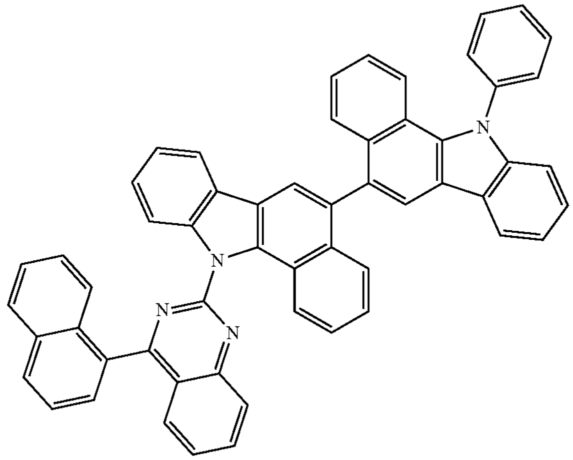
1-112
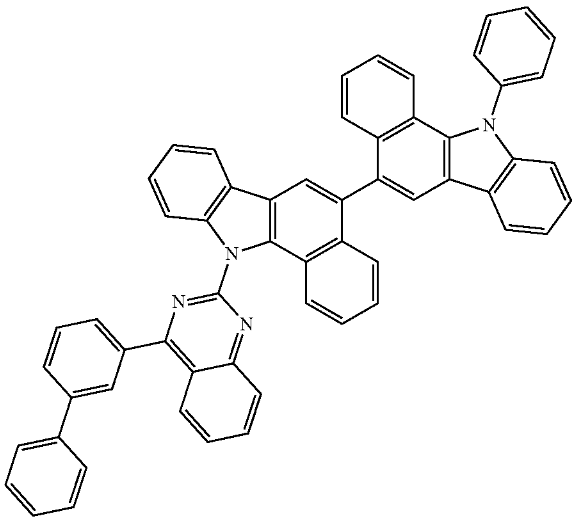
-continued
1-113
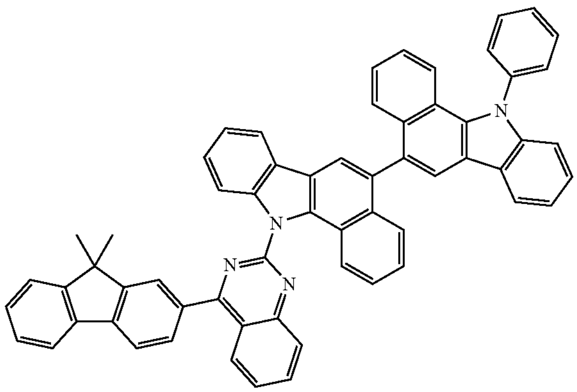
1-114
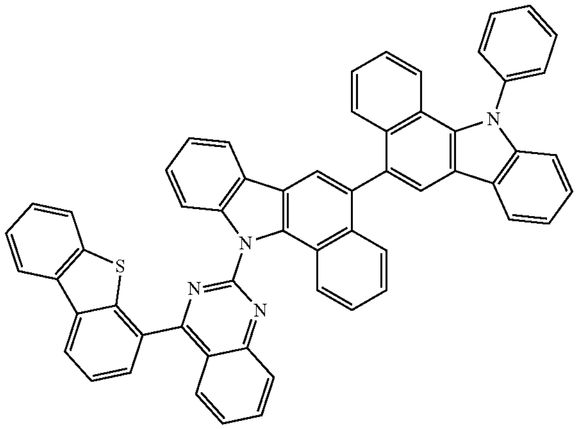
1-115
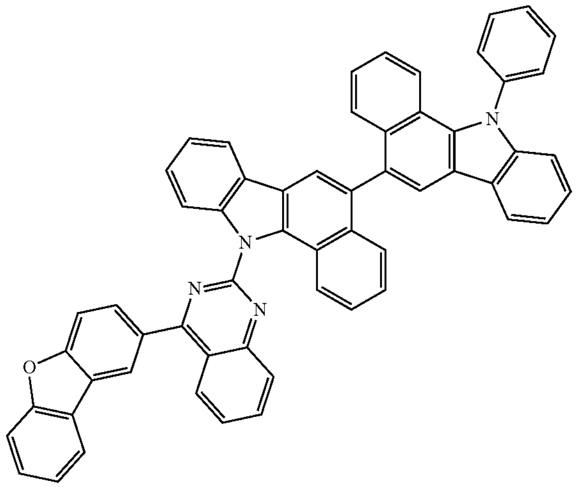

-continued
1-116
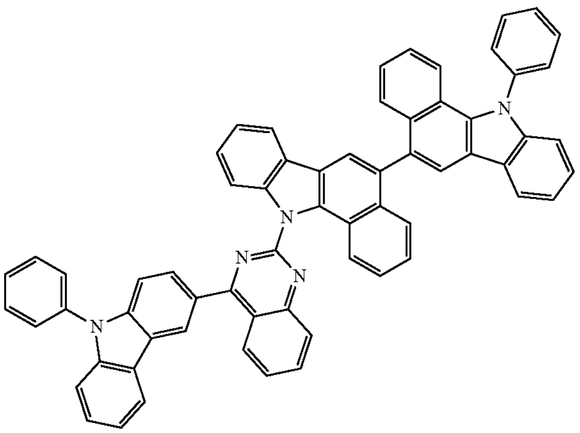
1-117
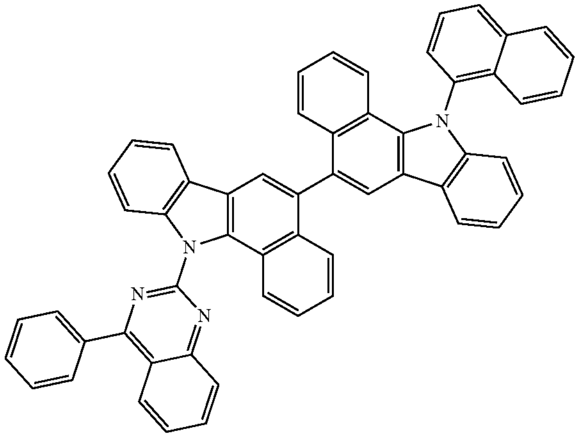
1-118
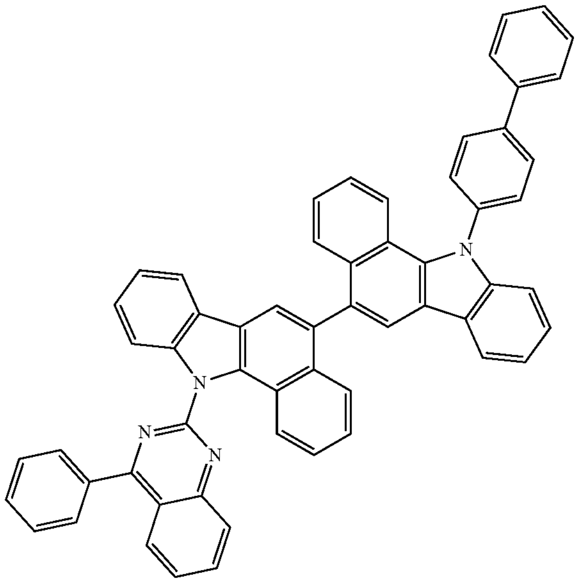
-continued
1-119
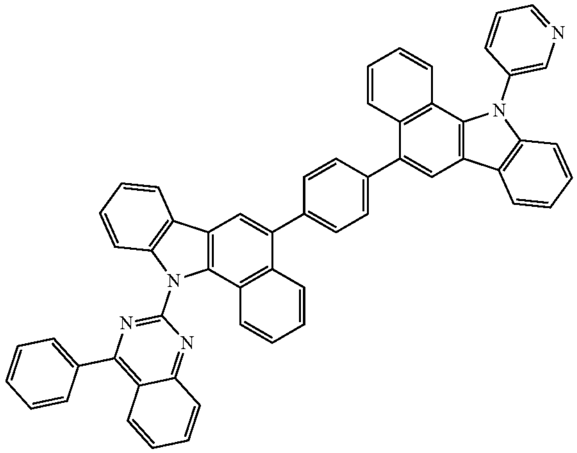
1-120
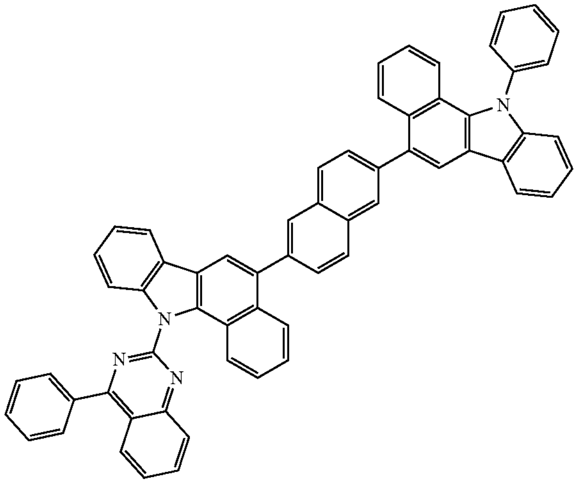
1-121
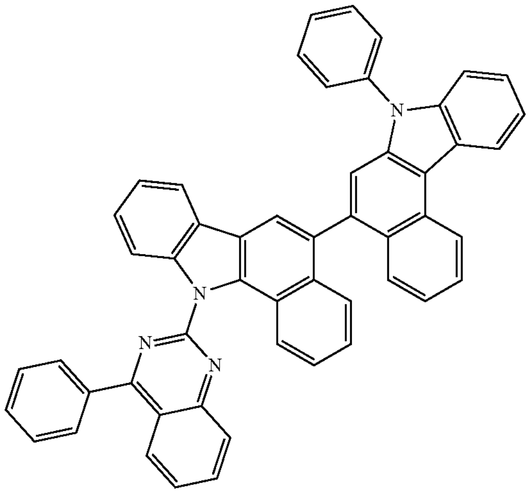

-continued
1-122
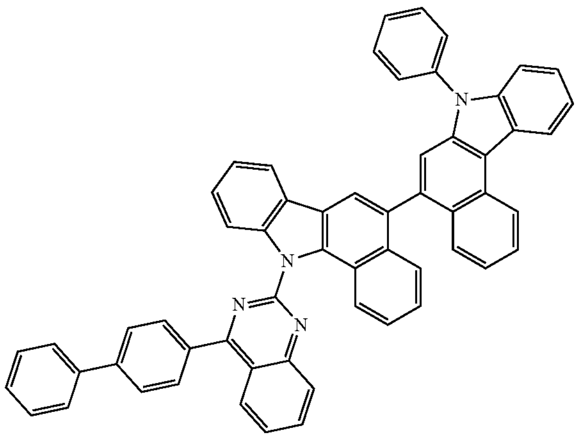
1-123
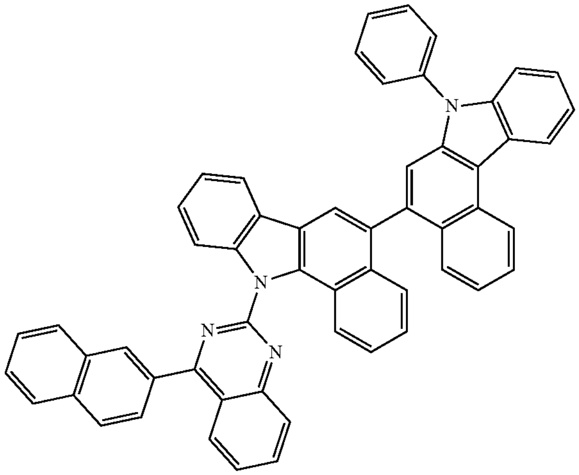
1-124
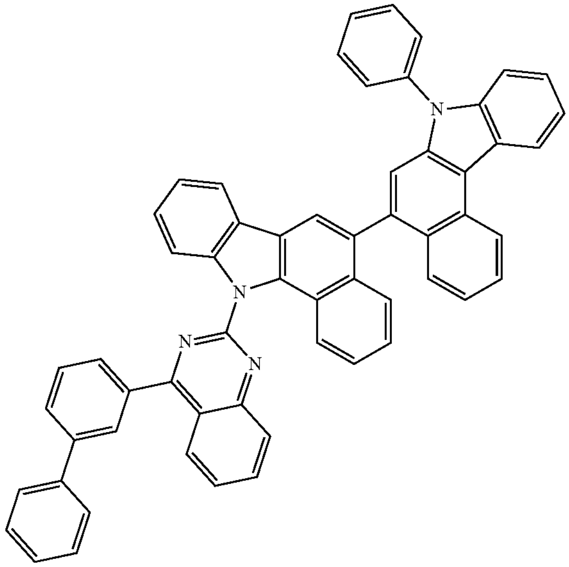
-continued
1-125
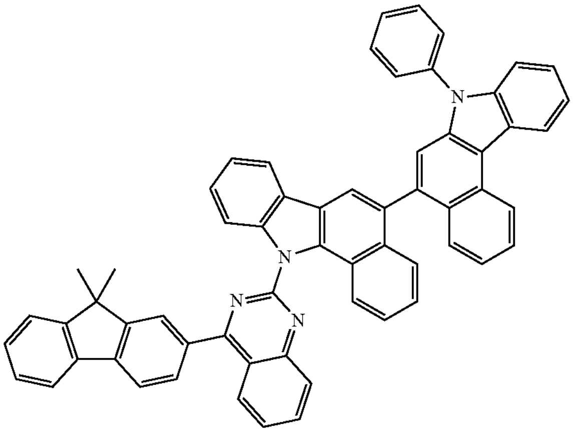
1-126
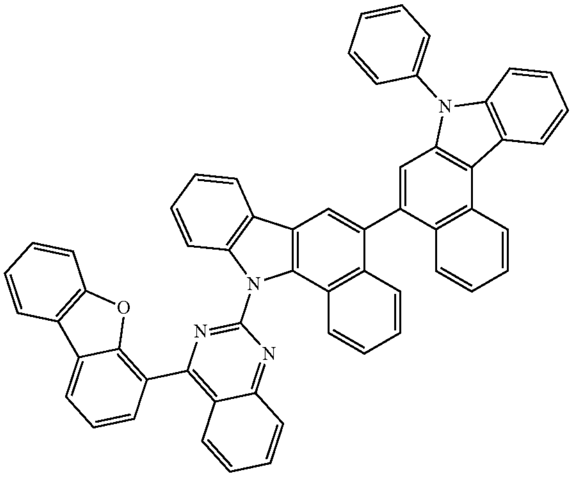
1-127
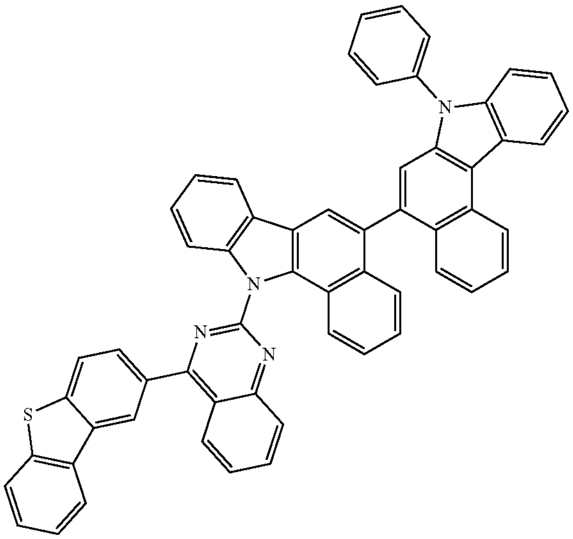

-continued
1-128
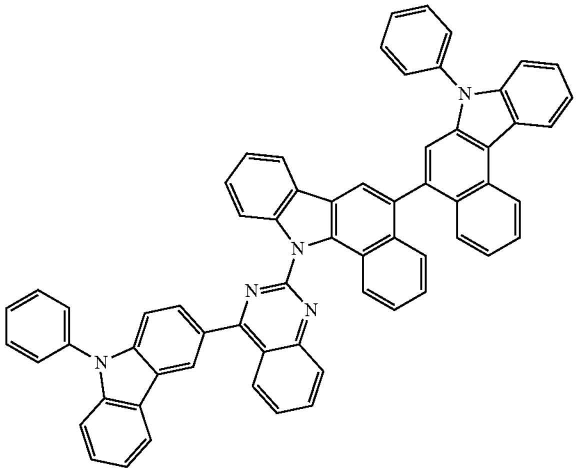
1-129
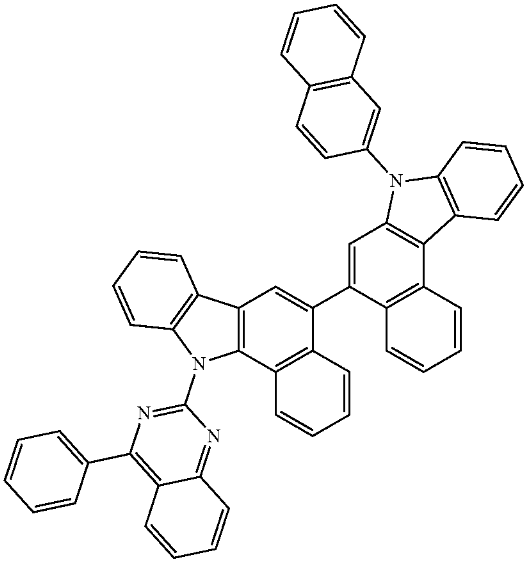
-continued
1-130
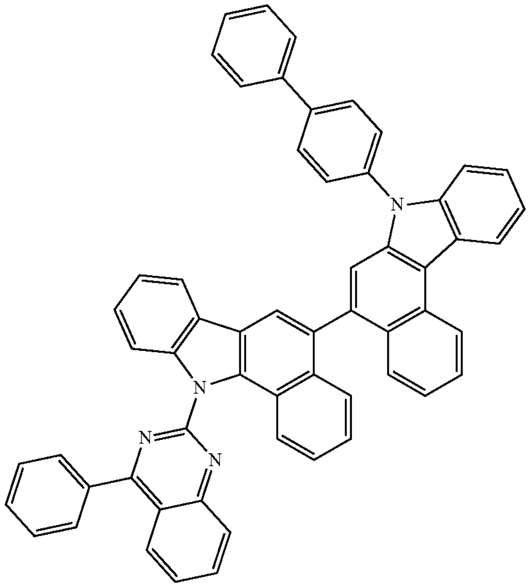
1-131
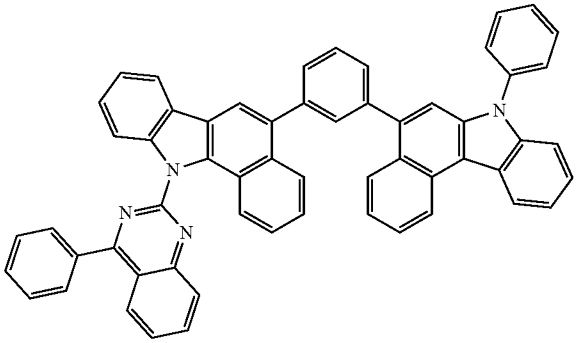
1-132
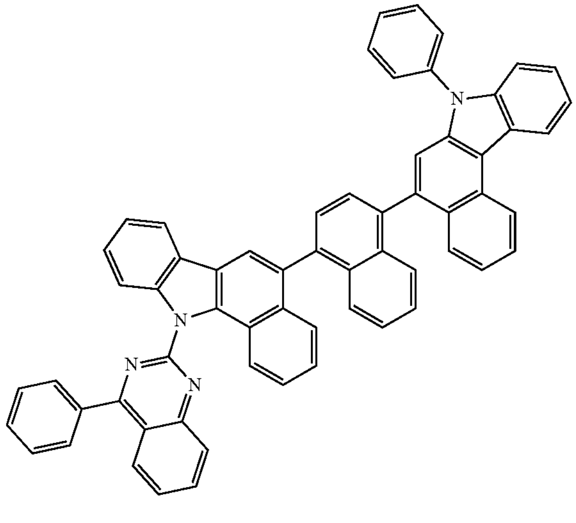

-continued
1-133
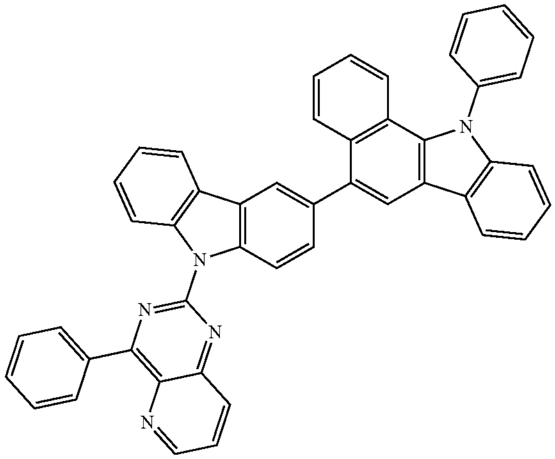
1-134
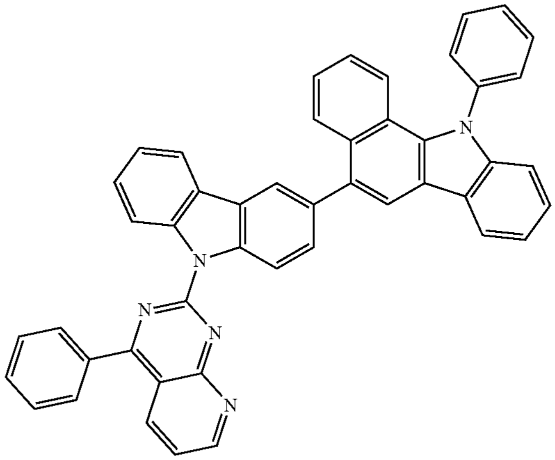
1-135
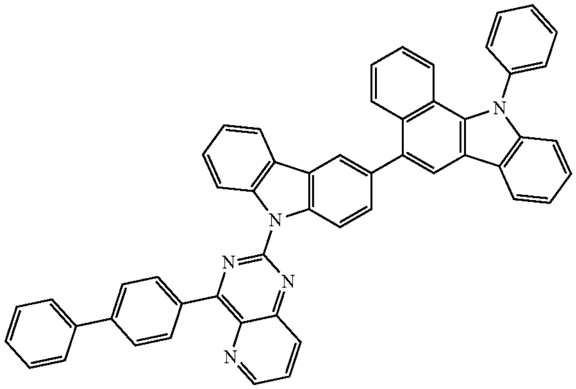
-continued
1-136
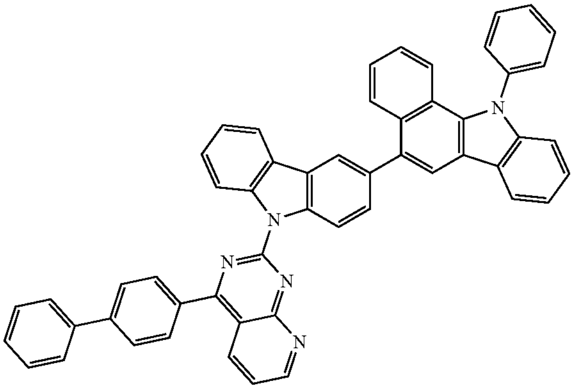
I-137
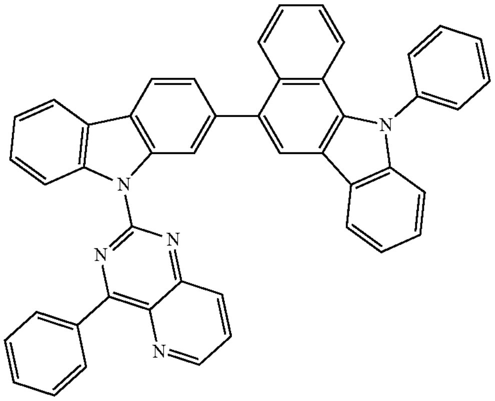
I-138
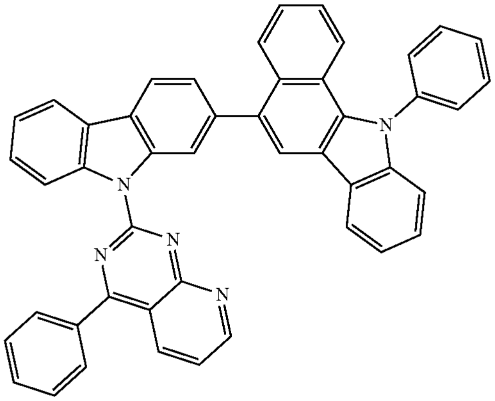

-continued
1-139
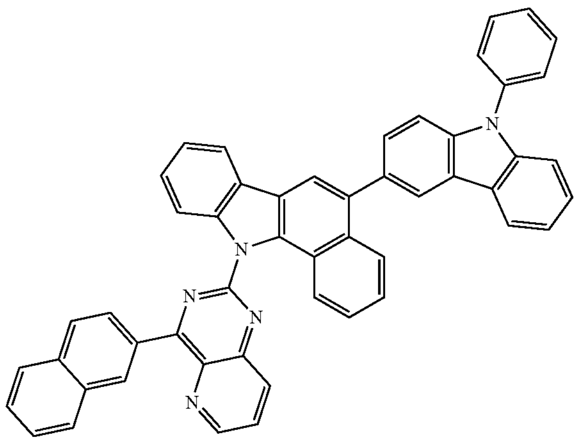
1-140
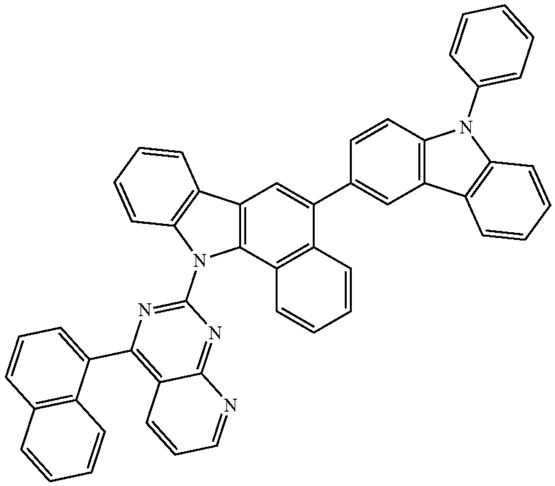
1-141
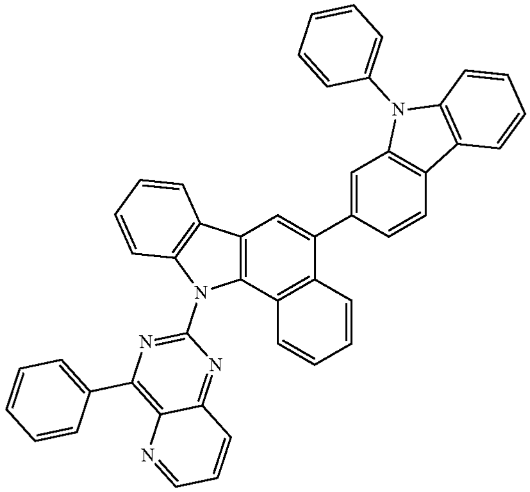
-continued
1-142
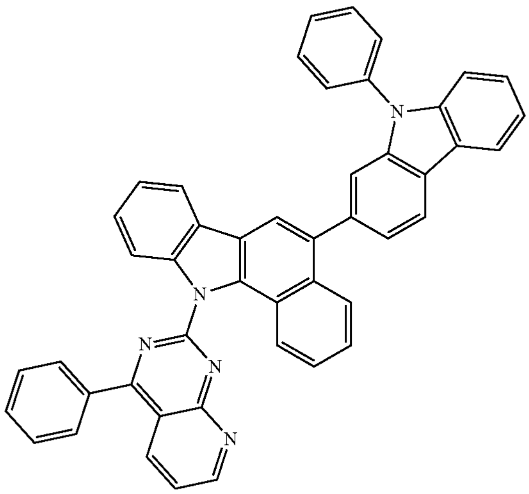
1-143
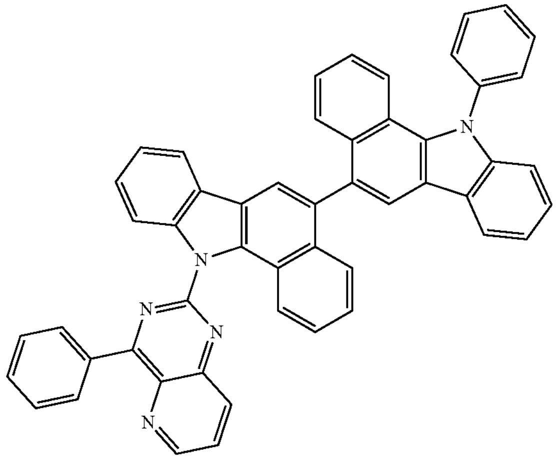
1-144
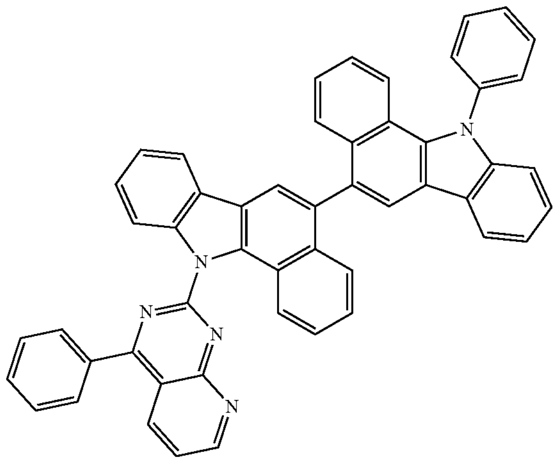

-continued
1-145
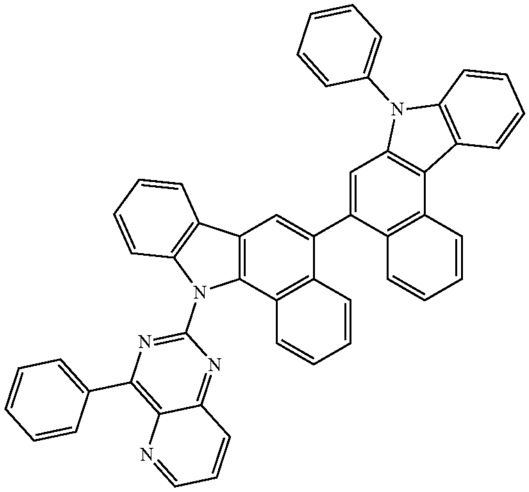
1-146
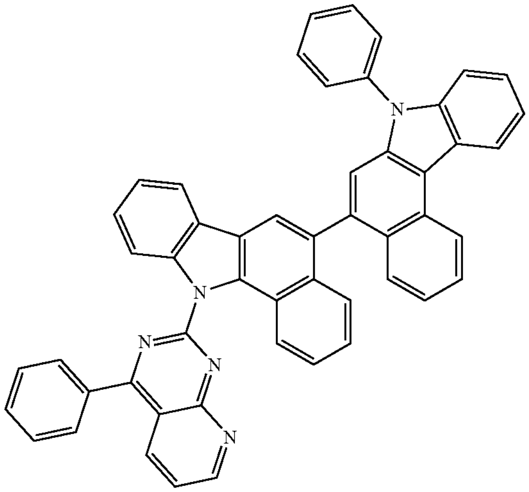
1-147
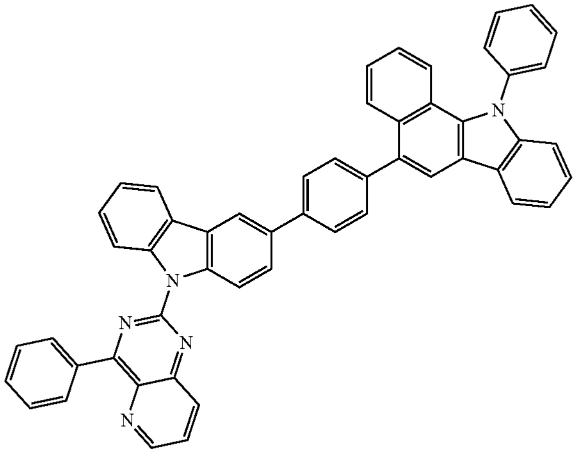
-continued
1-148
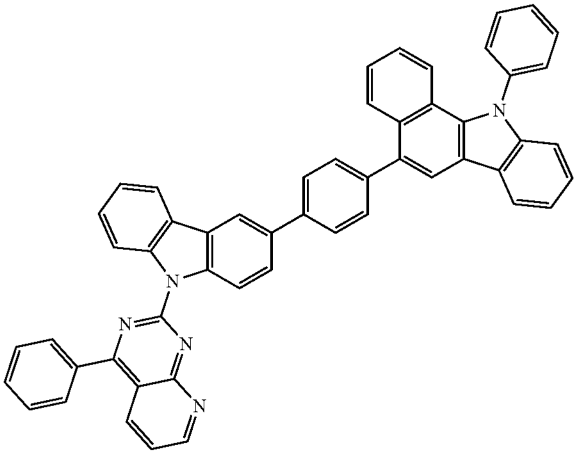
2-1
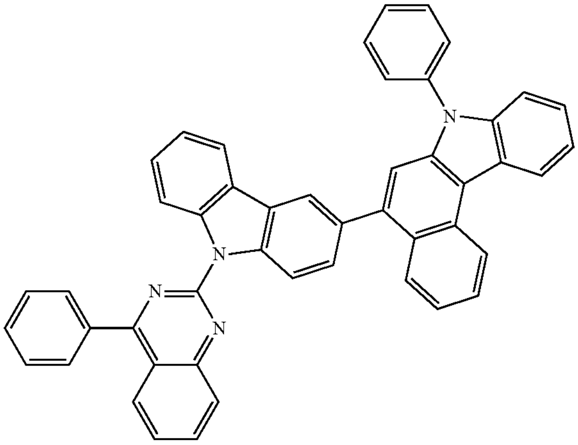
2-2
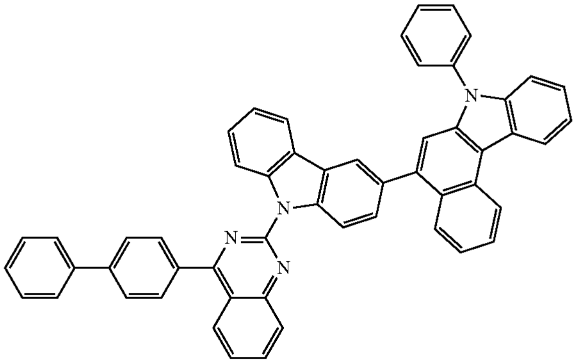

-continued
2-3
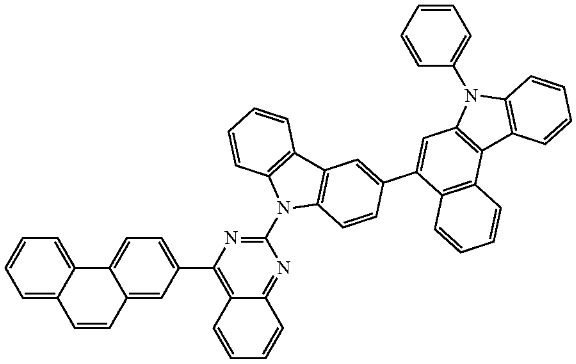
2-4
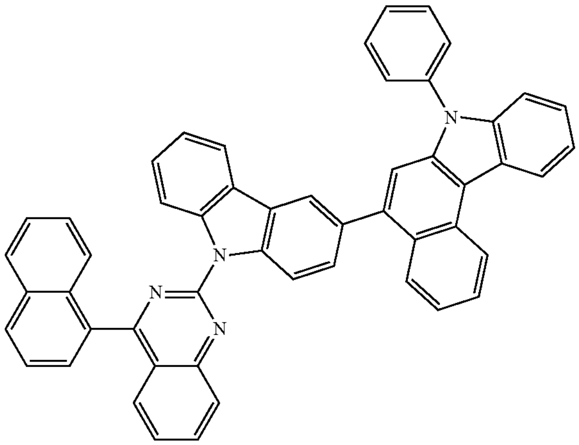
2-5
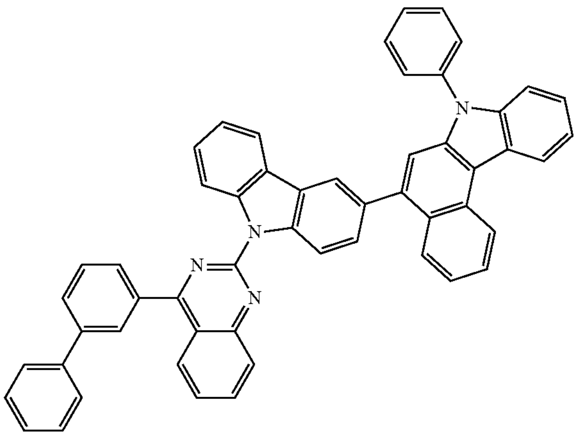
-continued
2-6
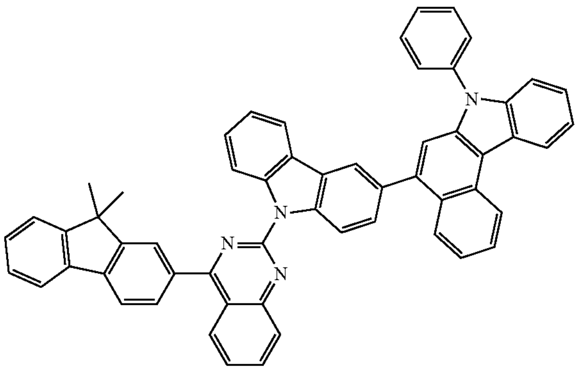
2-7
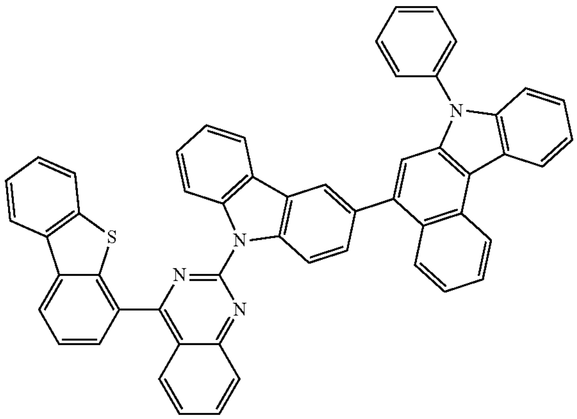
2-8
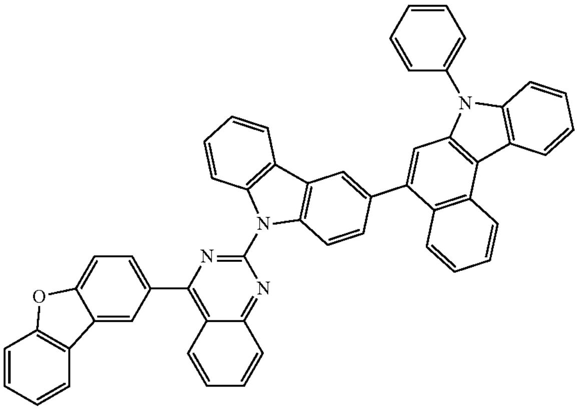
2-9
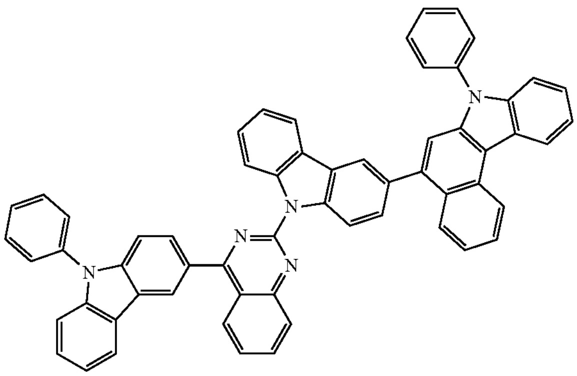

-continued
2-10
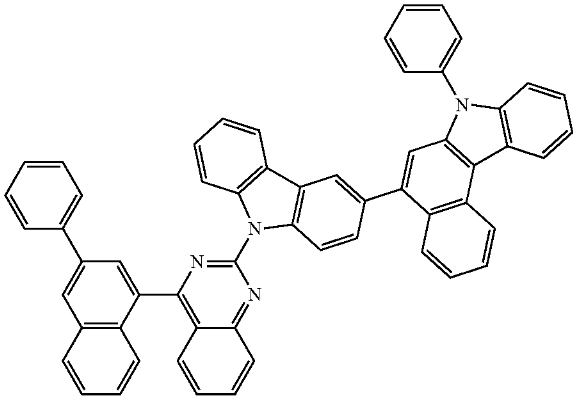
2-11
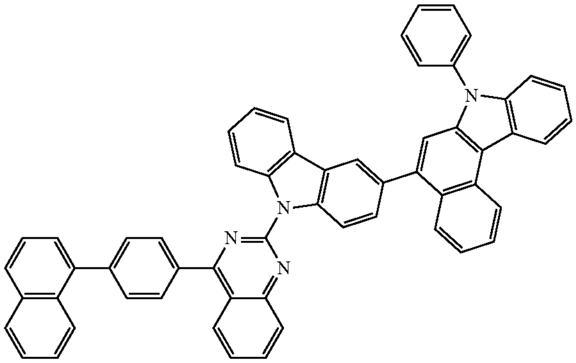
2-12
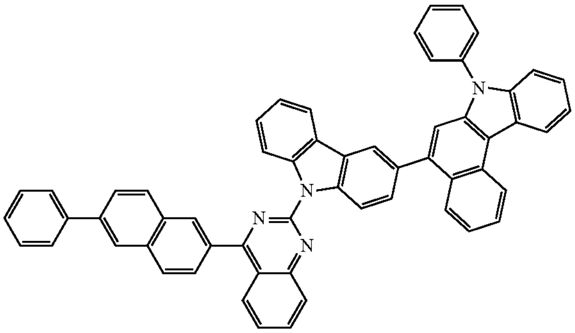
-continued
2-13
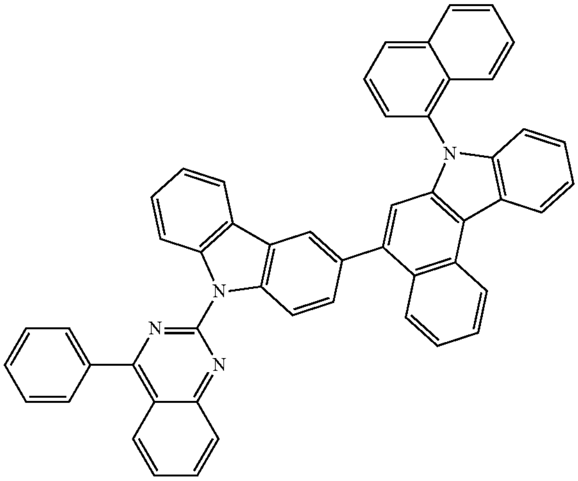
2-14
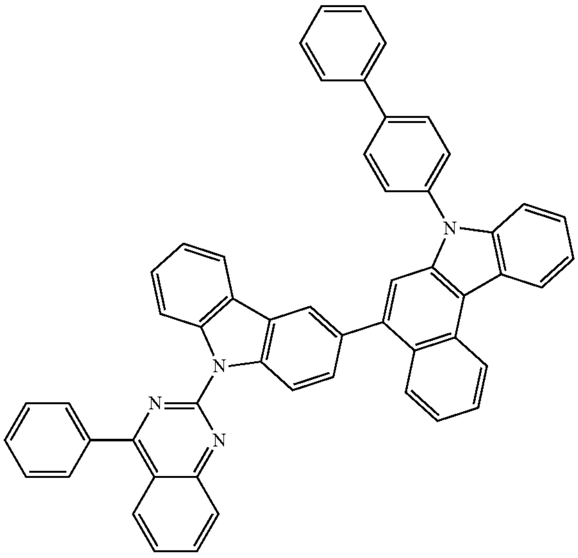
2-15
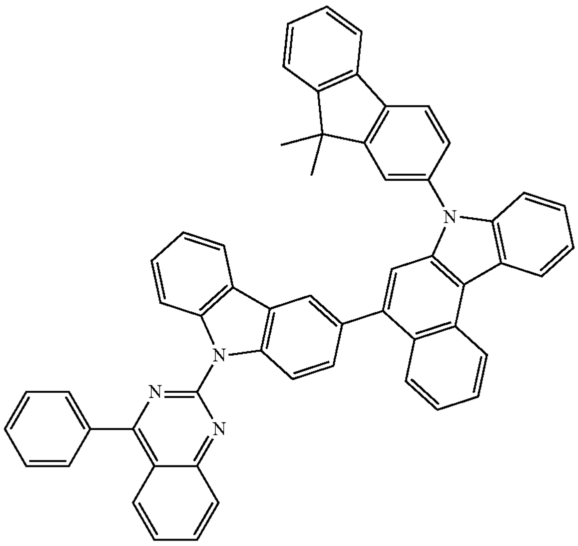

-continued
2-16
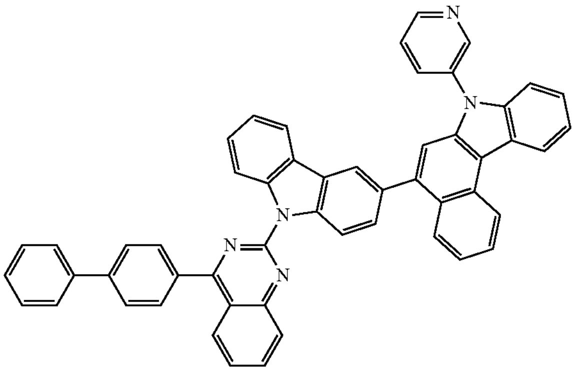
2-17
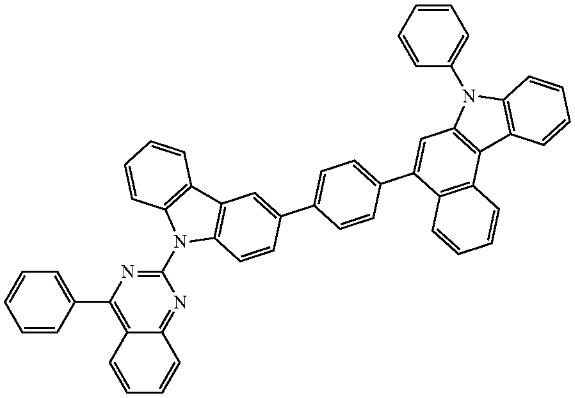
2-18
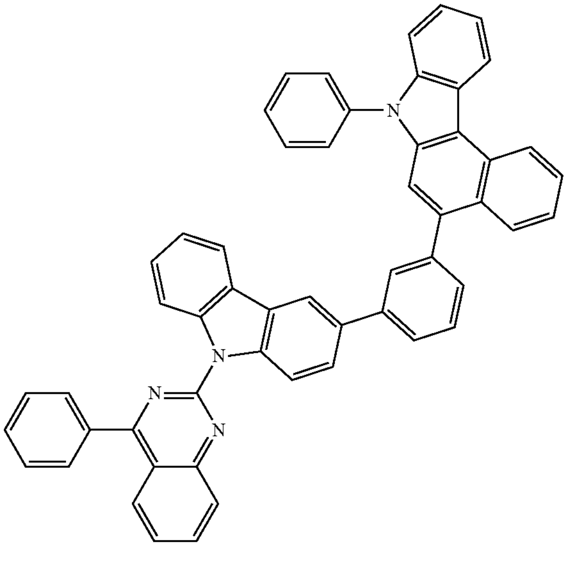
-continued
2-19
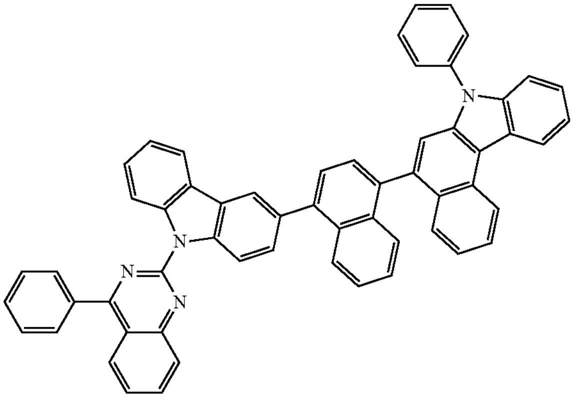
2-20
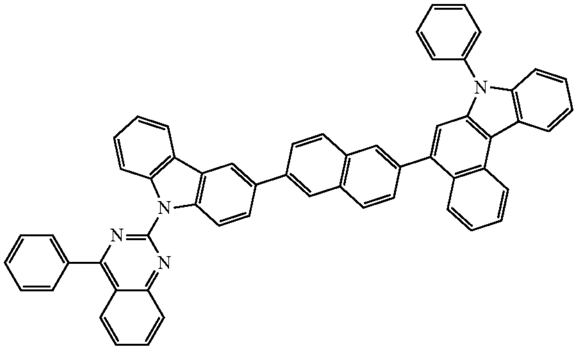
2-21
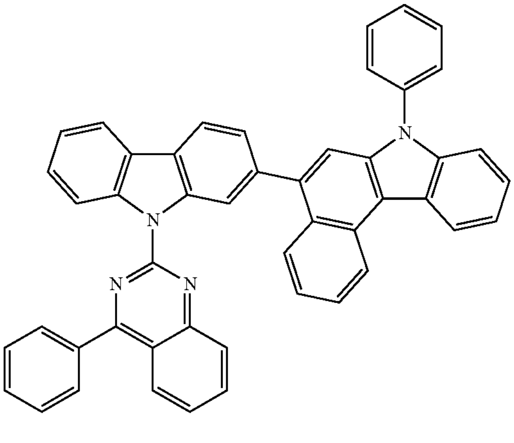

2-22
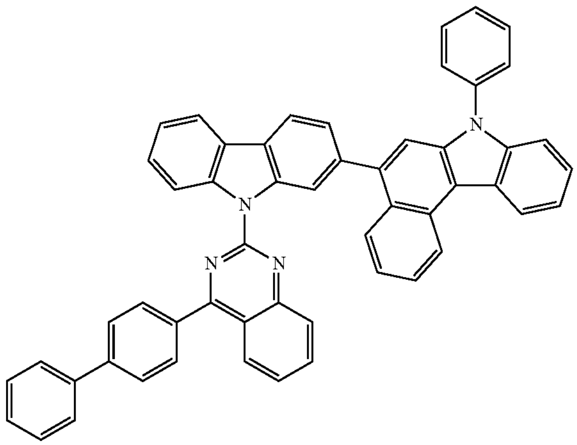
2-23
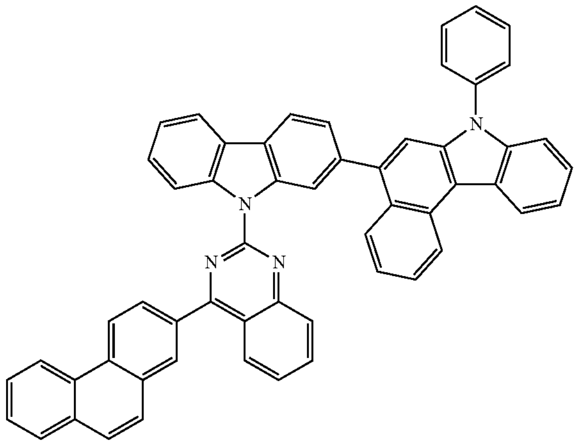
2-24
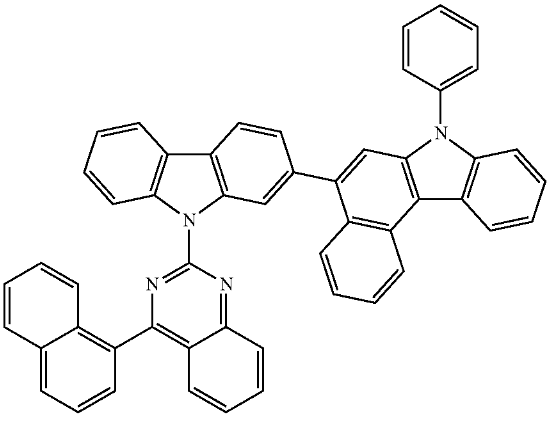
2-25
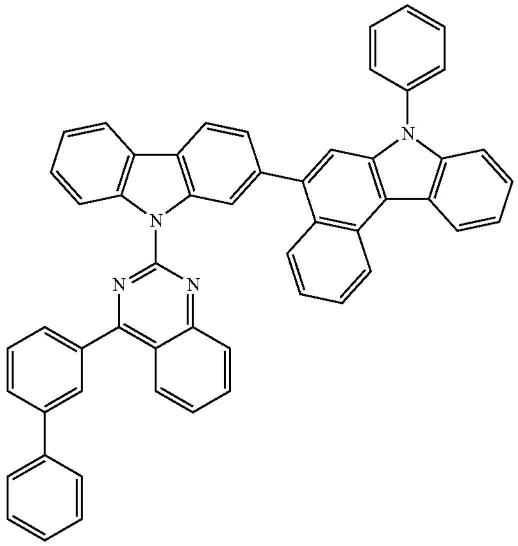
2-26
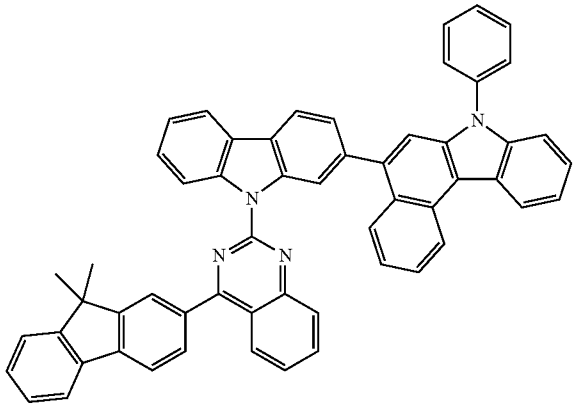
2-27
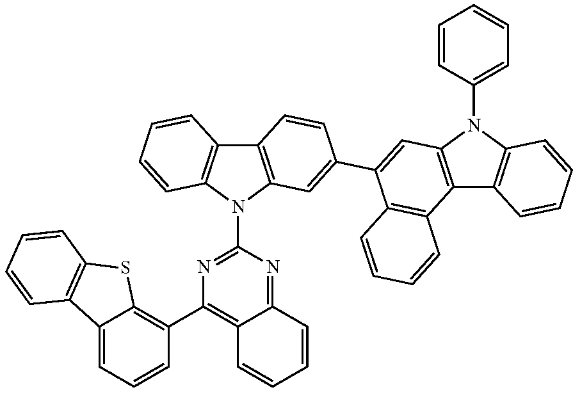

-continued
2-28
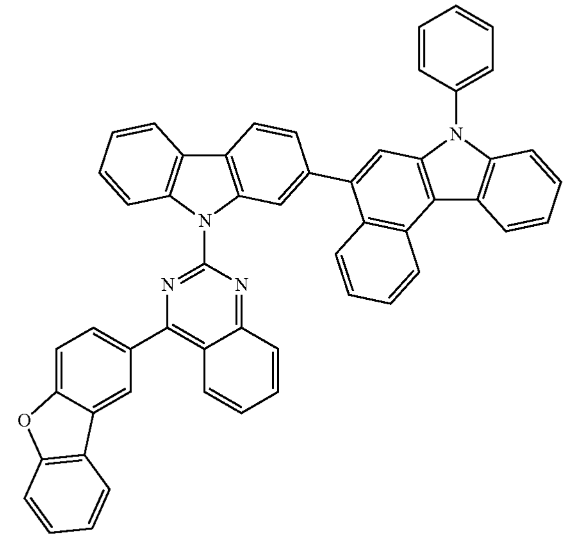
2-29
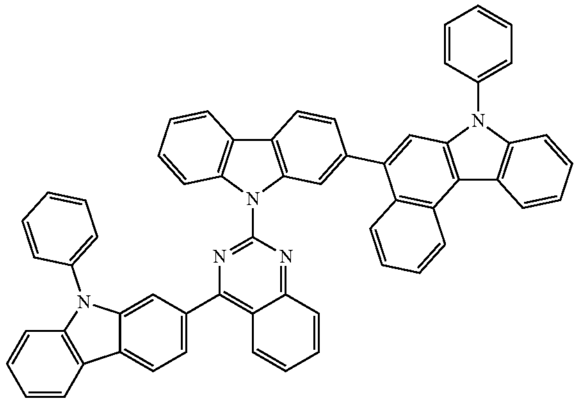
2-30
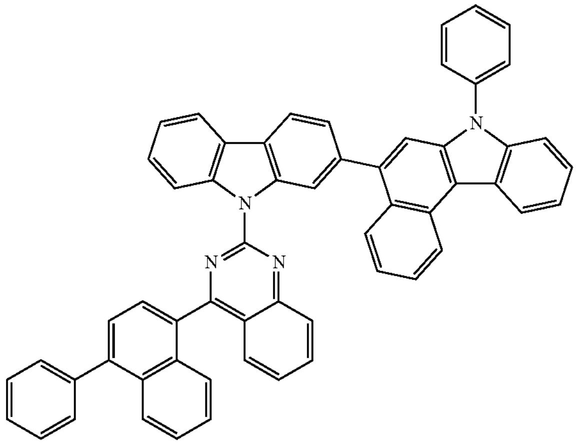
-continued
2-31
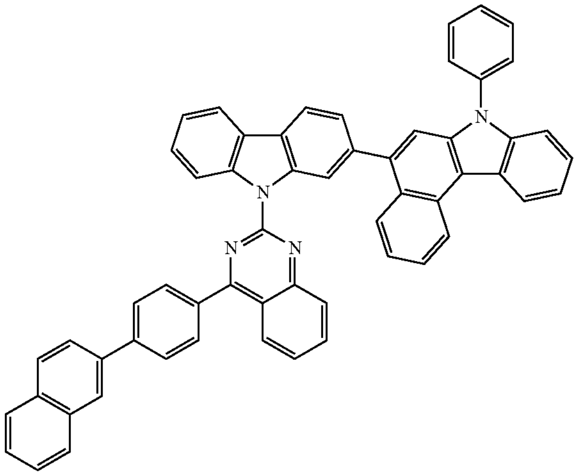
2-32
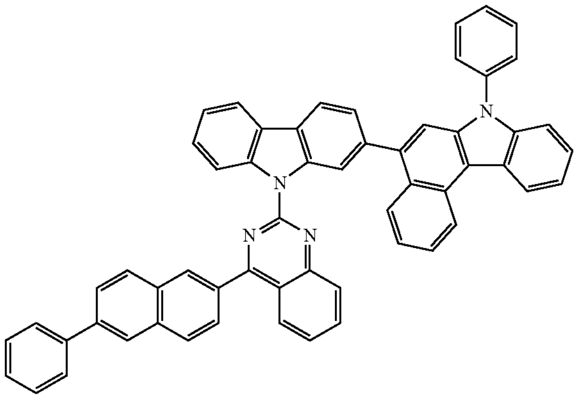
2-33
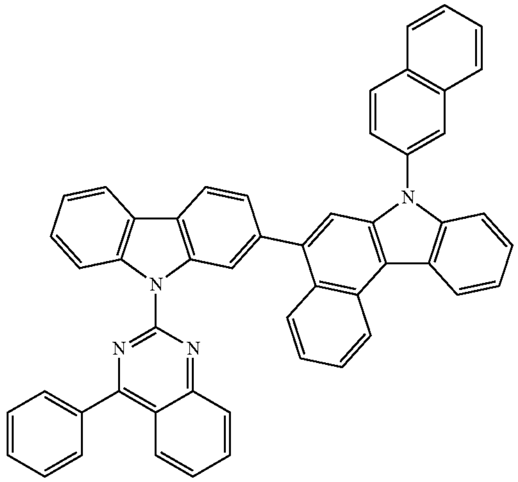

-continued
2-34
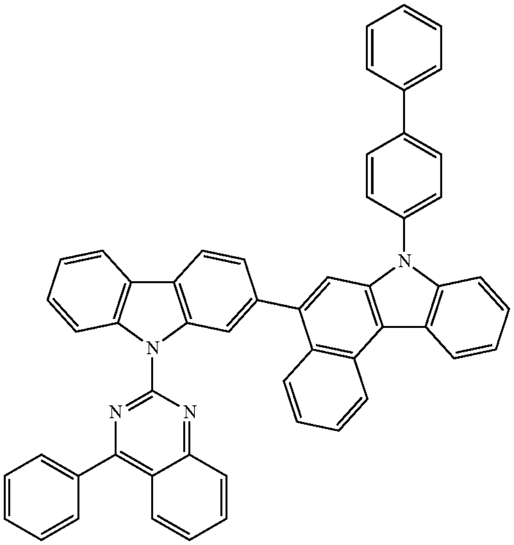
2-35
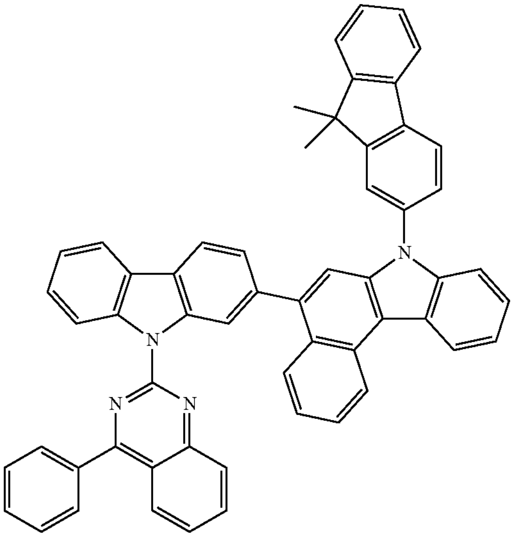
2-36
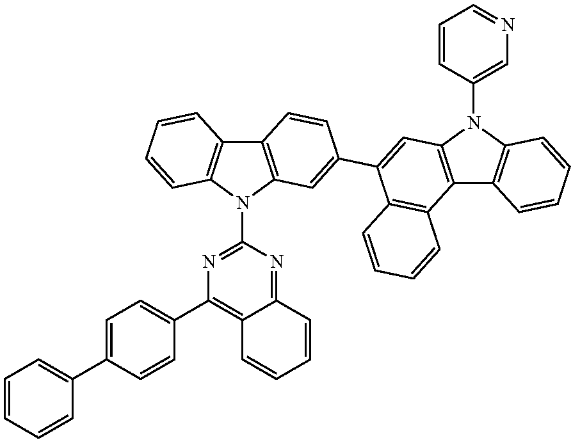
-continued
2-37
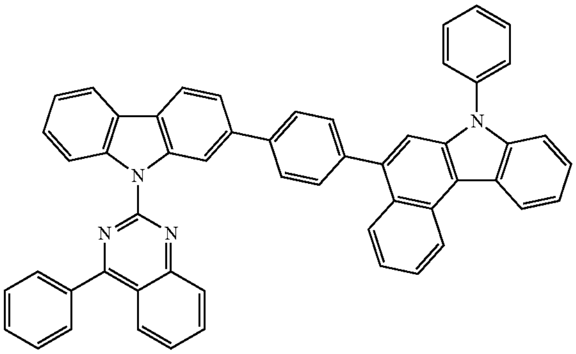
2-38
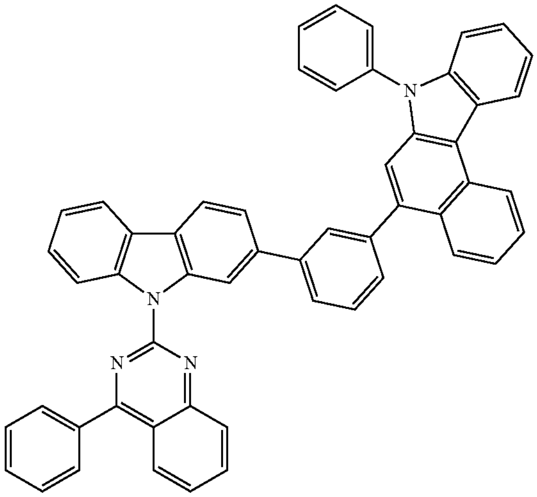
2-39
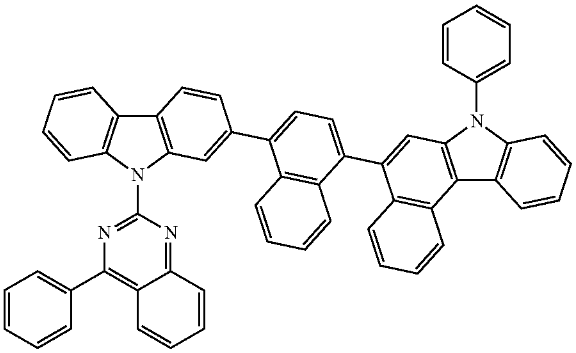
2-40
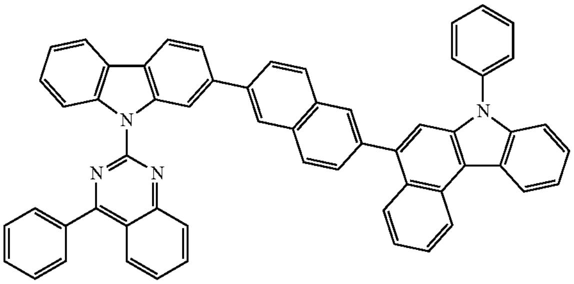

-continued
2-41
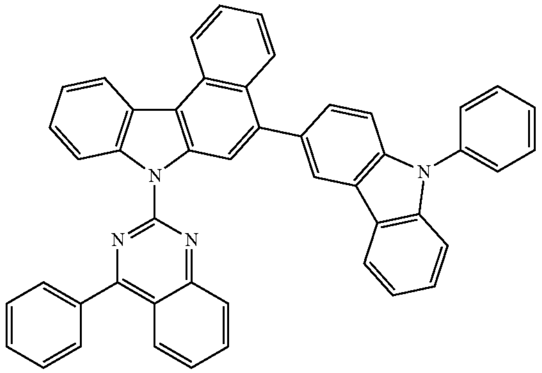
2-42
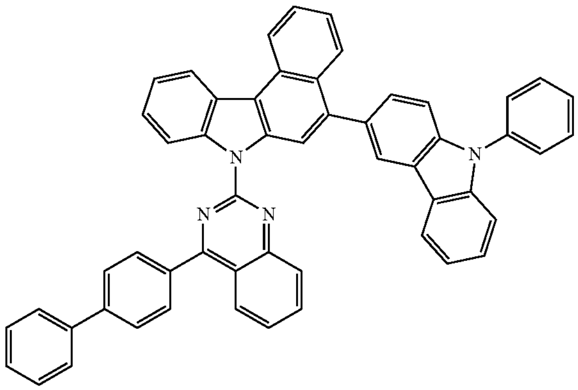
2-43
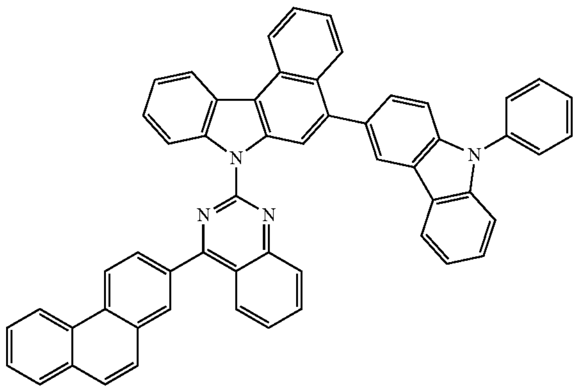
2-44
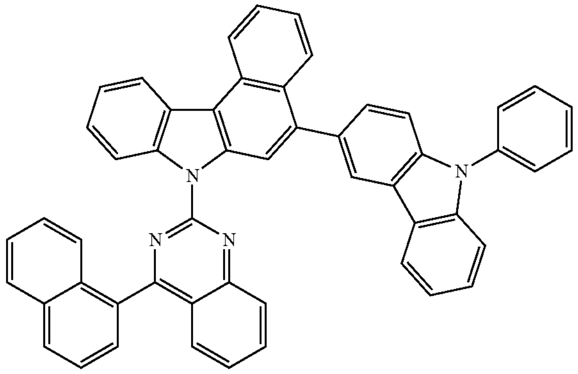
-continued
2-45
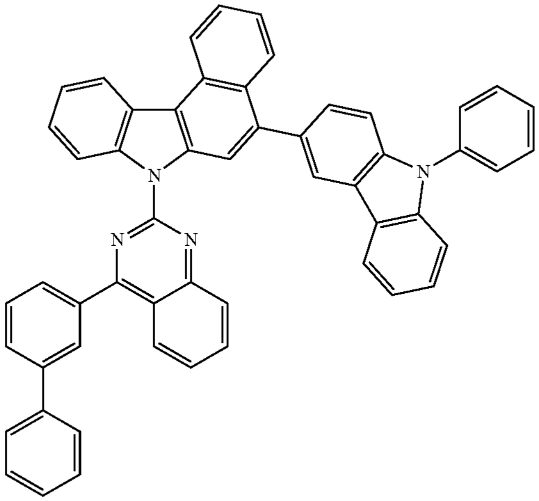
2-46
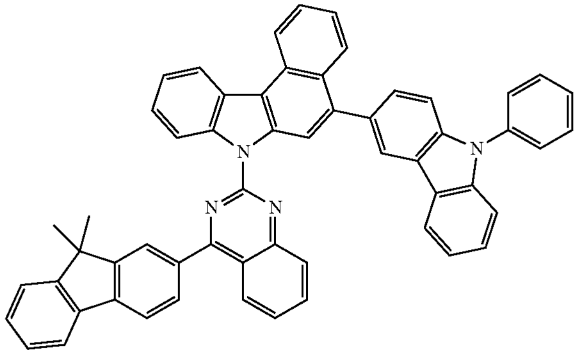
2-47
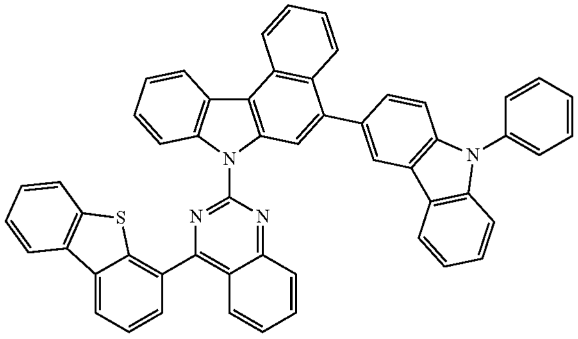

-continued
2-48
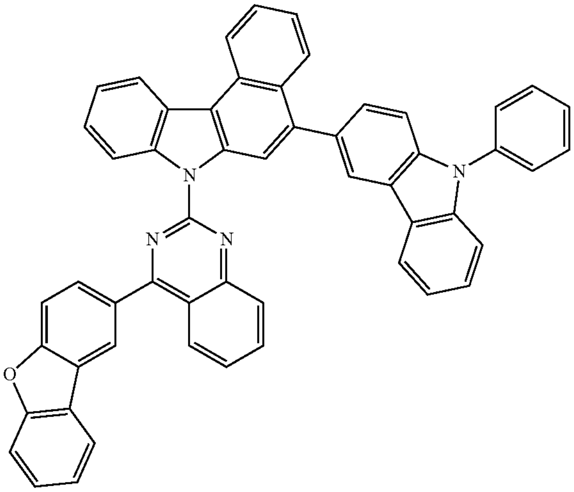
2-49
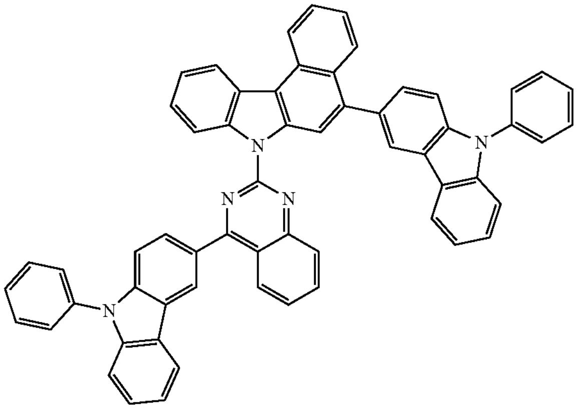
2-50
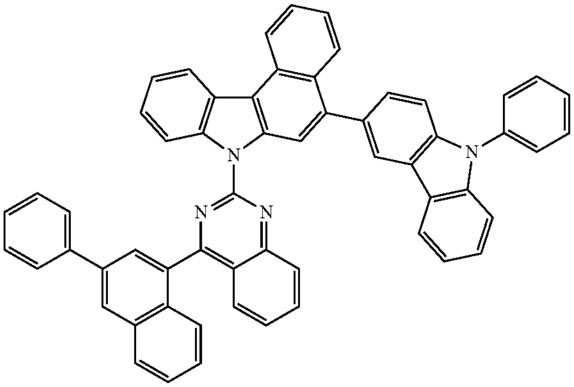
-continued
2-51
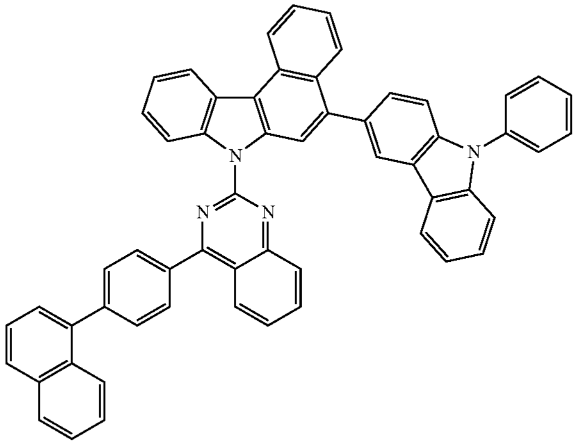
2-52
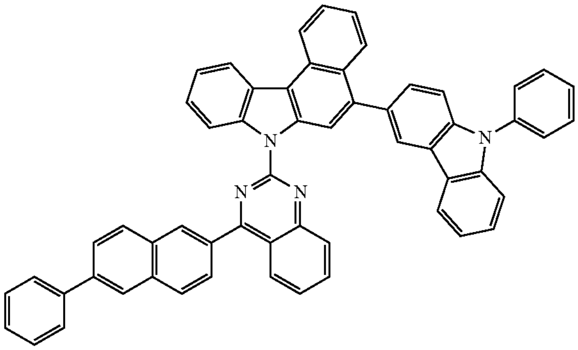
2-53
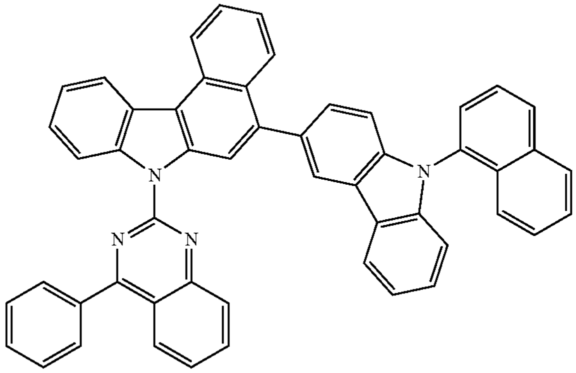
2-54
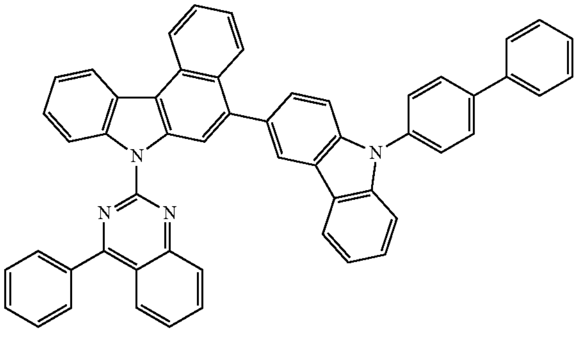

2-55
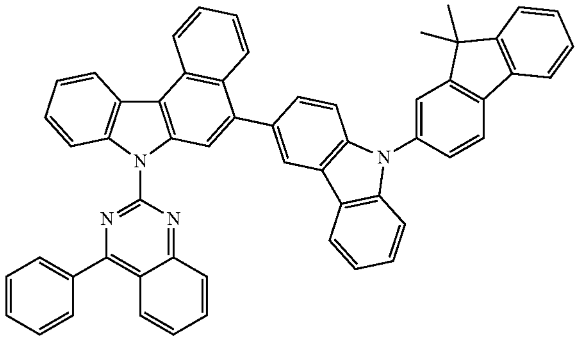
2-56
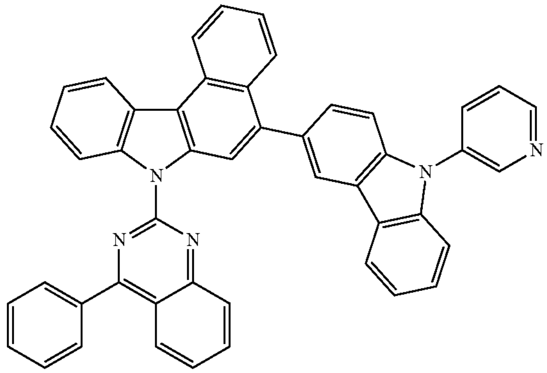
2-57
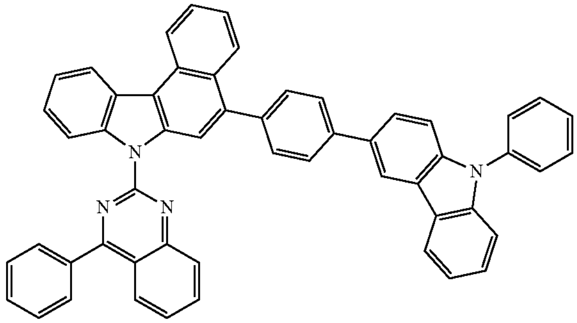
2-58
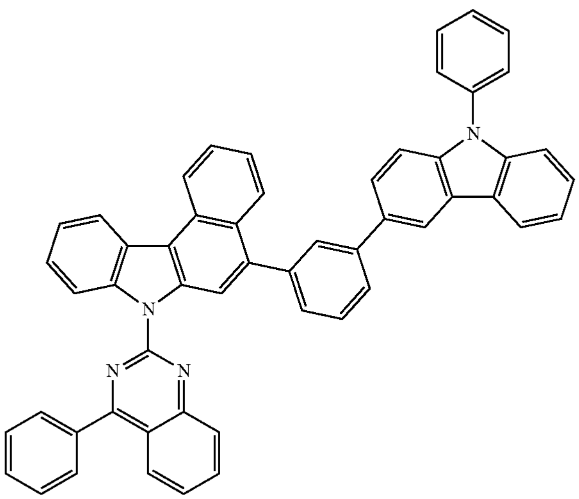
2-59
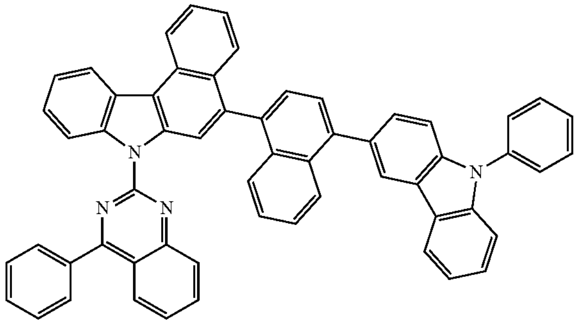
2-60
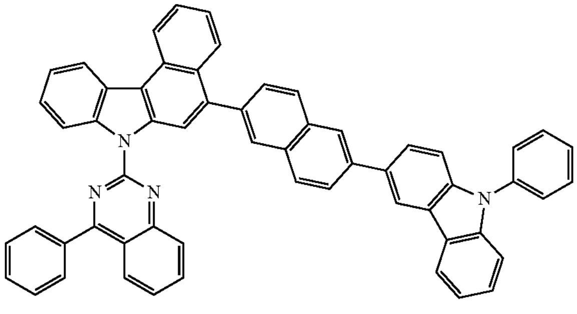
2-61
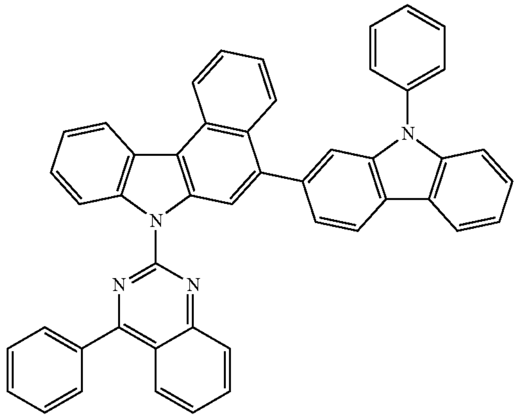
2-62
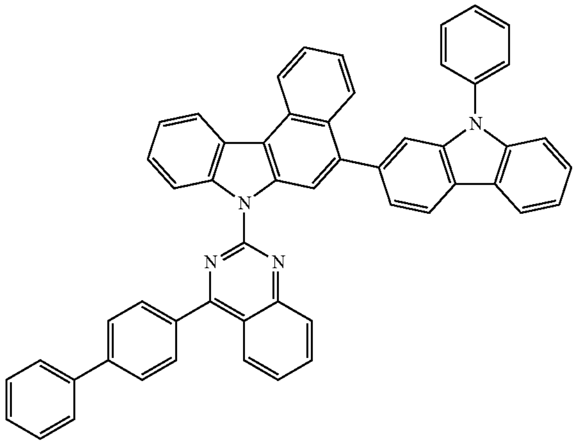

-continued
2-63
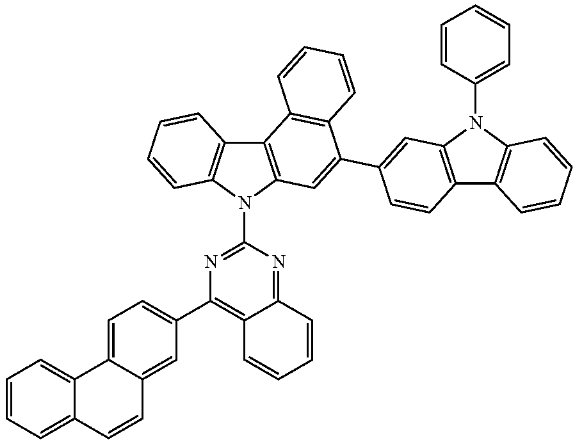
2-64
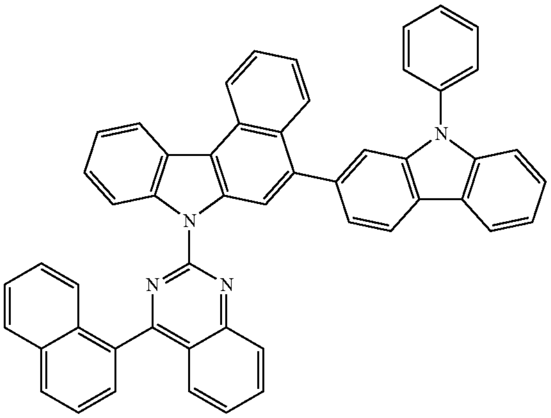
2-65
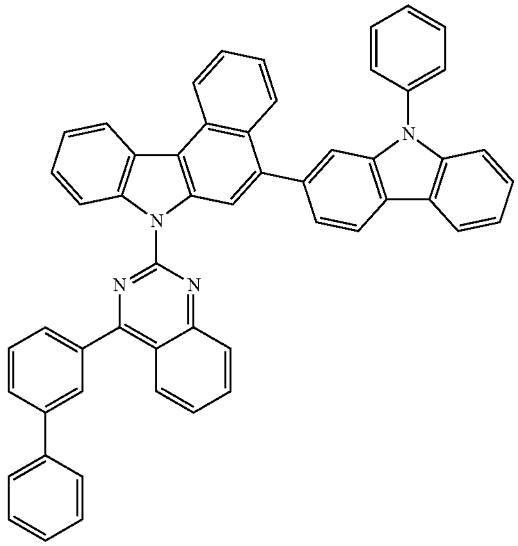
-continued
2-66
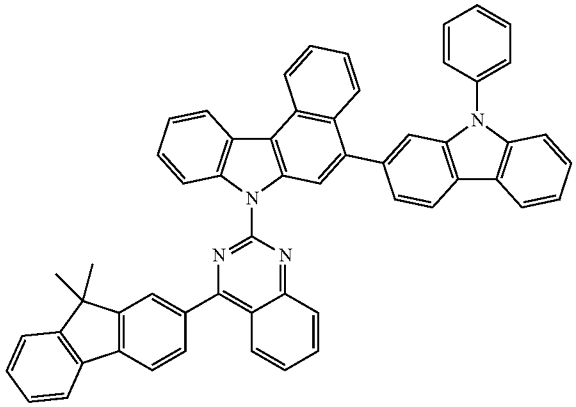
2-67
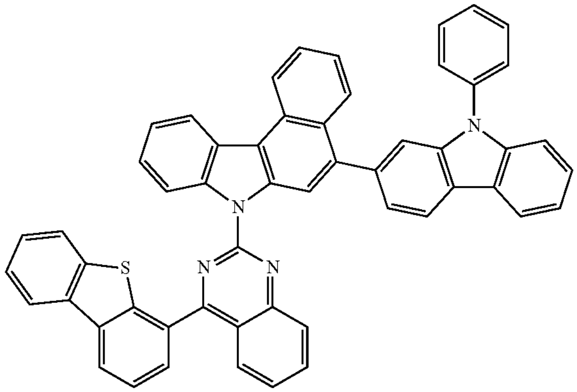
2-68
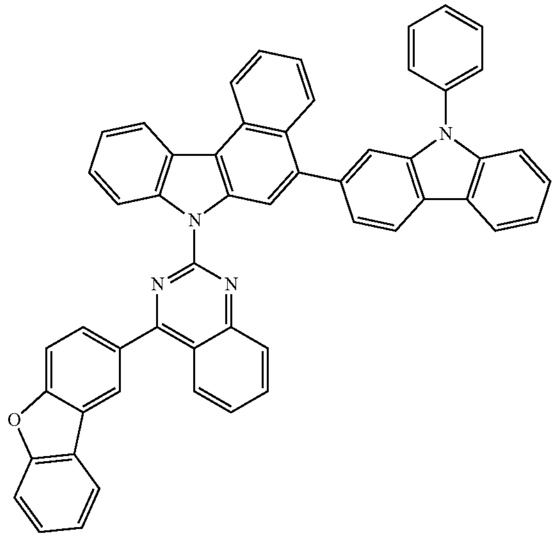

-continued
2-69
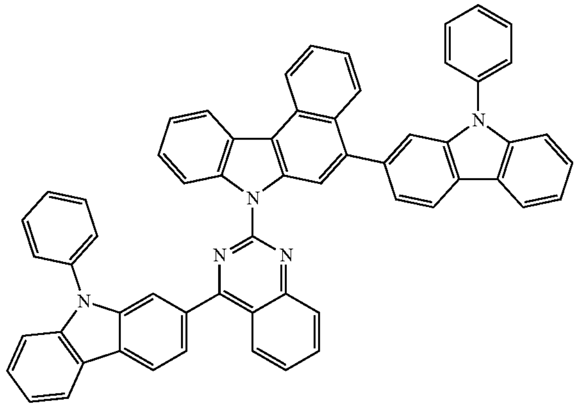
2-70
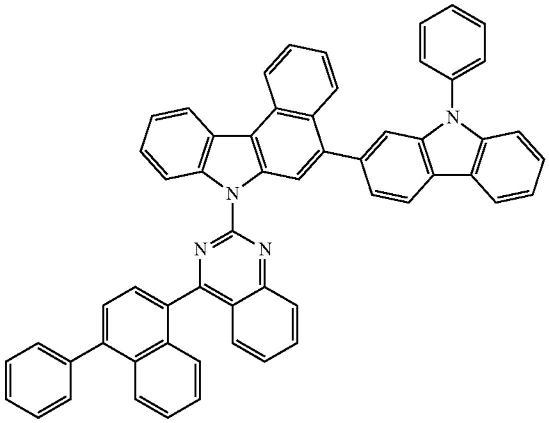
2-71
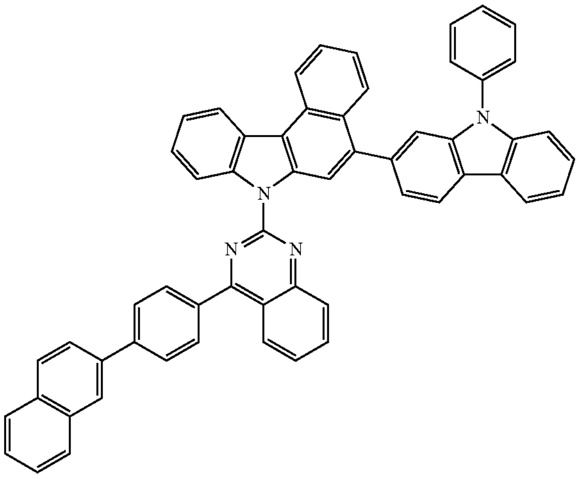
-continued
2-72
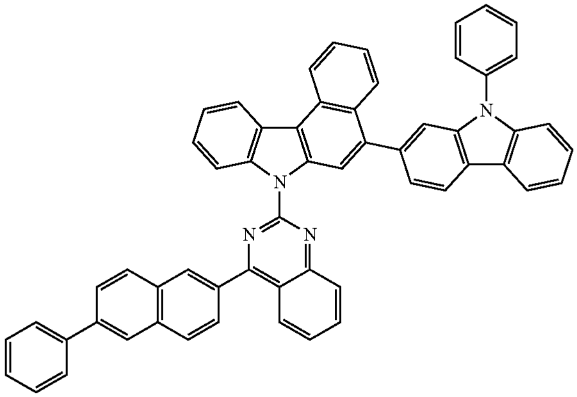
2-73
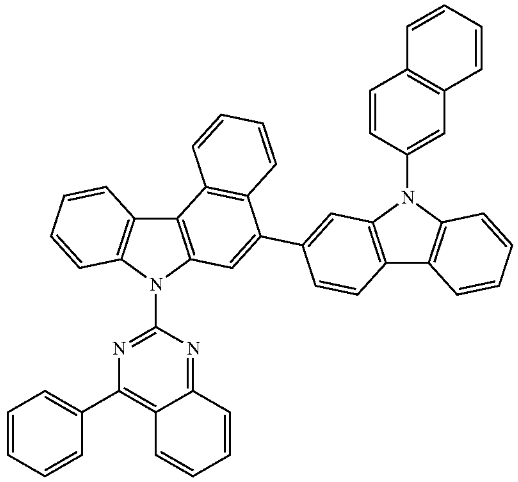
2-74
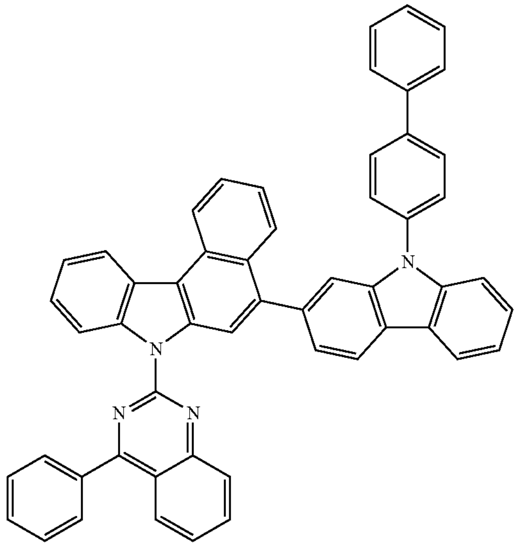

-continued
2-75
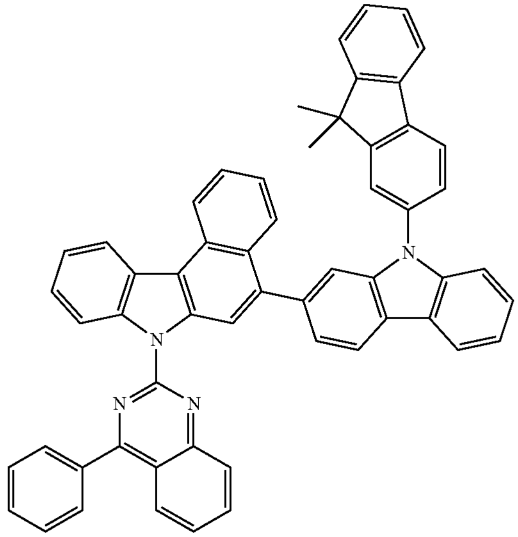
2-76
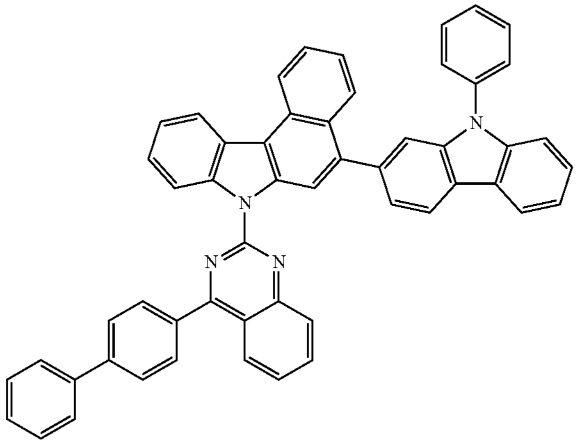
2-77
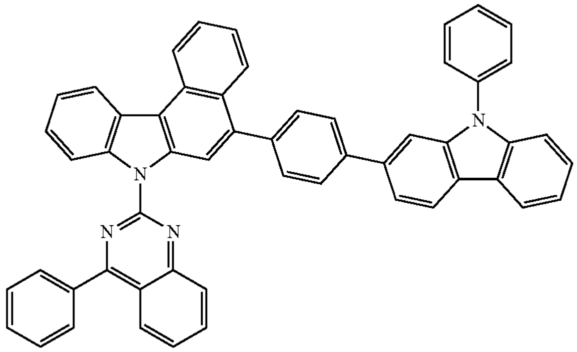
-continued
2-78
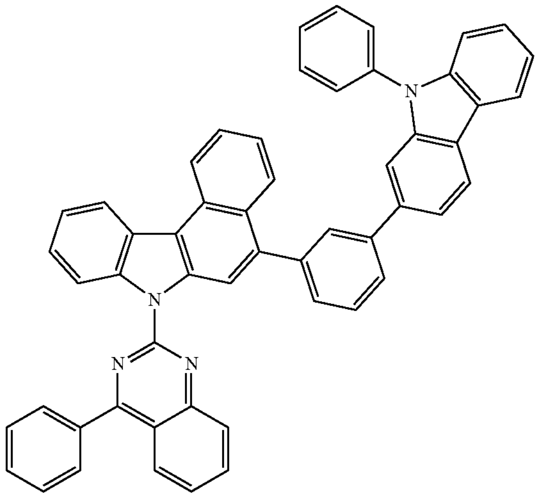
2-79
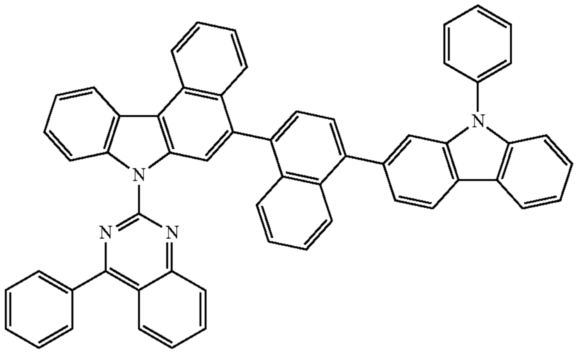
2-80
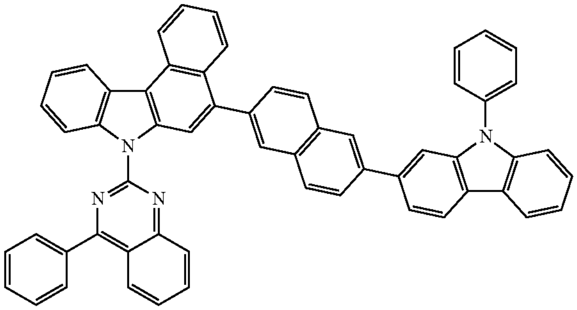
2-81
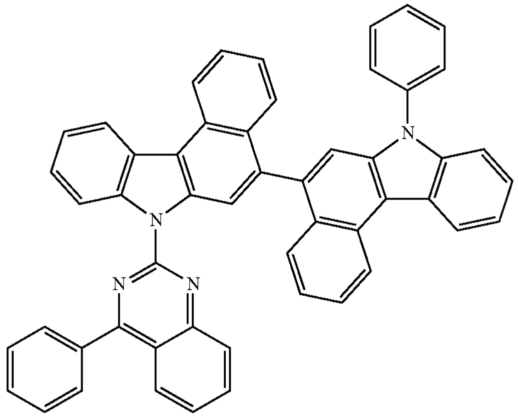

-continued
2-82
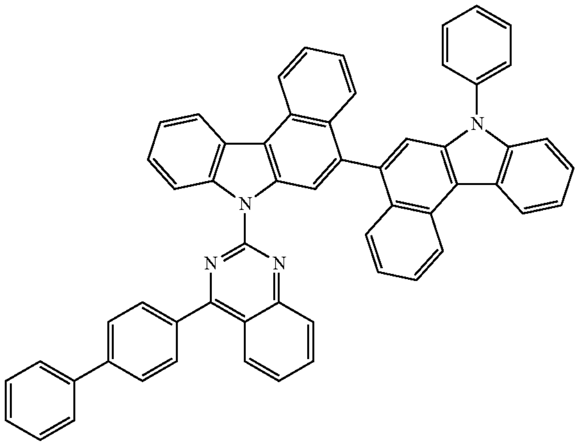
2-83
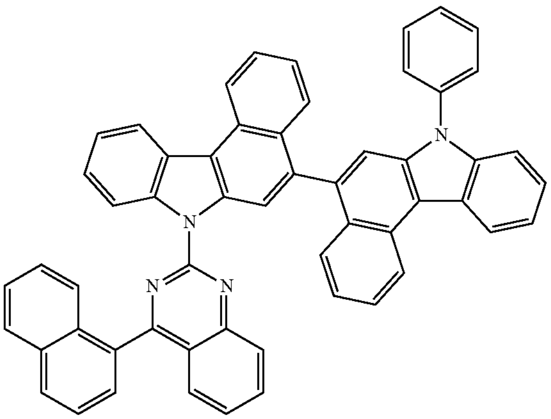
2-84
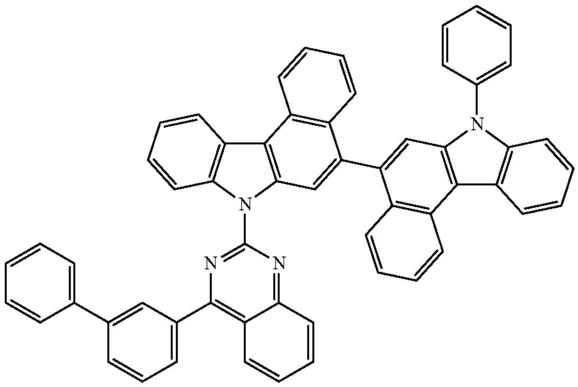
-continued
2-85
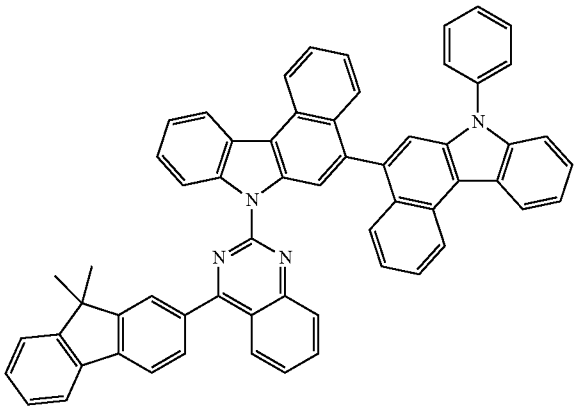
2-86
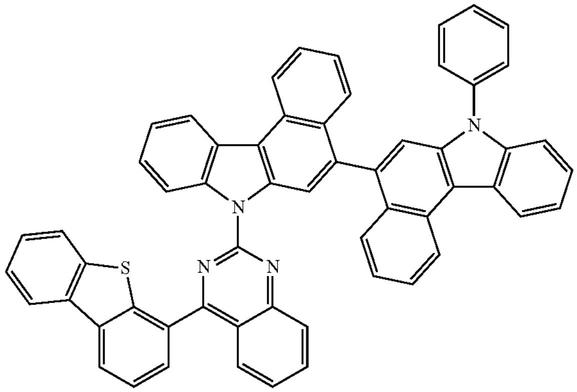
2-87
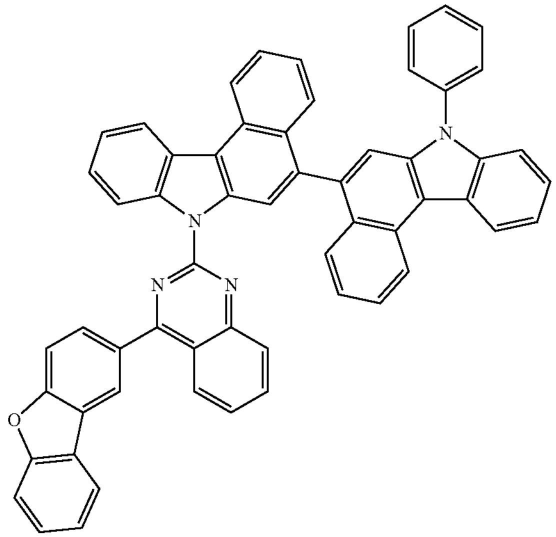

-continued
2-88
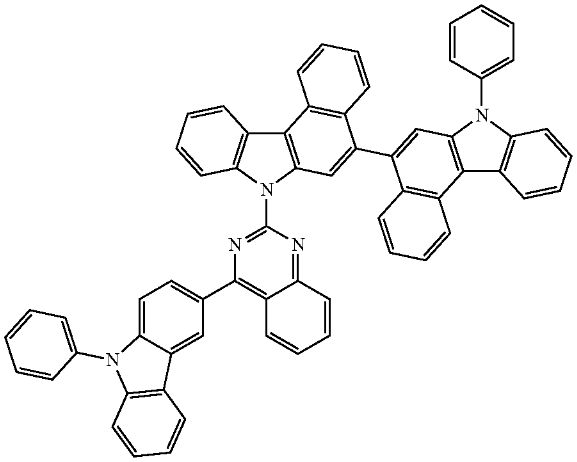
2-89
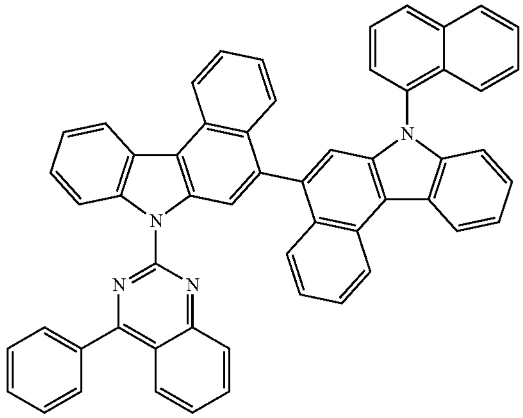
2-90
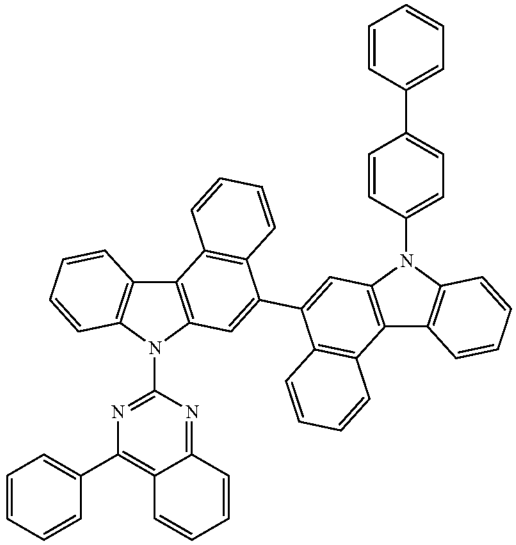
-continued
2-91
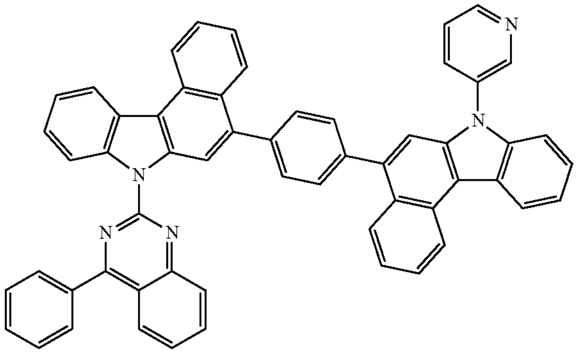
2-92
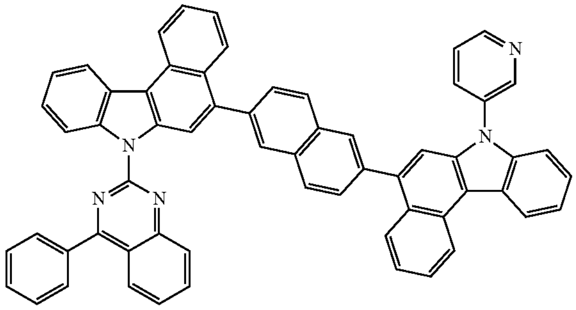
2-93
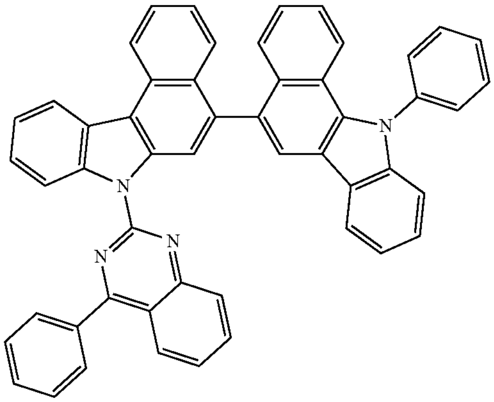
2-94
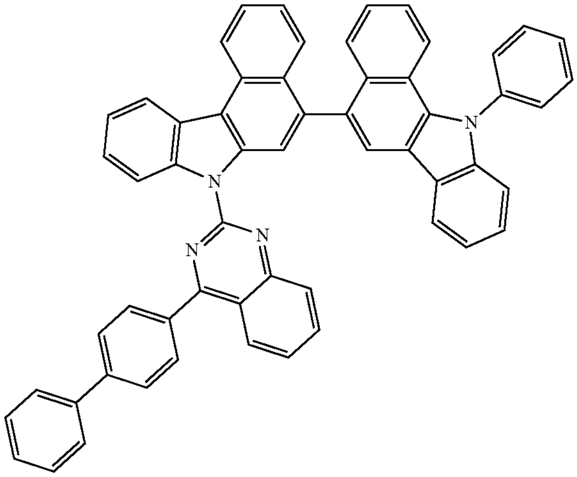

-continued
2-95
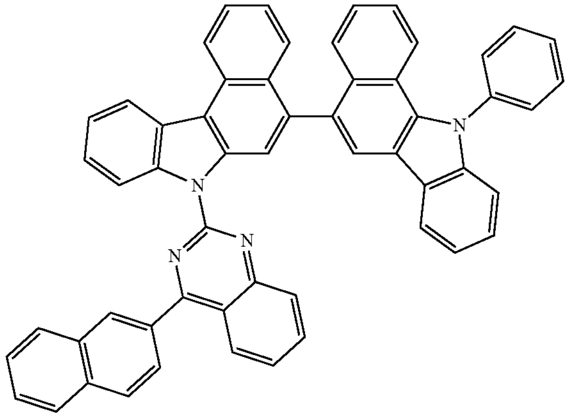
2-96
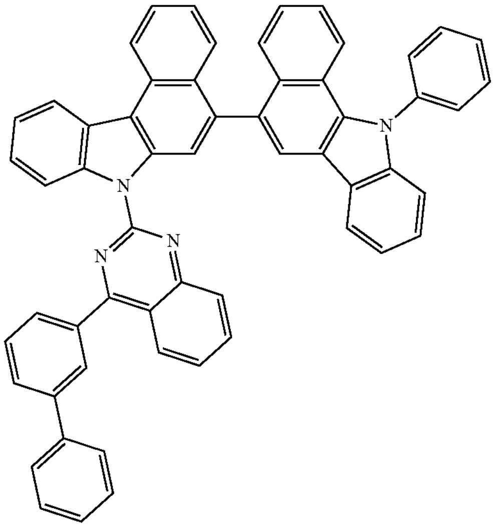
2-97
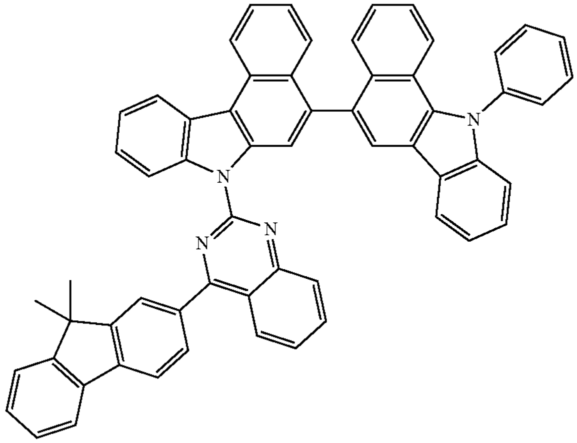
-continued
2-98
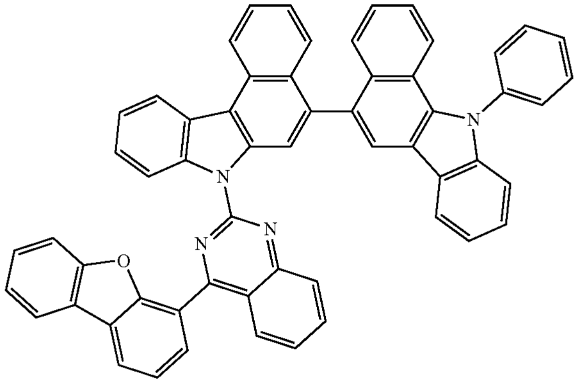
2-99
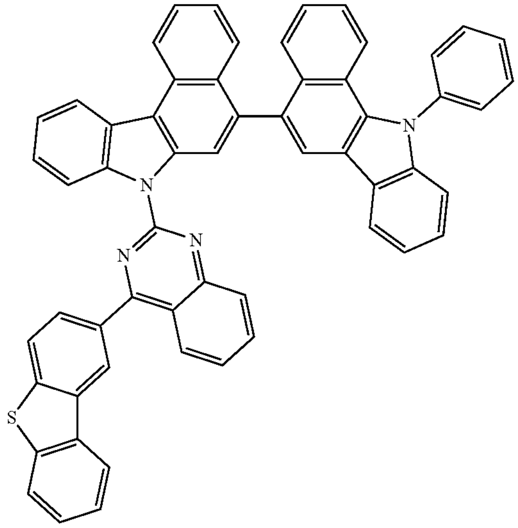
2-100
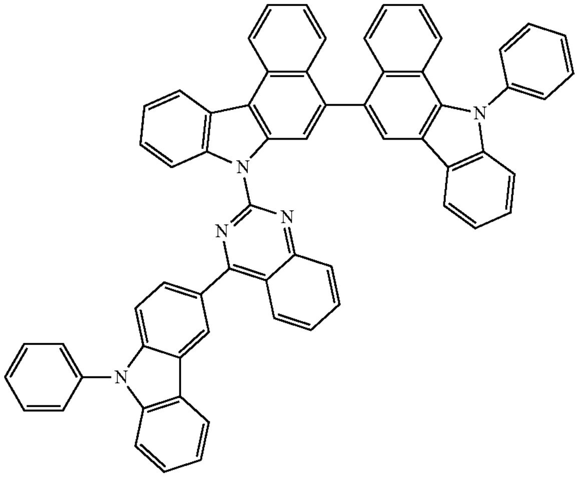

-continued
2-101
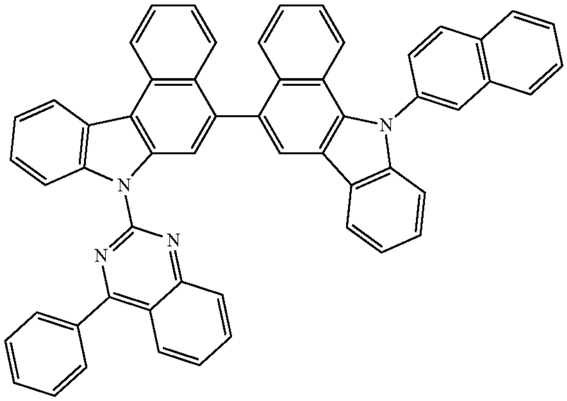
2-102
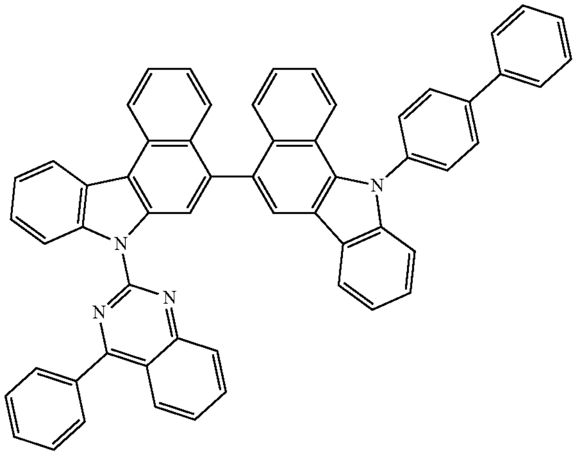
2-103
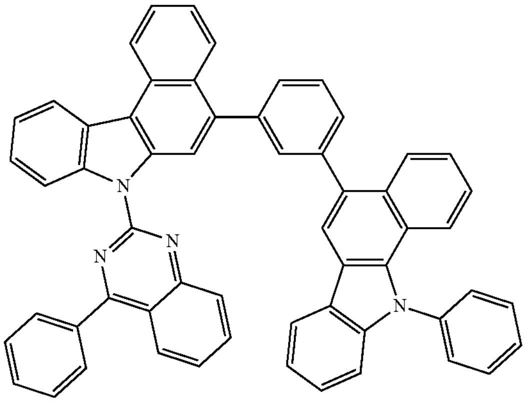
-continued
2-104
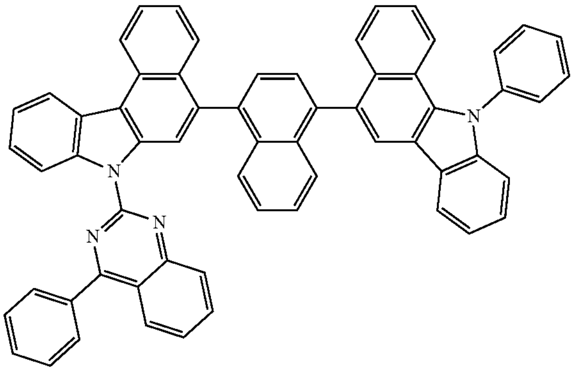
2-105
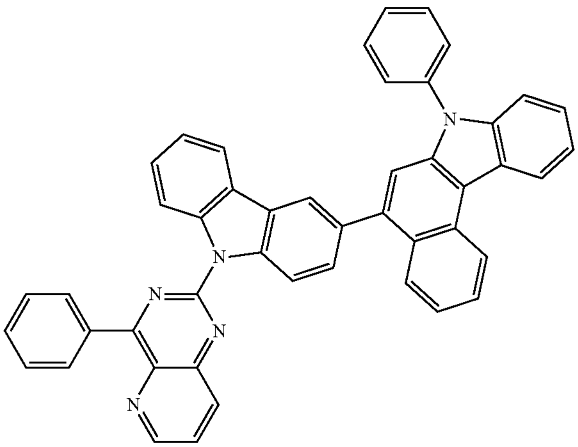
2-106
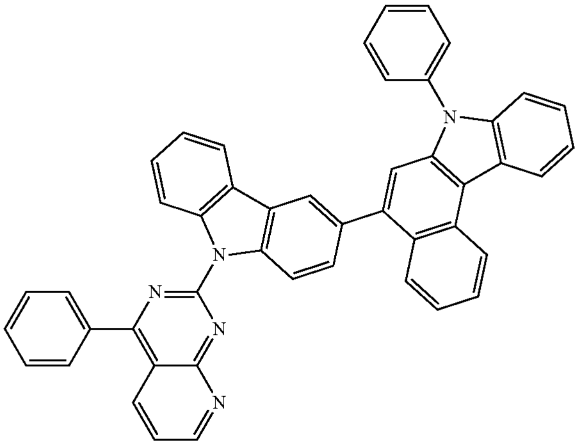

-continued
2-107
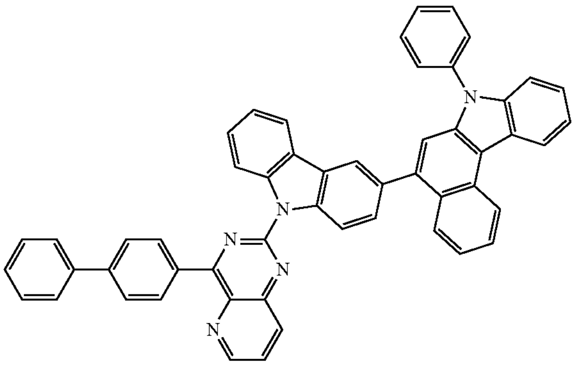
2-108
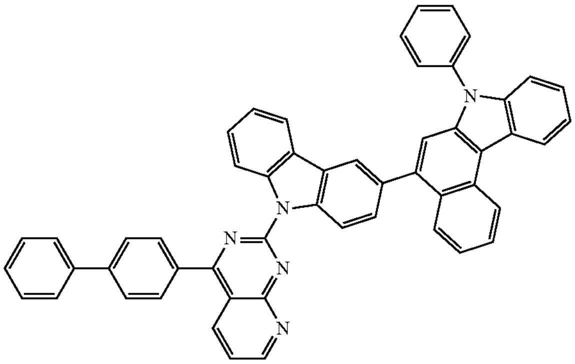
2-109
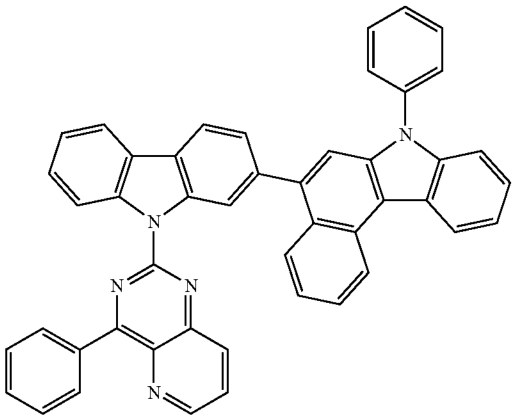
2-110
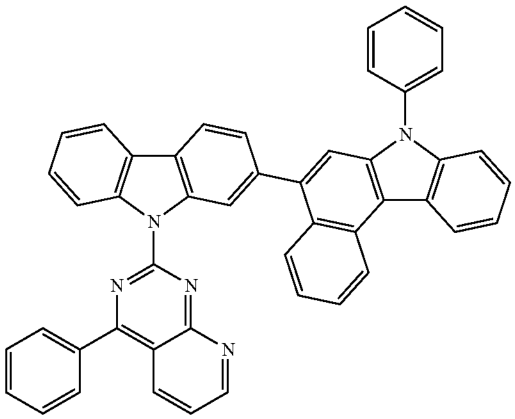
-continued
2-111
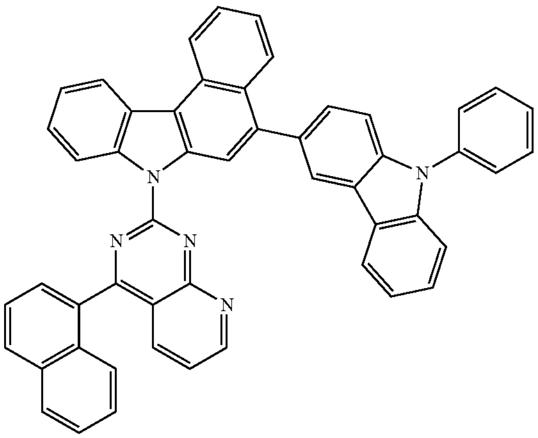
2-112
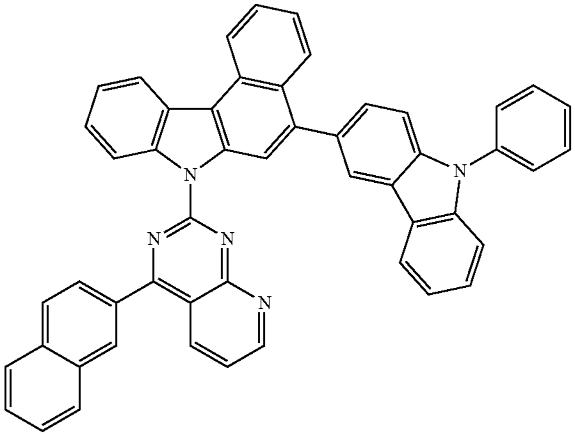
2-113
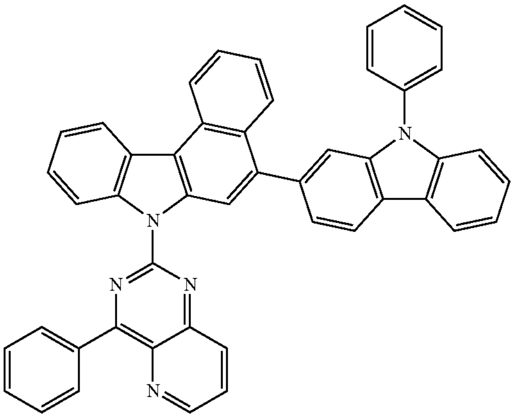

-continued
2-114
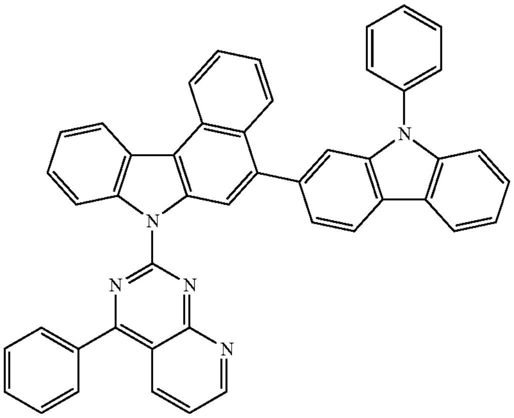
2-115
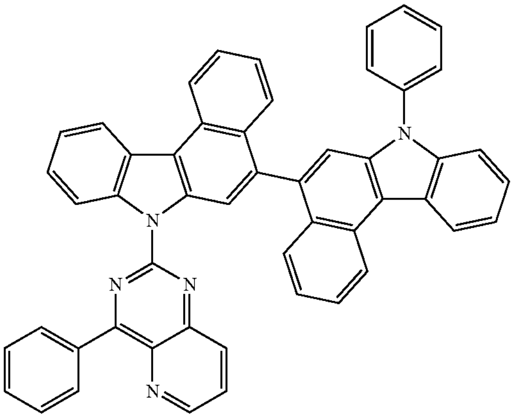
2-116
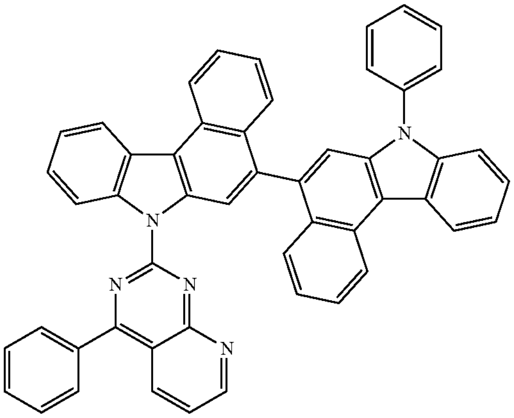
-continued
2-117
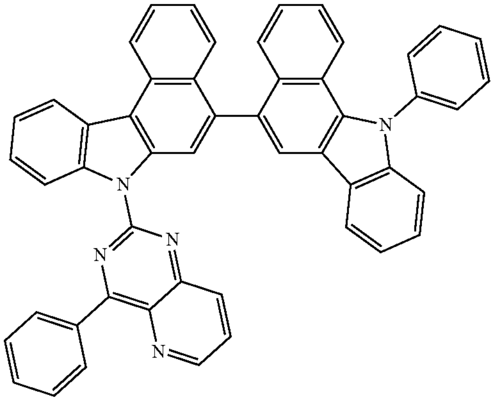
2-118
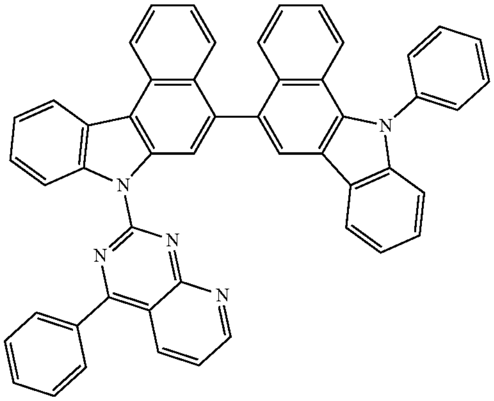
2-119
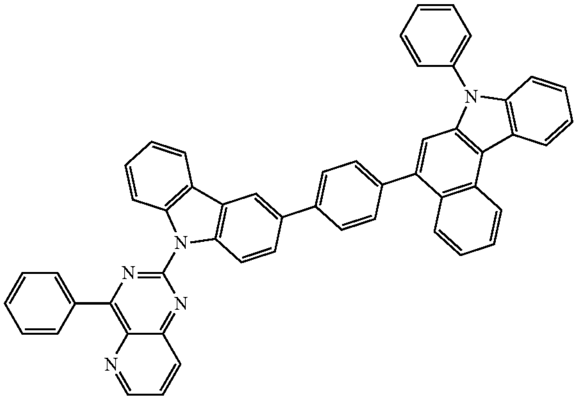

-continued 2-220

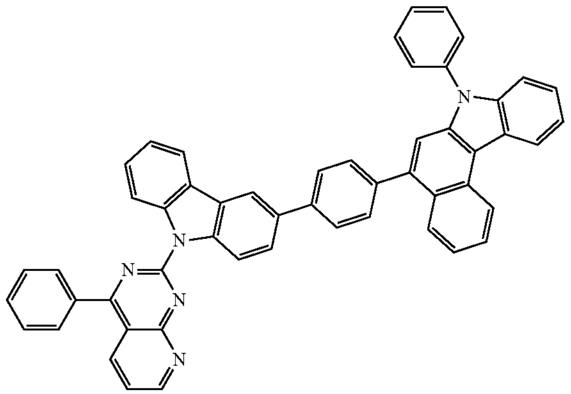

Hereinafter, synthesis examples of the compound represented by Formula 1 and manufacturing examples of the organic electronic element according to the present invention will be described in detail by way of example. However, the following examples are only for illustrative purposes and are not intended to limit the scope of the invention.

SYNTHESIS EXAMPLES

By way of example, the inventive compound (final product) is prepared by a reaction of sub 1 and sub 2 as shown in Reaction Scheme 1 below.

Reaction Scheme 1

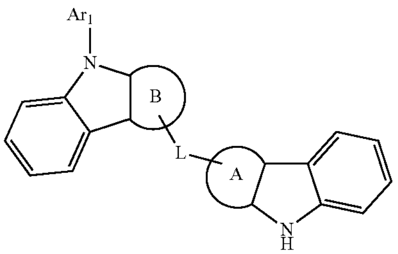

Sub 1

+

-continued

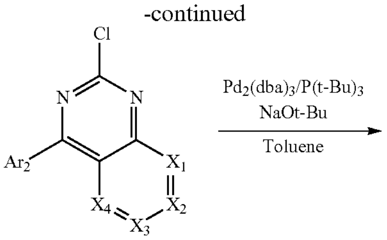

Sub 2

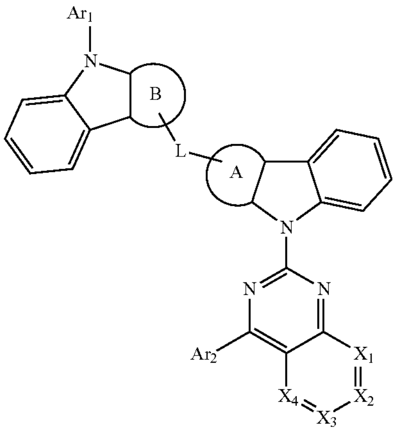

Final Products

1. Synthesis of Sub 1

Sub 1 may be synthesized by a reaction pathway of Reaction Scheme 2 below.

Reaction Scheme 2

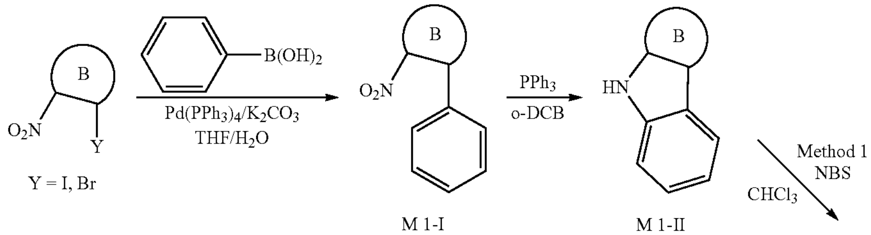

M 1-I

M 1-II

-continued
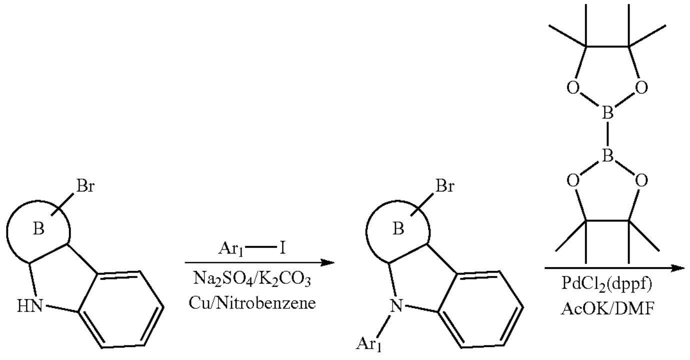
Sub 1-I Sub 1-II
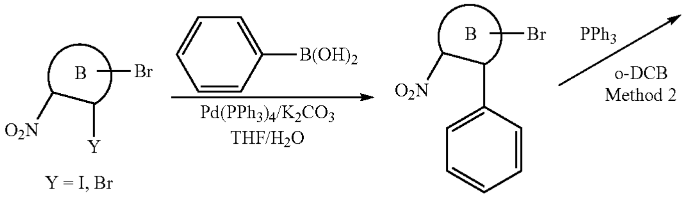
Y = I, Br
M 2-I
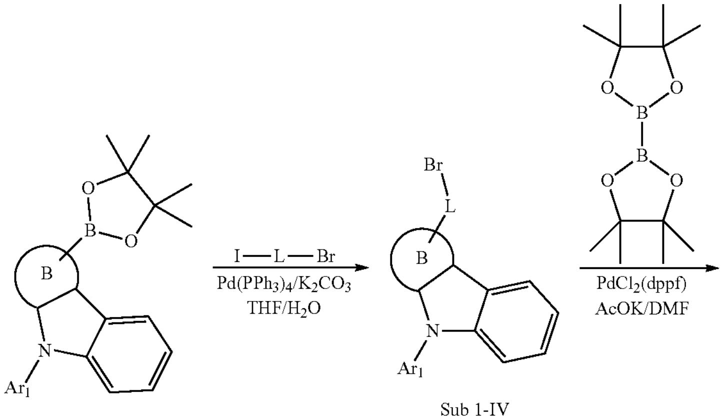
Sub 1-IV
Sub 1-III
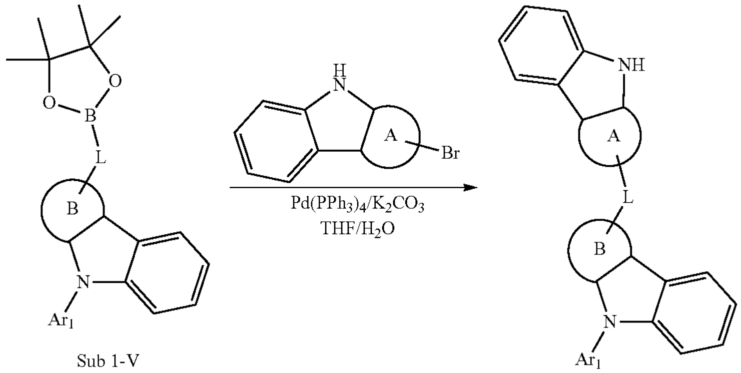
Sub 1-V
Sub 1

Synthesis examples of specific compounds belonging to Sub 1 are as follows.

(1) Synthesis example of Sub 1-1 (L=single bond)

Reaction Scheme 3

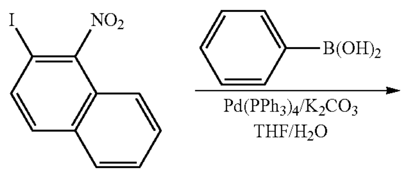

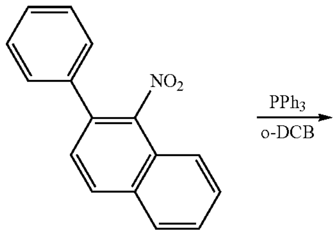

M1-I-1

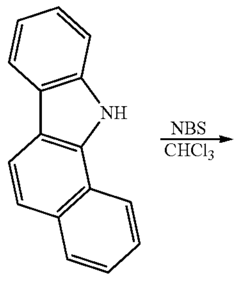

M1-II-1

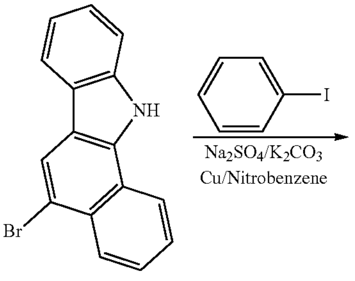

Sub 1-I-1

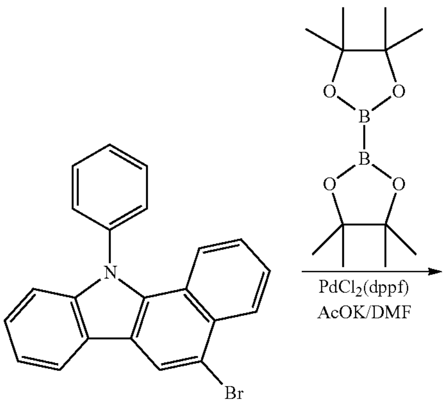

Sub 1-II-1

-continued

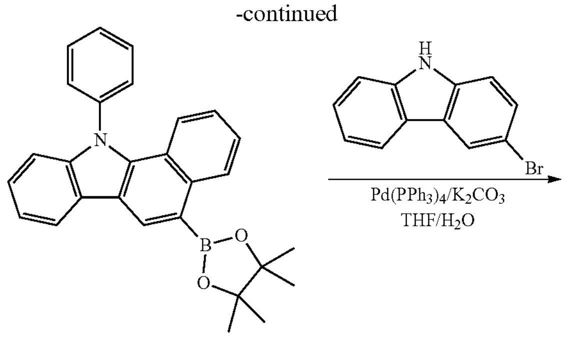

Sub 1-III-1

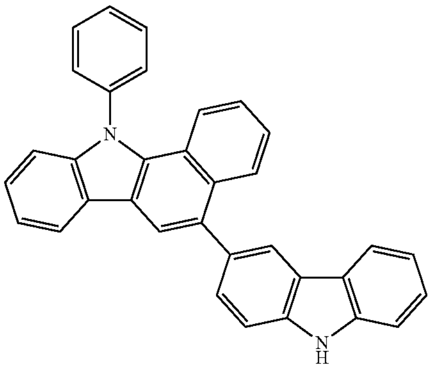

Sub 1-1

Synthesis of Intermediate M 1-I-1

Astartingmaterial, phenylboronicacid (89.06 g, 730.4 mmol) was dissolved in THF in a round bottom flask, and then 2-iodo-1-nitronaphthalene (262.13 g, 876.5 mmol), $Pd(PPh_3)_4$ (42.20 g, 36.5 mmol), $K_2CO_3$ (302.85 g, 2191.3 mmol), and water were added, followed by stirring at 80□. Upon completion of the reaction, the reaction product was extracted with $CH_2Cl_2$ and water. The organic layer was dried over $MgSO_4$ and concentrated, and then the thus generated compound was subjected to a silica gel column and recrystallization to give a product 158.4 g (yield: 87%).

Synthesis of Intermediate M 1-II-1

M 1-I-1 (158.4 g, 635.5 mmol) obtained in the above synthesis was dissolved in o-dichlorobenzene in a round bottom flask, and then triphenylphosphine (416.7 g, 1588.7 mmol) was added, followed by stirring at 200□. Upon completion of the reaction, o-dichlorobenzene was removed through distillation, followed by extraction with $CH_2Cl_2$ and water. The organic layer was dried over $MgSO_4$ and concentrated, and then the thus generated compound was subjected to a silica gel column and recrystallization to give a product 102.17 g (yield: 74%).

Synthesis of Intermediate Sub 1-I-1

After M 1-II-1 (102.17 g, 470.2 mmol) obtained in the above synthesis was dissolved in chloroform in a round bottom flask, the temperature of the reaction material was lowered to 0□, and then N-bromosuccinimide (83.70 g, 470.2 mmol) was slowly added dropwise, followed by stirring at room temperature. Upon completion of the reaction, the reaction product was extracted with $CH_2Cl_2$ and water. The organic layer was dried over $MgSO_4$ and concentrated, and then the thus generated compound was subjected to a silica gel column and recrystallization to give a product 90.52 g (yield: 65%).

Synthesis of Intermediate Sub 1-II-1

Sub 1-I-1 (90.52 g, 305.6 mmol) obtained in the above synthesis was dissolved in nitrobenzene in a round bottom flask, and then iodobenzene (93.53 g, 458.5 mmol), $Na_2SO_4$ (43.41 g, 305.6 mmol), $K_2CO_3$ (42.24 g, 305.6 mmol), and Cu (5.83 g, 91.7 mmol) were added, followed by stirring at 200□. Upon completion of the reaction, nitrobenzene was removed through distillation, followed by extraction with $CH_2Cl_2$ and water. The organic layer was dried over $MgSO_4$ and concentrated, and then the thus generated compound was subjected to a silica gel column and recrystallization to give a product 83.06 g (yield: 73%).

Synthesis of Intermediate Sub 1-III-1

Sub 1-II-1 (83.06 g, 223.1 mmol) obtained in the above synthesis was dissolved in DMF in a round bottom flask, and then Bis(pinacolato)diboron (62.33 g, 245.4 mmol), Pd(dppf)$Cl_2$ (5.47 g, 6.7 mmol), and KOAc (65.69 g, 669.4 mmol) were added, followed by stirring at 90□. Upon completion of the reaction, DMF was removed through distillation, followed by extraction with $CH_2Cl_2$ and water. The organic layer was dried over $MgSO_4$ and concentrated, and then the thus generated compound was subjected to a silica gel column and recrystallization to give a product 79.53 g (yield: 85%).

Synthesis Example of Sub 1-1

Sub 1-III-1 (50.21 g, 119.7 mmol) obtained in the above synthesis was dissolved in THF in a round bottom flask, and then 3-bromo-9H-carbazole (35.36 g, 143.7 mmol), $Pd(PPh_3)_4$ (6.92 g, 6 mmol), $K_2CO_3$ (49.65 g, 359.2 mmol), and water were added, followed by stirring at 80□. Upon completion of the reaction, the reaction product was extracted with $CH_2Cl_2$ and water. The organic layer was dried over $MgSO_4$ and concentrated, and then the thus generated compound was subjected to a silica gel column and recrystallization to give a product 40.63 g (yield: 74%).

(2) Synthesis example of Sub 1-18

Reaction Scheme 4

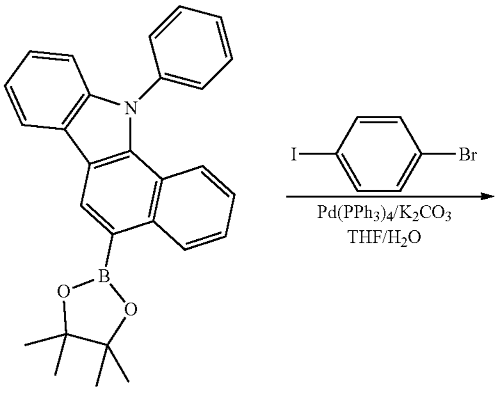

Sub 1-III-1

-continued

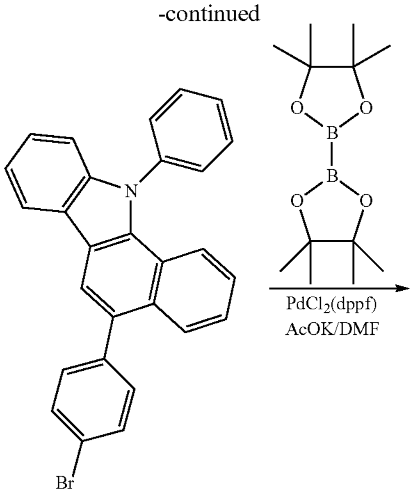

Sub 1-IV-18

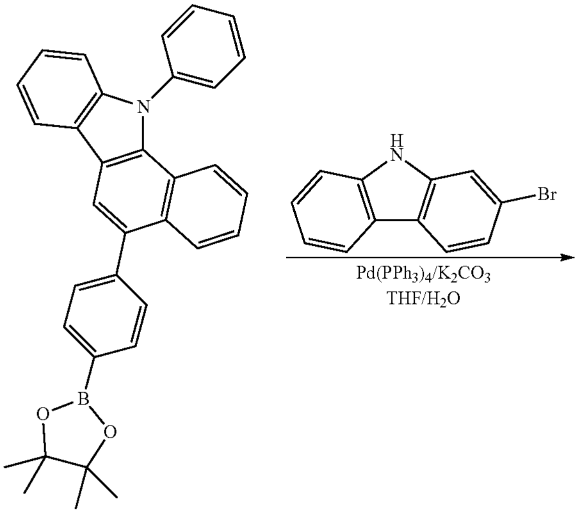

Sub 1-V-18

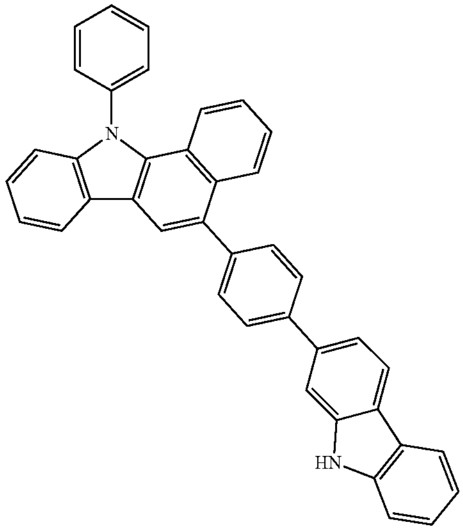

Sub 1-18

Synthesis of Intermediate Sub 1-IV-18

Sub 1-III-1 (29.32 g, 69.9 mmol) obtained in the above synthesis was dissolved in THF in a round bottom flask, and then 1-bromo-4-iodobenzene (29.67 g, 104.9 mmol), $Pd(PPh_3)_4$ (4.04 g, 3.5 mmol), $K_2CO_3$ (28.99 g, 209.8 mmol), and water were added, followed by stirring at 80□. Upon completion of the reaction, the reaction product was extracted with $CH_2Cl_2$ and water. The organic layer was dried over $MgSO_4$ and concentrated, and then the thus generated compound was subjected to a silica gel column and recrystallization to give a product 24.45 g (yield: 78%).

Synthesis of Intermediate Sub 1-V-18

Sub 1-IV-18 (24.45 g, 54.5 mmol) obtained in the above synthesis was dissolved in DMF in a round bottom flask, and then Bis(pinacolato)diboron (15.23 g, 60 mmol), Pd(dppf) $Cl_2$ (1.34 g, 1.6 mmol), and KOAc (16.06 g, 163.6 mmol) were added, followed by stirring at 90□. Upon completion of the reaction, DMF was removed through distillation, followed by extraction with $CH_2Cl_2$ and water. The organic layer was dried over $MgSO_4$ and concentrated, and then the thus generated compound was subjected to a silica gel column and recrystallization to give a product 23.23 g (yield: 86%).

Synthesis Example of Sub 1-18

Sub 1-V-18 (23.23 g, 46.9 mmol) obtained in the above synthesis was dissolved in THF in a round bottom flask, and then 2-bromo-9H-carbazole (13.85 g, 56.3 mmol), $Pd(PPh_3)_4$ (2.71 g, 2.3 mmol) $K_2CO_3$ (19.44 g, 140.7 mmol), and water were added, followed by stirring at 80□. Upon completion of the reaction, the reaction product was extracted with $CH_2Cl_2$ and water. The organic layer was dried over $MgSO_4$ and concentrated, and then the thus generated compound was subjected to a silica gel column and recrystallization to give a product 20.06 g (yield: 80%).

(3) Synthesis example of Sub 1-22 (L-single bond)

Scheme 5

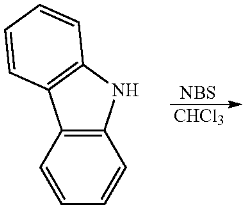

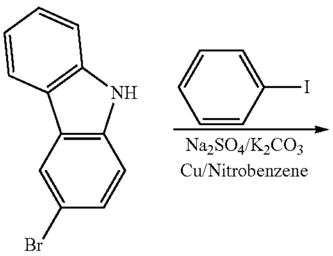

Sub 1-I-22

-continued

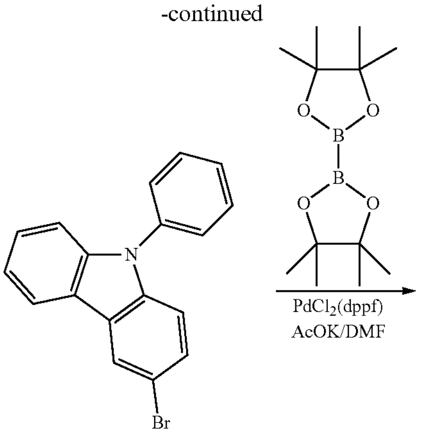

Sub 1-II-22

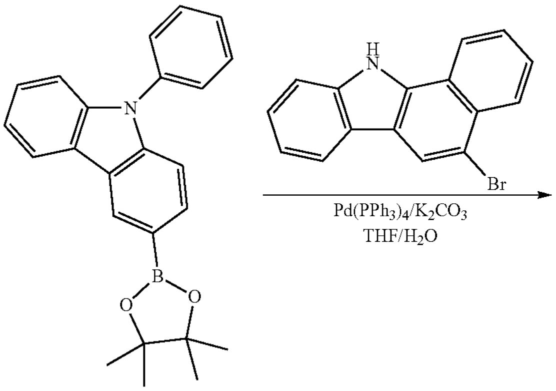

Sub 1-III-22

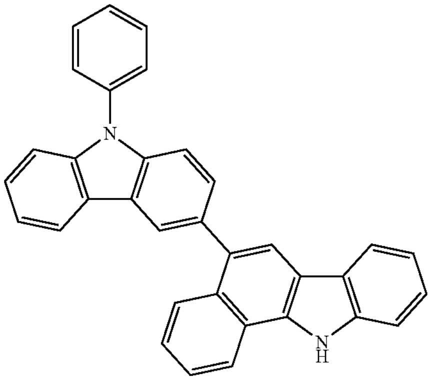

Sub 1-22

Synthesis of Intermediate Sub 1-I-22

In addition to 9H-carbazole (108.76 g, 650.4 mmol) as a starting material, N-bromosuccinimide (115.77 g, 650.4 mmol) and chloroform were used according to the synthesis method of Sub 1-I-1 of Example 1 above, to give a product 112.05 g (yield: 70%).

Synthesis of Intermediate Sub 1-II-22

In addition to Sub 1-I-22 (112.05 g, 455.3 mmol) obtained in the above synthesis, iodobenzene (139.33 g, 683 mmol), $Na_2SO_4$ (64.67 g, 455.3 mmol), $K_2CO_3$ (62.93 g, 455.3 mmol), Cu (8.68 g, 136.6 mmol), and nitrobenzene were used according to the synthesis method of Sub 1-II-1 of Example 1 above, to give a product 110.02 g (yield: 75%).

Synthesis of Intermediate Sub 1-III-22

In addition to Sub 1-II-22 (110.02 g, 341.5 mmol) obtained in the above synthesis, Bis(pinacolato)diboron (95.38 g, 375.6 mmol), $Pd(dppf)Cl_2$ (8.37 g, 10.2 mmol), KOAc (100.53 g, 1024.4 mmol), and DMF were used according to the synthesis method of Sub 1-III-1 of Example 1 above, to give a product 105.92 g (yield: 84%).

Synthesis Example of Sub 1-22

In addition to Sub 1-III-22 (55.3 g, 149.8 mmol) obtained in the above synthesis, 5-bromo-11H-benzo[a] carbazole (53.22 g, 179.7 mmol), $Pd(PPh_3)_4$ (8.65 g, 7.5 mmol), $K_2CO_3$ (62.09 g, 449.3 mmol), THF, and water were used according to the synthesis method of Sub 1-1 of Example 1 above, to give a product 48.76 g (yield: 71%).

(4) Synthesis Example of Sub 1-32 (L=single bond)

Reaction Scheme 6

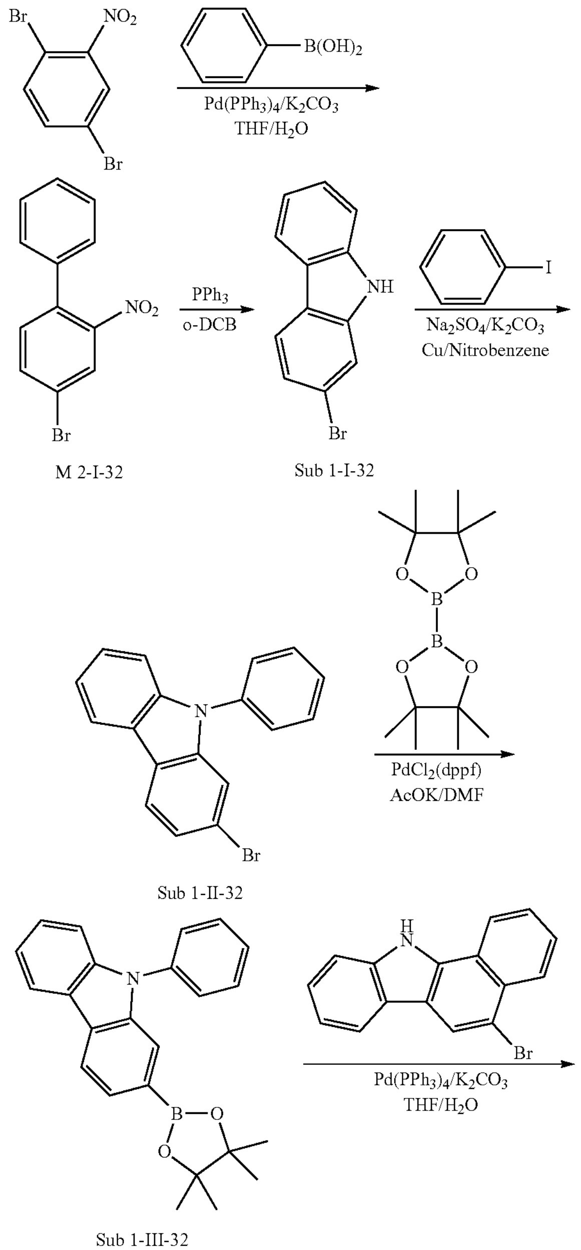

M 2-I-32

Sub 1-I-32

Sub 1-II-32

Sub 1-III-32

-continued

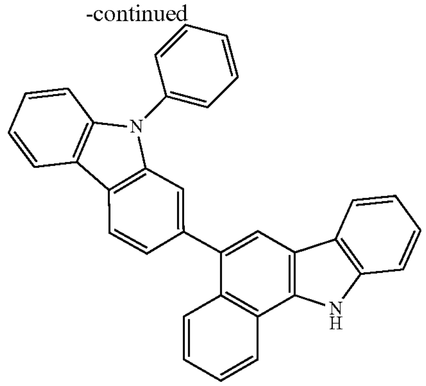

Sub 1-32

Synthesis of Intermediate M 2-I-32

A starting material, phenylboronic acid (89.13 g, 731 mmol) was dissolved in THF in a round bottom flask, and then 4-dibromo-2-nitrobenzene (308 g, 1096.5 mmol), $Pd(PPh_3)_4$ (42.24 g, 36.5 mmol), $K_2CO_3$ (303.09 g, 2193 mmol), and water were added, followed by stirring at 80□. Upon completion of the reaction, the reaction product was extracted with $CH_2Cl_2$ and water. The organic layer was dried over $MgSO_4$ and concentrated, and then the thus generated compound was subjected to a silica gel column and recrystallization to give a product 128.07 g (yield: 63%).

Synthesis of Intermediate Sub 1-I-32

M 2-I-32 (128.07 g, 460.5 mmol) obtained in the above synthesis was dissolved in o-dichlorobenzene in a round bottom flask, and then triphenylphosphine (301.97 g, 1151.3 mmol) was added, followed by stirring at 200□. Upon completion of the reaction, o-dichlorobenzene was removed through distillation, followed by extraction with $CH_2Cl_2$ and water. The organic layer was dried over $MgSO_4$ and concentrated, and then the thus generated compound was subjected to a silica gel column and recrystallization to give a product 80.47 g (yield: 71%).

Synthesis of Intermediate Sub 1-II-32

In addition to Sub 1-I-32 (80.47 g, 327 mmol) obtained in the above synthesis, iodobenzene (100.06 g, 490.5 mmol), $Na_2SO_4$ (46.44 g, 327 mol), $K_2CO_3$ (45.19 g, 327 mmol), Cu (6.23 g, 98.1 mmol), and nitrobenzene were used according to the synthesis method of Sub 1-II-1 of Example 1 above, to give a product 76.91 g (yield: 73%).

Synthesis of Intermediate Sub 1-III-32

In addition to Sub 1-II-32 (76.91 g, 238.7 mmol) obtained in the above synthesis, Bis(pinacolato)diboron (66.68 g, 262.6 mmol), Pd (dppf) $Cl_2$ (5.85 g, 7.2 mmol), KOAc (70.28 g, 716.1 mmol), and DMF were used according to the synthesis method of Sub 1-III-1 of Example 1 above, to give a product 69.63 g (yield: 79%).

Synthesis Example of Sub 1-32

In addition to Sub 1-III-32 (69.63 g, 188.6 mmol) obtained in the above synthesis, 5-bromo-11H-benzo[a] carbazole (67.01 g, 226.3 mmol), $Pd(PPh_3)_4$ (10.89 g, 9.4 mmol), $K_2CO_3$ (78.19 g, 565.7 mmol), THF, and water were used according to the synthesis method of Sub 1-1 of Example 1 above, to give a product 61.39 g (yield: 71%).

(5) Synthesis Example of Sub 1-46 (L=single bond)

Reaction Scheme 7

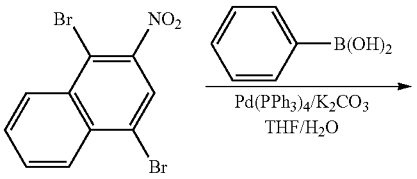

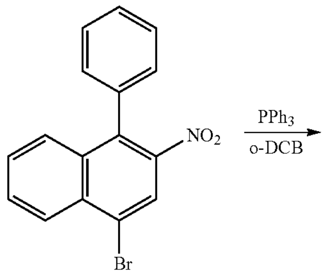

M 2-I-47

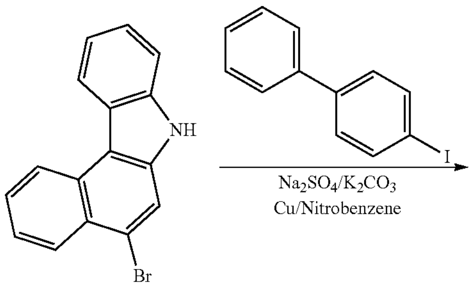

Sub 1-I-47

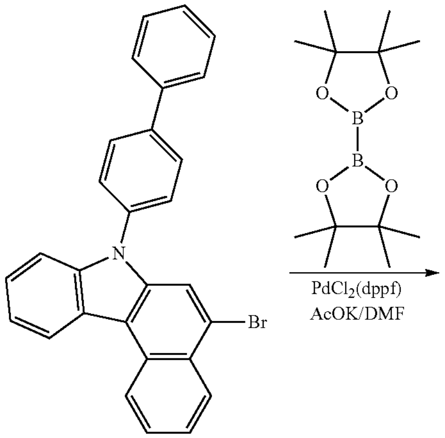

Sub 1-II-47

-continued

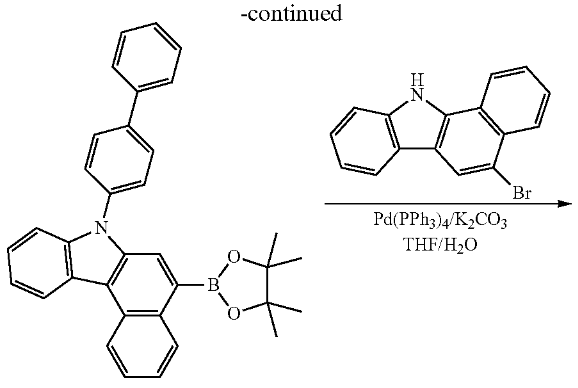

Sub 1-III-47

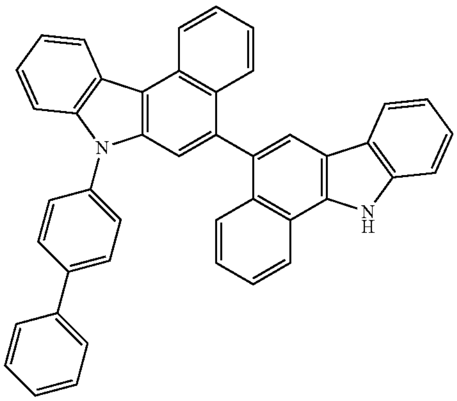

Sub 1-47

Synthesis of Intermediate M 2-I-47

In addition to phenylboronic acid (90.24 g, 740.1 mmol) as a starting material, 1,4-dibromo-2-nitronaphthalene (367.41 g, 1110.1 mmol), $Pd(PPh_3)_4$ (42.76 g, 37 mmol), $K_2CO_3$ (306.87 g, 2220.3 mmol), THF, and water were used according to the synthesis method of M 2-I-32 of Example 1, to give a product 148.15 g (yield: 61%).

Synthesis of Intermediate Sub 1-I-47

In addition to M 2-I-47 (148.15 g, 451.5 mmol) obtained in the above synthesis, triphenylphosphine (296.03 g, 1128.6 mmol) and o-dichlorobenzene were used according to the synthesis method of Sub 1-I-32 of Example 1, to give a product 92.26 g (yield: 69%).

Synthesis of Intermediate Sub 1-II-47

In addition to Sub 1-I-47 (92.26 g, 311.5 mmol) obtained in the above synthesis, 4-iodo-1,1'-biphenyl (130.89 g, 467.3 mmol), $Na_2SO_4$ (44.25 g, 311.5 mmol), $K_2CO_3$ (43.06 g, 311.5 mmol), Cu (5.94 g, 93.5 mmol), and nitrobenzene were used according to the synthesis method of Sub 1-II-1 of Example 1 above, to give a product 100.56 g (yield: 72%).

Synthesis of Intermediate Sub 1-III-47

In addition to Sub 1-II-47 (100.56 g, 224.3 mmol) obtained in the above synthesis, Bis(pinacolato)diboron (62.65 g, 246.7 mmol), $Pd(dppf)Cl_2$ (5.49 g, 6.7 mmol), KOAc (66.04 g, 672.9 mmol), and DMF were used according to the synthesis method of Sub 1-III-1 of Example 1 above, to give a product 85.56 g (yield: 77%).

Synthesis Example of Sub 1-47

In addition to Sub 1-III-47 (46.97 g, 94.8 mmol) obtained in the above synthesis, 5-bromo-11H-benzo[a]carbazole (33.69 g, 113.8 mmol), $Pd(PPh_3)_4$ (5.48 g, 4.7 mmol), $K_2CO_3$ (39.31 g, 284.4 mmol), THF, and water were used according to the synthesis method of Sub 1-1 of Example 1 above, to give a product 34.37 g (yield: 62%).

(6) Synthesis Example of Sub 1-52 (L-single bond)

Reaction Scheme 8

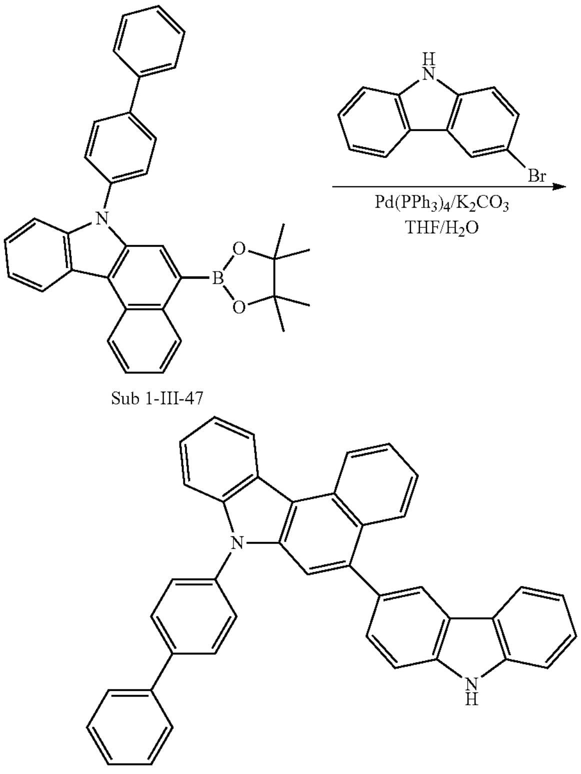

Sub 1-III-47

Sub 1-52

In addition to Sub 1-III-47 (38.59 g, 77.9 mmol) obtained in the above synthesis, 3-bromo-9H-carbazole (23 g, 93.5 mmol), $Pd(PPh_3)_4$ (4.5 g, 3.9 mmol), $K_2CO_3$ (32.3 g, 233.7 mmol), THF, and water were used according to the synthesis method of Sub 1-1 of Example 1 above, to give a product 30.4 g (yield: 73%).

(7) Synthesis example of Sub 1-76

Reaction Scheme 9

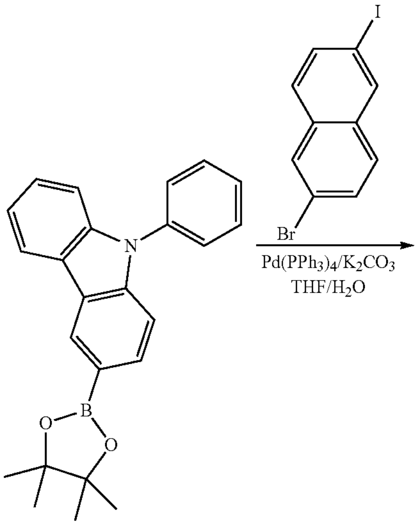

Sub 1-III-22

-continued

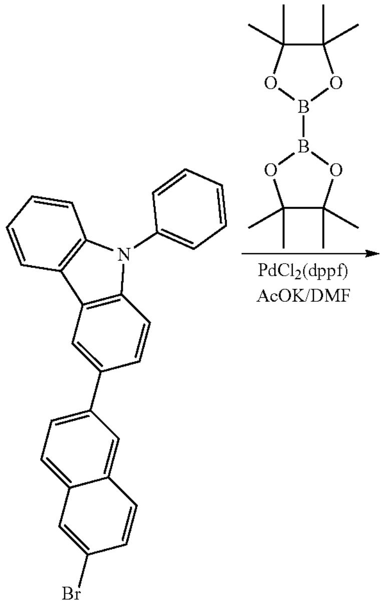

Sub 1-IV-76

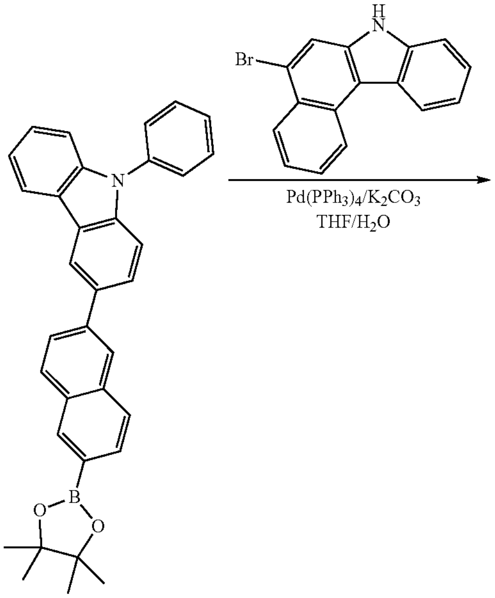

Sub 1-V-76

-continued

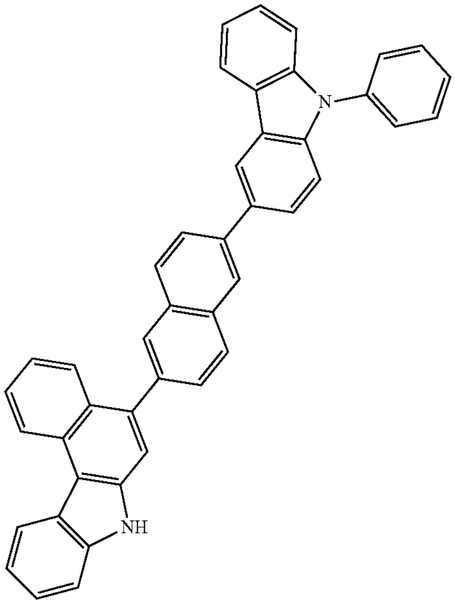

Sub 1-76

Synthesis of Intermediate Sub 1-IV-76

In addition to Sub 1-III-22 (50.62 g, 137.1 mmol) obtained in the above synthesis, 2-bromo-6-iodonaphthalene (68.47 g, 205.6 mmol), $Pd(PPh_3)_4$ (7.92 g, 6.9 mmol), $K_2CO_3$ (56.84 g, 411.3 mmol), THF, and water were used according to the synthesis method of Sub 1-IV-18 of Example 1 above, to give a product 44.87 g (yield: 73%).

Synthesis of Intermediate Sub 1-V-76

In addition to Sub 1-IV-76 (44.87 g, 100.1 mmol) obtained in the above synthesis, Bis(pinacolato)diboron (27.96 g, 110.1 mmol), $Pd(dppf)Cl_2$ (2.45 g, 3 mmol), KOAc (29.46 g, 300.2 mmol), and DMF were used according to the synthesis method of Sub 1-V-18 of Example 1 above, to give a product 40.16 g (yield: 81%).

Synthesis Example of Sub 1-76

In addition to Sub 1-V-76 (40.16 g, 81.1 mmol) obtained in the above synthesis, 5-bromo-7H-benzo[c]carbazole (28.81 g, 97.3 mmol), $Pd(PPh_3)_4$ (4.68 g, 4.1 mmol), $K_2CO_3$ (33.61 g, 243.2 mmol), THF, and water were used according to the synthesis method of Sub 1-18 of Example 1 above, to give a product 35.07 g (yield: 74%).

Meanwhile, examples of Sub 1 are as follows, but are limited thereto, and FD-MS values thereof are shown in Table 1 below.

Sub 1-1

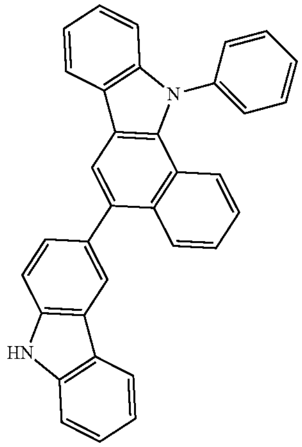

Sub 1-2

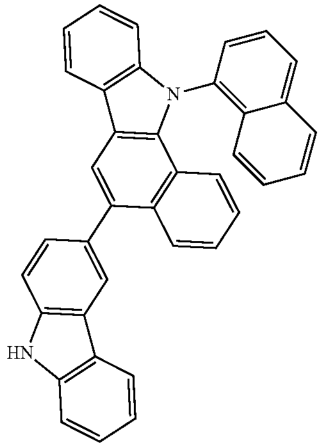

Sub 1-3

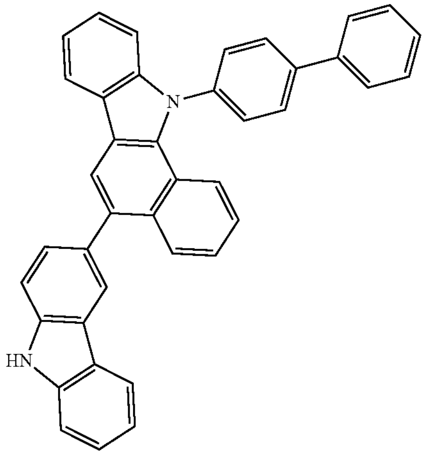

Sub 1-4
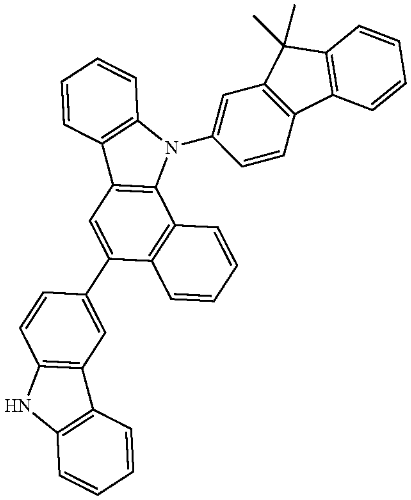
Sub 1-5
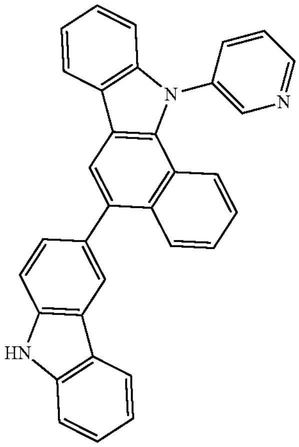
Sub 1-6
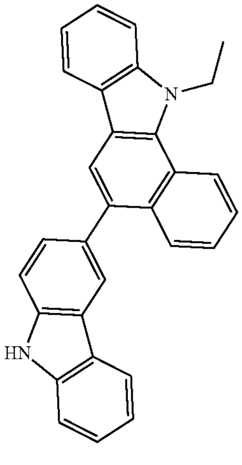
Sub 1-7
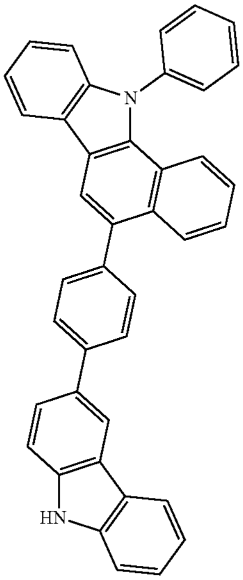
Sub 1-8
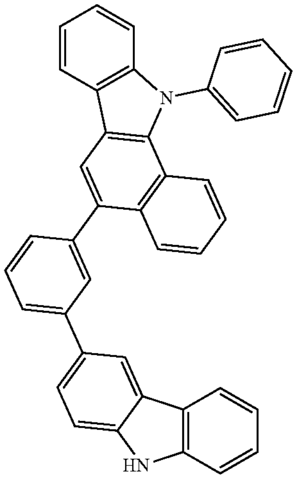
Sub 1-9
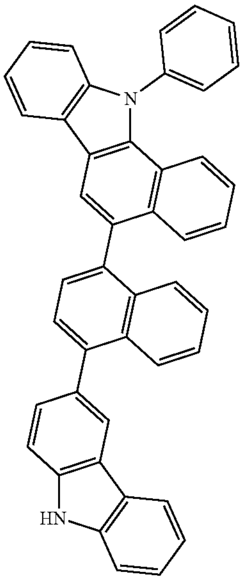

-continued
Sub 1-10
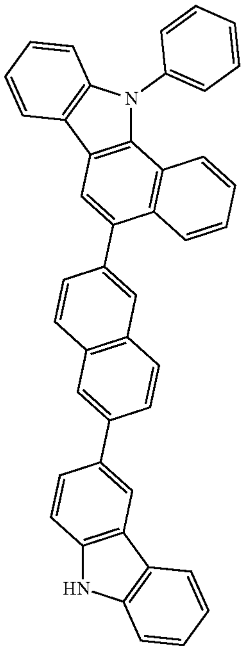
Sub 1-11
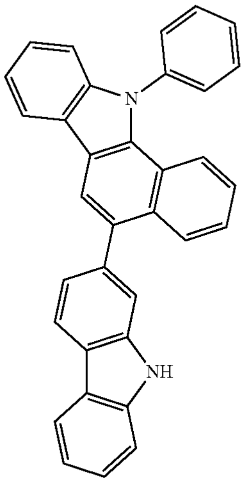
Sub 1-12
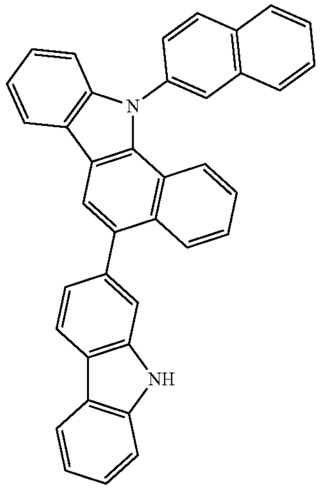
-continued
Sub 1-13
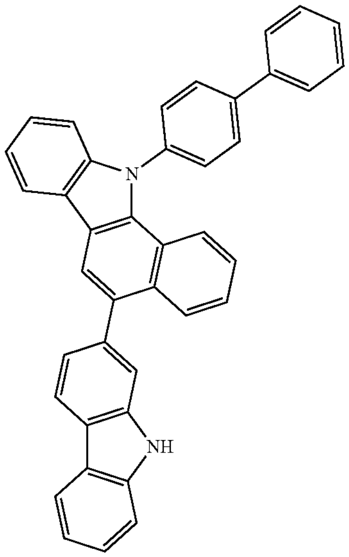
Sub 1-14
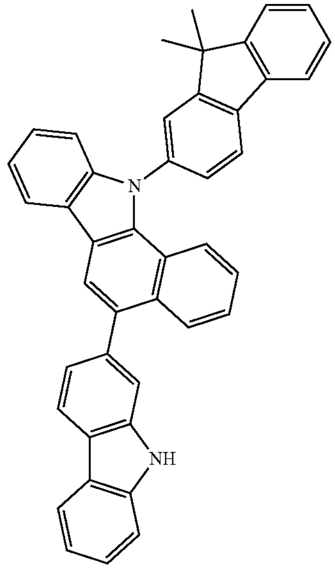
Sub 1-15
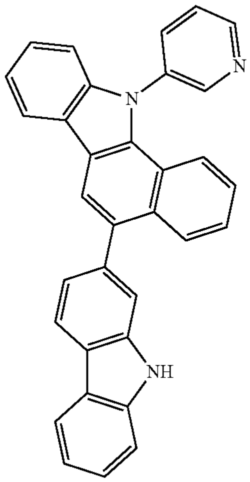

-continued
Sub 1-16
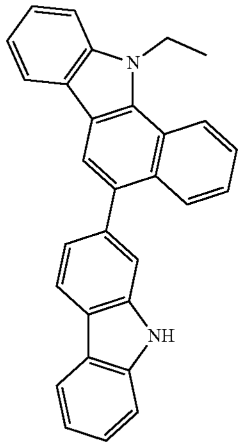
Sub 1-17
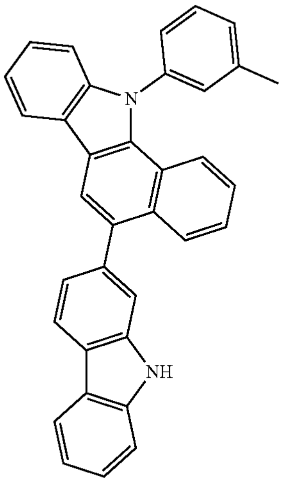
Sub 1-18
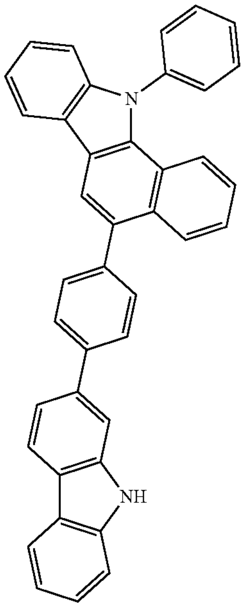
-continued
Sub 1-19
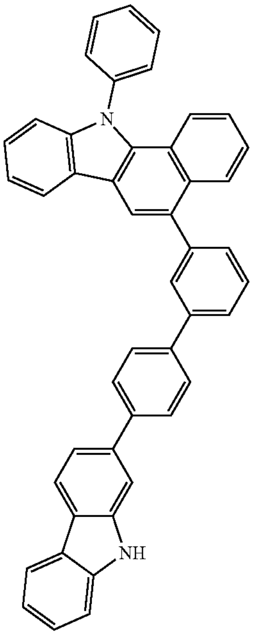
Sub 1-20
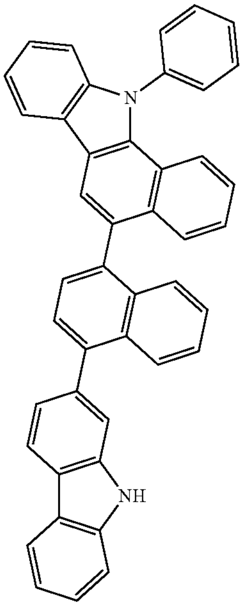

-continued
Sub 1-21
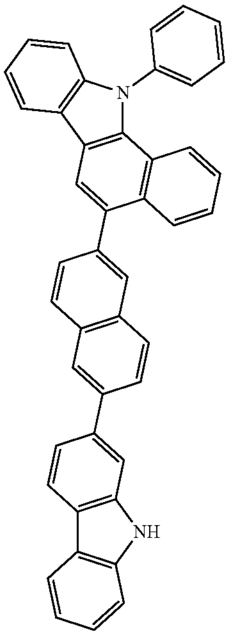
Sub 1-22
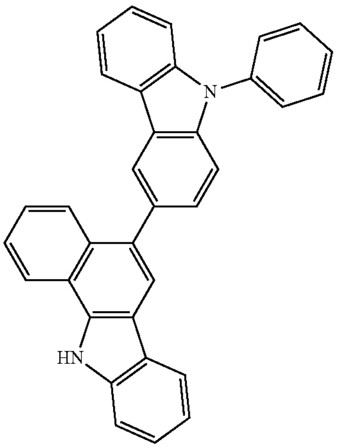
Sub 1-23
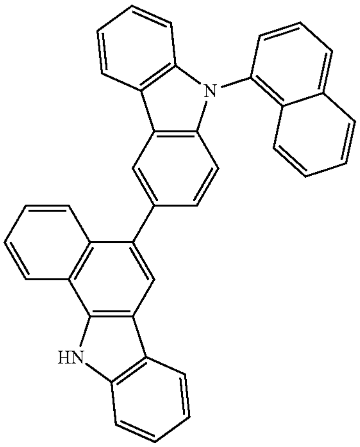
-continued
Sub 1-24
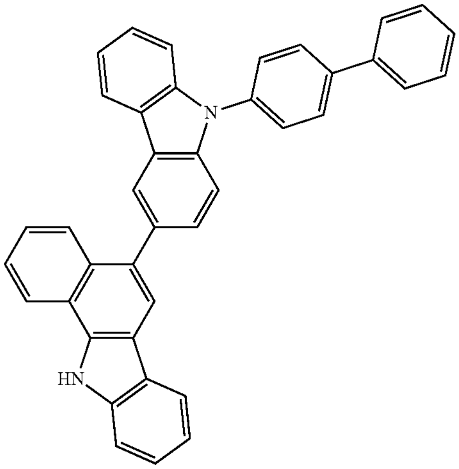
Sub 1-25
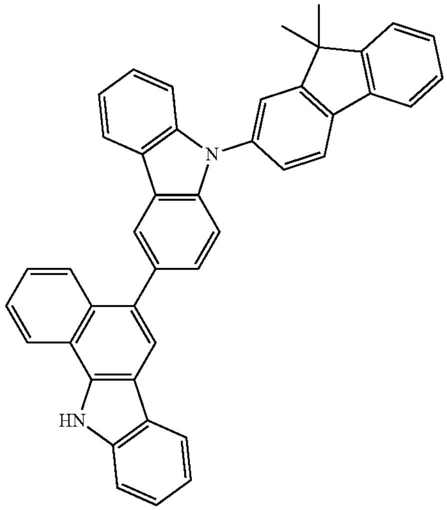
Sub 1-26
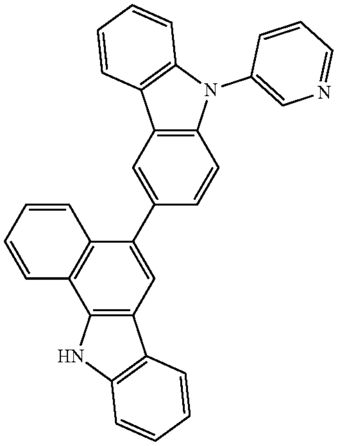

-continued
Sub 1-27
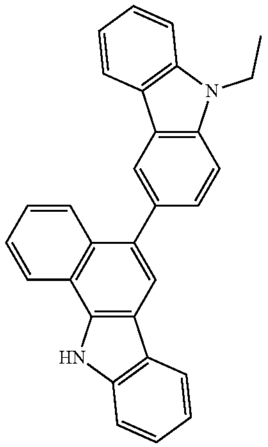
Sub 1-28
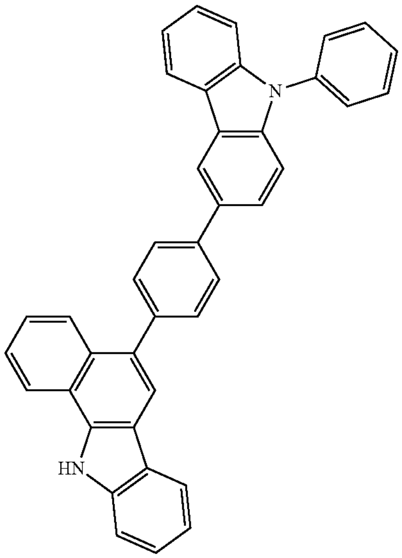
Sub 1-29
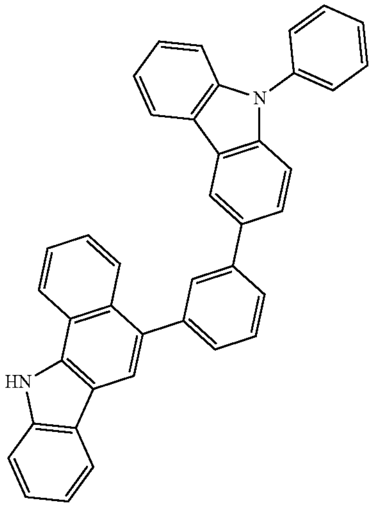
-continued
Sub 1-30
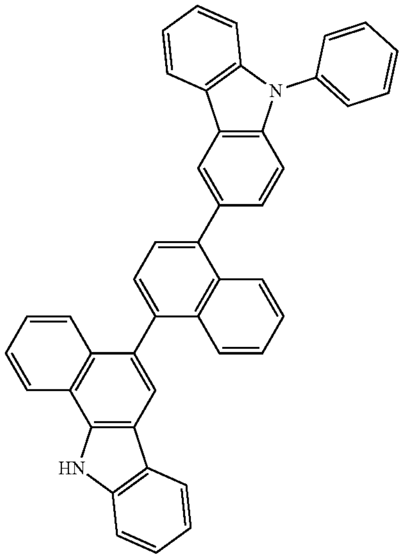
Sub 1-31
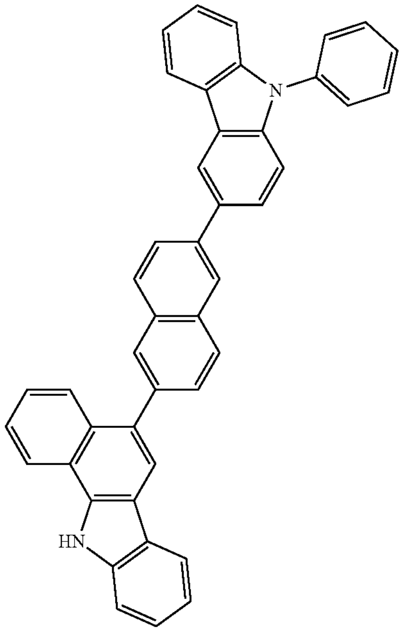
Sub 1-32
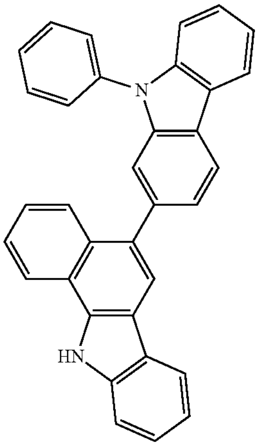

-continued
Sub 1-33
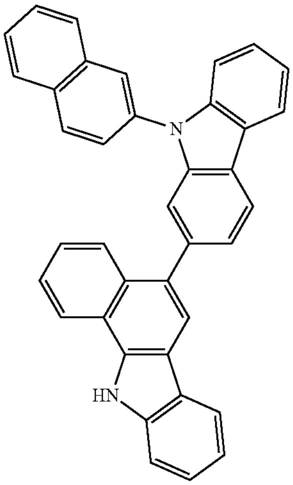
Sub 1-34
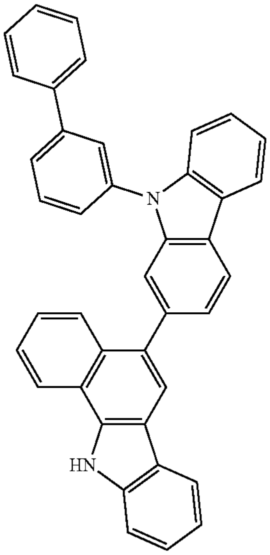
Sub 1-35
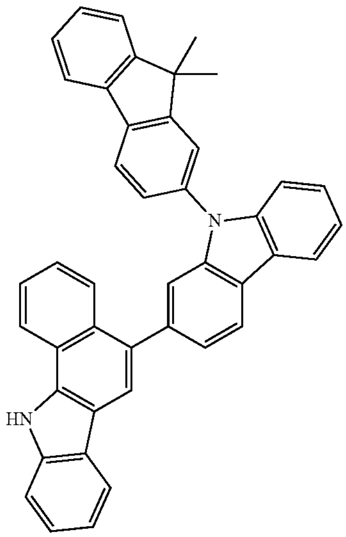
-continued
Sub 1-36
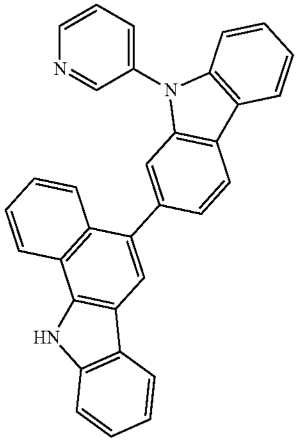
Sub 1-37
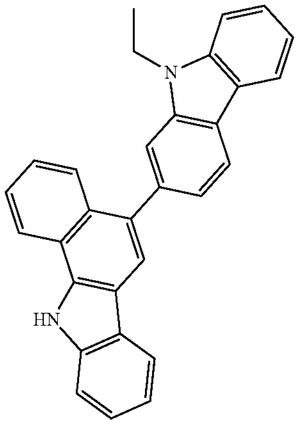
Sub 1-38
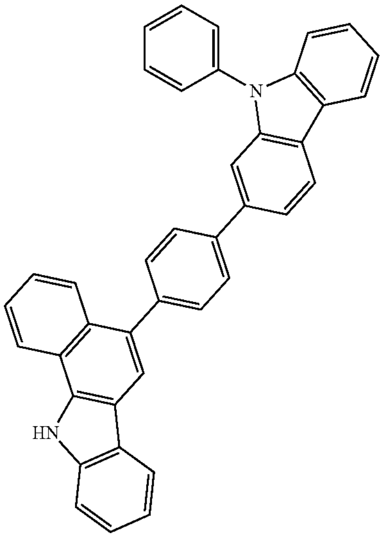

-continued
Sub 1-39
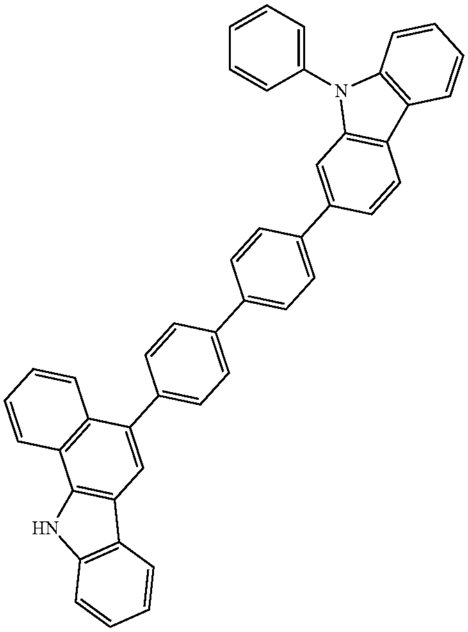
Sub 1-40
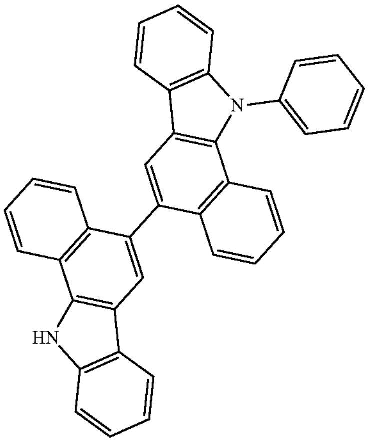
Sub 1-41
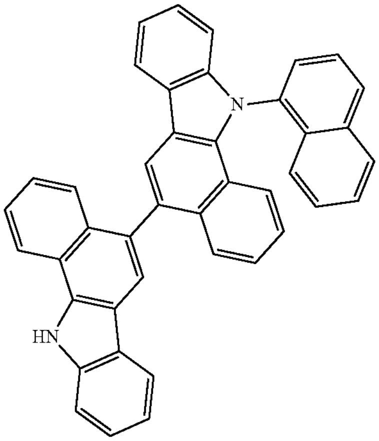
-continued
Sub 1-42
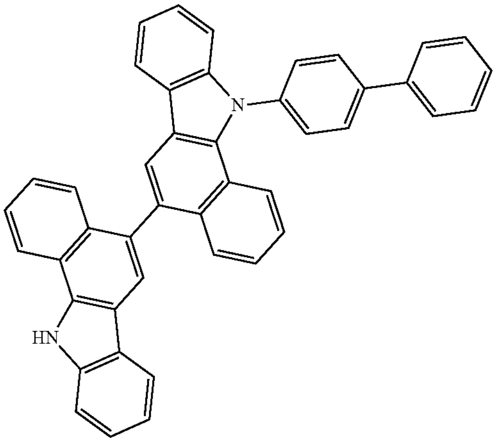
Sub 1-43
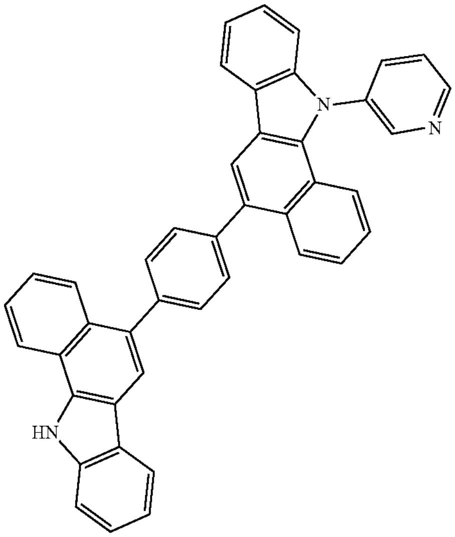
Sub 1-44
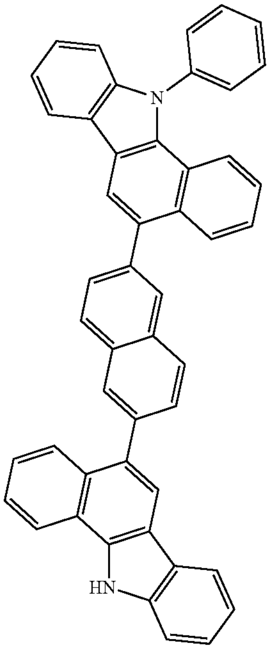

-continued
Sub 1-45
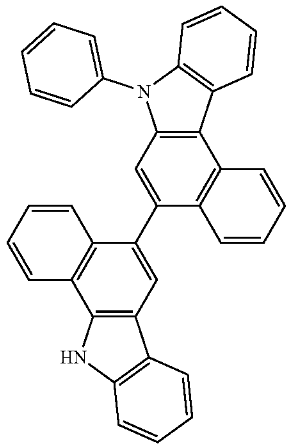
Sub 1-46
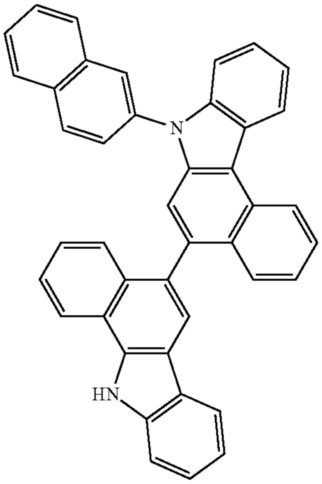
Sub 1-47
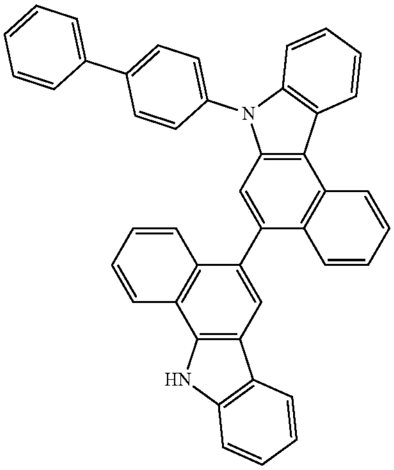
-continued
Sub 1-48
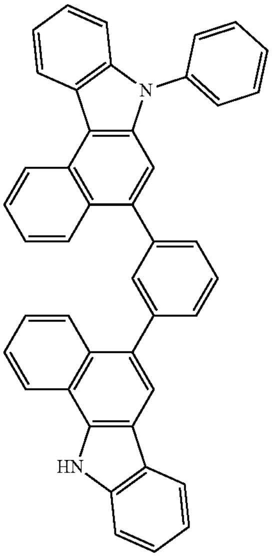
Sub 1-49
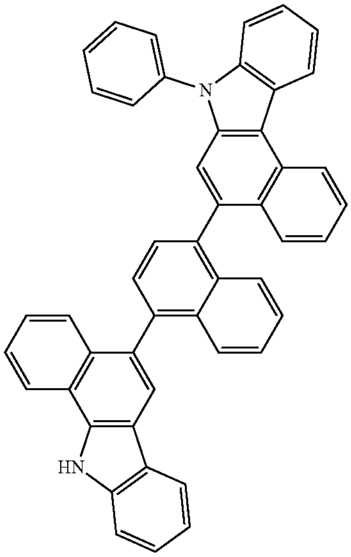
Sub 1-50
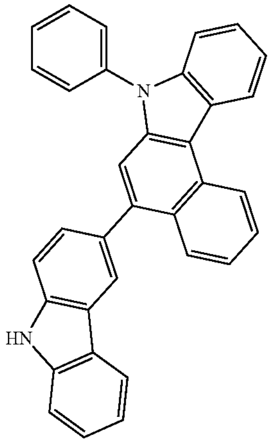

-continued
Sub 1-51
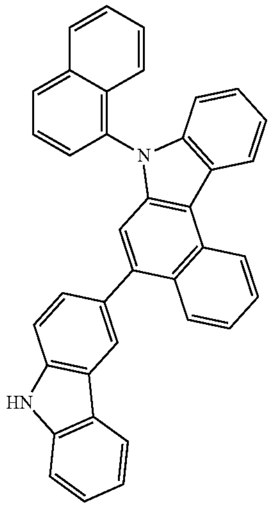
Sub 1-52
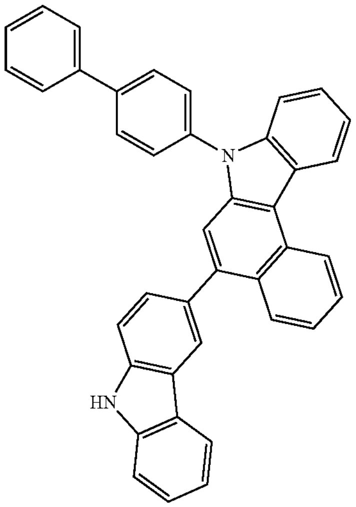
Sub 1-53
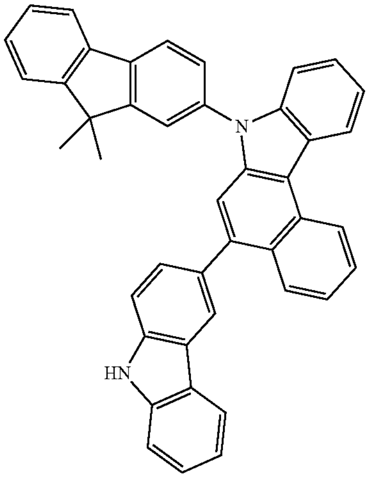
-continued
Sub 1-54
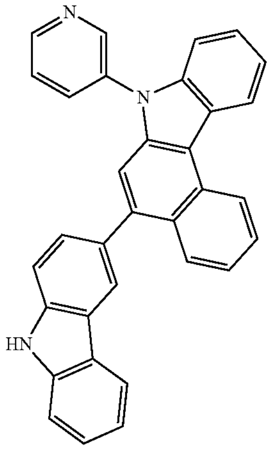
Sub 1-55
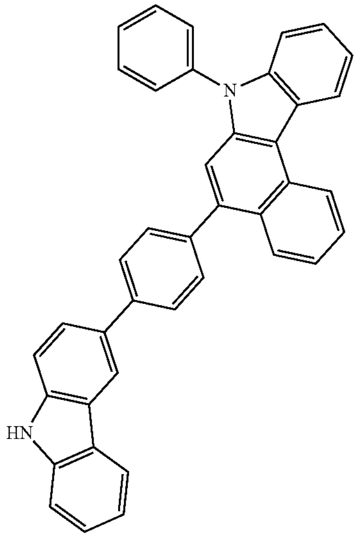
Sub 1-56
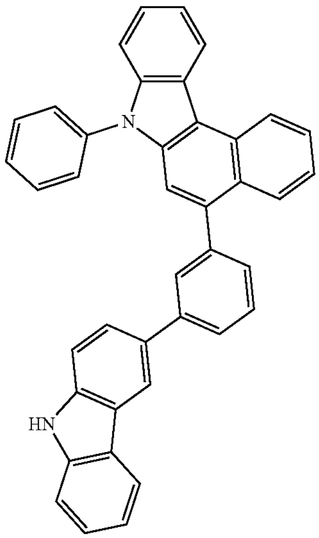

-continued
Sub 1-57
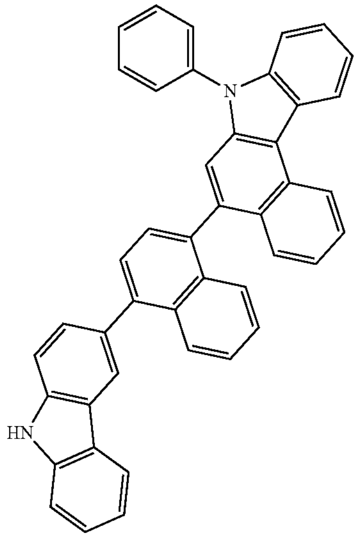
Sub 1-58
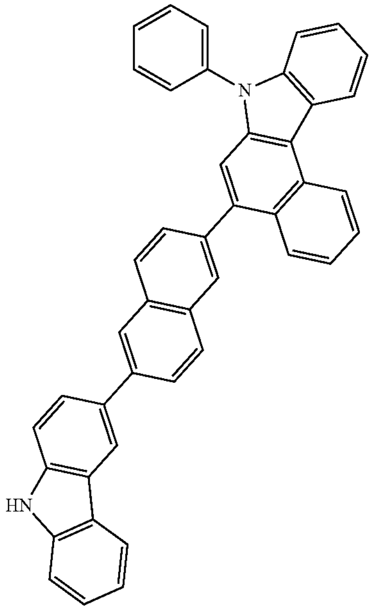
Sub 1-59
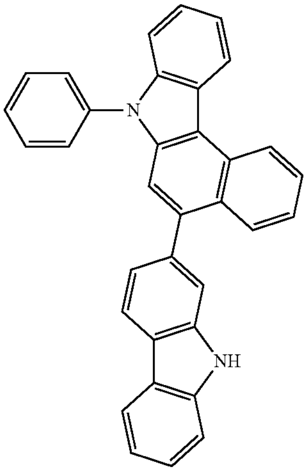
-continued
Sub 1-60
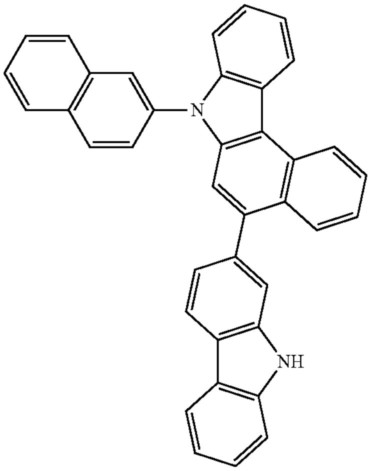
Sub 1-61
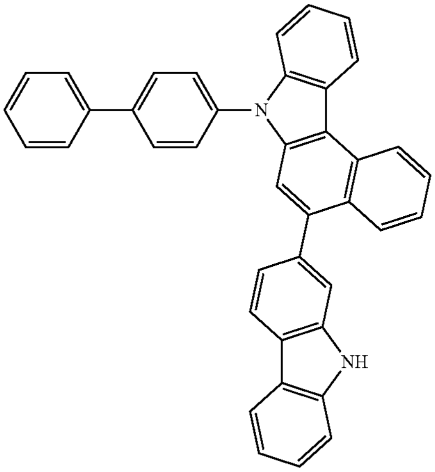
Sub 1-62
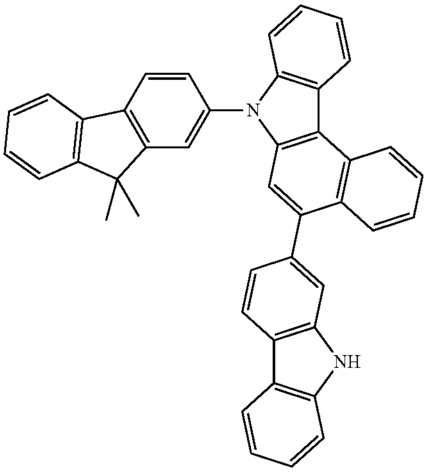

-continued
Sub 1-63
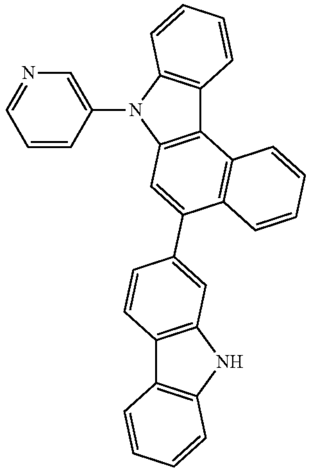
Sub 1-64
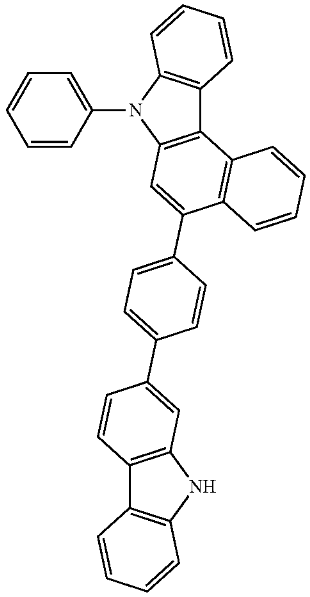
Sub 1-65
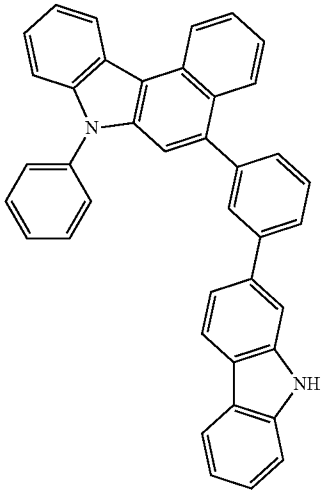
-continued
Sub 1-66
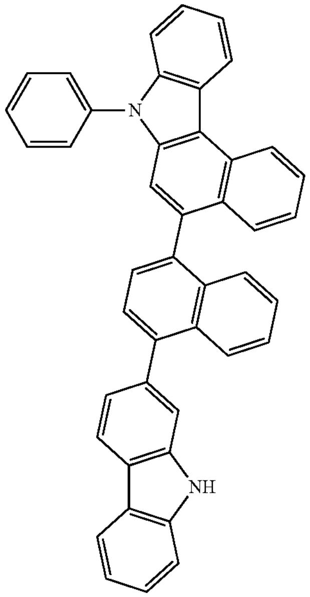
Sub 1-67
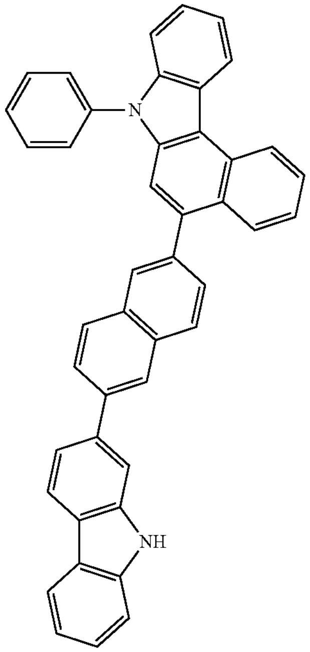

-continued
Sub 1-68
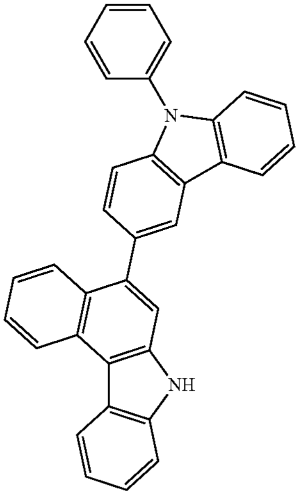
Sub 1-69
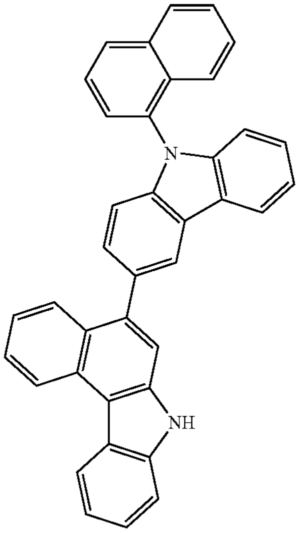
Sub 1-70
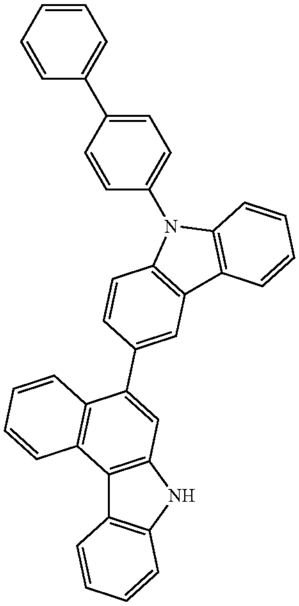
-continued
Sub 1-71
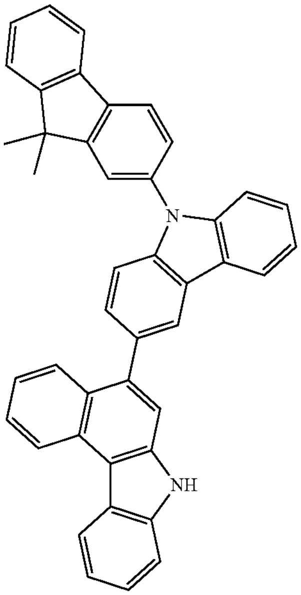
Sub 1-72
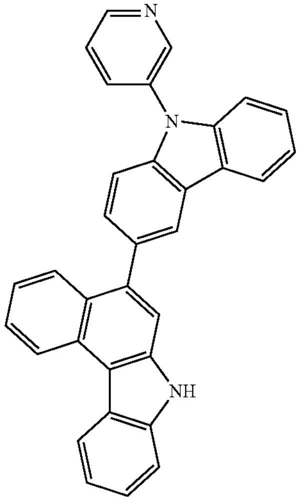

-continued
Sub 1-73
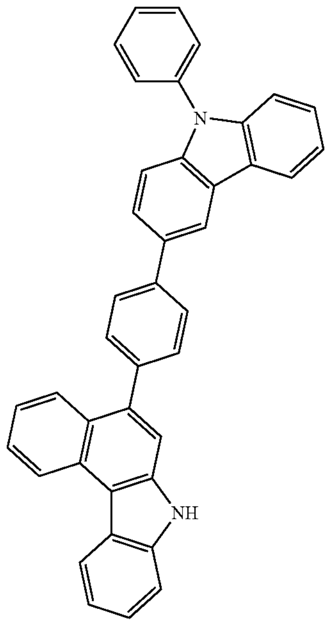
Sub 1-74
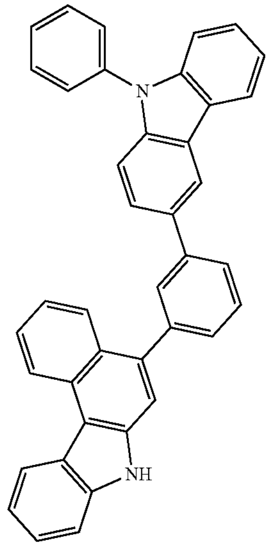
-continued
Sub 1-75
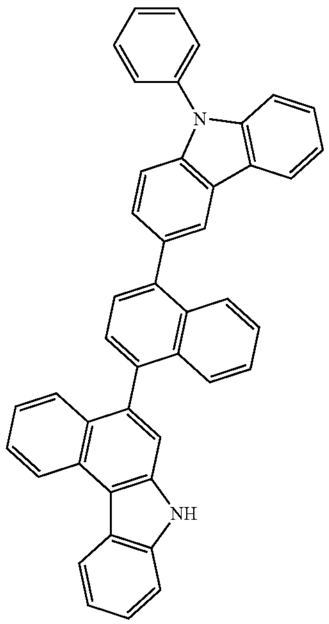
Sub 1-76
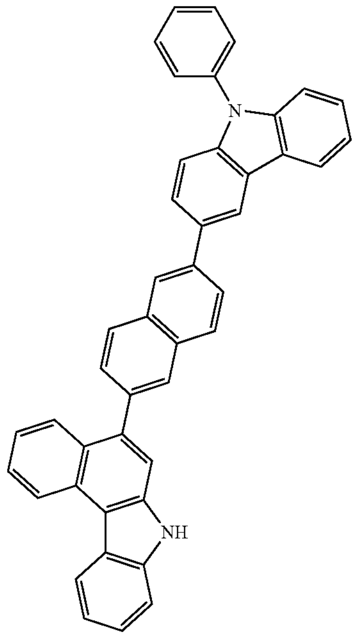

-continued
Sub 1-77
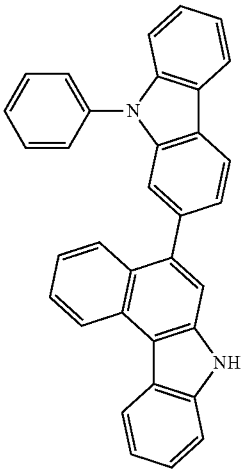
Sub 1-78
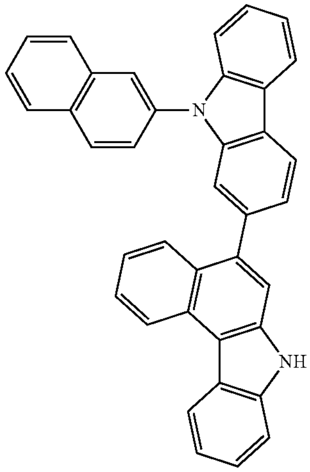
Sub 1-79
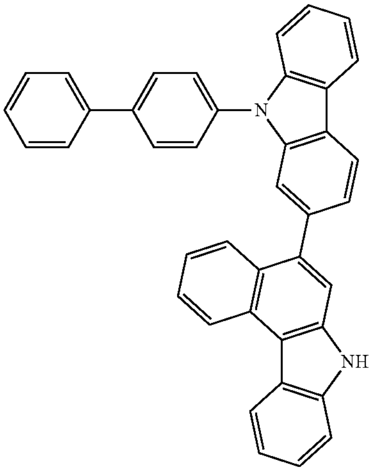
-continued
Sub 1-80
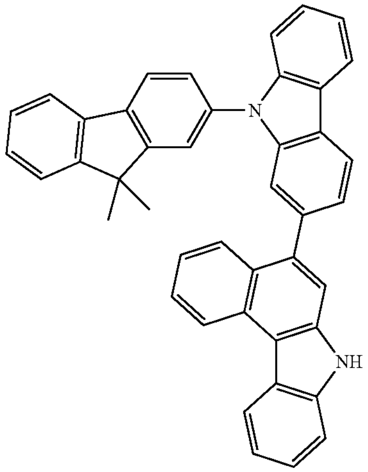
Sub 1-81
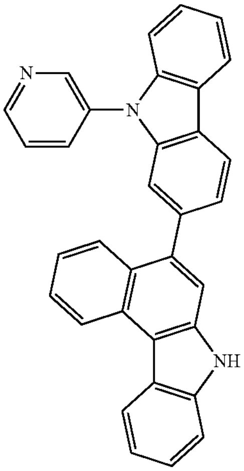
Sub 1-82
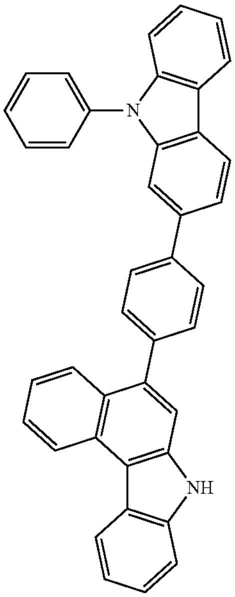

-continued
Sub 1-83
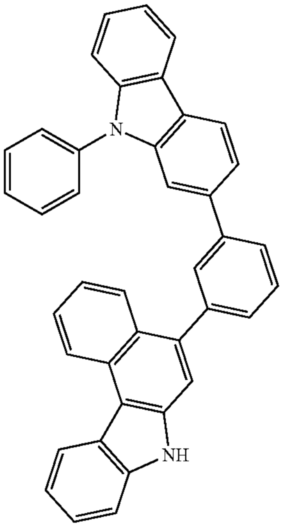
Sub 1-84
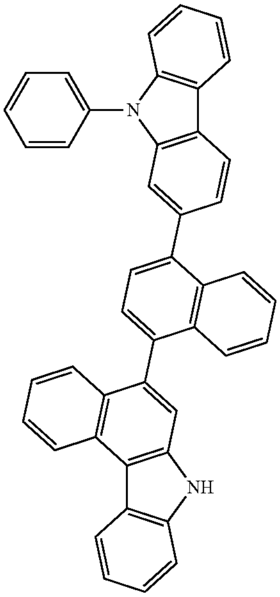
-continued
Sub 1-85
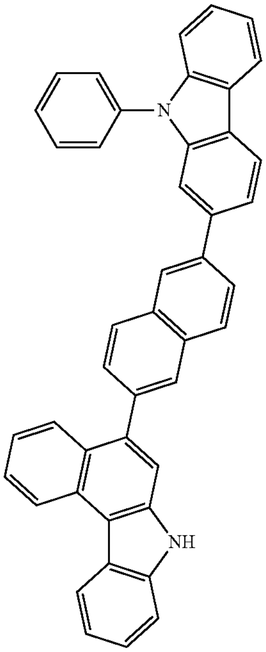
Sub 1-86
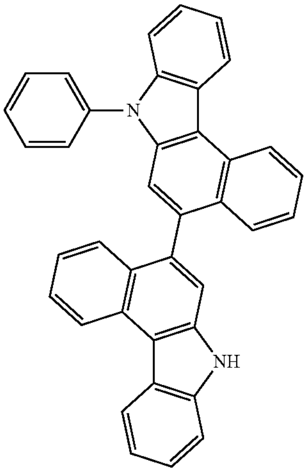
Sub 1-87
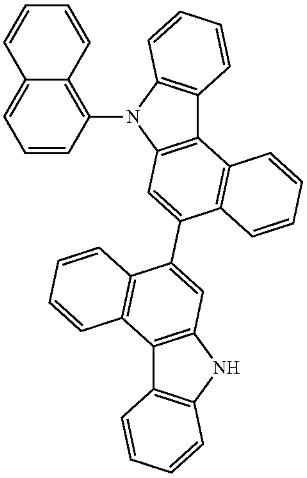

-continued
Sub 1-88
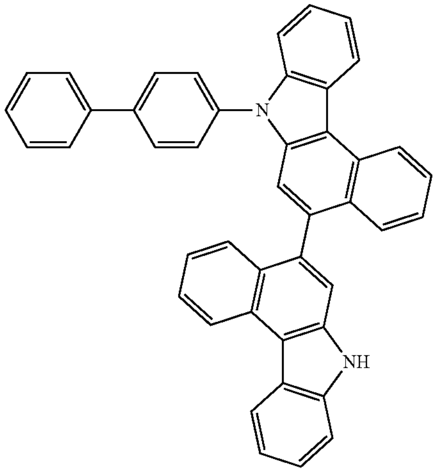
Sub 1-89
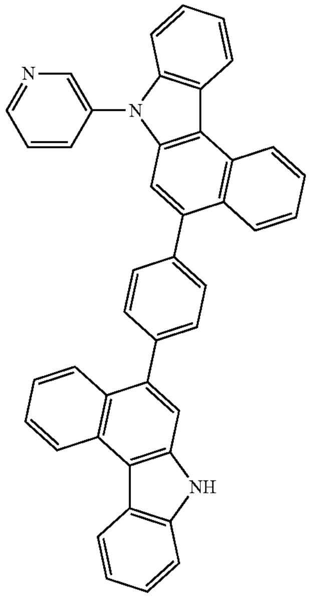
-continued
Sub 1-90
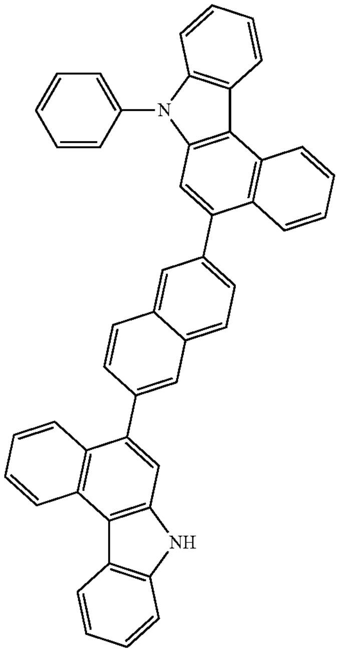
Sub 1-91
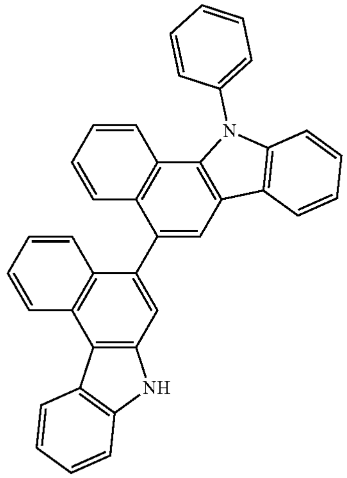

-continued

Sub 1-92

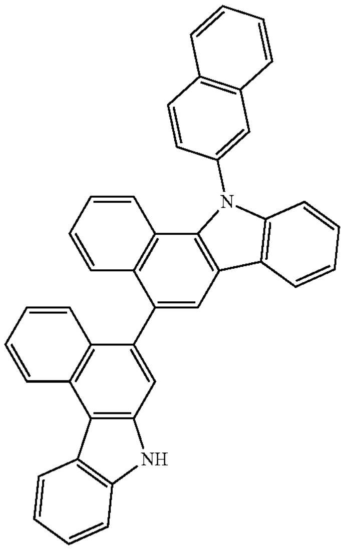

Sub 1-93

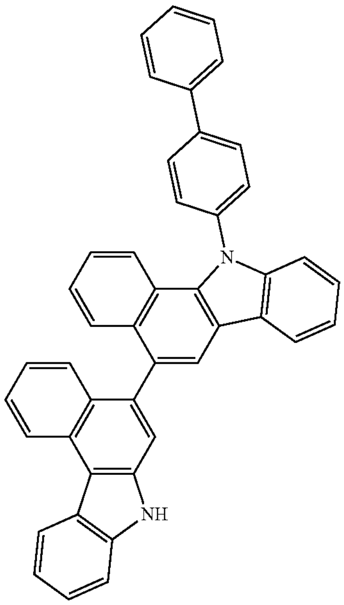

-continued

Sub 1-94

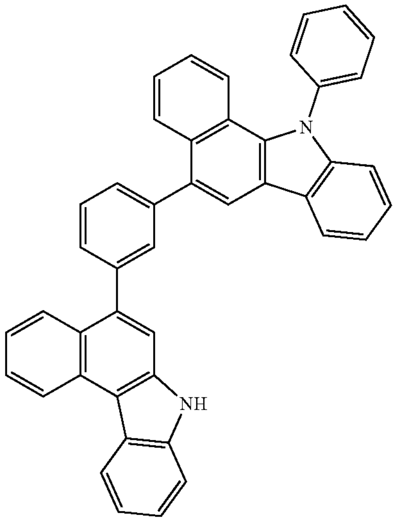

Sub 1-95

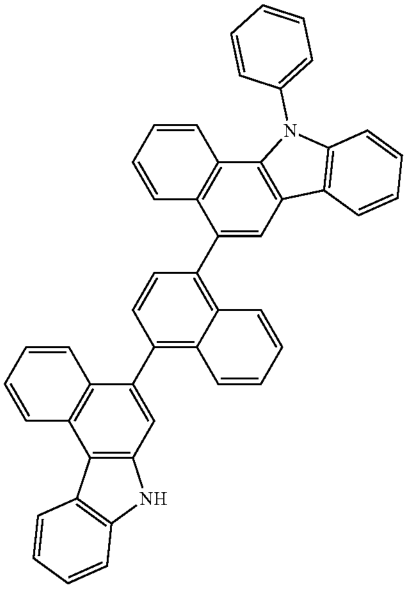

TABLE 1

| Compound | FD-MS | Compound | FD-MS |
|---|---|---|---|
| Sub 1-1 | m/z = 458.18 ($C_{34}H_{22}N_2$ = 458.55) | Sub 1-2 | m/z = 508.19 ($C_{38}H_{24}N_2$ = 508.61) |
| Sub 1-3 | m/z = 534.21 ($C_{40}H_{26}N_2$ = 534.65) | Sub 1-4 | m/z = 574.24 ($C_{43}H_{30}N_2$ = 574.71) |
| Sub 1-5 | m/z = 459.17 ($C_{33}H_{21}N_3$ = 459.54) | Sub 1-6 | m/z = 410.18 ($C_{30}H_{22}N_2$ = 410.51) |
| Sub 1-7 | m/z = 534.21 ($C_{40}H_{26}N_2$ = 534.65) | Sub 1-8 | m/z = 534.21 ($C_{40}H_{26}N_2$ = 534.65) |
| Sub 1-9 | m/z = 584.23 ($C_{44}H_{28}N_2$ = 584.71) | Sub 1-10 | m/z = 584.23 ($C_{44}H_{28}N_2$ = 584.71) |
| Sub 1-11 | m/z = 458.18 ($C_{34}H_{22}N_2$ = 458.55) | Sub 1-12 | m/z = 508.19 ($C_{38}H_{24}N_2$ = 508.61) |
| Sub 1-13 | m/z = 534.21 ($C_{40}H_{26}N_2$ = 534.65) | Sub 1-14 | m/z = 574.24 ($C_{43}H_{30}N_2$ = 574.71) |
| Sub 1-15 | m/z = 459.17 ($C_{33}H_{21}N_3$ = 459.54) | Sub 1-16 | m/z = 410.18 ($C_{30}H_{22}N_2$ = 410.51) |
| Sub 1-17 | m/z = 472.19 ($C_{35}H_{24}N_2$ = 472.58) | Sub 1-18 | m/z = 534.21 ($C_{40}H_{26}N_2$ = 534.65) |
| Sub 1-19 | m/z = 610.24 ($C_{46}H_{30}N_2$ = 610.74) | Sub 1-20 | m/z = 584.23 ($C_{44}H_{28}N_2$ = 584.71) |
| Sub 1-21 | m/z = 584.23 ($C_{44}H_{28}N_2$ = 584.71) | Sub 1-22 | m/z = 458.18 ($C_{34}H_{22}N_2$ = 458.55) |
| Sub 1-23 | m/z = 508.19 ($C_{38}H_{24}N_2$ = 508.61) | Sub 1-24 | m/z = 534.21 ($C_{40}H_{26}N_2$ = 534.65) |
| Sub 1-25 | m/z = 574.24 ($C_{43}H_{30}N_2$ = 574.71) | Sub 1-26 | m/z = 459.17 ($C_{33}H_{21}N_3$ = 459.54) |
| Sub 1-27 | m/z = 410.18 ($C_{30}H_{22}N_2$ = 410.51) | Sub 1-28 | m/z = 534.21 ($C_{40}H_{26}N_2$ = 534.65) |
| Sub 1-29 | m/z = 534.21 ($C_{40}H_{26}N_2$ = 534.65) | Sub 1-30 | m/z = 584.23 ($C_{44}H_{28}N_2$ = 584.71) |
| Sub 1-31 | m/z = 584.23 ($C_{44}H_{28}N_2$ = 584.71) | Sub 1-32 | m/z = 458.18 ($C_{34}H_{22}N_2$ = 458.55) |
| Sub 1-33 | m/z = 508.19 ($C_{38}H_{24}N_2$ = 508.61) | Sub 1-34 | m/z = 534.21 ($C_{40}H_{26}N_2$ = 534.65) |
| Sub 1-35 | m/z = 574.24 ($C_{43}H_{30}N_2$ = 574.71) | Sub 1-36 | m/z = 459.17 ($C_{33}H_{21}N_3$ = 459.54) |

TABLE 1-continued

| Compound | FD-MS | Compound | FD-MS |
|---|---|---|---|
| Sub 1-37 | m/z = 410.18 ($C_{30}H_{22}N_2$ = 410.51) | Sub 1-38 | m/z = 534.21 ($C_{40}H_{26}N_2$ = 534.65) |
| Sub 1-39 | m/z = 610.24 ($C_{46}H_{30}N_2$ = 610.74) | Sub 1-40 | m/z = 508.19 ($C_{38}H_{24}N_2$ = 508.61) |
| Sub 1-41 | m/z = 558.21 ($C_{42}H_{26}N_2$ = 558.67) | Sub 1-42 | m/z = 584.23 ($C_{44}H_{28}N_2$ = 584.71) |
| Sub 1-43 | m/z = 585.22 ($C_{43}H_{27}N_3$ = 585.69) | Sub 1-44 | m/z = 634.24 ($C_{48}H_{30}N_2$ = 634.77) |
| Sub 1-45 | m/z = 508.19 ($C_{38}H_{24}N_2$ = 508.61) | Sub 1-46 | m/z = 558.21 ($C_{42}H_{26}N_2$ = 558.67) |
| Sub 1-47 | m/z = 584.23 ($C_{44}H_{28}N_2$ = 584.71) | Sub 1-48 | m/z = 584.23 ($C_{44}H_{28}N_2$ = 584.71) |
| Sub 1-49 | m/z = 634.24 ($C_{48}H_{30}N_2$ = 634.77) | Sub 1-50 | m/z = 458.18 ($C_{34}H_{22}N_2$ = 458.55) |
| Sub 1-51 | m/z = 508.19 ($C_{38}H_{24}N_2$ = 508.61) | Sub 1-52 | m/z = 534.21 ($C_{40}H_{26}N_2$ = 534.65) |
| Sub 1-53 | m/z = 574.24 ($C_{43}H_{30}N_2$ = 574.71) | Sub 1-54 | m/z = 459.17 ($C_{33}H_{21}N_3$ = 459.54) |
| Sub 1-55 | m/z = 534.21 ($C_{40}H_{26}N_2$ = 534.65) | Sub 1-56 | m/z = 534.21 ($C_{40}H_{26}N_2$ = 534.65) |
| Sub 1-57 | m/z = 584.23 ($C_{44}H_{28}N_2$ = 584.71) | Sub 1-58 | m/z = 584.23 ($C_{44}H_{28}N_2$ = 584.71) |
| Sub 1-59 | m/z = 458.18 ($C_{34}H_{22}N_2$ = 458.55) | Sub 1-60 | m/z = 508.19 ($C_{38}H_{24}N_2$ = 508.61) |
| Sub 1-61 | m/z = 534.21 ($C_{40}H_{26}N_2$ = 534.65) | Sub 1-62 | m/z = 574.24 ($C_{43}H_{30}N_2$ = 574.71) |
| Sub 1-63 | m/z = 459.17 ($C_{33}H_{21}N_3$ = 459.54) | Sub 1-64 | m/z = 534.21 ($C_{40}H_{26}N_2$ = 534.65) |
| Sub 1-65 | m/z = 534.21 ($C_{40}H_{26}N_2$ = 534.65) | Sub 1-66 | m/z = 584.23 ($C_{44}H_{28}N_2$ = 584.71) |
| Sub 1-67 | m/z = 584.23 ($C_{44}H_{28}N_2$ = 584.71) | Sub 1-68 | m/z = 458.18 ($C_{34}H_{22}N_2$ = 458.55) |
| Sub 1-69 | m/z = 508.19 ($C_{38}H_{24}N_2$ = 508.61) | Sub 1-70 | m/z = 534.21 ($C_{40}H_{26}N_2$ = 534.65) |
| Sub 1-71 | m/z = 574.24 ($C_{43}H_{30}N_2$ = 574.71) | Sub 1-72 | m/z = 459.17 ($C_{33}H_{21}N_3$ = 459.54) |
| Sub 1-73 | m/z = 534.21 ($C_{40}H_{26}N_2$ = 534.65) | Sub 1-74 | m/z = 534.21 ($C_{40}H_{26}N_2$ = 534.65) |
| Sub 1-75 | m/z = 584.23 ($C_{44}H_{28}N_2$ = 584.71) | Sub 1-76 | m/z = 584.23 ($C_{44}H_{28}N_2$ = 584.71) |
| Sub 1-77 | m/z = 458.18 ($C_{34}H_{22}N_2$ = 458.55) | Sub 1-78 | m/z = 508.19 ($C_{38}H_{24}N_2$ = 508.61) |
| Sub 1-79 | m/z = 534.21 ($C_{40}H_{26}N_2$ = 534.65) | Sub 1-80 | m/z = 574.24 ($C_{43}H_{30}N_2$ = 574.71) |
| Sub 1-81 | m/z = 459.17 ($C_{33}H_{21}N_3$ = 459.54) | Sub 1-82 | m/z = 534.21 ($C_{40}H_{26}N_2$ = 534.65) |
| Sub 1-83 | m/z = 534.21 ($C_{40}H_{26}N_2$ = 534.65) | Sub 1-84 | m/z = 584.23 ($C_{44}H_{28}N_2$ = 584.71) |
| Sub 1-85 | m/z = 584.23 ($C_{44}H_{28}N_2$ = 584.71) | Sub 1-86 | m/z = 508.19 ($C_{38}H_{24}N_2$ = 508.61) |
| Sub 1-87 | m/z = 558.21 ($C_{42}H_{26}N_2$ = 558.67) | Sub 1-88 | m/z = 584.23 ($C_{44}H_{28}N_2$ = 584.71) |
| Sub 1-89 | m/z = 585.22 ($C_{43}H_{27}N_3$ = 585.69) | Sub 1-90 | m/z = 634.24 ($C_{48}H_{30}N_2$ = 634.77) |
| Sub 1-91 | m/z = 508.19 ($C_{38}H_{24}N_2$ = 508.61) | Sub 1-92 | m/z = 558.21 ($C_{42}H_{26}N_2$ = 558.67) |
| Sub 1-93 | m/z = 584.23 ($C_{44}H_{28}N_2$ = 584.71) | Sub 1-94 | m/z = 584.23 ($C_{44}H_{28}N_2$ = 584.71) |
| Sub 1-95 | m/z = 634.24 ($C_{48}H_{30}N_2$ = 634.77) | | |

2. Synthesis of Sub 2

Sub 2 of Reaction Scheme 1 may be synthesized by a reaction pathway of Reaction Scheme 10 below.

Reaction Scheme 10

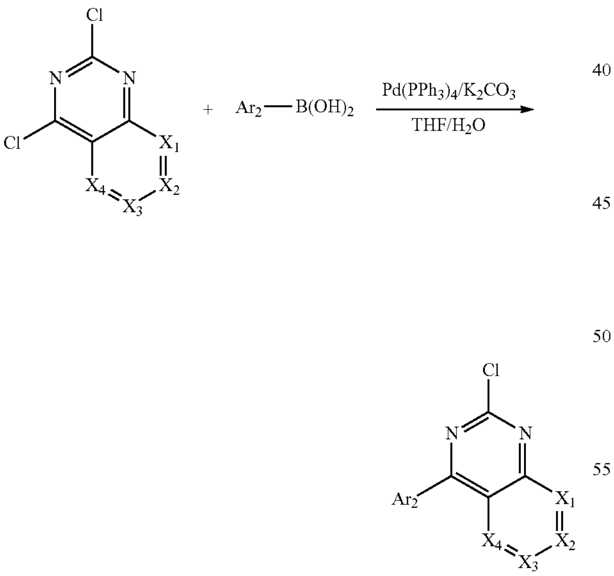

Sub 2

$X_1$~$X_4$ = CR′, N

Synthesis examples of specific compounds belonging to Sub 2 are as follows.

(1) Synthesis example of Sub 2-2

Reaction Scheme 11

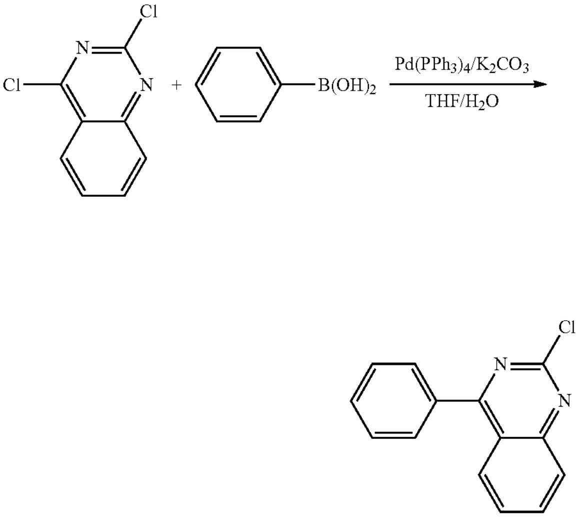

Sub 2-2

A starting material, 2,4-dichloroquinazoline (89.57 g, 450 mmol) was dissolved in THF in a round bottom flask, and then phenylboronic acid (65.84 g, 540 mmol), $Pd(PPh_3)_4$ (26 g, 22.5 mmol), $K_2CO_3$ (186.59 g, 1350 mmol), and water were added, followed by stirring at 70□. Upon completion of the reaction, the reaction product was extracted with $CH_2Cl_2$ and water. The organic layer was dried over $MgSO_4$ and concentrated, and then the thus generated compound was subjected to a silica gel column and recrystallization to give a product 71.49 g (yield: 66%).

(2) Synthesis example of Sub 2-8

Reaction Scheme 12

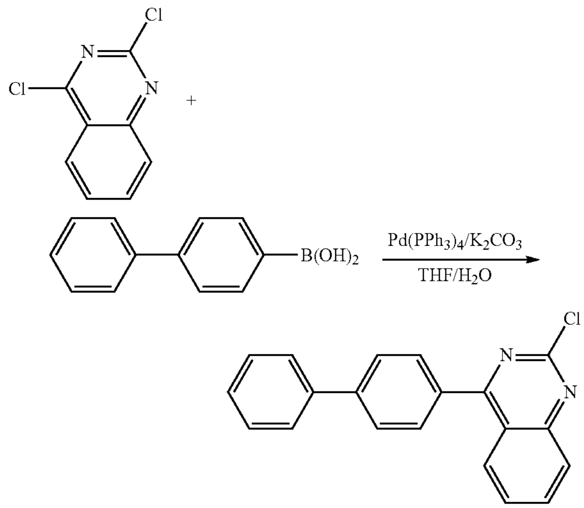

Sub 2-8

In addition to 2,4-dichloroquinazoline (76.59 g, 384.8 mmol) as a starting material, [1,1'-biphenyl]-4-ylboronic acid (91.44 g, 461.8 mmol), $Pd(PPh_3)_4$ (22.23 g, 19.2 mmol), $K_2CO_3$ (159.55 g, 1154.4 mmol), THF, and water were used according to the synthesis method of Sub 2-2 of Example 1, to give a product 74.36 g (yield: 61%).

(3) Synthesis example of Sub 2-14

Reaction Scheme 13

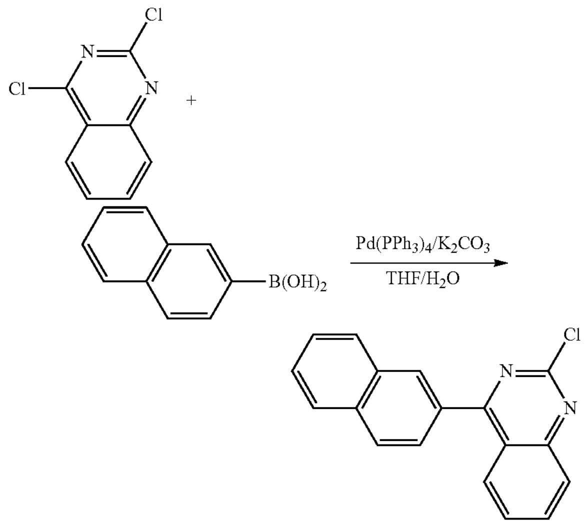

Sub 2-14

In addition to 2,4-dichloroquinazoline (78.48 g, 394.3 mmol) as a starting material, naphthalen-2-ylboronic acid (81.38 g, 473.2 mmol), $Pd(PPh_3)_4$ (22.78 g, 19.7 mmol), $K_2CO_3$ (163.49 g, 1182.9 mmol), THF, and water were used according to the synthesis method of Sub 2-2 of Example 1, to give a product 73.37 g (yield: 64%).

(4) Synthesis Example of Sub 2-27

Reaction Scheme 14

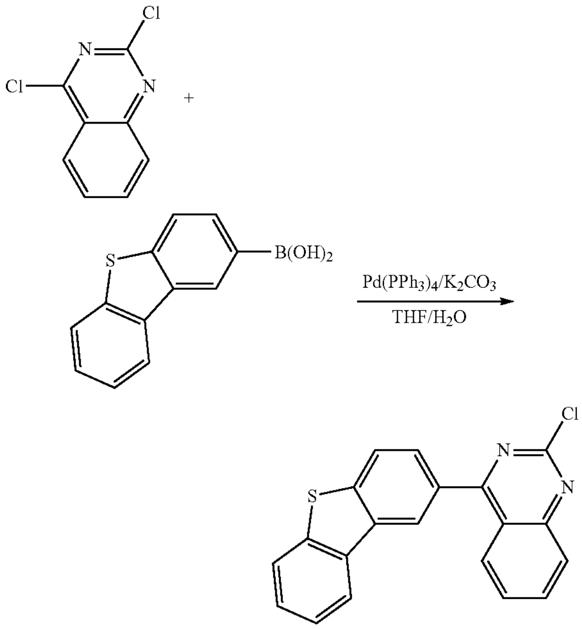

Sub 2-27

In addition to 2,4-dichloroquinazoline (70.43 g, 353.8 mmol) as a starting material, dibenzo[b,d]thiophen-2-ylboronic acid (96.84 g, 424.6 mmol), $Pd(PPh_3)_4$ (20.44 g, 17.7 mmol), $K_2CO_3$ (146.72 g, 1061.5 mmol), THF, and water were used according to the synthesis method of Sub 2-2 of Example 1, to give a product 77.32 g (yield: 63%).

(5) Synthesis Example of Sub 2-29

Reaction Scheme 15

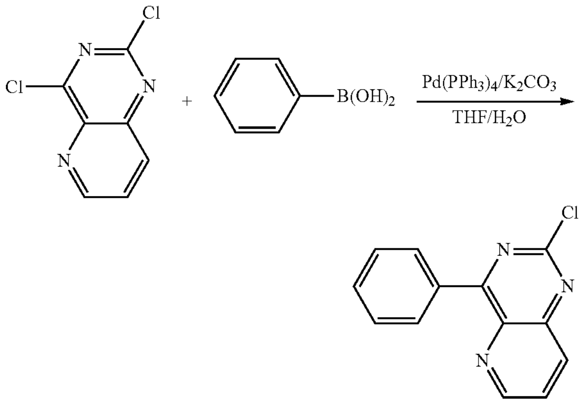

Sub 2-29

In addition to 2,4-dichloropyrido[3,2-d]pyrimidine (85.21 g, 426 mmol) as a starting material, phenylboronic acid (62.33 g, 511.2 mmol), $Pd(PPh_3)_4$ (24.61 g, 21.3 mmol), $K_2CO_3$ (176.64 g, 1278 mmol), THF, and water were used according to the synthesis method of Sub 2-2 of Example 1, to give a product 55.6 g (yield: 54%).

(6) Synthesis example of Sub 2-34

Reaction Scheme 16

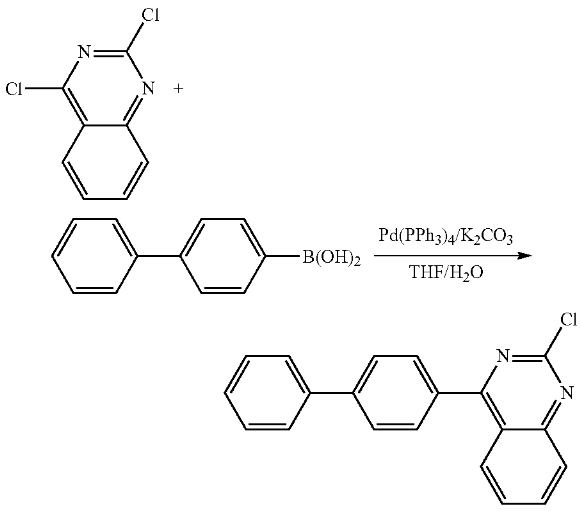

Sub 2-34

In addition to 2,4-dichloropyrido[2,3-d]pyrimidine (71.05 g, 355.2 mmol) as a starting material, [1,1'-biphenyl]-4-ylboronic acid (84.41 g, 426.3 mmol), $Pd(PPh_3)_4$ (20.52 g, 17.8 mmol), $K_2CO_3$ (147.28 g, 1065.6 mmol), THF, and water were used according to the synthesis method of Sub 2-2 of Example 1, to give a product 58.7 g (yield: 52%).

Meanwhile, examples of Sub 2 are as follows, but are not limited thereto, and FD-MS values thereof are shown in Table 2 below.

Sub 2-1

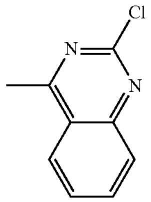

Sub 2-2

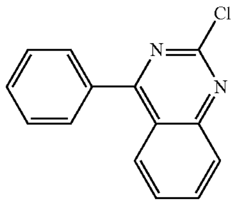

Sub 2-3

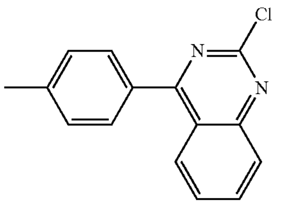

-continued

Sub 2-4

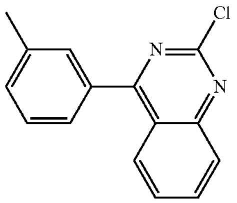

Sub 2-5

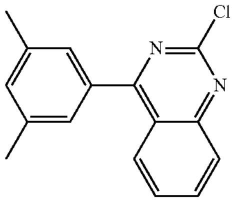

Sub 2-6

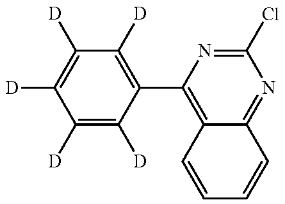

Sub 2-7

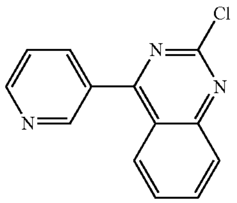

Sub 2-8

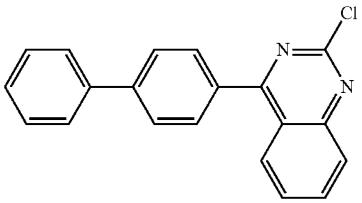

Sub 2-9

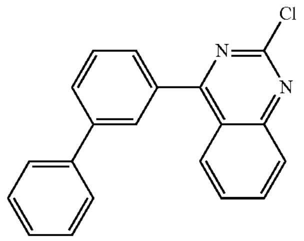

Sub 2-10

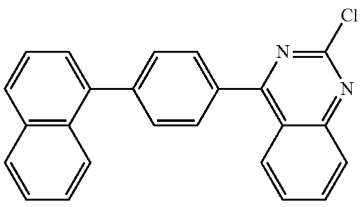

-continued
Sub 2-11
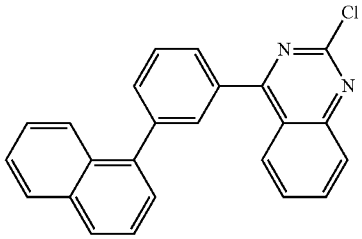
Sub 2-12
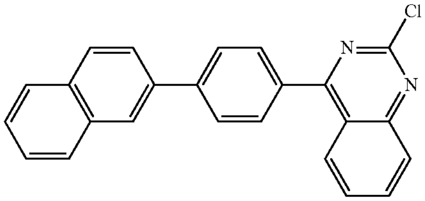
Sub 2-13
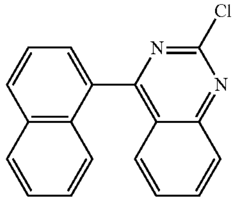
Sub 2-14
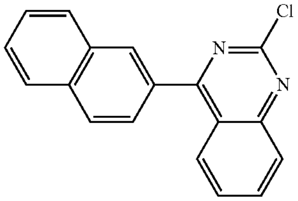
Sub 2-15
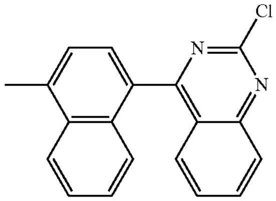
Sub 2-16
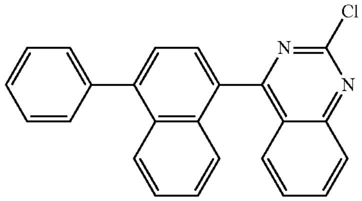
Sub 2-17
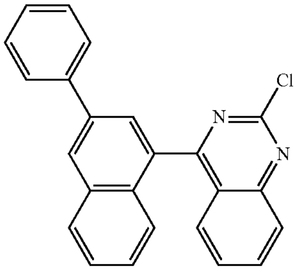
-continued
Sub 2-18
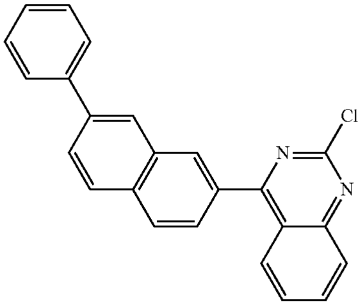
Sub 2-19
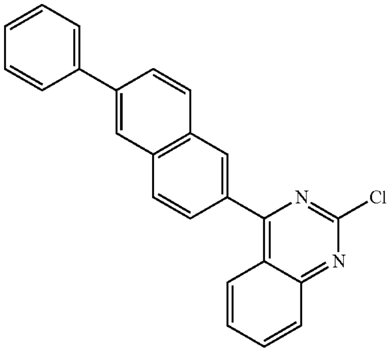
Sub 2-20
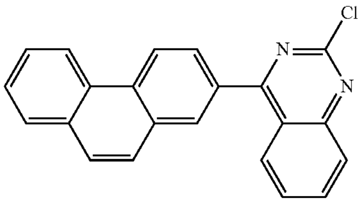
Sub 2-21
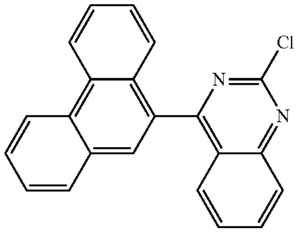
Sub 2-22
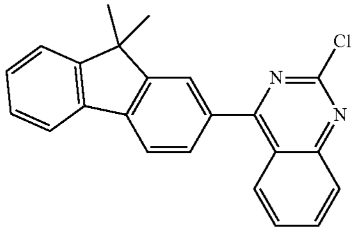
Sub 2-23
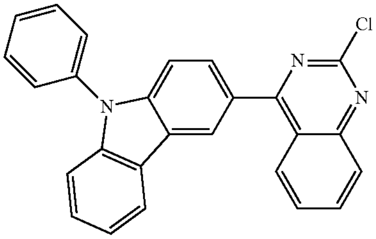

Sub 2-24
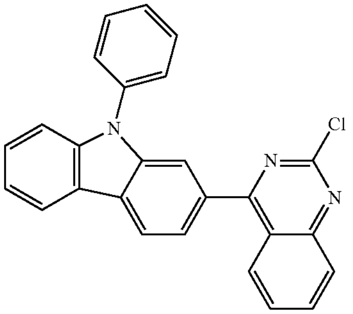
Sub 2-25
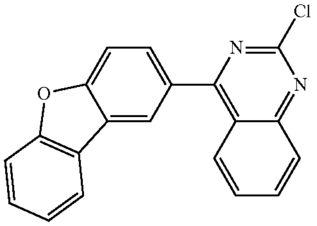
Sub 2-26
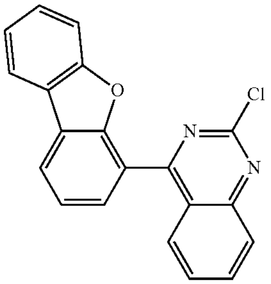
Sub 2-27
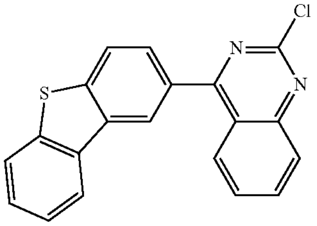
Sub 2-28
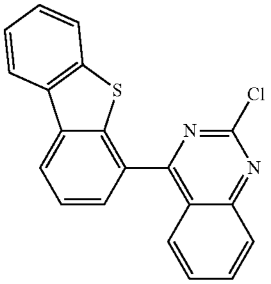
Sub 2-29
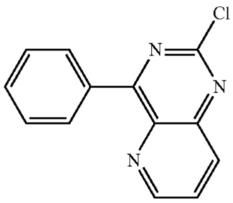
Sub 2-30
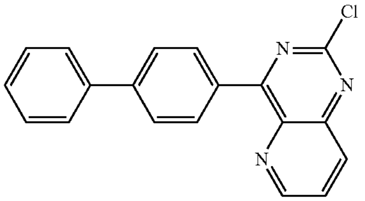
Sub 2-31
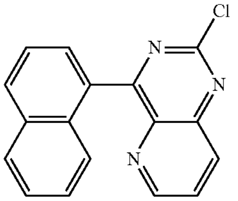
Sub 2-32
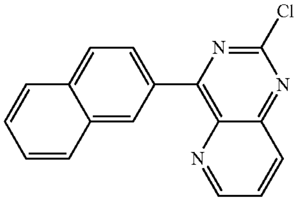
Sub 2-33
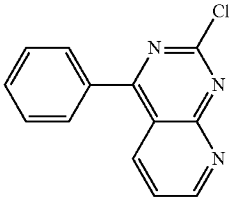
Sub 2-34
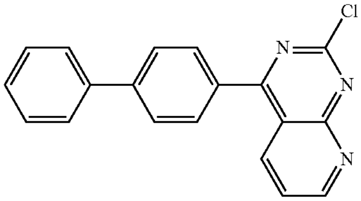
Sub 2-35
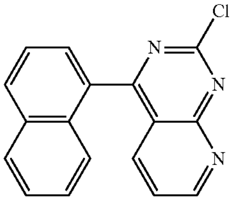
Sub 2-36
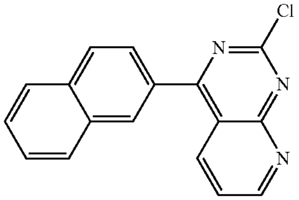

TABLE 2

| Compound | FD-MS | Compound | FD-MS |
|---|---|---|---|
| Sub 2-1 | m/z = 178.03 ($C_9H_7ClN_2$ = 178.62) | Sub 2-2 | m/z = 240.05 ($C_{14}H_9ClN_2$ = 240.69) |
| Sub 2-3 | m/z = 254.06 ($C_{15}H_{11}ClN_2$ = 254.71) | Sub 2-4 | m/z = 254.06 ($C_{15}H_{11}ClN_2$ = 254.71) |
| Sub 2-5 | m/z = 268.08 ($C_{16}H_{13}ClN_2$ = 268.74) | Sub 2-6 | m/z = 245.08 ($C_{14}H_4D_5ClN_2$ = 245.72) |
| Sub 2-7 | m/z = 241.04 ($C_{13}H_8ClN_3$ = 241.68) | Sub 2-8 | m/z = 316.08 ($C_{20}H_{13}ClN_2$ = 316.78) |
| Sub 2-9 | m/z = 316.08 ($C_{20}H_{13}ClN_2$ = 316.78) | Sub 2-10 | m/z = 366.09 ($C_{24}H_{15}ClN_2$ = 366.84) |
| Sub 2-11 | m/z = 366.09 ($C_{24}H_{15}ClN_2$ = 366.84) | Sub 2-12 | m/z = 366.09 ($C_{24}H_{15}ClN_2$ = 366.84) |
| Sub 2-13 | m/z = 290.06 ($C_{18}H_{11}ClN_2$ = 290.75) | Sub 2-14 | m/z = 290.06 ($C_{19}H_{11}ClN_2$ = 290.75) |
| Sub 2-15 | m/z = 304.08 ($C_{19}H_{13}ClN_2$ = 304.77) | Sub 2-16 | m/z = 366.09 ($C_{24}H_{15}ClN_2$ = 366.84) |
| Sub 2-17 | m/z = 366.09 ($C_{24}H_{15}ClN_2$ = 366.84) | Sub 2-18 | m/z = 366.09 ($C_{24}H_{15}ClN_2$ = 366.84) |
| Sub 2-19 | m/z = 366.09 ($C_{24}H_{15}ClN_2$ = 366.84) | Sub 2-20 | m/z = 340.08 ($C_{22}H_{13}ClN_2$ = 340.81) |
| Sub 2-21 | m/z = 340.08 ($C_{22}H_{13}ClN_2$ = 340.81) | Sub 2-22 | m/z = 356.11 ($C_{23}H_{17}ClN_2$ = 356.85) |
| Sub 2-23 | m/z = 405.1 ($C_{26}H_{16}ClN_3$ = 405.88) | Sub 2-24 | m/z = 405.1 ($C_{26}H_{16}ClN_3$ = 405.88) |
| Sub 2-25 | m/z = 330.06 ($C_{20}H_{11}ClN_2O$ = 330.77) | Sub 2-26 | m/z = 330.06 ($C_{20}H_{11}ClN_2O$ = 330.77) |
| Sub 2-27 | m/z = 346.03 ($C_{20}H_{11}ClN_2S$ = 346.83) | Sub 2-28 | m/z = 346.03 ($C_{20}H_{11}ClN_2S$ = 346.83) |
| Sub 2-29 | m/z = 241.04 ($C_{13}H_8ClN_3$ = 241.68) | Sub 2-30 | m/z = 317.07 ($C_{19}H_{12}ClN_3$ = 317.77) |
| Sub 2-31 | m/z = 291.06 ($C_{17}H_{10}ClN_3$ = 291.73) | Sub 2-32 | m/z = 291.06 ($C_{17}H_{10}ClN_3$ = 291.73) |
| Sub 2-33 | m/z = 241.04 ($C_{13}H_8ClN_3$ = 241.68) | Sub 2-34 | m/z = 317.07 ($C_{19}H_{12}ClN_3$ = 317.77) |
| Sub 2-35 | m/z = 291.06 ($C_{17}H_{10}ClN_3$ = 291.73) | Sub 2-36 | m/z = 291.06 ($C_{17}H_{10}ClN_3$ = 291.73) |

3. Final Product Synthesis

Sub 1 (1 eq.) was dissolved in toluene in a round bottom flask, and then Sub 2 (1.2 eq.), $Pd_2(dba)_3$ (0.03 eq.), $P(t\text{-}Bu)_3$ (0.08 eq.), and NaOt-Bu (3 eq.) were added, followed by stirring at 100□. Upon completion of the reaction, the reaction product was extracted with $CH_2Cl_2$ and water. The organic layer was dried over $MgSO_4$ and concentrated, and then the thus generated compound was subjected to a silica gel column and recrystallization, to give a final product.

(1) Synthesis example of Product 1-1

Reaction Scheme 17

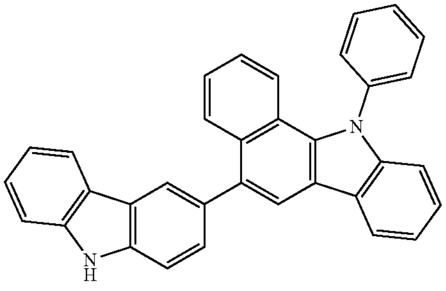

Sub 1-1

+

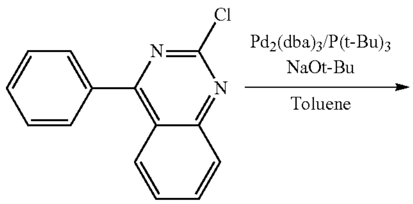

Sub 2-2

-continued

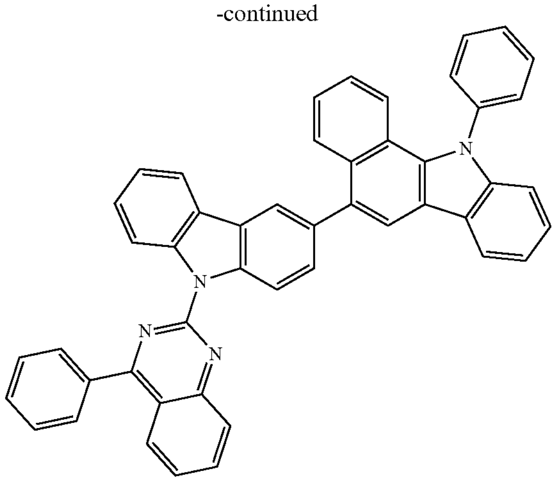

1-1

Sub 1-1 (7.65 g, 16.7 mmol) obtained in the above synthesis was dissolved in toluene in a round bottom flask, and then Sub 2-2 (4.82 g, 20 mmol), $Pd_2(dba)_3$ (0.46 g, 0.5 mmol), 50% $P(t\text{-}Bu)_3$ (0.7 ml, 1.3 mmol), and NaOt-Bu (4.81 g, 50 mmol) were added, followed by stirring at 100□. Upon completion of the reaction, the reaction product was extracted with $CH_2Cl_2$ and water. The organic layer was dried over $MgSO_4$ and concentrated, and then the thus generated compound was subjected to a silica gel column and recrystallization to give a product 7.96 g (yield: 72%).

(2) Synthesis Example of Product 1-10

Reaction Scheme 18

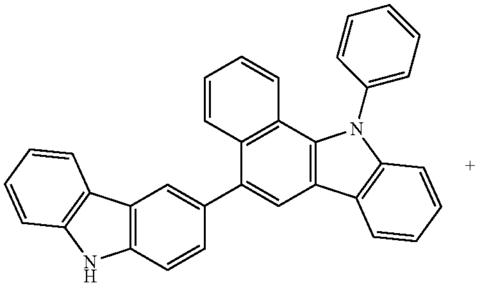

Sub 1-1

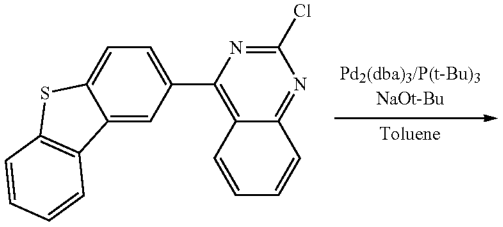

Sub 2-27

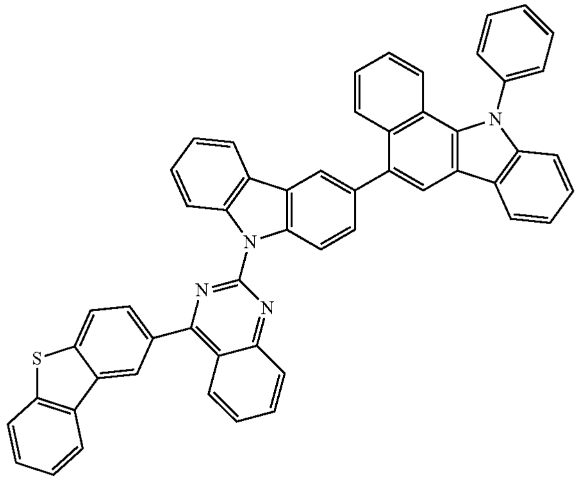

1-10

In addition to Sub 1-1 (6.94 g, 15.1 mmol) obtained in the above synthesis, Sub 2-27 (6.3 g, 18.2 mmol), $Pd_2(dba)_3$ (0.42 g, 0.5 mmol), 50% $P(t\text{-}Bu)_3$ (0.6 ml, 1.2 mmol), NaOt-Bu (4.36 g, 45.4 mmol), and toluene were used according to the synthesis method of Product 1-1 of example 3, to give a product 8.15 g (yield: 70%).

(3) Synthesis Example of Product 1-53

Reaction Scheme 19

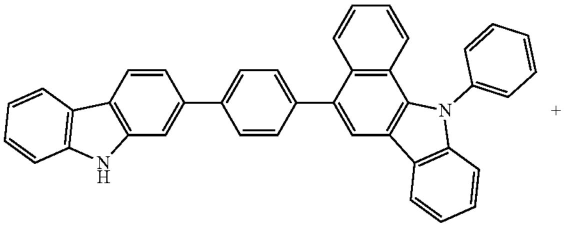

Sub 1-18

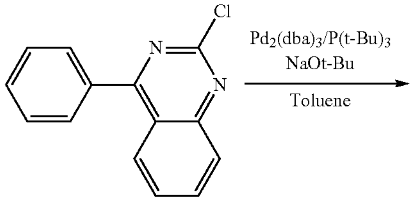

Sub 2-2

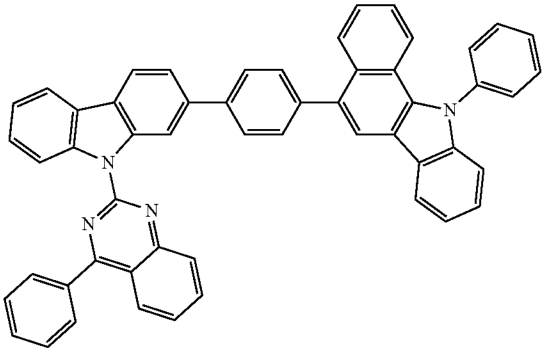

1-53

In addition to Sub 1-18 (7.74 g, 14.5 mmol) obtained in the above synthesis, Sub 2-2 (4.18 g, 17.4 mmol), $Pd_2(dba)_3$ (0.4 g, 0.4 mmol), 50% $P(t\text{-}Bu)_3$ (0.6 ml, 1.2 mmol), NaOt-Bu (4.17 g, 43.4 mmol), and toluene were used according to the synthesis method of Product 1-1 of example 3, to give a product 7.81 g (yield: 73%).

(4) Synthesis example of Product 1-58

Reaction Scheme 20

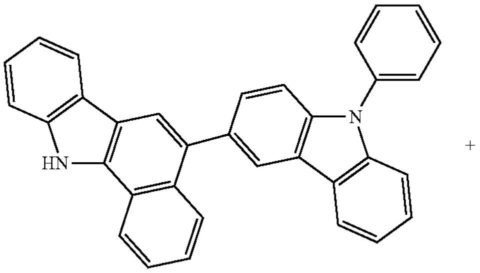

Sub 1-22

-continued

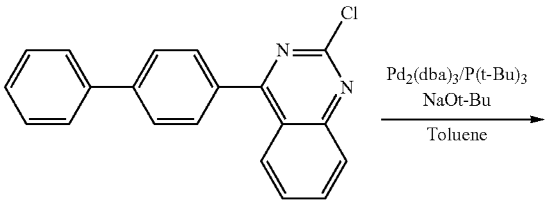

Sub 2-8

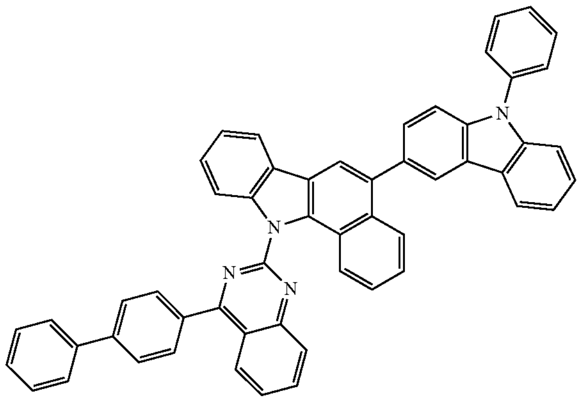

1-58

In addition to Sub 1-22 (7.06 g, 15.4 mmol) obtained in the above synthesis, Sub 2-8 (5.85 g, 18.5 mmol), $Pd_2(dba)_3$ (0.42 g, 0.5 mmol), 50% $P(t\text{-}Bu)_3$ (0.6 ml, 1.2 mmol), NaOt-Bu (4.44 g, 46.2 mmol), and toluene were used according to the synthesis method of Product 1-1 of example 3, to give a product 7.85 g (yield: 69%).

(5) Synthesis Example of Product 1-89

Reaction Scheme 21

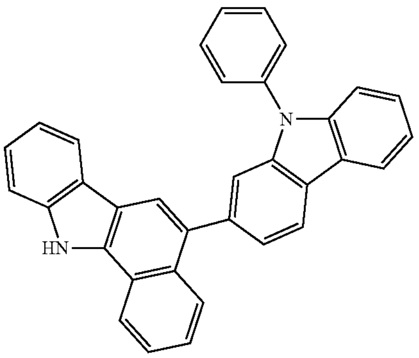

Sub 1-32

+

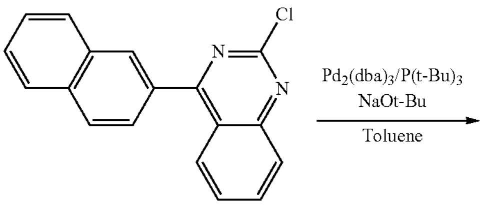

Sub 2-14

-continued

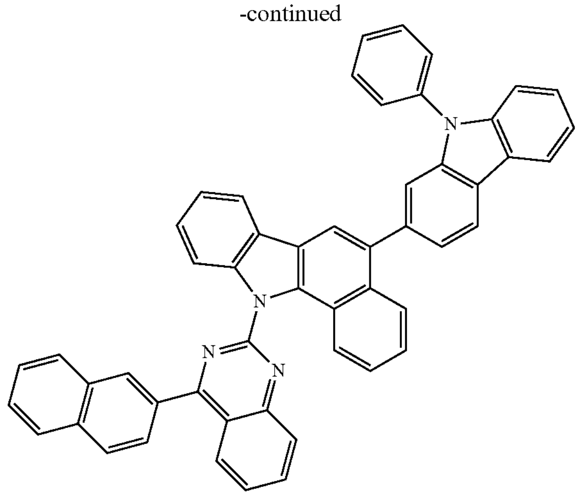

1-89

In addition to Sub 1-32 (7.54 g, 16.4 mmol) obtained in the above synthesis, Sub 2-14 (5.74 g, 19.7 mmol), $Pd_2(dba)_3$ (0.45 g, 0.5 mmol), 50% $P(t\text{-}Bu)_3$ (0.6 ml, 1.3 mmol), NaOt-Bu (4.74 g, 49.3 mmol), and toluene were used according to the synthesis method of Product 1-1 of example 3, to give a product 8.32 g (yield: 71%).

(6) Synthesis Example of Product 1-130

Reaction Scheme 22

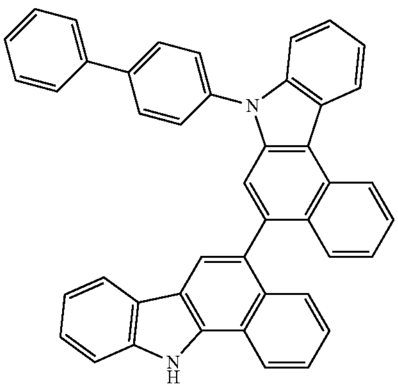

Sub 1-47

+

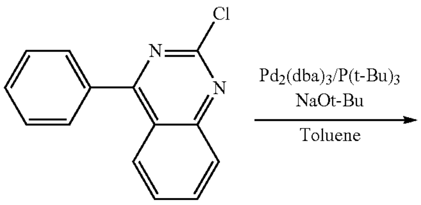

Sub 2-2

-continued

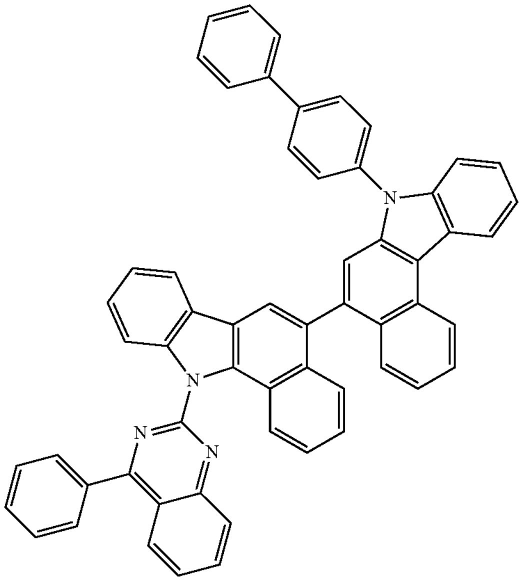

1-130

In addition to Sub 1-47 (8.29 g, 14.2 mmol) obtained in the above synthesis, Sub 2-2 (4.09 g, 17 mmol), $Pd_2(dba)_3$ (0.39 g, 0.4 mmol), 50% $P(t\text{-}Bu)_3$ (0.6 ml, 1.1 mmol), NaOt-Bu (4.09 g, 42.5 mmol), and toluene were used according to the synthesis method of Product 1-1 of example 3, to give a product 7.61 g (yield: 68%).

(7) Synthesis Example of Product 1-133

Reaction Scheme 23

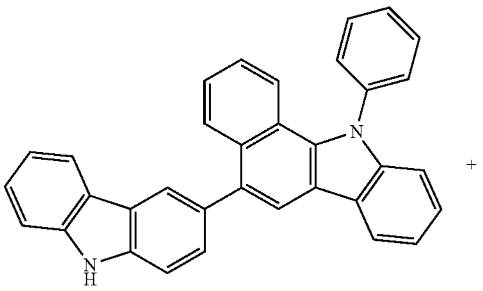

Sub 1-1

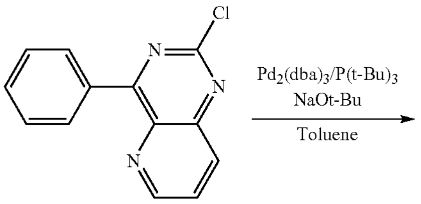

Sub 2-29

-continued

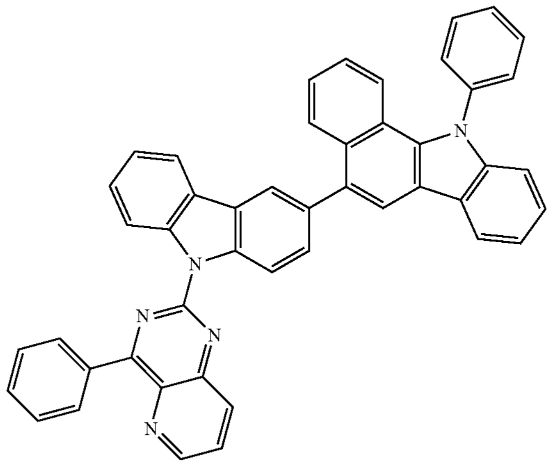

1-133

In addition to Sub 1-1 (8.11 g, 17.7 mmol) obtained in the above synthesis, Sub 2-29 (5.13 g, 21.2 mmol), $Pd_2(dba)_3$ (0.49 g, 0.5 mmol), 50% $P(t\text{-}Bu)_3$ (0.7 ml, 1.4 mmol), NaOt-Bu (5.1 g, 53.1 mmol), and toluene were used according to the synthesis method of Product 1-1 of example 3, to give a product 7.28 g (yield: 62%).

(8) Synthesis Example of Product 1-136

Reaction Scheme 24

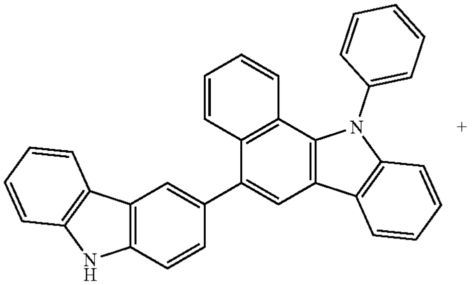

Sub 1-1

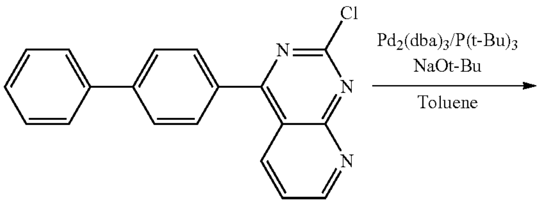

Sub 2-34

-continued

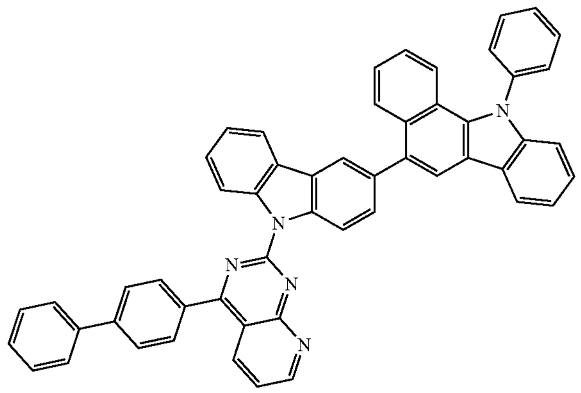

1-136

In addition to Sub 1-1 (8.32 g, 18.1 mmol) obtained in the above synthesis, Sub 2-34 (6.92 g, 21.8 mmol), $Pd_2(dba)_3$ (0.5 g, 0.5 mmol), 50% $P(t-Bu)_3$ (0.7 ml, 1.5 mmol), NaOt-Bu (5.23 g, 54.4 mmol), and toluene were used according to the synthesis method of Product 1-1 of example 3, to give a product 7.92 g (yield: 59%).

(9) Synthesis Example of Product 2-14

Reaction Scheme 25

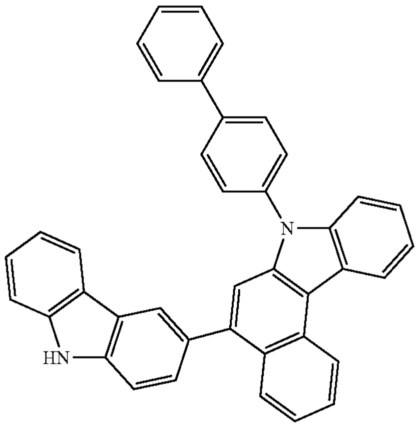

+

Sub 1-52

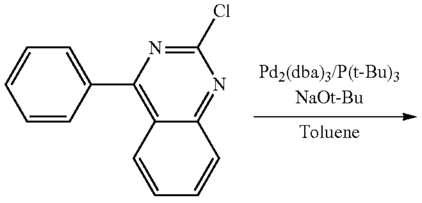

Sub 2-2

-continued

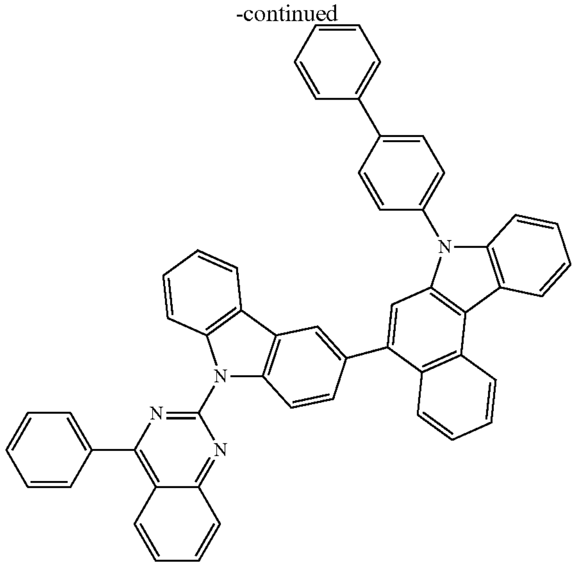

2-14

In addition to Sub 1-52 (7.92 g, 14.8 mmol) obtained in the above synthesis, Sub 2-2 (4.28 g, 17.8 mmol), $Pd_2(dba)_3$ (0.41 g, 0.4 mmol), 50% $P(t-Bu)_3$ (0.6 ml, 1.2 mmol), NaOt-Bu (4.27 g, 44.4 mmol), and toluene were used according to the synthesis method of Product 1-1 of example 3, to give a product 7.22 g (yield: 66%).

(10) Synthesis Example of Product 2-60

Reaction Scheme 26

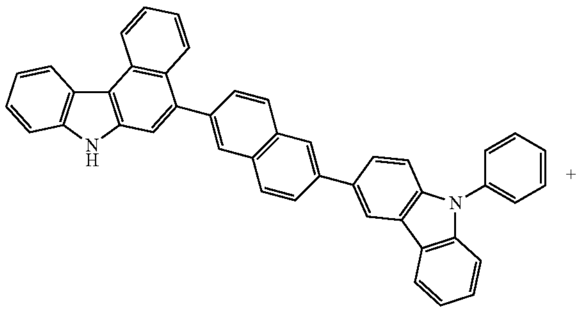

+

Sub 1-76

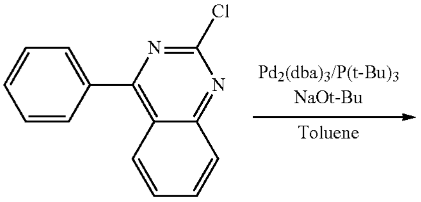

Sub 2-2

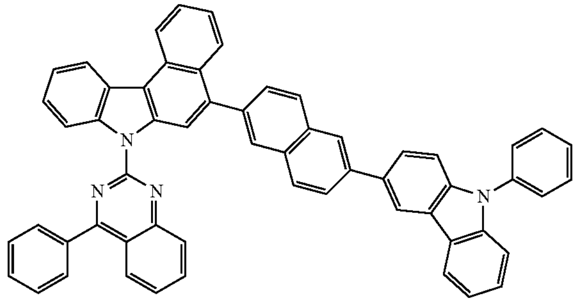

2-60

In addition to Sub 1-76 (8.01 g, 13.7 mmol) obtained in the above synthesis, Sub 2-2 (3.96 g, 16.4 mmol), $Pd_2(dba)_3$ (0.38 g, 0.4 mmol), 50% $P(t\text{-}Bu)_3$ (0.5 ml, 1.1 mmol), NaOt-Bu (3.95 g, 41.1 mmol), and toluene were used according to the synthesis method of Product 1-1 of example 3, to give a product 7.46 g (yield: 69%).

Meanwhile, FD-MS values of inventive compounds 1-1 to 1-148 and 2-1 to 2-120, which were prepared according to the synthesis examples above, are shown in Table 3 below.

TABLE 3

| Compound | FD-MS | Compound | FD-MS |
|---|---|---|---|
| 1-1 | m/z = 662.25 ($C_{48}H_{30}N_4$ = 662.78) | 1-2 | m/z = 738.28 ($C_{54}H_{34}N_4$ = 738.87) |
| 1-3 | m/z = 762.28 ($C_{56}H_{34}N_4$ = 762.90) | 1-4 | m/z = 712.26 ($C_{52}H_{32}N_4$ = 712.84) |
| 1-5 | m/z = 712.26 ($C_{52}H_{32}N_4$ = 712.84) | 1-6 | m/z = 738.28 ($C_{54}H_{34}N_4$ = 738.87) |
| 1-7 | m/z = 778.31 ($C_{57}H_{38}N_4$ = 778.94) | 1-8 | m/z = 768.23 ($C_{54}H_{32}N_4S$ = 768.92) |
| 1-9 | m/z = 752.26 ($C_{54}H_{32}N_4O$ = 752.86) | 1-10 | m/z = 768.23 ($C_{54}H_{32}N_4S$ = 768.92) |
| 1-11 | m/z = 752.26 ($C_{54}H_{32}N_4O$ = 752.86) | 1-12 | m/z = 827.30 ($C_{60}H_{37}N_5$ = 827.97) |
| 1-13 | m/z = 667.28 ($C_{48}H_{25}D_5N_4$ = 667.81) | 1-14 | m/z = 788.29 ($C_{58}H_{36}N_4$ = 788.93) |
| 1-15 | m/z = 788.29 ($C_{58}H_{36}N_4$ = 788.93) | 1-16 | m/z = 788.29 ($C_{58}H_{36}N_4$ = 788.93) |
| 1-17 | m/z = 788.29 ($C_{58}H_{36}N_4$ = 788.93) | 1-18 | m/z = 712.26 ($C_{52}H_{32}N_4$ = 712.84) |
| 1-19 | m/z = 738.28 ($C_{54}H_{34}N_4$ = 738.87) | 1-20 | m/z = 778.31 ($C_{57}H_{38}N_4$ = 778.94) |
| 1-21 | m/z = 739.27 ($C_{53}H_{33}N_5$ = 739.86) | 1-22 | m/z = 664.26 ($C_{48}H_{32}N_4$ = 664.79) |
| 1-23 | m/z = 676.26 ($C_{49}H_{32}N_4$ = 676.81) | 1-24 | m/z = 600.23 ($C_{43}H_{28}N_4$ = 600.71) |
| 1-25 | m/z = 738.28 ($C_{54}H_{34}N_4$ = 738.87) | 1-26 | m/z = 738.28 ($C_{54}H_{34}N_4$ = 738.87) |
| 1-27 | m/z = 788.29 ($C_{58}H_{36}N_4$ = 788.93) | 1-28 | m/z = 788.29 ($C_{58}H_{36}N_4$ = 788.93) |
| 1-29 | m/z = 662.25 ($C_{48}H_{30}N_4$ = 662.78) | 1-30 | m/z = 738.28 ($C_{54}H_{34}N_4$ = 738.87) |
| 1-31 | m/z = 762.28 ($C_{56}H_{34}N_4$ = 762.90) | 1-32 | m/z = 712.26 ($C_{52}H_{32}N_4$ = 712.84) |
| 1-33 | m/z = 712.26 ($C_{52}H_{32}N_4$ = 712.84) | 1-34 | m/z = 788.29 ($C_{58}H_{36}N_4$ = 788.93) |
| 1-35 | m/z = 778.31 ($C_{57}H_{38}N_4$ = 778.94) | 1-36 | m/z = 768.23 ($C_{54}H_{32}N_4S$ = 768.92) |
| 1-37 | m/z = 752.26 ($C_{54}H_{32}N_4O$ = 752.86) | 1-38 | m/z = 768.23 ($C_{54}H_{32}N_4S$ = 768.92) |
| 1-39 | m/z = 752.26 ($C_{54}H_{32}N_4O$ = 752.86) | 1-40 | m/z = 827.30 ($C_{60}H_{37}N_5$ = 827.97) |
| 1-41 | m/z = 667.28 ($C_{48}H_{25}D_5N_4$ = 667.81) | 1-42 | m/z = 788.29 ($C_{58}H_{36}N_4$ = 788.93) |
| 1-43 | m/z = 788.29 ($C_{58}H_{36}N_4$ = 788.93) | 1-44 | m/z = 788.29 ($C_{58}H_{36}N_4$ = 788.93) |
| 1-45 | m/z = 788.29 ($C_{58}H_{36}N_4$ = 788.93) | 1-46 | m/z = 712.26 ($C_{52}H_{32}N_4$ = 712.84) |
| 1-47 | m/z = 738.28 ($C_{54}H_{34}N_4$ = 738.87) | 1-48 | m/z = 778.31 ($C_{57}H_{38}N_4$ = 778.94) |
| 1-49 | m/z = 739.27 ($C_{53}H_{33}N_5$ = 739.86) | 1-50 | m/z = 664.26 ($C_{48}H_{32}N_4$ = 664.79) |
| 1-51 | m/z = 690.28 ($C_{50}H_{34}N_4$ = 690.83) | 1-52 | m/z = 690.28 ($C_{50}H_{34}N_4$ = 690.83) |
| 1-53 | m/z = 738.28 ($C_{54}H_{34}N_4$ = 738.87) | 1-54 | m/z = 814.31 ($C_{60}H_{38}N_4$ = 814.97) |
| 1-55 | m/z = 788.29 ($C_{58}H_{36}N_4$ = 788.93) | 1-56 | m/z = 788.29 ($C_{58}H_{36}N_4$ = 788.93) |
| 1-57 | m/z = 662.25 ($C_{48}H_{30}N_4$ = 662.78) | 1-58 | m/z = 738.28 ($C_{54}H_{34}N_4$ = 738.87) |
| 1-59 | m/z = 762.28 ($C_{56}H_{34}N_4$ = 762.90) | 1-60 | m/z = 712.26 ($C_{52}H_{32}N_4$ = 712.84) |
| 1-61 | m/z = 712.26 ($C_{52}H_{32}N_4$ = 712.84) | 1-62 | m/z = 738.28 ($C_{54}H_{34}N_4$ = 738.87) |
| 1-63 | m/z = 778.31 ($C_{57}H_{38}N_4$ = 778.94) | 1-64 | m/z = 768.23 ($C_{54}H_{32}N_4S$ = 768.92) |
| 1-65 | m/z = 752.26 ($C_{54}H_{32}N_4O$ = 752.86) | 1-66 | m/z = 768.23 ($C_{54}H_{32}N_4S$ = 768.92) |
| 1-67 | m/z = 752.26 ($C_{54}H_{32}N_4O$ = 752.86) | 1-68 | m/z = 827.30 ($C_{60}H_{37}N_5$ = 827.97) |
| 1-69 | m/z = 667.28 ($C_{48}H_{25}D_5N_4$ = 667.81) | 1-70 | m/z = 788.29 ($C_{58}H_{36}N_4$ = 788.93) |
| 1-71 | m/z = 788.29 ($C_{58}H_{36}N_4$ = 788.93) | 1-72 | m/z = 788.29 ($C_{58}H_{36}N_4$ = 788.93) |
| 1-73 | m/z = 788.29 ($C_{58}H_{36}N_4$ = 788.93) | 1-74 | m/z = 712.26 ($C_{52}H_{32}N_4$ = 712.84) |
| 1-75 | m/z = 738.28 ($C_{54}H_{34}N_4$ = 738.87) | 1-76 | m/z = 778.31 ($C_{57}H_{38}N_4$ = 778.94) |
| 1-77 | m/z = 739.27 ($C_{53}H_{33}N_5$ = 739.86) | 1-78 | m/z = 664.26 ($C_{48}H_{32}N_4$ = 664.79) |
| 1-79 | m/z = 726.28 ($C_{53}H_{34}N_4$ = 726.86) | 1-80 | m/z = 663.24 ($C_{47}H_{23}N_5$ = 663.77) |
| 1-81 | m/z = 738.28 ($C_{54}H_{34}N_4$ = 738.87) | 1-82 | m/z = 738.28 ($C_{54}H_{34}N_4$ = 738.87) |
| 1-83 | m/z = 788.29 ($C_{58}H_{36}N_4$ = 788.93) | 1-84 | m/z = 788.29 ($C_{58}H_{36}N_4$ = 788.93) |
| 1-85 | m/z = 662.25 ($C_{48}H_{30}N_4$ = 662.78) | 1-86 | m/z = 738.28 ($C_{54}H_{34}N_4$ = 738.87) |
| 1-87 | m/z = 762.28 ($C_{56}H_{34}N_4$ = 762.90) | 1-88 | m/z = 712.26 ($C_{52}H_{32}N_4$ = 712.84) |
| 1-89 | m/z = 712.26 ($C_{52}H_{32}N_4$ = 712.84) | 1-90 | m/z = 738.28 ($C_{54}H_{34}N_4$ = 738.87) |
| 1-91 | m/z = 778.31 ($C_{57}H_{38}N_4$ = 778.94) | 1-92 | m/z = 768.23 ($C_{54}H_{32}N_4S$ = 768.92) |
| 1-93 | m/z = 752.26 ($C_{54}H_{32}N_4O$ = 752.86) | 1-94 | m/z = 768.23 ($C_{54}H_{32}N_4S$ = 768.92) |
| 1-95 | m/z = 752.26 ($C_{54}H_{32}N_4O$ = 752.86) | 1-96 | m/z = 827.30 ($C_{60}H_{37}N_5$ = 827.97) |
| 1-97 | m/z = 667.28 ($C_{48}H_{25}D_5N_4$ = 667.81) | 1-98 | m/z = 788.29 ($C_{58}H_{36}N_4$ = 788.93) |
| 1-99 | m/z = 788.29 ($C_{58}H_{36}N_4$ = 788.93) | 1-100 | m/z = 788.29 ($C_{58}H_{36}N_4$ = 788.93) |
| 1-101 | m/z = 788.29 ($C_{58}H_{36}N_4$ = 788.93) | 1-102 | m/z = 712.26 ($C_{52}H_{32}N_4$ = 712.84) |
| 1-103 | m/z = 738.28 ($C_{54}H_{34}N_4$ = 738.87) | 1-104 | m/z = 778.31 ($C_{57}H_{38}N_4$ = 778.94) |
| 1-105 | m/z = 663.24 ($C_{47}H_{29}N_5$ = 663.77) | 1-106 | m/z = 614.25 ($C_{44}H_{30}N_4$ = 614.74) |
| 1-107 | m/z = 738.28 ($C_{54}H_{34}N_4$ = 738.87) | 1-108 | m/z = 814.31 ($C_{60}H_{38}N_4$ = 814.97) |
| 1-109 | m/z = 712.26 ($C_{52}H_{32}N_4$ = 712.84) | 1-110 | m/z = 788.29 ($C_{58}H_{36}N_4$ = 788.93) |
| 1-111 | m/z = 762.28 ($C_{56}H_{34}N_4$ = 762.90) | 1-112 | m/z = 788.29 ($C_{58}H_{36}N_4$ = 788.93) |
| 1-113 | m/z = 828.33 ($C_{61}H_{40}N_4$ = 829.00) | 1-114 | m/z = 818.25 ($C_{58}H_{34}N_4S$ = 818.98) |
| 1-115 | m/z = 802.27 ($C_{58}H_{34}N_4O$ = 802.92) | 1-116 | m/z = 877.32 ($C_{64}H_{39}N_5$ = 878.03) |
| 1-117 | m/z = 762.28 ($C_{56}H_{34}N_4$ = 762.90) | 1-118 | m/z = 788.29 ($C_{58}H_{36}N_4$ = 788.93) |
| 1-119 | m/z = 789.29 ($C_{57}H_{35}N_5$ = 789.92) | 1-120 | m/z = 838.31 ($C_{62}H_{38}N_4$ = 838.99) |
| 1-121 | m/z = 712.26 ($C_{52}H_{32}N_4$ = 712.84) | 1-122 | m/z = 788.29 ($C_{58}H_{36}N_4$ = 788.93) |
| 1-123 | m/z = 762.28 ($C_{56}H_{34}N_4$ = 762.90) | 1-124 | m/z = 788.29 ($C_{58}H_{36}N_4$ = 788.93) |
| 1-125 | m/z = 828.33 ($C_{61}H_{40}N_4$ = 829.00) | 1-126 | m/z = 802.27 ($C_{58}H_{34}N_4O$ = 802.92) |
| 1-127 | m/z = 818.25 ($C_{58}H_{34}N_4S$ = 818.98) | 1-128 | m/z = 877.32 ($C_{64}H_{39}N_5$ = 878.03) |
| 1-129 | m/z = 762.28 ($C_{56}H_{34}N_4$ = 762.90) | 1-130 | m/z = 788.29 ($C_{58}H_{36}N_4$ = 788.93) |
| 1-131 | m/z = 788.29 ($C_{58}H_{36}N_4$ = 788.93) | 1-132 | m/z = 838.31 ($C_{62}H_{38}N_4$ = 838.99) |
| 1-133 | m/z = 663.24 ($C_{47}H_{29}N_5$ = 663.77) | 1-134 | m/z = 663.24 ($C_{47}H_{29}N_5$ = 663.77) |
| 1-135 | m/z = 739.27 ($C_{53}H_{33}N_5$ = 739.86) | 1-136 | m/z = 739.27 ($C_{53}H_{33}N_5$ = 739.86) |
| 1-137 | m/z = 663.24 ($C_{47}H_{29}N_5$ = 663.77) | 1-138 | m/z = 663.24 ($C_{47}H_{29}N_5$ = 663.77) |
| 1-139 | m/z = 713.26 ($C_{51}H_{31}N_5$ = 713.83) | 1-140 | m/z = 713.26 ($C_{51}H_{31}N_5$ = 713.83) |

TABLE 3-continued

| Compound | FD-MS | Compound | FD-MS |
|---|---|---|---|
| 1-141 | m/z = 663.24 ($C_{47}H_{29}N_5$ = 663.77) | 1-142 | m/z = 663.24 ($C_{47}H_{29}N_5$ = 663.77) |
| 1-143 | m/z = 713.26 ($C_{51}H_{31}N_5$ = 713.83) | 1-144 | m/z = 713.26 ($C_{51}H_{31}N_5$ = 713.83) |
| 1-145 | m/z = 713.26 ($C_{51}H_{31}N_5$ = 713.83) | 1-146 | m/z = 713.26 ($C_{51}H_{31}N_5$ = 713.83) |
| 1-147 | m/z = 739.27 ($C_{53}H_{33}N_5$ = 739.86) | 1-148 | m/z = 739.27 ($C_{53}H_{33}N_5$ = 739.86) |
| 2-1 | m/z = 662.25 ($C_{48}H_{30}N_4$ = 662.78) | 2-2 | m/z = 738.28 ($C_{54}H_{34}N_4$ = 738.87) |
| 2-3 | m/z = 762.28 ($C_{56}H_{34}N_4$ = 762.90) | 2-4 | m/z = 712.26 ($C_{52}H_{32}N_4$ = 712.84) |
| 2-5 | m/z = 738.28 ($C_{54}H_{34}N_4$ = 738.87) | 2-6 | m/z = 778.31 ($C_{57}H_{38}N_4$ = 778.94) |
| 2-7 | m/z = 768.23 ($C_{54}H_{32}N_4S$ = 768.92) | 2-8 | m/z = 752.26 ($C_{54}H_{32}N_4O$ = 752.86) |
| 2-9 | m/z = 827.30 ($C_{60}H_{37}N_5$ = 827.97) | 2-10 | m/z = 788.29 ($C_{58}H_{36}N_4$ = 788.93) |
| 2-11 | m/z = 788.29 ($C_{58}H_{36}N_4$ = 788.93) | 2-12 | m/z = 788.29 ($C_{58}H_{36}N_4$ = 788.93) |
| 2-13 | m/z = 712.26 ($C_{52}H_{32}N_4$ = 712.84) | 2-14 | m/z = 738.28 ($C_{54}H_{34}N_4$ = 738.87) |
| 2-15 | m/z = 778.31 ($C_{57}H_{38}N_4$ = 778.94) | 2-16 | m/z = 739.27 ($C_{53}H_{33}N_5$ = 739.86) |
| 2-17 | m/z = 738.28 ($C_{54}H_{34}N_4$ = 738.87) | 2-18 | m/z = 738.28 ($C_{54}H_{34}N_4$ = 738.87) |
| 2-19 | m/z = 788.29 ($C_{58}H_{36}N_4$ = 788.93) | 2-20 | m/z = 788.29 ($C_{58}H_{36}N_4$ = 788.93) |
| 2-21 | m/z = 662.25 ($C_{48}H_{30}N_4$ = 662.78) | 2-22 | m/z = 738.28 ($C_{54}H_{34}N_4$ = 738.87) |
| 2-23 | m/z = 762.28 ($C_{56}H_{34}N_4$ = 762.90) | 2-24 | m/z = 712.26 ($C_{52}H_{32}N_4$ = 712.84) |
| 2-25 | m/z = 738.28 ($C_{54}H_{34}N_4$ = 738.87) | 2-26 | m/z = 778.31 ($C_{57}H_{38}N_4$ = 778.94) |
| 2-27 | m/z = 768.23 ($C_{54}H_{32}N_4S$ = 768.92) | 2-28 | m/z = 752.26 ($C_{54}H_{32}N_4O$ = 752.86) |
| 2-29 | m/z = 827.30 ($C_{60}H_{37}N_5$ = 827.97) | 2-30 | m/z = 788.29 ($C_{58}H_{36}N_4$ = 788.93) |
| 2-31 | m/z = 788.29 ($C_{58}H_{36}N_4$ = 788.93) | 2-32 | m/z = 788.29 ($C_{58}H_{36}N_4$ = 788.93) |
| 2-33 | m/z = 712.26 ($C_{52}H_{32}N_4$ = 712.84) | 2-34 | m/z = 738.28 ($C_{54}H_{34}N_4$ = 738.87) |
| 2-35 | m/z = 778.31 ($C_{57}H_{38}N_4$ = 778.94) | 2-36 | m/z = 739.27 ($C_{53}H_{33}N_5$ = 739.86) |
| 2-37 | m/z = 738.28 ($C_{54}H_{34}N_4$ = 738.87) | 2-38 | m/z = 738.28 ($C_{54}H_{34}N_4$ = 738.87) |
| 2-39 | m/z = 788.29 ($C_{58}H_{36}N_4$ = 788.93) | 2-40 | m/z = 788.29 ($C_{58}H_{36}N_4$ = 788.93) |
| 2-41 | m/z = 662.25 ($C_{48}H_{30}N_4$ = 662.78) | 2-42 | m/z = 738.28 ($C_{54}H_{34}N_4$ = 738.87) |
| 2-43 | m/z = 762.28 ($C_{56}H_{34}N_4$ = 762.90) | 2-44 | m/z = 712.26 ($C_{52}H_{32}N_4$ = 712.84) |
| 2-45 | m/z = 738.28 ($C_{54}H_{34}N_4$ = 738.87) | 2-46 | m/z = 778.31 ($C_{57}H_{38}N_4$ = 778.94) |
| 2-47 | m/z = 768.23 ($C_{54}H_{32}N_4S$ = 768.92) | 2-48 | m/z = 752.26 ($C_{54}H_{32}N_4O$ = 752.86) |
| 2-49 | m/z = 827.30 ($C_{60}H_{37}N_5$ = 827.97) | 2-50 | m/z = 788.29 ($C_{58}H_{36}N_4$ = 788.93) |
| 2-51 | m/z = 788.29 ($C_{58}H_{36}N_4$ = 788.93) | 2-52 | m/z = 788.29 ($C_{58}H_{36}N_4$ = 788.93) |
| 2-53 | m/z = 712.26 ($C_{52}H_{32}N_4$ = 712.84) | 2-54 | m/z = 738.28 ($C_{54}H_{34}N_4$ = 738.87) |
| 2-55 | m/z = 778.31 ($C_{57}H_{38}N_4$ = 778.94) | 2-56 | m/z = 663.24 ($C_{47}H_{29}N_5$ = 663.77) |
| 2-57 | m/z = 738.28 ($C_{54}H_{34}N_4$ = 738.87) | 2-58 | m/z = 738.28 ($C_{54}H_{34}N_4$ = 738.87) |
| 2-59 | m/z = 788.29 ($C_{58}H_{36}N_4$ = 788.93) | 2-60 | m/z = 788.29 ($C_{58}H_{36}N_4$ = 788.93) |
| 2-61 | m/z = 662.25 ($C_{48}H_{30}N_4$ = 662.78) | 2-62 | m/z = 738.28 ($C_{54}H_{34}N_4$ = 738.87) |
| 2-63 | m/z = 762.28 ($C_{56}H_{34}N_4$ = 762.90) | 2-64 | m/z = 712.26 ($C_{52}H_{32}N_4$ = 712.84) |
| 2-65 | m/z = 738.28 ($C_{54}H_{34}N_4$ = 738.87) | 2-66 | m/z = 778.31 ($C_{57}H_{38}N_4$ = 778.94) |
| 2-67 | m/z = 768.23 ($C_{54}H_{32}N_4S$ = 768.92) | 2-68 | m/z = 752.26 ($C_{54}H_{32}N_4O$ = 752.86) |
| 2-69 | m/z = 827.30 ($C_{60}H_{37}N_5$ = 827.97) | 2-70 | m/z = 788.29 ($C_{58}H_{36}N_4$ = 788.93) |
| 2-71 | m/z = 788.29 ($C_{58}H_{36}N_4$ = 788.93) | 2-72 | m/z = 788.29 ($C_{58}H_{36}N_4$ = 788.93) |
| 2-73 | m/z = 712.26 ($C_{52}H_{32}N_4$ = 712.84) | 2-74 | m/z = 738.28 ($C_{54}H_{34}N_4$ = 738.87) |
| 2-75 | m/z = 778.31 ($C_{57}H_{38}N_4$ = 778.94) | 2-76 | m/z = 739.27 ($C_{53}H_{33}N_5$ = 739.86) |
| 2-77 | m/z = 738.28 ($C_{54}H_{34}N_4$ = 738.87) | 2-78 | m/z = 738.28 ($C_{54}H_{34}N_4$ = 738.87) |
| 2-79 | m/z = 788.29 ($C_{58}H_{36}N_4$ = 788.93) | 2-80 | m/z = 788.29 ($C_{58}H_{36}N_4$ = 788.93) |
| 2-81 | m/z = 712.26 ($C_{52}H_{32}N_4$ = 712.84) | 2-82 | m/z = 788.29 ($C_{58}H_{36}N_4$ = 788.93) |
| 2-83 | m/z = 762.28 ($C_{56}H_{34}N_4$ = 762.90) | 2-84 | m/z = 788.29 ($C_{58}H_{36}N_4$ = 788.93) |
| 2-85 | m/z = 828.33 ($C_{61}H_{40}N_4$ = 829.00) | 2-86 | m/z = 818.25 ($C_{58}H_{34}N_4S$ = 818.98) |
| 2-87 | m/z = 802.27 ($C_{58}H_{34}N_4O$ = 802.92) | 2-88 | m/z = 877.32 ($C_{64}H_{39}N_5$ = 878.03) |
| 2-89 | m/z = 762.28 ($C_{56}H_{34}N_4$ = 762.90) | 2-90 | m/z = 788.29 ($C_{58}H_{36}N_4$ = 788.93) |
| 2-91 | m/z = 789.29 ($C_{57}H_{35}N_5$ = 789.92) | 2-92 | m/z = 838.31 ($C_{62}H_{38}N_4$ = 838.99) |
| 2-93 | m/z = 712.26 ($C_{52}H_{32}N_4$ = 712.84) | 2-94 | m/z = 788.29 ($C_{58}H_{36}N_4$ = 788.93) |
| 2-95 | m/z = 762.28 ($C_{56}H_{34}N_4$ = 762.90) | 2-96 | m/z = 788.29 ($C_{58}H_{36}N_4$ = 788.93) |
| 2-97 | m/z = 828.33 ($C_{61}H_{40}N_4$ = 829.00) | 2-98 | m/z = 802.27 ($C_{58}H_{34}N_4O$ = 802.92) |
| 2-99 | m/z = 818.25 ($C_{58}H_{34}N_4S$ = 818.98) | 2-100 | m/z = 877.32 ($C_{64}H_{39}N_5$ = 878.03) |
| 2-101 | m/z = 762.28 ($C_{56}H_{34}N_4$ = 762.90) | 2-102 | m/z = 788.29 ($C_{58}H_{36}N_4$ = 788.93) |
| 2-103 | m/z = 788.29 ($C_{58}H_{36}N_4$ = 788.93) | 2-104 | m/z = 838.31 ($C_{62}H_{38}N_4$ = 838.99) |
| 2-105 | m/z = 663.24 ($C_{47}H_{29}N_5$ = 663.77) | 2-106 | m/z = 663.24 ($C_{47}H_{29}N_5$ = 663.77) |
| 2-107 | m/z = 739.27 ($C_{53}H_{33}N_5$ = 739.86) | 2-108 | m/z = 739.27 ($C_{53}H_{33}N_5$ = 739.86) |
| 2-109 | m/z = 663.24 ($C_{47}H_{29}N_5$ = 663.77) | 2-110 | m/z = 663.24 ($C_{47}H_{29}N_5$ = 663.77) |
| 2-111 | m/z = 713.26 ($C_{51}H_{31}N_5$ = 713.83) | 2-112 | m/z = 713.26 ($C_{51}H_{31}N_5$ = 713.83) |
| 2-113 | m/z = 663.24 ($C_{47}H_{29}N_5$ = 663.77) | 2-114 | m/z = 663.24 ($C_{47}H_{29}N_5$ = 663.77) |
| 2-115 | m/z = 713.26 ($C_{51}H_{31}N_5$ = 713.83) | 2-116 | m/z = 713.26 ($C_{51}H_{31}N_5$ = 713.83) |
| 2-117 | m/z = 713.26 ($C_{51}H_{31}N_5$ = 713.83) | 2-118 | m/z = 713.26 ($C_{51}H_{31}N_5$ = 713.83) |
| 2-119 | m/z = 739.27 ($C_{53}H_{33}N_5$ = 739.86) | 2-120 | m/z = 739.27 ($C_{53}H_{33}N_5$ = 739.86) |

Meanwhile, the synthesis examples of the present invention, represented by Formula 1, have been described, but these are based on a Suzuki cross-coupling reaction, a Bromination reaction, an Ullmann reaction, a Miyaura boration reaction, and a Buchwald-Hartwig cross coupling reaction. A person skilled in the art could easily understand that the above reactions proceed even though, besides the substituents specified in the specific synthesis examples, the other substituents (substituents of $Ar_1$ to $Ar_2$, L, $X_1$ to $X_4$, and R') defined in Formula 1 are bonded. For example, all of the reactions of the starting material→M 1-I, a starting material→M 2-I, Sub 1-III→Sub 1-IV, Sub 1-V→Sub 1, in Reaction Scheme 2, and the reaction of the starting material→Sub 2 in Reaction Scheme 10 are based on the Suzuki cross-coupling reaction; the reaction of M 1-II→Sub 1-I in Reaction Scheme 2 is based on the Bromination reaction; the reaction of Sub 1-I→Sub 1-II in Reaction Scheme 2 is based on the Ullmann reaction; the reactions of Sub 1-II→Sub 1-III and Sub 1-IV→Sub 1-V are based on the Miyaura boration reaction. The reaction schemes for product synthesis (Reaction Schemes 17 to 26) are based on the Buchwald-Hartwig cross coupling reaction, and the above reactions will proceed even though substituents that are not specified therein are bonded.

Manufacture and Evaluation of Organic electronic Element

Example 1: Light Emitting Layer (Phosphorescent Red Host)

An organic light emitting diode was manufactured according to a normal method by using the inventive compounds obtained through synthesis as a host material of a light emitting layer.

First, an ITO layer (anode) was formed on a glass substrate, and then a film of 4,4',4"-Tris[2-naphthyl(phenyl)amino]triphenylamine (hereinafter, abbreviated as 2-TNATA) was vacuum-deposited on the ITO layer to form a hole injection layer with a thickness of 60 nm. Subsequently, a film then a film of 4,4-bis[N-(1-naphthyl)-N-phenylamino]biphenyl (hereinafter, abbreviated as NPD) was vacuum-deposited with a thickness of 20 nm on the hole injection layer to form a hole transport layer. Then, a light emitting layer with a thickness of 30 nm was deposited on the hole transport layer by doping the hole transport layer with the inventive compound as a host material and $(piq)_2Ir(acac)$ [bis-(1-phenylisoquinolyl) iridium(III) acetylacetonate] as a dopant material at a weight ratio of 95:5. Then, a film of (1,1'-bisphenyl)-4-olato)bis(2-methyl-8-quinolinolato)aluminum (hereinafter abbreviated as "BAlq") was vacuum-deposited with a thickness of 10 nm on the light emitting layer to forma hole blocking layer, and a film of tris(8-quinolinolato)aluminum (hereinafter abbreviated as "$Alq_3$") was formed with a thickness of 40 nm on the hole blocking layer to form an electron transport layer. Thereafter, LiF as halogenated alkali metal was deposited with a thickness of 0.2 nm to form an electron injection layer, and then Al was deposited with a thickness of 150 nm to form a negative electrode. In this way, an organic light emitting diode was manufactured.

Example 2 to EXAMPLE 268

Light Emitting Layer (Phosphorescent Red Host)

Organic light emitting diodes were manufactured by the same method as in Example 1 except that Compounds 1-2 to 1-148 and 2-1 to 2-120 listed in table 4, instead of inventive compound 1-1, were used as a host material of the light emitting layer.

Comparative Example 1

An organic light emitting diode was manufactured by the same method as in Example 1 except that comparative compound 1 below, instead of inventive compound 1-1, was used as a host material of the light emitting layer.

Comparative Compound 1

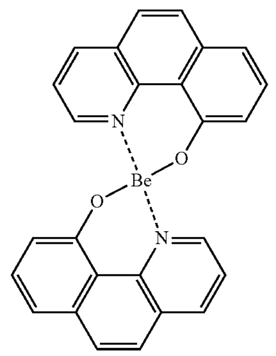

bis(10-hydroxybenzo[h] qinolinato) beryllium (hereinafter, abbreviated as "Bebq2")

Comparative Example 2

An organic light emitting diode was manufactured by the same method as in Example 1 except that comparative compound 2 below, instead of inventive compound 1-1, was used as a host material of the light emitting layer.

Comparative Compound 2

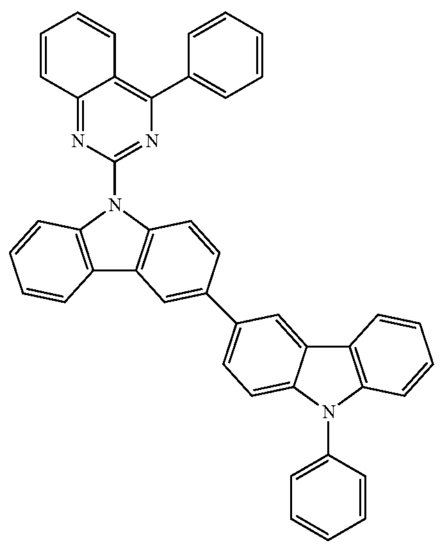 [SMILES: c1ccc(-c2nc(-n3c4ccccc4c4cc(-c5ccc6c(c5)c5ccccc5n6-c5ccccc5)ccc43)nc3ccccc23)cc1]

Comparative Example 3

An organic light emitting diode was manufactured by the same method as in Example 1 except that comparative compound 3 below, instead of inventive compound 1-1, was used as a host material of the light emitting layer.

Comparative Compound 3

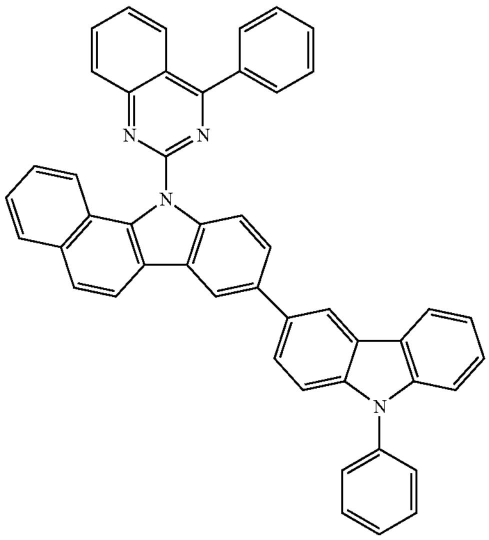 [SMILES: c1ccc(-c2nc(-n3c4ccc(-c5ccc6c(c5)c5ccccc5n6-c5ccccc5)cc4c4ccc5ccccc5c43)nc3ccccc23)cc1]

Comparative Example 4

An organic light emitting diode was manufactured by the same method as in Example 1 except that comparative compound 4 below, instead of inventive compound 1-1, was used as a host material of the light emitting layer.

Comparative Compound 4

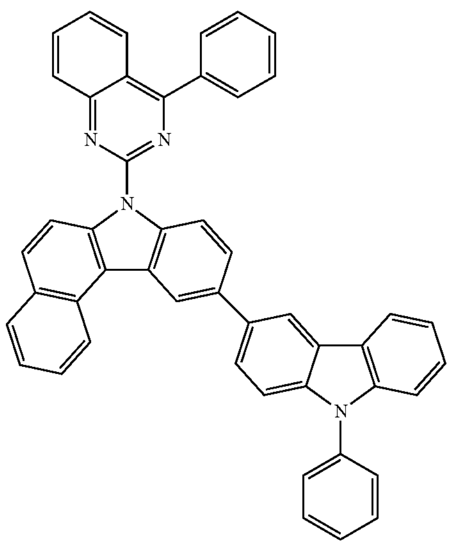 [SMILES: c1ccc(-c2nc(-n3c4ccc(-c5ccc6c(c5)c5ccccc5n6-c5ccccc5)cc4c4c5ccccc5ccc43)nc3ccccc23)cc1]

Comparative Example 5

An organic light emitting diode was manufactured by the same method as in Example 1 except that comparative compound 5 below, instead of inventive compound 1-1, was used as a host material of the light emitting layer.

Comparative Compound 5

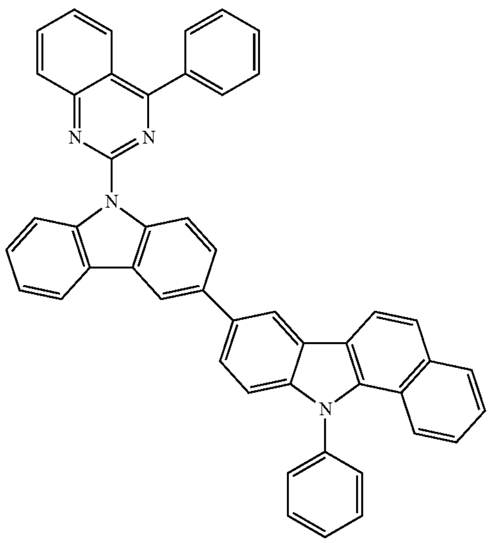 [SMILES: c1ccc(-c2nc(-n3c4ccccc4c4cc(-c5ccc6c(c5)c5ccc7ccccc7c5n6-c5ccccc5)ccc43)nc3ccccc23)cc1]

Comparative Example 6

An organic light emitting diode was manufactured by the same method as in Example 1 except that comparative compound 6 below, instead of inventive compound 1-1, was used as a host material of the light emitting layer.

Comparative Compound 6

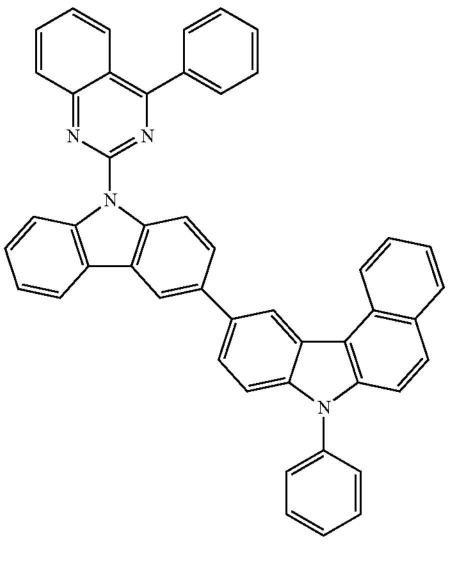 [SMILES: c1ccc(-c2nc(-n3c4ccccc4c4cc(-c5ccc6c(c5)c5c7ccccc7ccc5n6-c5ccccc5)ccc43)nc3ccccc23)cc1]

Comparative Example 7

An organic light emitting diode was manufactured by the same method as in Example 1 except that comparative compound 7 below, instead of inventive compound 1-1, was used as a host material of the light emitting layer.

Comparative Compound 7

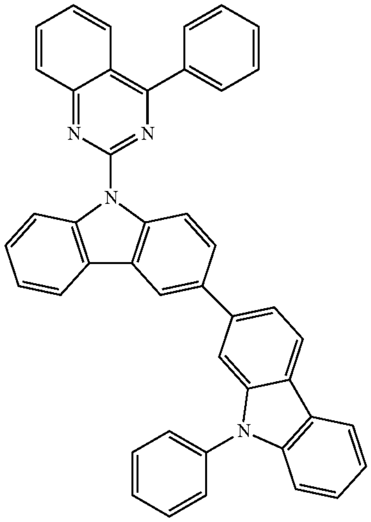 [SMILES: c1ccc(-c2nc(-n3c4ccccc4c4cc(-c5ccc6c7ccccc7n(-c7ccccc7)c6c5)ccc43)nc3ccccc23)cc1]

A forward bias DC voltage was applied to each of the thus manufactured organic light emitting diodes of Examples 1 to 268 and Comparative Examples 1 to 7, and electroluminescent (EL) characteristics thereof were measured by PR-650 from Photoresearch Company. Also, T95 lifespan was measured by lifespan measuring equipment from Mcscience Company at a reference brightness of 300 cd/m$^2$. The measurement results are shown in Table 4.

TABLE 4

| | Compound | Voltage (V) | Current Density (mA/cm$^2$) | Brightness (cd/m$^2$) | Efficiency (cd/A) | Lifetime T(90) | CIE x | CIE y |
|---|---|---|---|---|---|---|---|---|
| Comp. Ex. (1) | Comp. Com. 1 | 5.8 | 6.0 | 300.0 | 5.0 | 89.8 | 0.66 | 0.33 |
| Comp. Ex. (2) | Comp. com. 2 | 5.9 | 5.6 | 300.0 | 5.4 | 95.3 | 0.66 | 0.33 |
| Comp. Ex. (3) | Comp. com. 3 | 5.6 | 5.3 | 300.0 | 5.7 | 94.7 | 0.66 | 0.34 |
| Comp. Ex. (4) | Comp. com. 4 | 5.6 | 5.5 | 300.0 | 5.5 | 90.2 | 0.66 | 0.33 |
| Comp. Ex. (5) | Comp. com. 5 | 5.3 | 4.8 | 300.0 | 6.2 | 98.1 | 0.66 | 0.33 |
| Comp. Ex. (6) | Comp. com. 6 | 5.4 | 4.9 | 300.0 | 6.1 | 96.4 | 0.66 | 0.34 |
| Comp. Ex. (7) | Comp. com. 7 | 5.9 | 5.8 | 300.0 | 5.2 | 82.2 | 0.66 | 0.34 |
| Ex. (1) | Com. (1-1) | 5.2 | 3.3 | 300.0 | 9.0 | 145.9 | 0.66 | 0.34 |
| Ex. (2) | Com. (1-2) | 5.3 | 3.4 | 300.0 | 8.7 | 131.3 | 0.66 | 0.33 |
| Ex. (3) | Com. (1-3) | 5.4 | 3.6 | 300.0 | 8.3 | 126.5 | 0.66 | 0.33 |
| Ex. (4) | Com. (1-4) | 5.3 | 3.3 | 300.0 | 9.0 | 148.1 | 0.66 | 0.34 |
| Ex. (5) | Com. (1-5) | 5.2 | 3.3 | 300.0 | 9.0 | 141.3 | 0.66 | 0.33 |
| Ex. (6) | Com. (1-6) | 5.2 | 3.6 | 300.0 | 8.3 | 125.1 | 0.66 | 0.33 |
| Ex. (7) | Com. (1-7) | 5.3 | 3.5 | 300.0 | 8.6 | 124.3 | 0.66 | 0.33 |
| Ex. (8) | Com. (1-8) | 5.2 | 3.4 | 300.0 | 8.7 | 124.0 | 0.66 | 0.33 |
| Ex. (9) | Com. (1-9) | 5.4 | 3.6 | 300.0 | 8.4 | 126.8 | 0.66 | 0.33 |
| Ex. (10) | Com. (1-10) | 5.3 | 3.5 | 300.0 | 8.6 | 127.2 | 0.66 | 0.33 |
| Ex. (11) | Com. (1-11) | 5.3 | 3.5 | 300.0 | 8.6 | 128.3 | 0.66 | 0.34 |
| Ex. (12) | Com. (1-12) | 5.3 | 3.5 | 300.0 | 8.6 | 127.9 | 0.66 | 0.34 |
| Ex. (13) | Com. (1-13) | 5.2 | 3.5 | 300.0 | 8.6 | 127.8 | 0.66 | 0.34 |
| Ex. (14) | Com. (1-14) | 5.2 | 3.5 | 300.0 | 8.6 | 123.6 | 0.66 | 0.33 |
| Ex. (15) | Com. (1-15) | 5.4 | 3.5 | 300.0 | 8.5 | 125.7 | 0.66 | 0.34 |
| Ex. (16) | Com. (1-16) | 5.4 | 3.5 | 300.0 | 8.5 | 123.9 | 0.66 | 0.33 |
| Ex. (17) | Com. (1-17) | 5.3 | 3.4 | 300.0 | 8.7 | 128.4 | 0.66 | 0.33 |
| Ex. (18) | Com. (1-18) | 5.3 | 3.4 | 300.0 | 8.8 | 132.7 | 0.66 | 0.33 |
| Ex. (19) | Com. (1-19) | 5.2 | 3.4 | 300.0 | 8.9 | 133.2 | 0.66 | 0.34 |
| Ex. (20) | Com. (1-20) | 5.3 | 3.7 | 300.0 | 8.1 | 126.3 | 0.66 | 0.34 |
| Ex. (21) | Com. (1-21) | 5.4 | 3.6 | 300.0 | 8.4 | 126.4 | 0.66 | 0.33 |
| Ex. (22) | Com. (1-22) | 5.5 | 3.8 | 300.0 | 7.9 | 125.7 | 0.66 | 0.34 |
| Ex. (23) | Com. (1-23) | 5.3 | 3.8 | 300.0 | 8.0 | 125.0 | 0.66 | 0.33 |
| Ex. (24) | Com. (1-24) | 5.3 | 3.8 | 300.0 | 7.9 | 124.1 | 0.66 | 0.34 |
| Ex. (25) | Com. (1-25) | 5.4 | 3.8 | 300.0 | 7.8 | 123.8 | 0.66 | 0.33 |
| Ex. (26) | Com. (1-26) | 5.4 | 3.7 | 300.0 | 8.2 | 125.6 | 0.66 | 0.34 |
| Ex. (27) | Com. (1-27) | 5.4 | 3.7 | 300.0 | 8.1 | 124.5 | 0.66 | 0.33 |
| Ex. (28) | Com. (1-28) | 5.5 | 3.8 | 300.0 | 7.9 | 124.2 | 0.66 | 0.33 |

TABLE 4-continued

| | Compound | Voltage (V) | Current Density (mA/cm²) | Brightness (cd/m²) | Efficiency (cd/A) | Lifetime T(90) | CIE x | CIE y |
|---|---|---|---|---|---|---|---|---|
| Ex. (29) | Com. (1-29) | 5.3 | 3.4 | 300.0 | 8.7 | 135.6 | 0.66 | 0.34 |
| Ex. (30) | Com. (1-30) | 5.3 | 3.5 | 300.0 | 8.6 | 123.8 | 0.66 | 0.34 |
| Ex. (31) | Com. (1-31) | 5.3 | 3.6 | 300.0 | 8.4 | 126.5 | 0.66 | 0.33 |
| Ex. (32) | Com. (1-32) | 5.2 | 3.4 | 300.0 | 8.7 | 129.6 | 0.66 | 0.33 |
| Ex. (33) | Com. (1-33) | 5.3 | 3.4 | 300.0 | 8.9 | 134.4 | 0.66 | 0.33 |
| Ex. (34) | Com. (1-34) | 5.2 | 3.7 | 300.0 | 8.2 | 124.0 | 0.66 | 0.34 |
| Ex. (35) | Com. (1-35) | 5.3 | 3.5 | 300.0 | 8.5 | 126.9 | 0.66 | 0.33 |
| Ex. (36) | Com. (1-36) | 5.3 | 3.7 | 300.0 | 8.1 | 127.7 | 0.66 | 0.33 |
| Ex. (37) | Com. (1-37) | 5.3 | 3.7 | 300.0 | 8.1 | 126.8 | 0.66 | 0.33 |
| Ex. (38) | Com. (1-38) | 5.2 | 3.5 | 300.0 | 8.6 | 127.1 | 0.66 | 0.33 |
| Ex. (39) | Com. (1-39) | 5.4 | 3.7 | 300.0 | 8.2 | 127.9 | 0.66 | 0.33 |
| Ex. (40) | Com. (1-40) | 5.3 | 3.5 | 300.0 | 8.5 | 126.6 | 0.66 | 0.33 |
| Ex. (41) | Com. (1-41) | 5.2 | 3.6 | 300.0 | 8.4 | 128.7 | 0.66 | 0.33 |
| Ex. (42) | Com. (1-42) | 5.3 | 3.7 | 300.0 | 8.2 | 124.0 | 0.66 | 0.34 |
| Ex. (43) | Com. (1-43) | 5.4 | 3.6 | 300.0 | 8.3 | 126.7 | 0.66 | 0.33 |
| Ex. (44) | Com. (1-44) | 5.4 | 3.6 | 300.0 | 8.3 | 127.1 | 0.66 | 0.33 |
| Ex. (45) | Com. (1-45) | 5.3 | 3.7 | 300.0 | 8.2 | 126.5 | 0.66 | 0.33 |
| Ex. (46) | Com. (1-46) | 5.3 | 3.5 | 300.0 | 8.5 | 124.1 | 0.66 | 0.34 |
| Ex. (47) | Com. (1-47) | 5.2 | 3.5 | 300.0 | 8.6 | 126.3 | 0.66 | 0.34 |
| Ex. (48) | Com. (1-48) | 5.5 | 3.7 | 300.0 | 8.1 | 123.9 | 0.66 | 0.33 |
| Ex. (49) | Com. (1-49) | 5.4 | 4.0 | 300.0 | 7.5 | 126.6 | 0.66 | 0.33 |
| Ex. (50) | Com. (1-50) | 5.4 | 3.8 | 300.0 | 7.9 | 126.0 | 0.66 | 0.34 |
| Ex. (51) | Com. (1-51) | 5.3 | 4.0 | 300.0 | 7.5 | 125.8 | 0.66 | 0.34 |
| Ex. (52) | Com. (1-52) | 5.3 | 3.9 | 300.0 | 7.7 | 126.6 | 0.66 | 0.34 |
| Ex. (53) | Com. (1-53) | 5.4 | 3.8 | 300.0 | 7.8 | 127.9 | 0.66 | 0.34 |
| Ex. (54) | Com. (1-54) | 5.5 | 3.8 | 300.0 | 7.9 | 126.5 | 0.66 | 0.34 |
| Ex. (55) | Com. (1-55) | 5.4 | 4.0 | 300.0 | 7.5 | 127.1 | 0.66 | 0.33 |
| Ex. (56) | Com. (1-56) | 5.4 | 3.8 | 300.0 | 7.9 | 127.5 | 0.66 | 0.34 |
| Ex. (57) | Com. (1-57) | 5.2 | 3.3 | 300.0 | 9.1 | 153.9 | 0.66 | 0.34 |
| Ex. (58) | Com. (1-58) | 5.2 | 3.3 | 300.0 | 9.1 | 139.4 | 0.66 | 0.34 |
| Ex. (59) | Com. (1-59) | 5.2 | 3.4 | 300.0 | 8.9 | 132.2 | 0.66 | 0.33 |
| Ex. (60) | Com. (1-60) | 5.2 | 3.2 | 300.0 | 9.3 | 150.3 | 0.66 | 0.34 |
| Ex. (61) | Com. (1-61) | 5.2 | 3.3 | 300.0 | 9.1 | 153.2 | 0.66 | 0.34 |
| Ex. (62) | Com. (1-62) | 5.3 | 3.5 | 300.0 | 8.5 | 129.7 | 0.66 | 0.34 |
| Ex. (63) | Com. (1-63) | 5.2 | 3.5 | 300.0 | 8.5 | 130.8 | 0.66 | 0.34 |
| Ex. (64) | Com. (1-64) | 5.2 | 3.3 | 300.0 | 9.0 | 136.6 | 0.66 | 0.33 |
| Ex. (65) | Com. (1-65) | 5.2 | 3.4 | 300.0 | 8.8 | 134.8 | 0.66 | 0.34 |
| Ex. (66) | Com. (1-66) | 5.2 | 3.4 | 300.0 | 8.8 | 130.9 | 0.66 | 0.34 |
| Ex. (67) | Com. (1-67) | 5.2 | 3.4 | 300.0 | 8.9 | 126.4 | 0.66 | 0.33 |
| Ex. (68) | Com. (1-68) | 5.2 | 3.5 | 300.0 | 8.6 | 133.1 | 0.66 | 0.34 |
| Ex. (69) | Com. (1-69) | 5.2 | 3.4 | 300.0 | 8.8 | 126.3 | 0.66 | 0.33 |
| Ex. (70) | Com. (1-70) | 5.3 | 3.4 | 300.0 | 8.9 | 127.6 | 0.66 | 0.33 |
| Ex. (71) | Com. (1-71) | 5.3 | 3.4 | 300.0 | 8.9 | 132.9 | 0.66 | 0.34 |
| Ex. (72) | Com. (1-72) | 5.2 | 3.5 | 300.0 | 8.5 | 138.7 | 0.66 | 0.33 |
| Ex. (73) | Com. (1-73) | 5.3 | 3.5 | 300.0 | 8.6 | 124.5 | 0.66 | 0.34 |
| Ex. (74) | Com. (1-74) | 5.3 | 3.3 | 300.0 | 9.0 | 145.3 | 0.66 | 0.33 |
| Ex. (75) | Com. (1-75) | 5.2 | 3.3 | 300.0 | 9.0 | 141.4 | 0.66 | 0.33 |
| Ex. (76) | Com. (1-76) | 5.4 | 3.8 | 300.0 | 8.0 | 124.3 | 0.66 | 0.34 |
| Ex. (77) | Com. (1-77) | 5.3 | 3.5 | 300.0 | 8.5 | 125.9 | 0.66 | 0.33 |
| Ex. (78) | Com. (1-78) | 5.3 | 3.6 | 300.0 | 8.4 | 123.9 | 0.66 | 0.34 |
| Ex. (79) | Com. (1-79) | 5.3 | 3.6 | 300.0 | 8.3 | 128.6 | 0.66 | 0.33 |
| Ex. (80) | Com. (1-80) | 5.3 | 3.5 | 300.0 | 8.5 | 127.9 | 0.66 | 0.34 |
| Ex. (81) | Com. (1-81) | 5.3 | 3.7 | 300.0 | 8.1 | 127.3 | 0.66 | 0.33 |
| Ex. (82) | Com. (1-82) | 5.4 | 3.7 | 300.0 | 8.2 | 124.1 | 0.66 | 0.34 |
| Ex. (83) | Com. (1-83) | 5.3 | 3.7 | 300.0 | 8.1 | 125.9 | 0.66 | 0.34 |
| Ex. (84) | Com. (1-84) | 5.2 | 3.7 | 300.0 | 8.2 | 126.2 | 0.66 | 0.34 |
| Ex. (85) | Com. (1-85) | 5.2 | 3.3 | 300.0 | 9.0 | 145.1 | 0.66 | 0.33 |
| Ex. (86) | Com. (1-86) | 5.3 | 3.4 | 300.0 | 8.7 | 131.9 | 0.66 | 0.33 |
| Ex. (87) | Com. (1-87) | 5.2 | 3.5 | 300.0 | 8.6 | 124.5 | 0.66 | 0.33 |
| Ex. (88) | Com. (1-88) | 5.3 | 3.3 | 300.0 | 9.0 | 143.1 | 0.66 | 0.33 |
| Ex. (89) | Com. (1-89) | 5.2 | 3.4 | 300.0 | 8.9 | 143.6 | 0.66 | 0.34 |
| Ex. (90) | Com. (1-90) | 5.2 | 3.5 | 300.0 | 8.6 | 126.0 | 0.66 | 0.34 |
| Ex. (91) | Com. (1-91) | 5.2 | 3.4 | 300.0 | 8.8 | 128.4 | 0.66 | 0.33 |
| Ex. (92) | Com. (1-92) | 5.3 | 3.4 | 300.0 | 8.8 | 125.6 | 0.66 | 0.34 |
| Ex. (93) | Com. (1-93) | 5.2 | 3.6 | 300.0 | 8.4 | 125.6 | 0.66 | 0.34 |
| Ex. (94) | Com. (1-94) | 5.3 | 3.4 | 300.0 | 8.7 | 125.0 | 0.66 | 0.34 |
| Ex. (95) | Com. (1-95) | 5.3 | 3.5 | 300.0 | 8.5 | 124.6 | 0.66 | 0.34 |
| Ex. (96) | Com. (1-96) | 5.3 | 3.6 | 300.0 | 8.3 | 124.8 | 0.66 | 0.33 |
| Ex. (97) | Com. (1-97) | 5.2 | 3.5 | 300.0 | 8.6 | 127.9 | 0.66 | 0.34 |
| Ex. (98) | Com. (1-98) | 5.2 | 3.5 | 300.0 | 8.6 | 125.7 | 0.66 | 0.34 |
| Ex. (99) | Com. (1-99) | 5.2 | 3.6 | 300.0 | 8.4 | 126.5 | 0.66 | 0.33 |
| Ex. (100) | Com. (1-100) | 5.3 | 3.5 | 300.0 | 8.5 | 126.4 | 0.66 | 0.34 |
| Ex. (101) | Com. (1-101) | 5.3 | 3.5 | 300.0 | 8.6 | 127.8 | 0.66 | 0.34 |
| Ex. (102) | Com. (1-102) | 5.2 | 3.4 | 300.0 | 8.8 | 133.3 | 0.66 | 0.33 |
| Ex. (103) | Com. (1-103) | 5.3 | 3.6 | 300.0 | 8.4 | 127.3 | 0.66 | 0.33 |

TABLE 4-continued

| | Compound | Voltage (V) | Current Density (mA/cm$^2$) | Brightness (cd/m$^2$) | Efficiency (cd/A) | Lifetime T(90) | CIE x | CIE y |
|---|---|---|---|---|---|---|---|---|
| Ex. (104) | Com. (1-104) | 5.2 | 3.8 | 300.0 | 7.8 | 124.2 | 0.66 | 0.34 |
| Ex. (105) | Com. (1-105) | 5.3 | 3.8 | 300.0 | 8.0 | 125.1 | 0.66 | 0.33 |
| Ex. (106) | Com. (1-106) | 5.2 | 3.7 | 300.0 | 8.1 | 125.8 | 0.66 | 0.33 |
| Ex. (107) | Com. (1-107) | 5.4 | 3.9 | 300.0 | 7.7 | 124.6 | 0.66 | 0.34 |
| Ex. (108) | Com. (1-108) | 5.4 | 3.6 | 300.0 | 8.3 | 127.5 | 0.66 | 0.34 |
| Ex. (109) | Com. (1-109) | 5.3 | 3.5 | 300.0 | 8.5 | 137.0 | 0.66 | 0.34 |
| Ex. (110) | Com. (1-110) | 5.2 | 3.6 | 300.0 | 8.4 | 127.8 | 0.66 | 0.33 |
| Ex. (111) | Com. (1-111) | 5.3 | 3.5 | 300.0 | 8.6 | 132.0 | 0.66 | 0.33 |
| Ex. (112) | Com. (1-112) | 5.4 | 3.6 | 300.0 | 8.3 | 126.0 | 0.66 | 0.34 |
| Ex. (113) | Com. (1-113) | 5.4 | 3.7 | 300.0 | 8.1 | 126.1 | 0.66 | 0.33 |
| Ex. (114) | Com. (1-114) | 5.4 | 3.7 | 300.0 | 8.2 | 124.6 | 0.66 | 0.34 |
| Ex. (115) | Com. (1-115) | 5.3 | 3.8 | 300.0 | 8.0 | 128.7 | 0.66 | 0.34 |
| Ex. (116) | Com. (1-116) | 5.3 | 3.8 | 300.0 | 8.0 | 127.2 | 0.66 | 0.33 |
| Ex. (117) | Com. (1-117) | 5.5 | 3.6 | 300.0 | 8.4 | 127.3 | 0.66 | 0.34 |
| Ex. (118) | Com. (1-118) | 5.5 | 3.6 | 300.0 | 8.4 | 124.6 | 0.66 | 0.33 |
| Ex. (119) | Com. (1-119) | 5.5 | 4.0 | 300.0 | 7.5 | 124.8 | 0.66 | 0.34 |
| Ex. (120) | Com. (1-120) | 5.5 | 3.9 | 300.0 | 7.7 | 126.8 | 0.66 | 0.33 |
| Ex. (121) | Com. (1-121) | 5.2 | 3.5 | 300.0 | 8.6 | 135.1 | 0.66 | 0.34 |
| Ex. (122) | Com. (1-122) | 5.3 | 3.5 | 300.0 | 8.5 | 125.1 | 0.66 | 0.33 |
| Ex. (123) | Com. (1-123) | 5.3 | 3.5 | 300.0 | 8.5 | 134.2 | 0.66 | 0.33 |
| Ex. (124) | Com. (1-124) | 5.3 | 3.7 | 300.0 | 8.1 | 126.9 | 0.66 | 0.34 |
| Ex. (125) | Com. (1-125) | 5.3 | 3.7 | 300.0 | 8.1 | 124.0 | 0.66 | 0.33 |
| Ex. (126) | Com. (1-126) | 5.5 | 3.7 | 300.0 | 8.1 | 128.1 | 0.66 | 0.33 |
| Ex. (127) | Com. (1-127) | 5.4 | 3.6 | 300.0 | 8.4 | 125.2 | 0.66 | 0.34 |
| Ex. (128) | Com. (1-128) | 5.3 | 3.8 | 300.0 | 8.0 | 126.7 | 0.66 | 0.33 |
| Ex. (129) | Com. (1-129) | 5.4 | 3.5 | 300.0 | 8.5 | 126.9 | 0.66 | 0.34 |
| Ex. (130) | Com. (1-130) | 5.5 | 3.6 | 300.0 | 8.4 | 127.7 | 0.66 | 0.33 |
| Ex. (131) | Com. (1-131) | 5.5 | 4.0 | 300.0 | 7.5 | 125.6 | 0.66 | 0.34 |
| Ex. (132) | Com. (1-132) | 5.5 | 3.8 | 300.0 | 7.8 | 123.9 | 0.66 | 0.33 |
| Ex. (133) | Com. (1-133) | 5.3 | 3.4 | 300.0 | 8.8 | 136.5 | 0.66 | 0.33 |
| Ex. (134) | Com. (1-134) | 5.3 | 3.4 | 300.0 | 8.8 | 129.1 | 0.66 | 0.33 |
| Ex. (135) | Com. (1-135) | 5.3 | 3.5 | 300.0 | 8.5 | 123.6 | 0.66 | 0.33 |
| Ex. (136) | Com. (1-136) | 5.2 | 3.6 | 300.0 | 8.3 | 124.8 | 0.66 | 0.34 |
| Ex. (137) | Com. (1-137) | 5.2 | 3.5 | 300.0 | 8.6 | 124.4 | 0.66 | 0.33 |
| Ex. (138) | Com. (1-138) | 5.3 | 3.5 | 300.0 | 8.5 | 125.9 | 0.66 | 0.33 |
| Ex. (139) | Com. (1-139) | 5.3 | 3.3 | 300.0 | 9.1 | 149.2 | 0.66 | 0.34 |
| Ex. (140) | Com. (1-140) | 5.2 | 3.3 | 300.0 | 9.0 | 139.4 | 0.66 | 0.34 |
| Ex. (141) | Com. (1-141) | 5.2 | 3.4 | 300.0 | 8.8 | 131.3 | 0.66 | 0.33 |
| Ex. (142) | Com. (1-142) | 5.3 | 3.4 | 300.0 | 8.9 | 129.3 | 0.66 | 0.34 |
| Ex. (143) | Com. (1-143) | 5.5 | 3.5 | 300.0 | 8.5 | 123.9 | 0.66 | 0.33 |
| Ex. (144) | Com. (1-144) | 5.5 | 3.6 | 300.0 | 8.4 | 125.5 | 0.66 | 0.33 |
| Ex. (145) | Com. (1-145) | 5.4 | 3.6 | 300.0 | 8.4 | 124.7 | 0.66 | 0.33 |
| Ex. (146) | Com. (1-146) | 5.5 | 3.5 | 300.0 | 8.5 | 125.7 | 0.66 | 0.33 |
| Ex. (147) | Com. (1-147) | 5.3 | 3.6 | 300.0 | 8.4 | 126.4 | 0.66 | 0.34 |
| Ex. (148) | Com. (1-148) | 5.5 | 3.8 | 300.0 | 8.0 | 128.4 | 0.66 | 0.34 |
| Ex. (149) | Com. (2-1) | 5.3 | 3.4 | 300.0 | 8.9 | 134.8 | 0.66 | 0.33 |
| Ex. (150) | Com. (2-2) | 5.2 | 3.5 | 300.0 | 8.5 | 124.1 | 0.66 | 0.33 |
| Ex. (151) | Com. (2-3) | 5.3 | 3.6 | 300.0 | 8.4 | 128.1 | 0.66 | 0.34 |
| Ex. (152) | Com. (2-4) | 5.2 | 3.5 | 300.0 | 8.8 | 130.8 | 0.66 | 0.34 |
| Ex. (153) | Com. (2-5) | 5.2 | 3.7 | 300.0 | 8.1 | 127.3 | 0.66 | 0.34 |
| Ex. (154) | Com. (2-6) | 5.3 | 3.6 | 300.0 | 8.4 | 125.1 | 0.66 | 0.34 |
| Ex. (155) | Com. (2-7) | 5.3 | 3.7 | 300.0 | 8.2 | 124.8 | 0.66 | 0.34 |
| Ex. (156) | Com. (2-8) | 5.3 | 3.5 | 300.0 | 8.6 | 125.0 | 0.66 | 0.33 |
| Ex. (157) | Com. (2-9) | 5.2 | 3.5 | 300.0 | 8.6 | 124.7 | 0.66 | 0.33 |
| Ex. (158) | Com. (2-10) | 5.4 | 3.5 | 300.0 | 8.5 | 126.4 | 0.66 | 0.33 |
| Ex. (159) | Com. (2-11) | 5.3 | 3.5 | 300.0 | 8.5 | 126.9 | 0.66 | 0.34 |
| Ex. (160) | Com. (2-12) | 5.2 | 3.7 | 300.0 | 8.2 | 127.3 | 0.66 | 0.33 |
| Ex. (161) | Com. (2-13) | 5.2 | 3.5 | 300.0 | 8.5 | 126.3 | 0.66 | 0.34 |
| Ex. (162) | Com. (2-14) | 5.4 | 3.5 | 300.0 | 8.6 | 124.0 | 0.66 | 0.34 |
| Ex. (163) | Com. (2-15) | 5.4 | 3.9 | 300.0 | 7.6 | 126.5 | 0.66 | 0.34 |
| Ex. (164) | Com. (2-16) | 5.5 | 3.8 | 300.0 | 8.0 | 127.3 | 0.66 | 0.33 |
| Ex. (165) | Com. (2-17) | 5.4 | 3.9 | 300.0 | 7.7 | 126.8 | 0.66 | 0.34 |
| Ex. (166) | Com. (2-18) | 5.3 | 4.0 | 300.0 | 7.5 | 128.6 | 0.66 | 0.33 |
| Ex. (167) | Com. (2-19) | 5.5 | 3.8 | 300.0 | 7.8 | 127.2 | 0.66 | 0.34 |
| Ex. (168) | Com. (2-20) | 5.4 | 3.7 | 300.0 | 8.1 | 125.9 | 0.66 | 0.34 |
| Ex. (169) | Com. (2-21) | 5.2 | 3.5 | 300.0 | 8.6 | 138.4 | 0.66 | 0.34 |
| Ex. (170) | Com. (2-22) | 5.2 | 3.6 | 300.0 | 8.4 | 127.3 | 0.66 | 0.34 |
| Ex. (171) | Com. (2-23) | 5.3 | 3.8 | 300.0 | 8.0 | 124.7 | 0.66 | 0.33 |
| Ex. (172) | Com. (2-24) | 5.3 | 3.5 | 300.0 | 8.6 | 129.2 | 0.66 | 0.34 |
| Ex. (173) | Com. (2-25) | 5.3 | 3.7 | 300.0 | 8.1 | 127.4 | 0.66 | 0.34 |
| Ex. (174) | Com. (2-26) | 5.2 | 3.8 | 300.0 | 7.9 | 128.0 | 0.66 | 0.34 |
| Ex. (175) | Com. (2-27) | 5.3 | 3.6 | 300.0 | 8.4 | 124.9 | 0.66 | 0.34 |
| Ex. (176) | Com. (2-28) | 5.3 | 3.7 | 300.0 | 8.2 | 125.9 | 0.66 | 0.34 |
| Ex. (177) | Com. (2-29) | 5.3 | 3.6 | 300.0 | 8.3 | 128.1 | 0.66 | 0.33 |
| Ex. (178) | Com. (2-30) | 5.3 | 3.6 | 300.0 | 8.3 | 124.6 | 0.66 | 0.33 |

TABLE 4-continued

| | Compound | Voltage (V) | Current Density (mA/cm$^2$) | Brightness (cd/m$^2$) | Efficiency (cd/A) | Lifetime T(90) | CIE x | CIE y |
|---|---|---|---|---|---|---|---|---|
| Ex. (179) | Com. (2-31) | 5.3 | 3.8 | 300.0 | 7.9 | 125.4 | 0.66 | 0.33 |
| Ex. (180) | Com. (2-32) | 5.4 | 3.7 | 300.0 | 8.2 | 127.3 | 0.66 | 0.33 |
| Ex. (181) | Com. (2-33) | 5.3 | 3.6 | 300.0 | 8.3 | 127.7 | 0.66 | 0.33 |
| Ex. (182) | Com. (2-34) | 5.3 | 3.6 | 300.0 | 8.3 | 125.9 | 0.66 | 0.33 |
| Ex. (183) | Com. (2-35) | 5.5 | 3.8 | 300.0 | 7.9 | 126.7 | 0.66 | 0.34 |
| Ex. (184) | Com. (2-36) | 5.5 | 3.8 | 300.0 | 7.8 | 124.1 | 0.66 | 0.34 |
| Ex. (185) | Com. (2-37) | 5.4 | 3.8 | 300.0 | 7.8 | 127.7 | 0.66 | 0.34 |
| Ex. (186) | Com. (2-38) | 5.5 | 3.9 | 300.0 | 7.6 | 123.6 | 0.66 | 0.34 |
| Ex. (187) | Com. (2-39) | 5.5 | 3.8 | 300.0 | 7.8 | 123.9 | 0.66 | 0.34 |
| Ex. (188) | Com. (2-40) | 5.3 | 3.9 | 300.0 | 7.7 | 125.5 | 0.66 | 0.33 |
| Ex. (189) | Com. (2-41) | 5.2 | 3.3 | 300.0 | 9.0 | 147.8 | 0.66 | 0.34 |
| Ex. (190) | Com. (2-42) | 5.2 | 3.4 | 300.0 | 8.8 | 133.0 | 0.66 | 0.33 |
| Ex. (191) | Com. (2-43) | 5.2 | 3.6 | 300.0 | 8.3 | 125.0 | 0.66 | 0.33 |
| Ex. (192) | Com. (2-44) | 5.2 | 3.4 | 300.0 | 8.9 | 145.9 | 0.66 | 0.34 |
| Ex. (193) | Com. (2-45) | 5.3 | 3.4 | 300.0 | 8.7 | 126.9 | 0.66 | 0.33 |
| Ex. (194) | Com. (2-46) | 5.3 | 3.6 | 300.0 | 8.4 | 127.7 | 0.66 | 0.34 |
| Ex. (195) | Com. (2-47) | 5.3 | 3.6 | 300.0 | 8.4 | 128.0 | 0.66 | 0.34 |
| Ex. (196) | Com. (2-48) | 5.3 | 3.5 | 300.0 | 8.5 | 127.3 | 0.66 | 0.33 |
| Ex. (197) | Com. (2-49) | 5.3 | 3.6 | 300.0 | 8.4 | 125.7 | 0.66 | 0.34 |
| Ex. (198) | Com. (2-50) | 5.3 | 3.5 | 300.0 | 8.6 | 126.8 | 0.66 | 0.34 |
| Ex. (199) | Com. (2-51) | 5.3 | 3.5 | 300.0 | 8.6 | 126.2 | 0.66 | 0.33 |
| Ex. (200) | Com. (2-52) | 5.3 | 3.6 | 300.0 | 8.4 | 125.3 | 0.66 | 0.33 |
| Ex. (201) | Com. (2-53) | 5.3 | 3.4 | 300.0 | 8.7 | 130.6 | 0.66 | 0.33 |
| Ex. (202) | Com. (2-54) | 5.2 | 3.4 | 300.0 | 8.7 | 131.9 | 0.66 | 0.34 |
| Ex. (203) | Com. (2-55) | 5.2 | 3.7 | 300.0 | 8.2 | 127.5 | 0.66 | 0.33 |
| Ex. (204) | Com. (2-56) | 5.3 | 3.6 | 300.0 | 8.3 | 128.0 | 0.66 | 0.34 |
| Ex. (205) | Com. (2-57) | 5.3 | 3.7 | 300.0 | 8.2 | 123.7 | 0.66 | 0.34 |
| Ex. (206) | Com. (2-58) | 5.5 | 3.7 | 300.0 | 8.2 | 124.5 | 0.66 | 0.34 |
| Ex. (207) | Com. (2-59) | 5.4 | 3.7 | 300.0 | 8.2 | 124.9 | 0.66 | 0.33 |
| Ex. (208) | Com. (2-60) | 5.4 | 3.8 | 300.0 | 8.0 | 126.7 | 0.66 | 0.34 |
| Ex. (209) | Com. (2-61) | 5.3 | 3.4 | 300.0 | 8.8 | 135.3 | 0.66 | 0.34 |
| Ex. (210) | Com. (2-62) | 5.2 | 3.5 | 300.0 | 8.5 | 126.7 | 0.66 | 0.34 |
| Ex. (211) | Com. (2-63) | 5.2 | 3.6 | 300.0 | 8.4 | 128.6 | 0.66 | 0.33 |
| Ex. (212) | Com. (2-64) | 5.3 | 3.4 | 300.0 | 8.8 | 137.3 | 0.66 | 0.34 |
| Ex. (213) | Com. (2-65) | 5.3 | 3.7 | 300.0 | 8.2 | 124.9 | 0.66 | 0.34 |
| Ex. (214) | Com. (2-66) | 5.2 | 3.5 | 300.0 | 8.5 | 126.5 | 0.66 | 0.34 |
| Ex. (215) | Com. (2-67) | 5.2 | 3.5 | 300.0 | 8.6 | 127.3 | 0.66 | 0.34 |
| Ex. (216) | Com. (2-68) | 5.2 | 3.5 | 300.0 | 8.5 | 124.1 | 0.66 | 0.34 |
| Ex. (217) | Com. (2-69) | 5.3 | 3.6 | 300.0 | 8.3 | 125.6 | 0.66 | 0.34 |
| Ex. (218) | Com. (2-70) | 5.2 | 3.6 | 300.0 | 8.4 | 126.1 | 0.66 | 0.33 |
| Ex. (219) | Com. (2-71) | 5.2 | 3.6 | 300.0 | 8.4 | 127.9 | 0.66 | 0.33 |
| Ex. (220) | Com. (2-72) | 5.2 | 3.5 | 300.0 | 8.5 | 126.4 | 0.66 | 0.34 |
| Ex. (221) | Com. (2-73) | 5.3 | 3.4 | 300.0 | 8.7 | 124.5 | 0.66 | 0.34 |
| Ex. (222) | Com. (2-74) | 5.3 | 3.5 | 300.0 | 8.6 | 123.9 | 0.66 | 0.34 |
| Ex. (223) | Com. (2-75) | 5.5 | 3.9 | 300.0 | 7.6 | 125.0 | 0.66 | 0.34 |
| Ex. (224) | Com. (2-76) | 5.3 | 3.8 | 300.0 | 7.9 | 127.5 | 0.66 | 0.34 |
| Ex. (225) | Com. (2-77) | 5.3 | 3.8 | 300.0 | 8.0 | 125.3 | 0.66 | 0.34 |
| Ex. (226) | Com. (2-78) | 5.3 | 3.9 | 300.0 | 7.6 | 127.6 | 0.66 | 0.34 |
| Ex. (227) | Com. (2-79) | 5.2 | 3.8 | 300.0 | 7.8 | 128.4 | 0.66 | 0.34 |
| Ex. (228) | Com. (2-80) | 5.4 | 3.7 | 300.0 | 8.1 | 127.5 | 0.66 | 0.34 |
| Ex. (229) | Com. (2-81) | 5.3 | 3.4 | 300.0 | 8.7 | 134.5 | 0.66 | 0.33 |
| Ex. (230) | Com. (2-82) | 5.3 | 3.6 | 300.0 | 8.4 | 125.0 | 0.66 | 0.34 |
| Ex. (231) | Com. (2-83) | 5.2 | 3.5 | 300.0 | 8.6 | 138.9 | 0.66 | 0.33 |
| Ex. (232) | Com. (2-84) | 5.4 | 3.8 | 300.0 | 8.0 | 125.1 | 0.66 | 0.33 |
| Ex. (233) | Com. (2-85) | 5.4 | 3.7 | 300.0 | 8.1 | 128.0 | 0.66 | 0.33 |
| Ex. (234) | Com. (2-86) | 5.5 | 3.7 | 300.0 | 8.1 | 126.6 | 0.66 | 0.33 |
| Ex. (235) | Com. (2-87) | 5.4 | 3.7 | 300.0 | 8.1 | 128.1 | 0.66 | 0.33 |
| Ex. (236) | Com. (2-88) | 5.5 | 3.6 | 300.0 | 8.3 | 128.4 | 0.66 | 0.34 |
| Ex. (237) | Com. (2-89) | 5.5 | 3.6 | 300.0 | 8.4 | 128.2 | 0.66 | 0.33 |
| Ex. (238) | Com. (2-90) | 5.4 | 3.6 | 300.0 | 8.3 | 127.6 | 0.66 | 0.33 |
| Ex. (239) | Com. (2-91) | 5.4 | 4.0 | 300.0 | 7.5 | 123.6 | 0.66 | 0.33 |
| Ex. (240) | Com. (2-92) | 5.5 | 3.8 | 300.0 | 7.9 | 126.8 | 0.66 | 0.34 |
| Ex. (241) | Com. (2-93) | 5.3 | 3.5 | 300.0 | 8.6 | 140.0 | 0.66 | 0.33 |
| Ex. (242) | Com. (2-94) | 5.2 | 3.5 | 300.0 | 8.5 | 128.5 | 0.66 | 0.33 |
| Ex. (243) | Com. (2-95) | 5.3 | 3.5 | 300.0 | 8.5 | 132.5 | 0.66 | 0.34 |
| Ex. (244) | Com. (2-96) | 5.3 | 3.6 | 300.0 | 8.3 | 128.0 | 0.66 | 0.34 |
| Ex. (245) | Com. (2-97) | 5.4 | 3.7 | 300.0 | 8.2 | 124.6 | 0.66 | 0.33 |
| Ex. (246) | Com. (2-98) | 5.4 | 3.8 | 300.0 | 7.9 | 124.1 | 0.66 | 0.33 |
| Ex. (247) | Com. (2-99) | 5.4 | 3.7 | 300.0 | 8.1 | 123.9 | 0.66 | 0.34 |
| Ex. (248) | Com. (2-100) | 5.4 | 3.7 | 300.0 | 8.2 | 125.2 | 0.66 | 0.33 |
| Ex. (249) | Com. (2-101) | 5.4 | 3.6 | 300.0 | 8.4 | 125.9 | 0.66 | 0.33 |
| Ex. (250) | Com. (2-102) | 5.4 | 3.6 | 300.0 | 8.3 | 125.1 | 0.66 | 0.33 |
| Ex. (251) | Com. (2-103) | 5.4 | 3.9 | 300.0 | 7.6 | 125.8 | 0.66 | 0.34 |
| Ex. (252) | Com. (2-104) | 5.4 | 4.0 | 300.0 | 7.5 | 124.6 | 0.66 | 0.33 |
| Ex. (253) | Com. (2-105) | 5.3 | 3.5 | 300.0 | 8.6 | 127.1 | 0.66 | 0.33 |

TABLE 4-continued

| | Compound | Voltage (V) | Current Density (mA/cm²) | Brightness (cd/m²) | Efficiency (cd/A) | Lifetime T(90) | CIE x | CIE y |
|---|---|---|---|---|---|---|---|---|
| Ex. (254) | Com. (2-106) | 5.3 | 3.5 | 300.0 | 8.6 | 127.1 | 0.66 | 0.33 |
| Ex. (255) | Com. (2-107) | 5.3 | 3.7 | 300.0 | 8.2 | 126.4 | 0.66 | 0.33 |
| Ex. (256) | Com. (2-108) | 5.3 | 3.5 | 300.0 | 8.6 | 127.7 | 0.66 | 0.34 |
| Ex. (257) | Com. (2-109) | 5.2 | 3.6 | 300.0 | 8.3 | 124.3 | 0.66 | 0.34 |
| Ex. (258) | Com. (2-110) | 5.3 | 3.5 | 300.0 | 8.5 | 127.1 | 0.66 | 0.33 |
| Ex. (259) | Com. (2-111) | 5.3 | 3.4 | 300.0 | 8.8 | 129.3 | 0.66 | 0.34 |
| Ex. (260) | Com. (2-112) | 5.2 | 3.4 | 300.0 | 8.8 | 135.0 | 0.66 | 0.34 |
| Ex. (261) | Com. (2-113) | 5.3 | 3.5 | 300.0 | 8.6 | 126.3 | 0.66 | 0.34 |
| Ex. (262) | Com. (2-114) | 5.2 | 3.4 | 300.0 | 8.7 | 124.9 | 0.66 | 0.34 |
| Ex. (263) | Com. (2-115) | 5.3 | 3.5 | 300.0 | 8.5 | 127.3 | 0.66 | 0.33 |
| Ex. (264) | Com. (2-116) | 5.5 | 3.6 | 300.0 | 8.3 | 128.3 | 0.66 | 0.34 |
| Ex. (265) | Com. (2-117) | 5.5 | 3.6 | 300.0 | 8.3 | 125.3 | 0.66 | 0.33 |
| Ex. (266) | Com. (2-118) | 5.3 | 3.5 | 300.0 | 8.5 | 128.5 | 0.66 | 0.34 |
| Ex. (267) | Com. (2-119) | 5.5 | 4.0 | 300.0 | 7.5 | 124.8 | 0.66 | 0.34 |
| Ex. (268) | Com. (2-120) | 5.5 | 3.9 | 300.0 | 7.7 | 128.6 | 0.66 | 0.34 |

It can be seen from the results in Table 4 above that the compounds of comparative examples 1 to 7 exhibited a lower driving voltage, lower efficiency, and a lower lifespan than the inventive compounds.

Especially, Comparative Examples 2 to 7 have similar biscarbazole types to the inventive compounds, but produce different results depending on the presence or absence and location of a ring on the carbazole backbone.

It can be confirmed that Comparative Examples 2 and 7, in which a ring is not formed on the carbazole backbone, exhibited the highest driving voltage, lowest efficiency, and lowest lifespan among the comparative examples, and Comparative Examples 3 to 6, in which a ring is formed on the outside phenyl of the carbazole backbone, exhibited a lower driving voltage and relatively higher efficiency and lifespan than Comparative Examples 2 and 7.

However, the inventive compounds, in which a ring is formed on the backbone connecting two carbazole moieties, exhibited very excellent efficiency and lifespan characteristics and lower or similar driving voltages compared with Comparative Examples 3 to 6.

The reason is that, the compound in which a ring is present on the backbone connecting two carbazole moieties has a deeper HOMO energy level compared with the compound in which a ring is formed on the outside portion of the carbazole backbone, and thus holes overflow to the light emitting layer more promptly to increase the lifespan, and the light emission occurs inside the light emitting layer but not at the light emitting layer-hole transport layer interface, thereby achieving higher efficiency.

Although exemplary embodiments of the present invention have been described for illustrative purposes, a person skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

EXPLANATION OF NUMERICAL REFERENCES

100: organic electronic device 110: substrate.
120: First electrode 130: hole injection layer.
140: hole transport layer 141: buffer layer.
150: light emitting layer 151: emission-auxiliary layer.
160: electron transport layer 170: electron injection layer.
180: cathode.

What is claimed is:

1. A compound represented by Formula 4:

Formula 4

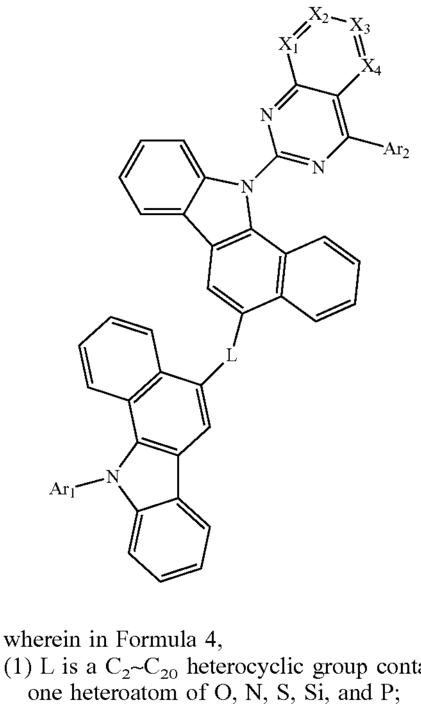

wherein in Formula 4, (1) L is a $C_2$~$C_{20}$ heterocyclic group containing at least one heteroatom of O, N, S, Si, and P;

(2) $Ar_1$ and $Ar_2$ are each independently selected from the group consisting of a fluorenyl group; a silane group; a $C_6$~$C_{60}$ aryl group; a $C_2$~$C_{20}$ alkenyl group; a $C_2$~$C_{60}$ heterocyclic group containing at least one heteroatom of O, N, S, Si, and P; a $C_1$~$C_{50}$ alkyl group; and a fused cyclic group of a $C_6$~$C_{60}$ aromatic ring and a $C_3$~$C_{60}$ aliphatic ring;

(3) $X_1$ to $X_4$ are each independently CR' or N; and (4) R' is selected from the group consisting of hydrogen; a $C_6$~$C_{60}$ aryl group; a fluorenyl group; a $C_2$~$C_{60}$ heterocyclic group containing at least one heteroatom of O, N, S, Si, and P; a $C_1$~$C_{50}$ alkyl group; and a fused cyclic group of a $C_6$~$C_{60}$ aromatic ring and a $C_3$~$C_{60}$ aliphatic ring; and a $C_2$~$C_{20}$ alkenyl group.

2. An organic electronic element comprising a first electrode, a second electrode, and an organic material layer disposed between the first electrode and the second electrode, wherein the organic material layer contains the compound of claim 1.

3. The organic electronic element of claim 2, wherein the organic material layer is formed by a soluble process using the compound.

4. The organic electronic element of claim 2, wherein the organic material layer includes at least one of a light emitting layer, a hole injection layer, a hole transport layer, an electron injection layer, an electron transport layer, and an emission-auxiliary layer.

5. The organic electronic element of claim 3, wherein the compound is used as a host material for a light emitting layer.

6. An electronic device, comprising:

a display device including the organic electronic element of claim 3; and a controller driving the display device.

7. The electronic device of claim 6, wherein the organic electronic element is at least one of an organic light emitting diode, an organic solar cell, an organic solar cell, an organic photo conductor, an organic transistor, and an element for a monochromatic or white lighting.

* * * * *